(12) United States Patent
De Palma et al.

(10) Patent No.: US 11,591,407 B2
(45) Date of Patent: Feb. 28, 2023

(54) ENGINEERED ANTIGEN PRESENTING CELLS AND USES THEREOF

(71) Applicant: ECOLE POLYTECHNIQUE FEDERALE DE LAUSANNE (EPFL), Lausanne (CH)

(72) Inventors: Michele De Palma, Lausanne (CH); Mario Leonardo Squadrito, Varese (IT)

(73) Assignee: ECOLE POLYTECHNIQUE FEDERALE DE LAUSANNE (EPPFL), Lausanne (CH)

(*) Notice: Subject to any disclaimer, the term of this patent is extended or adjusted under 35 U.S.C. 154(b) by 1246 days.

(21) Appl. No.: 16/074,446

(22) PCT Filed: Feb. 1, 2017

(86) PCT No.: PCT/EP2017/052145
§ 371 (c)(1),
(2) Date: Aug. 1, 2018

(87) PCT Pub. No.: WO2017/134100
PCT Pub. Date: Aug. 10, 2017

(65) Prior Publication Data
US 2019/0062450 A1    Feb. 28, 2019

(30) Foreign Application Priority Data
Feb. 2, 2016 (EP) .................................. 16153966

(51) Int. Cl.
| | | |
|---|---|---|
| *C07K 16/32* | (2006.01) | |
| *C07K 14/705* | (2006.01) | |
| *C07K 14/735* | (2006.01) | |
| *C07K 14/71* | (2006.01) | |
| *C07K 14/715* | (2006.01) | |
| *A61P 35/00* | (2006.01) | |
| *A61K 39/00* | (2006.01) | |

(52) U.S. Cl.
CPC ........ *C07K 16/32* (2013.01); *A61K 39/00119* (2018.08); *A61K 39/001171* (2018.08); *A61P 35/00* (2018.01); *C07K 14/705* (2013.01); *C07K 14/70535* (2013.01); *C07K 14/70553* (2013.01); *C07K 14/70596* (2013.01); *C07K 14/71* (2013.01); *C07K 14/715* (2013.01); *C07K 14/7153* (2013.01); *C07K 14/7158* (2013.01); *A61K 2039/5154* (2013.01); *C07K 2317/622* (2013.01); *C07K 2319/00* (2013.01); *C07K 2319/02* (2013.01); *C07K 2319/03* (2013.01); *C07K 2319/70* (2013.01); *C07K 2319/74* (2013.01)

(58) Field of Classification Search
CPC .................. C07K 16/32; C07K 14/705; C07K 14/70535; C07K 14/70553; C07K 14/7158; C07K 2317/622; C07K 2319/00; C07K 2319/02; C07K 2319/03; C07K 2319/70; C07K 2319/74; C07K 14/70596; C07K 14/71; C07K 14/715; C07K 14/7153; A61K 39/00119; A61K 2039/5154; A61K 35/14; A61P 35/00; C12N 5/0634; C12N 2510/00
See application file for complete search history.

(56) References Cited

U.S. PATENT DOCUMENTS

| | | | |
|---|---|---|---|
| 8,273,550 B2 | 9/2012 | Cizeau et al. | |
| 8,586,547 B2 | 11/2013 | Nishimura et al. | |
| 8,999,334 B2 | 4/2015 | Chahal et al. | |
| 2011/0038865 A1* | 2/2011 | Shin ................... | A61K 47/6811 424/134.1 |
| 2013/0247233 A1* | 9/2013 | Gaitanaris .............. | A61P 11/00 435/325 |
| 2015/0284463 A1* | 10/2015 | Tamaskovic ............ | A61P 35/00 530/387.3 |
| 2016/0015796 A1* | 1/2016 | Savelyeva ............ | A61K 47/646 424/185.1 |
| 2017/0267742 A1* | 9/2017 | Jensen ................... | A61P 43/00 |
| 2018/0009895 A1* | 1/2018 | Smith ................ | C07K 16/2866 |

FOREIGN PATENT DOCUMENTS

| | | | | |
|---|---|---|---|---|
| CN | 101925612 A | 12/2010 | | |
| CN | 101970498 A | 2/2011 | | |
| CN | 102459589 A | 5/2012 | | |
| WO | WO-2004012817 A2 * | 2/2004 | ......... | C07K 14/4703 |
| WO | WO-2007094005 A2 * | 8/2007 | ............. | A61P 19/02 |
| WO | WO-2010014629 A1 * | 2/2010 | ............. | A61P 19/02 |
| WO | WO 2010/042904 | 4/2010 | | |

(Continued)

OTHER PUBLICATIONS

Stone et al. "A sensitivity scale for targeting T cells with chimeric antigen receptors (CARs) and bispecific T-cell Engagers (BiTEs)." Oncoimmunology. Sep. 1, 2012; 1(6): 863-873. (Year: 2012).*
Xie et al. "Breast Cancer Migration and Invasion Depend on Proteasome Degradation of Regulator of G-Protein Signaling 4." Cancer Res. Jul. 15, 2009; 69(14): 5743-5751. (Year: 2009).*
Ahmed, N. et al. "Immunotherapy for Osteosarcoma: Genetic Modification of T cells Overcomes Low Levels of Tumor Antigen Expression" *Molecular Therapy*, Oct. 2009, pp. 1779-1787, vol. 17, No. 10.

(Continued)

*Primary Examiner* — Titilayo Moloye
(74) *Attorney, Agent, or Firm* — Saliwanchik, Lloyd & Eisenschenk

(57) ABSTRACT

The present invention relates to engineered extra-cellular vesicle internalizing receptors that have the ability to enhance uptake, processing, and presentation to T-cells of tumor-associated antigens by an antigen-presenting cell. It further relates to vectors or antigen presenting cells expressing said receptors, composition and uses thereof for the prevention and/or treatment of a cancer.

18 Claims, 9 Drawing Sheets

Specification includes a Sequence Listing.

(56) References Cited

FOREIGN PATENT DOCUMENTS

| WO | WO-2010117448 A2 * | 10/2010 | ............ C07K 14/52 |
|---|---|---|---|
| WO | WO 2015/092024 | 6/2015 | |

OTHER PUBLICATIONS

Ahmed, N. et al. "Human Epidermal Growth Factor Receptor 2 (HER2)—Specific Chimeric Antigen Receptor—Modified T Cells for the Immunotherapy of HER2-Positive Sarcoma" *Journal of Clinical Oncology*, May 20, 2015, pp. 1688-1696, vol. 33, No. 15, Supplemental Information—pp. 1-7.

Amendola, M. et al. "Coordinate dual-gene transgenesis by lentiviral vectors carrying synthetic bidirectional promoters" *Nature Biotechnology*, Jan. 2005, pp. 108-116, vol. 23, No. 1.

Baer, C. et al. "Suppression of microRNA activity amplifies IFN-γ-induced macrophage activation and promotes anti-tumour immunity" *Nature Cell Biology*, Jul. 2016, pp. 790-802, vol. 18, No. 7, Methods—pp. 1-4, Supplementary Information—pp. 1-13.

Biglari, A. et al. "Human monocytes expressing a CEA-specific chimeric CD64 receptor specifically target CEA-expressing tumour cells in vitro and in vivo" *Gene Therapy*, 2006, pp. 602-610, vol. 13.

De Palma, M. et al. "Transduction of a Gene Expression Cassette Using Advanced Generation Lentiviral Vectors" *Methods in Enzymology*, 2002, pp. 514-529, vol. 346.

Dolan, B. P. et al. "Dendritic Cells Cross-Dressed with Peptide MHC Class I Complexes Prime CD8$^+$ T Cells" *The Journal of Immunology*, 2006, pp. 6018-6024, vol. 177.

Franklin, M. C. et al. "Insights into ErbB signaling from the structure of the ErbB2-pertuzumab complex" *Cancer Cell*, Apr. 2004, pp. 317-328, vol. 5.

Gardner, T. et al. "Sipuleucel-T (Provenge) autologous vaccine approved for treatment of men with asymptomatic or minimally symptomatic castrate-resistant metastatic prostate cancer" *Human Vaccines & Immunotherapeutics*, Apr. 1, 2012, pp. 534-539, vol. 8, No. 4.

Gu, X. et al. "Improved vaccine efficacy of tumor exosome compared to tumor lysate loaded dendritic cells in mice" *International Journal of Cancer*, 2015, pp. E74-E84, vol. 136.

Hartman, Z. C. et al. "Increasing vaccine potency through exosome antigen targeting" *Vaccine*, 2011, pp. 9361-9367, vol. 29.

Kastenmüller, W. et al. "Dendritic cell-targeted vaccines—hope or hype?" *Nature Reviews—Immunology*, Oct. 2014, pp. 705-711, vol. 14.

Koller, B. H. et al. "Normal Development of Mice Deficient in β$_2$ M, MHC Class I Proteins, and CD8$^+$ T Cells" *Science*, Jun. 8, 1990, pp. 1227-1230, vol. 248.

Leto, S. M. et al. "Sustained Inhibition of HER3 and EGFR Is Necessary to Induce Regression of HER2-Amplified Gastrointestinal Carcinomas" *Clinical Cancer Research*, Dec. 15, 2015, pp. 5519-5531, vol. 21, No. 24.

Liu, Y. et al. "The exosomes in tumor immunity" *OncoImmunology*, Sep. 2015, pp. e1027472-1-e1027472-8, vol. 4, No. 9.

Mahnke, K. et al. "The Dendritic Cell Receptor for Endocytosis, DEC-205, Can Recycle and Enhance Antigen Presentation via Major Histocompatibility Complex Class II-positive Lysosomal Compartments" *The Journal of Cell Biology*, Oct. 30, 2000, pp. 673-683, vol. 151, No. 3.

Miller, J. F.A.P. et al. "The Journey from Discoveries in Fundamental Immunology to Cancer Immunotherapy" *Cancer Cell*, Apr. 13, 2015, pp. 439-449, vol. 27.

Morgan, R. A. et al. "Case Report of a Serious Adverse Event Following the Administration of T Cells Transduced With a Chimeric Antigen Receptor Recognizing ERBB2" *Molecular Therapy*, Apr. 2010, pp. 843-851, vol. 18, No. 4.

Mulcahy, L. A. et al. "Routes and mechanisms of extracellular vesicle uptake" *Journal of Extracellular Vesicles*, Aug. 4, 2014, pp. 1-14, vol. 3, No. 24641.

Newick, K. et al. "Chimeric antigen receptor T-cell therapy for solid tumors" *Molecular Therapy—Oncolytics*, 2016, pp. 1-7, vol. 3, No. 16006.

Palucka, K. et al. "Cancer immunotherapy via dendritic cells" *Nature Reviews Cancer*, 2012, pp. 1-30, vol. 12, No. 4.

Robbins, P. D. et al. "Regulation of immune responses by extracellular vesicles" *Nature Reviews—Immunology*, Mar. 2014, pp. 195-208, vol. 14.

Sadelain, M. et al. "The basic principles of chimeric antigen receptor (CAR) design" *Cancer Discovery*, Apr. 2013, pp. 1-21, vol. 3, No. 4.

Saenger, Y. M. et al. "Improved tumor immunity using anti-tyrosinase related protein-1 mAb combined with DNA vaccines in murine melanoma" *Cancer Research*, Dec. 1, 2008, pp. 1-19, vol. 68, No. 23.

Schölzel, K. et al. "Transfer of MHC-class-I molecules among liver sinusoidal cells facilitates hepatic immune surveillance" *Journal of Hepatology*, 2014, pp. 600-608, vol. 61.

Schönfeld, K. et al. "Selective Inhibition of Tumor Growth by Clonal NK Cells Expressing an ErbB2/HER2-Specific Chimeric Antigen Receptor" *Molecular Therapy*, Feb. 2015, pp. 330-338, vol. 23, No. 2.

Squadrito, M. L. et al. "miR-511-3p Modulates Genetic Programs of Tumor-Associated Macrophages" *Cell Reports*, Feb. 23, 2012, pp. 141-154, vol. 1.

Squadrito, M. L. et al. "Endogenous RNAs Modulate MicroRNA Sorting to Exosomes and Transfer to Acceptor Cells" *Cell Reports*, Sep. 11, 2014, pp. 1432-1446, vol. 8.

Squadrito, M. L. et al. "EVIR: chimeric receptors that enhance dendritic cell cross-dressing with tumor antigens" *Nature Methods*, Mar. 2018, pp. 183-186, vol. 15, No. 3, Online Methods—pp. 1-5.

Théry, C. et al. "Isolation and Characterization of Exosomes from Cell Culture Supernatants and Biological Fluids" *Current Protocols in Cell Biology*, 2006, pp. 3.22.1-3.22.29, Suppl. 30.

Théry, C. et al. "Membrane vesicles as conveyors of immune responses" *Nature Reviews—Immunology*, Aug. 2009, pp. 581-593, vol. 9.

Villadangos, J. A. et al. "Antigen-Presentation Properties of Plasmacytoid Dendritic Cells" *Immunity*, Sep. 19, 2008, pp. 352-361, vol. 29.

Von Heijne, G. et al. "Membrane-protein topology" *Nature Reviews—Molecular Cell Biology*, Dec. 2006, pp. 909-918, vol. 7.

Wakim, L. M. et al. "Cross-dressed dendritic cells drive memory CD8$^+$ T-cell activation after viral infection" *Nature*, Mar. 31, 2011, pp. 629-632, vol. 471.

Waldmann, T. A. "Immunotherapy: past, present and future" *Nature Medicine*, Mar. 2003, pp. 269-277, vol. 9, No. 3.

Yáñez-Mó, M. et al. "Biological properties of extracellular vesicles and their physiological functions" *Journal of Extracellular Vesicles*, 2015, pp. 1-60, vol. 4, No. 27066.

Yvon, E. et al. "Immunotherapy of metastatic melanoma using genetically engineered GD2-specific T cells" *Clinical Cancer Research*, Sep. 15, 2009, pp. 1-16, vol. 15, No. 18.

Zeelenberg, I. S. et al. "Antigen Localization Controls T Cell-Mediated Tumor Immunity" *The Journal of Immunology*, 2011, pp. 1281-1288, vol. 187.

Zhou, H. et al. "Structural Insights into the Down-regulation of Overexpressed p185$^{her2/neu}$ Protein of Transformed Cells by the Antibody chA21" *The Journal of Biological Chemistry*, Sep. 9, 2011, pp. 31676-31683, vol. 286, No. 36.

Written Opinion in International Application No. PCT/EP2017/052145, dated Apr. 5, 2017, pp. 1-6.

* cited by examiner

ENGINEERED ANTIGEN PRESENTING CELLS AND USES THEREOF

CROSS-REFERENCE TO RELATED APPLICATION

This application is the U.S. national stage application of International Patent Application No. PCT/EP2017/052145, filed Feb. 1, 2017.

The Sequence Listing for this application is labeled "Seq-List.txt" which was created on Jul. 5, 2018 and is 201 KB. The entire content of the sequence listing is incorporated herein by reference in its entirety.

FIELD OF THE INVENTION

The present invention relates to a vaccine comprising cells expressing extra-cellular vesicle internalizing receptors and their use in the immunotherapy for prevention and/or treatment of cancers.

BACKGROUND OF THE INVENTION

Immunotherapy is gaining increasing importance for the treatment and prevention of various human diseases including infections, inflammatory and degenerative conditions, and cancers.

In cancer, immunotherapy includes stimulating the patient's own immune system to attack cancer cells or other cellular components of the tumor (Waldmann et al., 2003, *Nat Med*, 9: 269-277; Miller et al., 2015, *Cancer Cell*, 27(4):439-49). The main types of immunotherapy now being used to treat cancer include use of monoclonal antibodies, immune checkpoint inhibitors, and cancer vaccines (Miller et al., 2015, supra).

In cancer-related applications, immunotherapy is based on the assumption that cancer cells express on their surface molecules that are not expressed (or are expressed at lower levels) by normal cells and that can be detected by the immune system. These molecules are known as cancer antigens and are often proteins (normal or mutated) or other macromolecules such as carbohydrates and lipids. In the last decade, an increasing number of molecules derived from the processing of tumor proteins have been identified and classified as tumor-associated antigens (TAAs). So-called active immunotherapy is used to engage the immune system into attacking the tumor cells by targeting TAAs. TAAs can be recognized by different cell types including CD8+ cytotoxic T lymphocytes (CTLs). After cancer-cell recognition by CTLs, these can subsequently engage in eliminating cancer cells.

One of the main goals of current research on immunotherapy approaches is to elicit or enhance cancer-specific CTLs by vaccinating the patient against potential or known TAAs.

Approaches developed and transferred to clinical trials include adoptive immunotherapy with ex vivo TAA-loaded antigen presenting cells (APCs), hereon referred to as APC-TAA.

Indeed, the generation of potent and persisting anti-tumor immunity requires the presentation of TAAs by professional APCs, such as dendritic cells (DCs), to the CTLs (Palucka et al, 2012, *Nat Rev Cancer*, 12(4):265-77). DCs are generated ex vivo by culturing hematopoietic progenitors or monocytes, obtained from the patient, with specific cytokine/growth factor combinations. Once generated, the DCs are exposed to total tumor lysates or specific TAAs ex vivo, before reinfusion of the APC-TAA in the patient. During the past decade, preclinical studies in mice and several clinical trials have shown the safety of the procedure, its ability to induce the expansion of circulating $CD^{4+}$ T cells and $CD^{8+}$ T cells that are specific for tumor antigens, and objective clinical responses in some patients (Palucka et al., 2012, supra).

Currently, only one APC-TAA vaccine, Sipuleucel-T (Provenge®), is approved in the US to treat advanced prostate cancer that is no longer being helped by hormone therapy (Gardner et al., 2012, *Hum Vaccin Immunother,* 8(4): 534-9). This example demonstrates the feasibility of active immunization for the treatment of established cancer.

However, the use of ex vivo cultured APC-TAA is typically labour-intensive (the APCs need to be isolated, manipulated ex vivo, and then re-infused), expensive, and is generally not individualized to each patient (Kastenmueller et al., 2014, *Nat Rev Immunol.*, 14(10):705-11).

An alternative vaccination approach consists of targeting a selected TAA to APCs in vivo, without ex vivo manipulation (Palucka et al., 2012, supra; Kastenmueller et al., 2014, supra).

This can be achieved by several means, e.g., by using chimeric proteins that are comprised of an antibody, specific for an APC receptor (e.g. CD205, CLEC9A, CD11c), that is also fused to a selected TAA. The chimeric protein can target APCs and promote TAA internalization, processing, and presentation by the APC to the T cells. However, these approaches are not very efficient and only one TAA can be delivered. Furthermore, the induction of CTLs by the targeted APCs also requires the provision of DC maturation and/or activation signals, as the absence thereof can induce antigen-specific tolerance (Kastenmueller et al., 2014, supra).

In one approach, DCs were exposed ex vivo to cancer cell lysates or extracellular vesicles (EVs) and then inoculated back into the subject to activate antigen-specific T cells and induce anti-tumor immune responses (Gu et al., 2015, *Intern Journal of Cancer,* 136, E74-84).

Another approach used monocytes/macrophages engineered to express an anti-carcinoembryonic antigen (CEA) chimeric antigen receptor (CAR), or DCs engineered to express an anti-HER2 (human epidermal growth factor receptor 2) CAR to directly target and lyse cancer cells in vitro and in vivo (Biglari et al., 2006, *Gene therapy,* 13: 602-610; Wei et al., 2008, *Cancer research,* 68: 3854-62). In a different type of approach, CTLs or natural killer (NK) cells were engineered to express a CAR designed against a specific TAA. The CAR-engineered T or NK cells then recognized cancer cells that expressed the specific antigen and killed them (Ahmed et al., 2015, *Journal of clinical oncology,* 33, 1688-1696; Schonfeld et al., 2015, *Molecular therapy,* 23, 330-338). However, the efficacy of the aforementioned approaches is limited by the ability of the engineered cells to traffic to solid tumors once re-infused.

Therefore, there is still a need for developing anti-tumor vaccines able to induce strong and broad T-cell responses that are specific for multiple known and unknown TAAs on a personalized manner, but at the same time applicable to a broad range of patients.

SUMMARY OF THE INVENTION

The invention is based on the design of new Extra-cellular Vesicle Internalizing Receptors (EVIRs) directed against a surface molecule expressed by cancer cells, and the genetic engineering of APCs such as monocytes, macrophages, DCs, or B cells, in order to stably express those new EVIRs. The invention is further based on the observation that APCs engineered to express an EVIR of the present invention efficiently take and/or internalize extra-cellular vesicles (EVs), comprising any cancer-cell derived particles or membranes, that are derived from surface molecule-positive cancer cells but not surface molecule-negative cells, independent of cell contact. It was further observed that EVs uptake by the EVIR-expressing APCs advantageously enhances the presentation of TAAs that are unrelated to the selected surface molecule but are related to the cancer cell of origin, and promotes the expansion of TAA-specific T cells, thereby offering a promising tool for cancer treatment or diagnosis.

One aspect of the invention relates to a recombinant EVIR directed against at least one cancer-cell surface molecule.

Another aspect of the invention relates to an isolated nucleic acid molecule encoding an EVIR according to the invention.

In another aspect, the invention provides a recombinant vector comprising a nucleic acid molecule encoding an EVIR according to the invention.

Another aspect of the invention relates to an isolated cell expressing at least one EVIR of the invention, in particular an APC and compositions thereof.

Another aspect of the invention provides an ex vivo method (i.e., in culture) of inducing expression of at least one EVIR of the invention in an APC or a stem/progenitor cell thereof comprising the steps of:
(i) ex vivo transducing said cell with a vector according to the invention; and
(ii) optionally inducing APC differentiation, maturation or activation.

Another aspect of the invention provides an ex vivo method of preparing EVIR-expressing, TAAs-presenting cells, comprising the steps of:
(i) providing at least one cancer cell or at least one cancer cell-derived EV obtained from a cancer subject;
(ii) providing an EVIR-expressing cell of the invention;
(iii) contacting, ex vivo, an EVIR-expressing cell provided under (ii) with said at least one cancer cell or EV provided under (i);
(iv) collecting cells obtained in step (iii);
wherein cells obtained under (iv) have an enhanced ability to present TAAs from said cancer subject as compared to a cell not expressing an EVIR and treated as in (iii), once administered to said subject.

Another aspect of the invention relates to an isolated EVIR-expressing cell, or an EVIR-expressing TAAs-presenting cell obtainable by a method according to the invention.

Another aspect of the invention relates to an EVIR-expressing cell, an EVIR-expressing TAAs-presenting cell or a recombinant vector according to the invention for use as a medicament.

Another aspect of the invention provides a pharmaceutical composition comprising cells of the invention or at least one recombinant vector according to the invention and at least one pharmaceutically acceptable carrier, diluent or excipient thereof.

Another aspect of the invention relates to an EVIR-expressing cell, an EVIR-expressing TAAs-presenting cell or a recombinant vector according to the invention for use in the prevention and/or treatment of a cancer.

Another aspect of the invention relates to a use of an isolated EVIR-expressing cell or an isolated EVIR-expressing TAAs-presenting cell for the preparation of a pharmaceutical composition for the prevention and/or treatment of a cancer.

Another aspect of the invention provides a vaccine composition comprising an EVIR-expressing cell or an EVIR-expressing TAAs-presenting cell according to the invention.

Another aspect of the invention provides an ex vivo method of identifying new TAAs from a cancer subject comprising the steps of:
(i) providing EVIR-expressing APCs obtained from said subject which had been administered a vector encoding an EVIR according to the invention under suitable conditions for inducing transduction of the subject's APCs or stem/progenitor cell thereof or EVIR-expressing cells according to the invention; or
(ii) providing EVIR-expressing APCs wherein EVIR-expressing APCs has been contacted ex vivo with at least one cancer cell or at least one cancer cell-derived EV obtained from a cancer subject; and
(iii) identifying the peptides loaded on MHCI or MHCII molecules in the cells provided under (i) or (ii), wherein said peptides comprise new TAAs.

Another aspect of the invention provides an ex vivo method of identifying new T-cell receptors (TCRs) from a cancer subject comprising the steps of:
(i) providing T cells that have been isolated from a tumor from a subject that has been administered a vector encoding an EVIR according to the invention under suitable conditions for inducing transduction of the subject's APCs or stem/progenitor cell thereof or EVIR-expressing cells according to the invention; or
(ii) providing isolated T cells from a cancer subject that have been contacted ex vivo with EVIR-expressing, TAA presenting APCs obtained by a method of the invention wherein EVIR-expressing, TAA presenting APCs present TAAs of the same cancer subject; and
(iii) sequencing T cells receptors (TCRs) from isolated T cells provided in step (i) or (ii).

Another aspect of the invention provides a method of inducing in vivo the expression of at least one EVIR of the invention in an APC or a stem/progenitor cell thereof in a subject in need thereof, said method comprising the steps of:
(i) administering a vector encoding an EVIR according to the invention to said subject under suitable conditions for inducing transduction of the subject's APCs or stem/progenitor cell thereof in vivo with said vector; and
(ii) optionally inducing APC differentiation, maturation or activation in vivo.

Another aspect of the invention provides a method of preventing and/or treating a cancer comprising administering an effective amount of EVIR-expressing cells or at least one recombinant vector according to the invention in a subject in need thereof.

Another aspect of the invention relates to a method of preventing and/or treating a cancer comprising administering an effective amount of EVIR-expressing, TAA-presenting cells in a subject in need thereof.

Another aspect of the invention provides a kit for carrying out methods according to the invention comprising at least one EVIR, or at least one recombinant expression vector, or at least one EVIR-expressing cell according to the invention.

DESCRIPTION OF THE FIGURES

Statistical p values were calculated in Prism (GraphPad Software) and are indicated in the figures as follows. * $p<0.05$,  $p<0.01$, * $p<0.001$.

DETAILED DESCRIPTION

Figure 1:
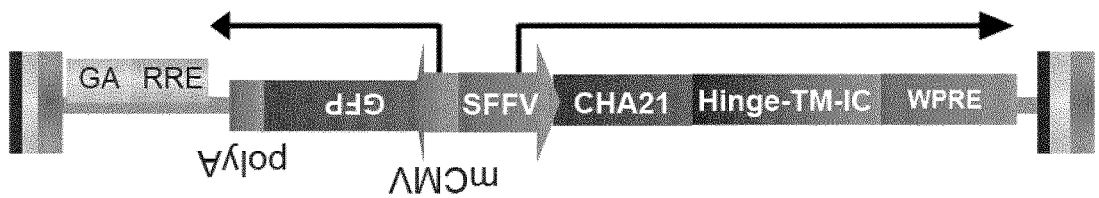
FIG. 1. EVIR-expressing LV. Schematic representation of the bidirectional proviral LV used to simultaneously express a representative EVIR (e.g., anti-HER2) and a second gene, in this case, Green Fluorescent Protein (GFP).

The term "antibody" as referred to herein designates a polypeptide that binds to an antigen.

This includes whole antibodies and any antigen binding fragments. The term "antibody" is used in its broadest sense and includes monoclonal antibodies, polyclonal antibodies, human antibodies, humanized antibodies, chimeric antibodies and the like as long as the characteristic properties of the invention are retained, in particular the ability of binding to the target antigen, more specifically to the membrane-associated molecules of cancer cells.

Examples of antibodies and fragments thereof include a variable domain fragment ("Fv", consisting of the VH and VL domains of a single arm of an antibody), Fab fragment (monovalent fragment consisting of the VH, VL, CH1 and CL domains), Fab2 fragment (bivalent), Fab3 fragment (trivalent), Fab' fragment (Fab with hinge region), F(ab')2 fragment (bivalent fragment including two Fab fragments linked by a disulfide bridge at the hinge region), Fd fragment (consisting of the VH and CH1 domains), rIgG (reduced IgG or half-IgG), diabodies, triabodies, tetrabodies, minibodies, monovalent antibodies, divalent or multivalent antibodies comprising a fragment of more than one antibody, single chain variable fragment (ScFv), bis-scFv (bispecific), and derivatives of antibodies such as disulfide stabilized Fv fragments, CDR-comprising peptides, as well as epitope-binding fragments of any of the above (Holliger et al., 2005, *Nature Biotechnology*, 23(9): 1126-1136).

The term "a membrane-associated molecule" or "surface molecule" as used herein refers to any molecule that is physically embedded in the lipid bilayer or bound or anchored to a cell membrane permanently or transiently under specific conditions. The molecule may be associated with any membrane of the cancer cell, including the plasma membrane or intracellular membranes. These molecules could perform a variety of functions and belong to different functional groups including, but not limited to glycoproteins, membrane receptor proteins, transport proteins, membrane enzymes, cell adhesion molecules, and their mutated forms. These molecules can be expressed either on the cancer cell's plasma membrane or any membrane associated with cancer-cell derived particles, such as extra-cellular vesicles (EVs).

The term includes known and unknown cancer cell membrane-associated molecules.

Examples of membrane-associated molecules include, but are not limited to, human epidermal growth factor receptor 2 (HER2), tyrosinase-related protein-1 (TYRP1), carcinoembryonic antigen (CEA), mesothelin, PMEL (gp100), gangliosides (GD2, GD3), and mucins.

The term "extra-cellular vesicle internalizing receptor" or "EVIR" refers to a recombinant receptor directed against a surface molecule expressed by a cancer cell or any cancer-cell derived particle/vesicle. An EVIR according to the invention comprises the following elements that are referred to as "an extracellular antibody domain", "proteinic domain" and optionally "a domain to increase EVIR export to the cellular membrane".

The term "extracellular antibody domain" refers to any antibody domain with specificity for any membrane-associated molecule expressed by a cancer cell or cancer-cell derived particle/vesicle. Examples of antibody domains according the invention include, but are not limited to: (i) anti-HER2 scFv, such as CHA21 (Zhou et al., 2011, *The Journal of Biological Chemistry*, 286: 31676-31683), a trastuzumab-based scFv (Morgan et al., 2010, *Mol Ther.*, 18(4):843-51), a pertuzumab-based scFv (Franklin et al., 2004, *Cancer Cell*, 5(4):317-28) and a FRP5-based scFv (Ahmed et al., 2009, *Mol Ther.*, 17(10):1779-87); (ii) anti-GD2 scFv (Newik et al., 2016, *Mol Ther Oncolytics*, 68:139-152); or (iii) anti-TYRP1 scFv (Saenger et al., 2008, *Cancer Res*, 68(23): 9884-91); among others.

The terms "transmembrane domain" and "intracellular domain" refer to portions of the protein fragments of the EVIR of the invention comprising polypeptides that anchor the "extracellular antibody domain" of the EVIR to the cell surface and extend to the cell cytoplasm. According to a particular aspect, the transmembrane domain of the EVIR according to the invention can allow the EVIR to anchor to the antigen presenting cell membrane. According to a particular aspect, the intracellular domain of the EVIR according to the invention can have a signalling or non-signalling capacity.

In particular, those "transmembrane domains" and "intracellular domains" forming the proteinic domain can be the corresponding domains from the native membrane associated protein they are derived from or domains that are derived from those through some truncations and/or homologous sequence modifications that would not affect their anchoring ability to the cell membranes, such as for example the removal of the endogenous signal peptides. For example, according to a particular aspect, the proteinic domain may comprise more than one of transmembrane domains that are linked together by extracellular "non hinge" domains (peptidic fragments that bridges two "transmembrane domains" in the native membrane protein), such as found in certain membrane proteins such as CCR1, -2, -4 and -5.

When the intracellular domain of the EVIR has a signalling ability (e.g. comprising a signalling peptidic portion) it may be referred as a "signalling domain" and when the intracellular domain of the EVIR does not have a signalling capacity, it may be referred as "an inert intracellular domain". According to a particular aspect, the proteinic domain may comprise more than one of transmembrane domains that are linked by an intracellular domain.

Figure 13:
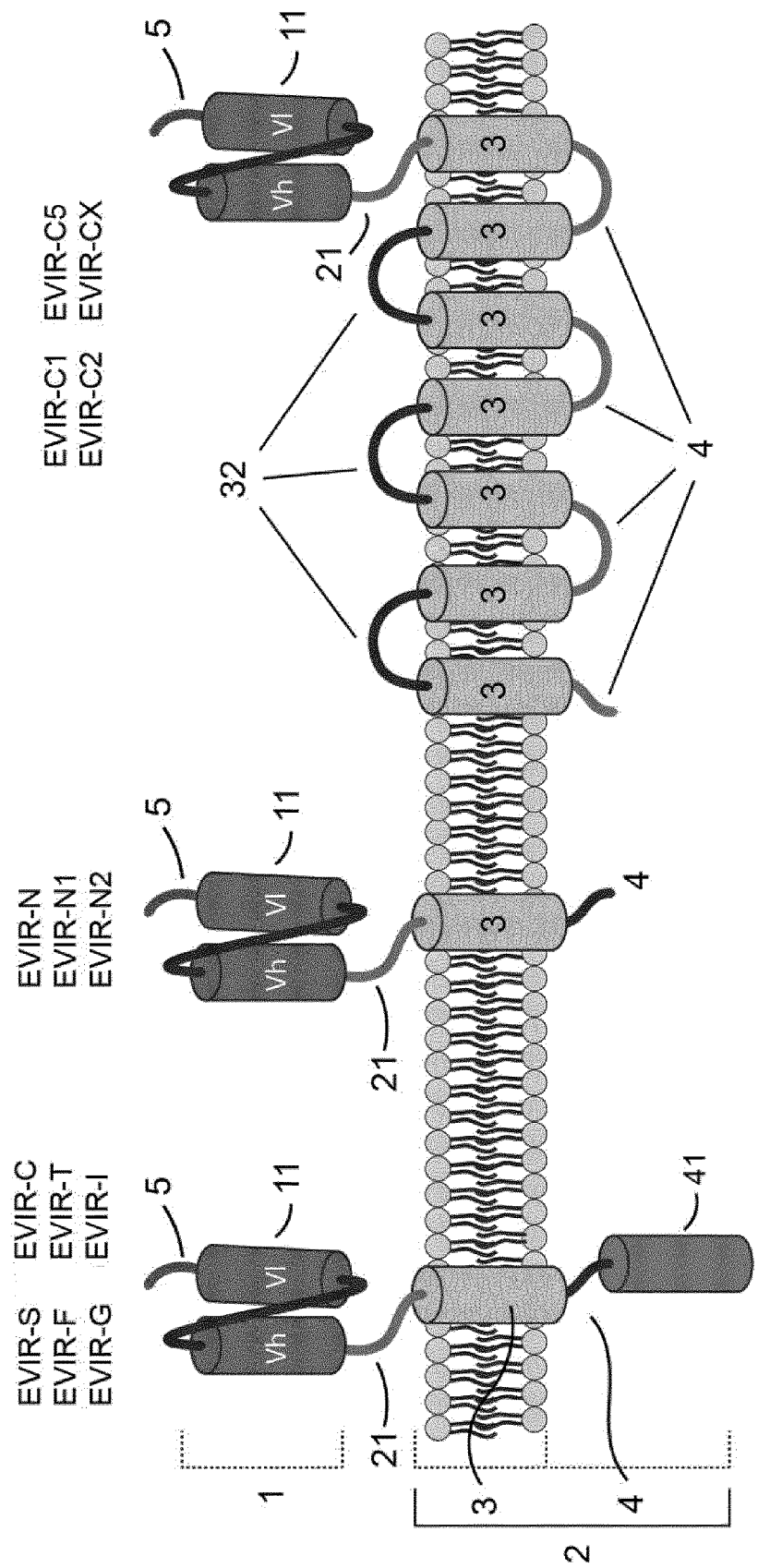
FIG. 13. The illustration represents schematically and generically some examples of constructs for the EVIR of the invention comprising an extracellular antibody domain specific for a membrane-associated molecule of a cancer cell (1) such as a scFv (11), a proteinic domain (2) comprising at least one transmembrane domain (3) and at least one intracellular domain (4). The proteinic domain may comprise a hinge domain (21) connecting the transmembrane domain (3) to the extracellular antibody domain (1). The proteinic domain (2) can be varied to either comprise one transmembrane domain (3) and one intracellular domain (4) such as the example represented on the left and the middle or more than one of each, wherein the transmembrane domains (3) are linked together on the extracellular side by extracellular non-hinge domains (32) and by the more than one intracellular domains (4) on the intracellular side, as in the example represented on the right. Further, the EVIR comprises a cell membrane export domain (5) linked to the extracellular antibody domain (1). The intracellular domain (4) may also comprise a signalling sequence (41). The specific names of the constructs of the invention are indicating under which type of constructs of the invention those are falling.

Various examples of constructs for the EVIRs and in particular various types of proteinic domains are illustrated on FIG. 13. The proteinic domain of the EVIRs according to the invention can comprise "transmembrane domain", "intracellular domain" and optionally further "extracellular non hinge domain" linking the transmembrane domains derived from the same or different proteins. The transmembrane domains, intracellular domains and optional extracellular non hinge domains can be derived from any protein that induces at least one of the following functions: cell survival, differentiation, proliferation, activation, maturation, phagocytosis, endocytosis, antigen-processing and presentation, T-cell recruitment, among other functions. Preferably, that includes any protein fragment that induces monocyte and/or macrophage and/or DC cell survival, differentiation, proliferation, activation, maturation, phagocytosis, endocytosis, antigen-processing and presentation, T-cell recruitment, among other functions (Holliger et al., 2005, supra; Palucka et al., 2012, supra; Kastenmueller et al., 2014, supra). Examples of proteinic domains or the transmembrane/intracellular and optional extracellular non hinge domains of those include domains from a membrane associated protein such as growth factor receptors, Fcγ receptor family, toll-like receptors, C—C chemokine receptors, and other protein molecules, either native or recombinant, that are expressed on the surface of any cell and that can promote monocyte and/or macrophage and/or DC cell survival, differentiation, proliferation, activation, maturation, phagocytosis, endocytosis, antigen-processing and presentation, T-cell recruitment, among other functions. Specific examples of those domains include FcγRIIIA receptor (a member of the Fcγ receptor family expressed by cells of the innate immune system), receptor tyrosine kinase (FLT3, also termed CD135), toll-like receptor 4 (TLR4), C—C chemokine receptor type 2 (CCR2), integrin beta chain beta 2 receptor (ITGB2), colony-stimulating factor-2 receptor B (CSF2RB), C—C chemokine receptor type 1 (CCR1), C—C chemokine receptor type 5 (CCR5), chemokine receptor CXCR4 and P-selectin glycoprotein-1 ligand receptor (SELPLG), or a fragment of the human nerve growth factor receptor (NGFR).

The proteinic domain may further comprise a "hinge region", which is a peptidic fragment that bridges the "transmembrane domain" to the "extracellular antibody domain" of the EVIR of the invention, thereby providing flexibility to the recombinant receptor (Sadelain et al., 2013, Cancer Discov, 3(4):388-98). In a particular embodiment, the proteinic domain containing a transmembrane domain, an intracellular domain and a hinge region is obtained by simply removing the extracellular domain from the membrane associated protein from which the transmembrane and intracellular domains are derived as exemplified herein. In this case, the hinge region corresponds to a peptidic region naturally linking the transmembrane and the original extracellular domain of the membrane associated protein.

An EVIR of the invention may also contain a "cell membrane export domain", which refers to any protein fragment, either cellular or viral, that increases sorting of the EVIR to the cell membrane. A non-limiting example is an IgK domain (von Heijne et al., 2006, Nat Rev Mol Cell Biol., 7:909-18), for example inserted at the N-terminus of the EVIR.

The term "an antigen-presenting cell" or "APC" as referred to herein, refers to a cell that displays foreign antigens complexed with major histocompatibility complexes (MHCs) on its surface; this process is known as antigen presentation. Those cells are also sometimes referred to as or "accessory cell". T-cells may recognize these complexes using their T-cell receptors (TCRs), so APCs process antigens and present them to T-cells. Examples of APCs include, but are not limited to, dendritic cells (DCs), monocytes, macrophages, certain B-cells, and certain activated epithelial cells.

The term "hematopoietic cells" refers to cells having the ability to differentiate into mature blood cells, including monocytes, macrophages and dendritic cells and includes hematopoietic stem cell (HSCs) and hematopoietic progenitor cells (HPCs).

The term "EVIR-expressing, TAA-presenting cell" refers herein to a cell expressing an EVIR according to the invention and, optionally, a protein capable of inducing APC differentiation, survival, activation and/or cross-presentation, or attracting and/or activating T cells, which after being contacted with cancer cells and/or cancer-cell derived particles, such as EVs, has internalized the cancer cell and/or cancer-cell derived particles and processed TAAs, so that TAAs presentation was achieved within the antigen presenting cell expressing the EVIR.

The term "extracellular vesicles" or "EVs" refers herein to any membrane-containing particles or fragments derived from cancer cells. EVs may comprise exosomes, microvesicles, microparticles, apoptotic bodies, cell debris, membrane fragments and similar subcellular material of tumor origin that, therefore, may be associated with known and unknown tumor antigens. After fusion of the EV with the engineered APC, the EV-associated tumor antigens are presented by the engineered APCs to T cells in order to initiate an immune response against cancer. EVs can be isolated as described (Squadrito et al., 2014, Cell Rep, 8(5):1432-46; Thery et al., 2006, Curr Protoc Cell Biol, Chapter 3; Unit 3:22). Presentation of the tumor antigens by the APCs may occur after processing and loading of the antigens on the APC's MHCI or MHCII molecules (conventional and cross-presentation) as described in Villadangos et al., 2014, Immunity, 29(3):352-61, but also by direct presentation of EV-derived antigen/MHC complexes via cross-dressing as described in Schölzel et al., 2014, J Hepatol., 61(3):600-8.

The terms "cancers" or "tumors" as defined herewith are diseases involving abnormal cell growth with the potential to invade or spread to other parts of the body. Term "cancers" designate diseases exemplified by, but not limited to, carcinomas (such as breast, prostate, lung, pancreas, and colon cancers), melanomas, sarcomas (such as bone, cartilage, nerve cancer), lymphomas and leukemias (hematopoietic cancers), germ cell tumors (such as seminoma and dysgerminoma) and blastomas.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a cancer in a mammal, particularly a human, and includes inhibiting the disease, i.e., arresting its development; or relieving the disease, i.e., causing regression of the disease and/or its symptoms or conditions such as improvement or remediation of damage. In particular, the cells, methods, uses, formulations and compositions according to the invention are useful in the treatment of cancer and/or in the prevention of evolution of a cancer into an advanced or metastatic stage in patients with early stage cancer, thereby improving the cancer staging and patient prognosis. In particular, prevention and/or treatment of a cancer may include administration of cells according to the invention.

The term "efficacy" of a treatment or method according to the invention can be measured based on changes in the course of disease or condition in response to a use or a method according to the invention. For example, the efficacy of a treatment or method according to the invention can be measured by its impact on signs or symptoms of illness. A response is achieved when the patient experiences partial or total alleviation, or reduction of unwanted symptoms of illness. According to a particular embodiment, the efficacy can be measured through the measuring of the elicited immune response against cancer cells such as by analyzing tumor-specific T cells or by assessing cancer cell death and/or inhibition of tumor growth, progression and dissemination.

The term "effective amount" as used herein refers to an amount of at least one cell according to the invention, or a pharmaceutical formulation thereof, that elicits a detectable reduction of the symptoms of the disease in a subject that is being administered said cells, these symptoms can include, for instance decrease in solid tumor mass.

The term "subject" as used herein refers to mammals. For examples, mammals contemplated by the present invention include human, primates, domesticated animals such as cattle, sheep, pigs, horses, laboratory rodents, other pets and the like.

The term "variant" as used herein means a polypeptide substantially homologous to the original peptide sequence, but which has at least one an amino acid sequence different from that of the original sequence because of one or more deletions, insertions or substitutions.

Substantially homologous means a variant amino acid sequence that is at least 80%, at least 85%, at least 90%, at least 95%, at least 96%, at least 97%, at least 98% or at least 99% identical to the original amino acid sequences, as disclosed above. The percent identity of two amino acid sequences can be determined by visual inspection and/or mathematical calculation, or more easily by comparing sequence information using known computer program used for sequence comparison such as Clustal package version 1.83. A variant may comprise a sequence having at least one conservatively substituted amino acid, meaning that a given amino acid residue is replaced by a residue having similar physiochemical characteristics. Generally, substitutions for one or more amino acids present in the original polypeptide should be made conservatively. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known (Kyte, et al, 1982, *J. Mol. Biol.,* 157: 105-131). For example, a "conservative amino acid substitution" may involve a substitution of a native amino acid residue with a non-native residue such that there is little or no effect on the polarity or charge of the amino acid residue at that position. Desired amino acid substitutions (whether conservative or non-conservative) can be determined by those skilled in the art at the time such substitutions are desired.

EVIRs According to the Invention

Extra-cellular vesicle internalizing receptors (EVIRs) of the invention comprise:
 (i) an extracellular antibody domain specific for a membrane-associated molecule of a cancer cell;
 (ii) a proteinic domain comprising at least one transmembrane domain and at least one intracellular domain; and
 (iii) optionally a cell membrane export domain increasing the export of the EVIR to the cellular membrane of antigen-presenting cells.

Extra-cellular vesicle internalizing receptors of the invention comprise:
 (i) an extracellular antibody domain specific for a membrane-associated molecule of a cancer cell;
 (ii) a proteinic domain comprising one transmembrane domain and one intracellular domain; and
 (iii) optionally a cell membrane export domain increasing the export of the EVIR to the cellular membrane of antigen-presenting cells.

In a particular embodiment, is provided an EVIR according to the invention wherein the proteinic domain further comprises a hinge region linking the extracellular antibody domain to the transmembrane domain.

In a particular embodiment, is provided an EVIR according to the invention wherein the proteinic domain comprises at least two, at least three, at least four, at least five, at least six or at least seven transmembrane domains (for example seven transmembrane domains).

In a further particular embodiment, is provided an EVIR according to the invention wherein the proteinic domain comprises at least two, at least three, at least four, at least five, at least six or at least seven transmembrane domains linked together by intracellular domains of the EVIR of the invention and/or extracellular non hinge domains.

In a particular embodiment, is provided an EVIR according to the invention wherein the proteinic domain comprises at least two, at least three or at least four intracellular domains (for example four intracellular domains).

In a further particular embodiment, is provided an EVIR according to the invention wherein the proteinic domain comprises at least two, at least three, at least four, at least five, at least six or at least seven transmembrane domains linked together by at least one, at least two, or at least three intracellular domains and optionally further linked together by extracellular at least one, at least two, or at least three non-hinge domains.

In a particular embodiment, is provided an EVIR according to the invention that further comprises an amino acid sequence that facilitates DNA engineering (e.g. a cloning site) such as TG.

In a particular embodiment, is provided an EVIR according to the invention wherein an amino acid sequence that facilitates DNA engineering (e.g. a cloning site) is of SEQ ID NO: 104.

In a particular embodiment, is provided an EVIR according to the invention wherein an amino acid sequence that facilitates DNA engineering is present between the transmembrane domain and extracellular antibody domain.

In a particular embodiment, is provided an EVIR according to the invention wherein the extracellular antibody domain is a scFv.

In a further particular embodiment, is provided an EVIR according to the invention wherein the extracellular antibody domain comprises a sequence of an antibody, or a fragment thereof specific for human epidermal growth factor receptor 2 (HER2).

In another further particular embodiment, is provided an EVIR according to the invention wherein the extracellular antibody domain comprises a sequence of an antibody specific for at least one cancer cell membrane-associated molecule corresponding to a tumor-associated antigen, including but not limited to, human epidermal growth factor receptor 2 (HER2), tyrosinase-related protein-1 (TYRP1), carcinoembryonic antigen (CEA), mesothelin, PMEL (gp100), gangliosides (GD2, GD3), and mucins.

In a more particular embodiment, is provided an EVIR according to the invention wherein the extracellular antibody domain comprises a sequence of an antibody specific for an anti-human epidermal growth factor receptor 2 (HER2).

In another more particular embodiment, is provided an EVIR according to the invention wherein the extracellular antibody domain comprises a sequence of an antibody specific for a tyrosinase-related protein-1 (TYRP1).

In another more particular embodiment, is provided an EVIR according to the invention wherein the extracellular antibody domain comprises a sequence of an antibody specific for a ganglioside GD2 (GD2).

In a more particular embodiment, is provided an EVIR according to the invention wherein the sequence of an anti-human epidermal growth factor receptor 2 (HER2) comprises the sequence of CHA21 (SEQ ID NO: 27), or a variant thereof.

In another more particular embodiment, is provided an EVIR according to the invention wherein the sequence of an anti-human epidermal growth factor receptor 2 (HER2) comprises the sequence of a trastuzumab-based scFv (SEQ ID NO: 28), or a variant thereof.

In another more particular embodiment, is provided an EVIR according to the invention wherein the sequence of an anti-human epidermal growth factor receptor 2 (HER2) comprises the sequence of a pertuzumab-based scFv (SEQ ID NO: 29), or a variant thereof.

In another more particular embodiment, is provided an EVIR according to the invention wherein the sequence of an anti-human epidermal growth factor receptor 2 (HER2) comprises the sequence of a FRP5-based scFv (SEQ ID NO: 30), or a variant thereof.

In another more particular embodiment, is provided an EVIR according to the invention wherein the sequence of an anti-tyrosinase-related protein-1 (TYRP1) comprises the sequence of TA99-based anti-TYRP1 scFv (SEQ ID NO: 113), or a variant thereof.

In another more particular embodiment, is provided an EVIR according to the invention wherein the sequence of an anti-ganglioside GD2 (GD2) comprises the sequence of 14G2a-based anti-GD2 scFv (SEQ ID NO: 114), or a variant thereof.

In a particular embodiment, is provided an EVIR according to the invention wherein the proteinic domain is a fragment of a transmembrane receptor expressed by myeloid cells.

In a particular embodiment, is provided an EVIR according to the invention wherein the proteinic domain comprises a G protein-coupled receptor, a fragment or a variant thereof, expressed by myeloid cells.

In a particular embodiment, is provided an EVIR according to the invention wherein the proteinic domain comprises a seven-transmembrane domain receptor, a fragment or a variant thereof, expressed by myeloid cells.

In a more particular embodiment, is provided the EVIR according to the invention wherein it comprises a proteinic domain comprising at least one transmembrane and at least one intracellular domain, and optionally at least one extracellular non-hinge domain, and optionally a hinge domain from a receptor selected from a growth factor receptor, Fcγ receptor family, toll-like receptor, C—C chemokine receptor, or other signalling receptor that that can promote monocyte and/or macrophage and/or DC cell survival, differentiation, proliferation, activation, maturation, phagocytosis, endocytosis, antigen-processing and presentation, T-cell recruitment, among other functions.

In a more particular embodiment, is provided an EVIR according to the invention wherein the proteinic domain comprises a hinge domain, at least one transmembrane and at least one intracellular domain from a receptor selected from the human nerve growth factor receptor (proteinic domain of SEQ ID NO: 31), FcγRIIIA receptor (proteinic domain of SEQ ID NO: 32), the receptor tyrosine kinase FLT3 (proteinic domain of SEQ ID NO: 33), the toll-like receptor 4 (proteinic domain of SEQ ID NO: 34), the C—C chemokine receptor type 2 (proteinic domain of SEQ ID NO: 35), the integrin beta chain beta 2 receptor (proteinic domain of SEQ ID NO: 36), the colony-stimulating factor-2 receptor B (CSF2RB) (proteinic domain of SEQ ID NO: 37), the chemokine receptor CCR1 (proteinic domain of SEQ ID NO: 38), the chemokine receptor CCR5 (S proteinic domain of SEQ ID NO: 39), the chemokine receptor CXCR4 (proteinic domain of SEQ ID NO: 40) and the P-selectin glycoprotein-1 ligand receptor (proteinic domain of SEQ ID NO: 41), or variants thereof.

In a more particular embodiment, is provided an EVIR according to the invention wherein the proteinic domain is selected from SEQ ID NO: 35, SEQ ID NO: 38, SEQ ID NO: 39 and SEQ ID NO: 40, or a fragment or variant thereof.

In a more particular embodiment, is provided an EVIR according to the invention comprising proteinic domains derived from isoforms of the proteins described herein.

In a more particular embodiment, is provided an EVIR according to the invention wherein the proteinic domain comprises a hinge domain selected from SEQ ID NO: 79, SEQ ID NO: 82, SEQ ID NO: 85, SEQ ID NO: 88, SEQ ID NO: 91, SEQ ID NO: 92, SEQ ID NO: 95, SEQ ID NO: 98, SEQ ID NO: 99, SEQ ID NO: 100 and SEQ ID NO: 101, or variants thereof.

In a more particular embodiment, is provided an EVIR according to the invention wherein the proteinic domain comprises a transmembrane domain selected from SEQ ID NO: 80, SEQ ID NO: 83, SEQ ID NO: 86, SEQ ID NO: 89, SEQ ID NO: 93), SEQ ID NO: 96, and SEQ ID NO: 102, or variants thereof.

In a more particular embodiment, is provided an EVIR according to the invention wherein the proteinic domain comprises an intracellular domain selected from SEQ ID NO: 81, SEQ ID NO: 84, SEQ ID NO: 87, SEQ ID NO: 90, SEQ ID NO: 94, SEQ ID NO: 97, and SEQ ID NO: 103, or variants thereof.

In a more particular embodiment, is provided an EVIR according to the invention wherein the proteinic domain derived from a receptor selected from the human nerve growth factor receptor, the chemokine receptor CCR5, and the P-selectin glycoprotein-1 ligand receptor.

In a further more particular embodiment, is provided an EVIR according to the invention wherein the proteinic domain comprises a sequence selected from SEQ ID NO: 31, 39 and 41 or a variant thereof.

According to a particular embodiment, an EVIR according to the invention comprises a cell membrane export domain, for example at the N-terminus of the EVIR sequence.

According to a more particular embodiment, an EVIR according to the invention comprises a cell membrane export domain comprising an IgK domain (von Heijne, 2006, supra).

According to a further particular embodiment an EVIR according to the invention comprises a cell membrane export domain of SEQ ID NO: 42 or a variant thereof.

EVIRs according to the invention can be obtained by any known methods of molecular cloning for polypeptide expression, as described in the following examples.

According to a further particular embodiment EVIRs of the invention comprise:
  (i) an anti-HER2 CHA21 comprising an amino acid sequence of SEQ ID NO: 27;
  (ii) a proteinic domain comprising an amino acid sequence selected from: SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40 and SEQ ID NO: 41;
  (iii) optionally an amino acid sequence that facilitates DNA engineering of SEQ ID NO: 104; and
  (iv) a cell membrane export domain IgK of SEQ ID NO: 42.

According to a further particular embodiment an EVIR of the invention comprises:
  (i) an anti-TYRP1 comprising an amino acid sequence of SEQ ID NO: 113;
  (ii) a proteinic domain comprising an amino acid sequence of SEQ ID NO: 31;
  (iii) optionally an amino acid sequence that facilitates DNA engineering of SEQ ID NO: 104; and
  (iv) a cell membrane export domain IgK of SEQ ID NO: 42.

According to a further particular embodiment EVIRs of the invention comprise:
  (i) an anti-GD2 comprising an amino acid sequence of SEQ ID NO: 114;
  (ii) a proteinic domain comprising an amino acid sequence of SEQ ID NO: 31;
  (iii) optionally an amino acid sequence that facilitates DNA engineering of SEQ ID NO: 104; and
  (iv) a cell membrane export domain IgK of SEQ ID NO: 42.

According to a further particular embodiment, an EVIR according to the invention has an amino acid sequence selected from SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63 and SEQ ID NO: 64, or variants thereof.

According to a further particular embodiment, an EVIR according to the invention has an amino acid sequence of SEQ ID NO: 132, or variants thereof.

According to a further particular embodiment, an EVIR according to the invention has an amino acid sequence of SEQ ID NO: 133 or variants thereof.

According to a further particular embodiment, a proteinic domain of EVIRs of the invention comprises:
  (i) a hinge domain comprising an amino acid sequence selected from: SEQ ID NO: 79, SEQ ID NO: 82, SEQ ID NO: 85, SEQ ID NO: 88, SEQ ID NO: 92, SEQ ID NO: 95, and 101;
  (ii) a transmembrane domain comprising an amino acid sequence selected from: SEQ ID NO: 80, SEQ ID NO: 83, SEQ ID NO: 86, SEQ ID NO: 89, SEQ ID NO: 93, SEQ ID NO: 96 and SEQ ID NO: 102;
  (iii) an intracellular domain comprising an amino acid sequence selected from: SEQ ID NO: 81, SEQ ID NO: 84, SEQ ID NO: 87, SEQ ID NO: 90, SEQ ID NO: 94, SEQ ID NO: 97 and SEQ ID NO: 103.

Nucleic Acids of the Invention

Isolated nucleic acid encoding an EVIR according to the invention may be, for instance, natural DNA or RNA or a recombinant or synthetic DNA, RNA or LNA or a recombinant nucleic acid molecule comprising any of the nucleic acid molecules according to the invention either alone or in combination. In a particular embodiment, the nucleic acid molecules according to the invention are cDNA.

In a particular embodiment, is provided an isolated nucleic acid molecule encoding an EVIR according to the invention, wherein the extracellular antibody domain comprises a sequence of an antibody specific for at least one cancer cell membrane-associated molecule corresponding to a tumor-associated antigen, including but not limited to, human epidermal growth factor receptor 2 (HER2), tyrosinase-related protein-1 (TYRP1), carcinoembryonic antigen (CEA), mesothelin, PMEL (gp100), gangliosides (GD2, GD3), and mucins.

In a more particular embodiment, is provided an isolated nucleic acid molecule encoding an EVIR according to the invention comprising an extracellular antibody domain consisting of CHA21 sequence, wherein the said nucleic acid molecule comprises SEQ ID NO: 1 or a variant thereof.

In a more particular embodiment, is provided an isolated nucleic acid molecule encoding an EVIR according to the invention comprising an extracellular antibody domain consisting of CHA21 sequence, wherein the said nucleic acid molecule comprises SEQ ID NO: 1.

In a more particular embodiment, is provided an isolated nucleic acid molecule encoding an EVIR according to the invention comprising an extracellular antibody domain consisting of CHA21 sequence, wherein the said nucleic acid molecule comprises SEQ ID NO: 128.

In another more particular embodiment, is provided an isolated nucleic acid molecule encoding an EVIR according to the invention comprising an extracellular antibody domain consisting of a trastuzumab-based scFv, wherein the said nucleic acid molecule comprises SEQ ID NO: 76.

In another more particular embodiment, is provided an isolated nucleic acid molecule encoding an EVIR according to the invention comprising an extracellular antibody domain consisting of a pertuzumab-based scFv sequence, wherein the said nucleic acid molecule comprises SEQ ID NO: 77.

In another more particular embodiment, is provided an isolated nucleic acid molecule encoding an EVIR according to the invention comprising an extracellular antibody domain consisting of a FRP5-based scFv sequence, wherein the said nucleic acid molecule comprises SEQ ID NO: 78.

In another more particular embodiment, is provided an isolated nucleic acid molecule encoding an EVIR according to the invention comprising an extracellular antibody domain consisting of an anti-TYRP1 scFv sequence, wherein the said nucleic acid molecule comprises SEQ ID NO: 111.

In a further particular embodiment, is provided an isolated nucleic acid molecule encoding an EVIR according to the invention comprising an extracellular antibody domain consisting of an anti-GD2 scFv sequence, wherein the said nucleic acid molecule comprises SEQ ID NO: 112.

In a more particular embodiment, is provided an isolated nucleic acid molecule encoding an EVIR according to the invention comprising at least one transmembrane and at least one intracellular domain from a receptor selected from the human nerve growth factor receptor (SEQ ID NO: 43), FcγRIIIA receptor (SEQ ID NO: 44), the receptor tyrosine kinase (SEQ ID NO: 45), the toll-like receptor 4 (SEQ ID NO: 46), the C—C chemokine receptor type 2 (SEQ ID NO: 47), the integrin beta chain beta 2 receptor (SEQ ID NO: 48), the colony-stimulating factor-2 receptor B (SEQ ID NO: 49), the chemokine receptor CCR1 (SEQ ID NO: 50), the chemokine receptor CCR5 (SEQ ID NO: 51), the chemokine receptor CXCR4 (SEQ ID NO: 52) and the P-selectin glycoprotein-1 ligand receptor (SEQ ID NO: 53).

In another embodiment, is provided an isolated nucleic acid molecule encoding an EVIR according to the invention comprising a cell membrane export domain comprising an IgK domain, wherein the said nucleic acid molecule comprises SEQ ID NO: 2, in particular SEQ ID NO: 129, wherein an isolated nucleic acid molecule encoding said EVIR is further comprising a nucleic acid sequence encoding an extracellular antibody domain consisting of CHA21 (SEQ ID NO: 1).

In another embodiment, is provided an isolated nucleic acid molecule encoding an EVIR according to the invention comprising a cell membrane export domain comprising an IgK domain, wherein the said nucleic acid molecule comprises SEQ ID NO: 129, wherein an isolated nucleic acid molecule encoding said EVIR is further comprising a nucleic acid sequence encoding an extracellular antibody domain consisting of CHA21 (SEQ ID NO: 128).

In another embodiment, is provided an isolated nucleic acid molecule encoding an EVIR according to the invention comprising a cell membrane export domain comprising an IgK domain, wherein the said nucleic acid molecule comprises SEQ ID NO: 105 wherein an isolated nucleic acid molecule encoding said EVIR is further comprising an extracellular antibody domain consisting of a trastuzumab-based scFv of SEQ ID NO: 76 or an extracellular antibody domain consisting of a FRP5-based scFv sequence of SEQ ID NO: 78.

In another embodiment, is provided an isolated nucleic acid molecule encoding an EVIR according to the invention comprising a cell membrane export domain comprising an IgK domain, wherein the said nucleic acid molecule comprises SEQ ID NO: 106, wherein an isolated nucleic acid molecule encoding said EVIR is further comprising an extracellular antibody domain consisting of a pertuzumab-based scFv sequence of SEQ ID NO: 77.

In a particular embodiment, is provided an isolated nucleic acid molecule encoding an EVIR according to the invention comprising an amino acid sequence that facilitates DNA engineering (e.g. cloning site).

In a particular embodiment, is provided an isolated nucleic acid molecule encoding an EVIR according to the invention comprising an amino acid sequence that facilitates DNA engineering (e.g. cloning site), wherein the said nucleic acid molecule comprises SEQ ID NO: 107 or SEQ ID NO: 108.

According to another embodiment, is provided an isolated nucleic acid molecule encoding an EVIR according to the invention comprising a nucleic acid sequence encoding a functional protein that promotes in cells, preferably in monocytes, macrophages and/or DCs, survival, differentiation, proliferation, activation, maturation, phagocytosis, endocytosis, M1-polarization, antigen-processing and presentation, T-cell recruitment, among other functions, or a protein capable of inducing APC differentiation, survival, activation and/or cross-presentation (for example CD40 (cluster of differentiation 40), GM-CSF (CSF2, colony stimulating factor 2), Type I and II interferon (e.g. interferon gamma (IFNγ)), LIN28, or Rab34), or attracting and/or activating T cells (for example IL-2 or CXCL9 (chemokine (C—X—C motif) ligand 9)).

According to another embodiment, is provided an isolated nucleic acid molecule encoding an EVIR according to the invention further comprising a nucleic acid sequence encoding a protein capable of inducing APC differentiation, survival, activation and/or cross-presentation (for example CD40, GM-CSF (CSF2), Type I and II interferon (e.g. IFNγ), or Rab34), or attracting and/or activating T cells (for example IL-2 or CXCL9).

According to another embodiment, is provided an isolated nucleic acid molecule encoding an EVIR according to the invention comprising a nucleic acid sequence encoding a functional protein capable of inducing APC differentiation, survival, activation and/or cross-presentation such as LIN28 (protein encoded by the Lin28 gene).

According to another embodiment, is provided an isolated nucleic acid molecule encoding an EVIR according to the invention further comprising a nucleic acid sequence encoding a protein capable of inducing APC differentiation, survival, activation and/or cross-presentation selected from: SEQ ID NO: 117 (CXCL9), SEQ ID NO: 120 (GM-CSF), SEQ ID NO: 123 (IFNγ), SEQ ID NO: 126 (LIN28) and SEQ ID NO: 127 (CD40).

According to a further particular embodiment an isolated nucleic acid encoding EVIRs of the invention comprises:
  (i) a nucleic acid sequence of SEQ ID NO: 1 or variants thereof encoding anti-HER2 CHA21;
  (ii) a nucleic acid sequence encoding a proteinic domain selected from: SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52 and SEQ ID NO: 53 or variants thereof; and
  (iii) a nucleic acid sequence of SEQ ID NO: 2 or variants thereof encoding a cell membrane export domain IgK.

According to a further particular embodiment an isolated nucleic acid encoding an EVIR of the invention comprises:
  (i) a nucleic acid sequence of SEQ ID NO: 111 or variants thereof encoding anti-TYRP1;
  (ii) a nucleic acid sequence encoding a proteinic domain of SEQ ID NO: 43 or variants thereof; and
  (iii) a nucleic acid sequence of SEQ ID NO: 109 or variants thereof encoding cell membrane export domain IgK.

According to a further particular embodiment an isolated nucleic acid encoding an EVIR of the invention comprises:

(i) a nucleic acid sequence of SEQ ID NO: 112 or variants thereof encoding anti-GD2;
(ii) a nucleic acid sequence encoding a proteinic domain of SEQ ID NO: 43 or variants thereof; and
(iii) a nucleic acid sequence of SEQ ID NO: 110 or variants thereof encoding cell membrane export domain IgK.

According to a further particular embodiment, is provided an isolated nucleic acid encoding an EVIR according to the invention selected from SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74 and SEQ ID NO: 75.

According to a further particular embodiment, is provided an isolated nucleic acid encoding an EVIR according to the invention selected from SEQ ID NO: 130 and SEQ ID NO: 131.

In a more particular embodiment, is provided an isolated nucleic acid encoding an EVIR according to the invention comprising orthologous human sequences encoding proteinic domain of the invention.

Vectors and Methods for Cell Transduction

In one embodiment, the invention provides a recombinant expression vector comprising a nucleic acid molecule according to the invention, wherein the vector optionally comprises an expression controlling sequence, allowing expression in eukaryotic host cells of the encoded sequence, operably linked to said nucleic acid molecule.

Numerous expression systems can be used, including without limitation chromosomes, episomes, plasmids, and virus-derived vectors. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses, lentiviruses, adeno-associated viruses (AAV). These recombinant vectors can equally be cosmid or phagemid derivatives.

In one embodiment, the recombinant vectors are any viral vectors selected from retroviral vectors (both replication-competent and replication-defective retroviral vectors), lentiviral vectors, in particular bidirectional lentiviral vectors, adenoviral vectors and adeno-associated vectors.

In a particular embodiment, the recombinant vector is a retroviral vector.

In one embodiment, the invention provides a recombinant expression vector comprising nucleic acid molecules encoding for one or more than one EVIR sequence of the invention.

In one embodiment, the invention provides a recombinant expression vector comprising at least one nucleic acid molecule encoding for a functional protein that promotes in cells, preferably in monocytes, macrophages and/or DCs, survival, differentiation, proliferation, activation, maturation, phagocytosis, endocytosis, antigen-processing and presentation, T-cell recruitment, among other functions.

In one embodiment, the invention provides a recombinant expression vector comprising nucleic acid molecules encoding for one or more than one EVIR sequence of the invention further comprising at least one nucleic acid molecule encoding for a functional protein that promotes in cells, preferably in monocytes, macrophages and/or DCs, survival, differentiation, proliferation, activation, maturation, phagocytosis, endocytosis, antigen-processing and presentation, T-cell recruitment, among other functions.

According to a particular embodiment, the expression vectors according to the invention may also encode for a protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9).

According to a particular embodiment, the invention provides a recombinant expression vector comprising nucleic acid molecules encoding for a protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9).

In another embodiment, a bidirectional or bicistronic expression vector can be used to co-express at least one EVIR according to the invention together with a protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9).

The nucleic acid sequence can be inserted in the recombinant expression vector by methods well known to a person skilled in the art such as, for example, those that are described in *Molecular Cloning: A Laboratory Manual*, Sambrook et al., 4th Ed., Cold Spring Harbor Laboratory Press, Cold Spring Harbor, N.Y., 2001.

Recombinant vectors can include nucleotide sequences that allow, control or regulate the expression and the transcription of a polynucleotide of the invention as well as the translation of an EVIR of the invention, these sequences being selected according to the host cells that are used. For example, an appropriate secretion signal can be integrated in the recombinant vector so that the EVIR, encoded by the nucleic acid molecule of the invention, will be directed to the membrane.

In a further embodiment, is provided a host cell comprising a recombinant vector according to the invention.

The introduction of the recombinant vector in a host cell can be carried out according to methods that are well known to a person skilled in the art, such as those described in *Basic Methods in Molecular Biology*, Davis et al., $2^{nd}$ ed., McGraw-Hill Professional Publishing, 1995, and *Molecular Cloning: A Laboratory Manual*, supra, such as transfection by calcium phosphate, transfection by DEAE dextran, transfection, microinjection, transfection by cationic lipids, electroporation, transduction or infection.

In another embodiment, the invention provides a process for producing APCs capable of expressing an EVIR, optionally along with a protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9), comprising contacting cells with a vector or a nucleic acid according to the invention.

According to an embodiment, EVIRs according to the invention are optionally co-expressed with the said protein or alternatively, the expression of said protein is achieved in APCs expressing EVIRs by using an independent vector.

According to a particular aspect is provided an ex vivo method (i.e., in culture) of inducing expression of at least one EVIR of the invention in an APC or a stem/progenitor cell thereof comprising the steps of:
(i) ex vivo transducing said cell with a vector according to the invention; and (ii) optionally inducing APC differentiation, maturation or activation;

wherein an EVIR according to the invention is expressed in said APC cells with a protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9).

Another aspect of the invention provides a method of inducing in vivo the expression of at least one EVIR of the invention in an APC or a stem/progenitor cell thereof in a subject in need thereof, said method comprising the steps of:
 (i) administering a vector encoding an EVIR according to the invention to said subject under suitable conditions for inducing transduction of the subject's APCs or stem/progenitor cell thereof in vivo with said vector; and
 (ii) optionally inducing APC differentiation, maturation or activation in vivo, wherein an EVIR according to the invention is expressed in vivo in said APC cells with a protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9).

The EVIRs can be delivered to APCs using a lentiviral vector (or alternative viral or non-viral vectors), either ex vivo on isolated APCs (or precursors thereof) or in vivo via systemic (e.g., intravenous) or local (e.g., intra-tumoral, peri-tumoral, lymphnodal, etc.) delivery of a vector of the invention encoding said EVIRs.

In particular, the invention provides a process for producing an antigen-presenting cell or any stem of progenitor cell thereof, expressing at least one EVIR according to the invention, comprising contacting said APCs or stem of progenitor cell thereof, in particular DCs, monocytes or macrophages, either ex vivo or in vivo with a vector or a nucleic acid according to the invention.

EVIR-Expressing APCs

According to an embodiment, the invention provides an antigen-presenting cell expressing at least one EVIR according to the invention.

According to an embodiment, the invention provides a cell expressing one EVIR according to the invention.

According to a further embodiment, the invention provides a cell expressing at least an EVIR along with a protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9).

According to a particular embodiment, the invention provides a cell expressing at least 2, at least 3, at least 4 different EVIRs of the invention.

According to a particular embodiment, the invention provides a cell expressing at least one EVIR according to the invention, for example from about 1 to about 3 different EVIRs of the invention.

According to an embodiment, is provided a cell composition comprising APCs expressing at least one EVIR of the invention, wherein at least 1%, at least 10%, at least 20%, at least 30%, at least 40%, at least 50%, at least 60%, at least 70%, at least 80%, or at least 90% of the APCs, in particular monocytes, macrophages or DCs, express at least one EVIR of the invention.

According to a further embodiment, is provided a cell composition of the invention, wherein at least 1% of the cell population expresses at least one EVIR of the invention.

According to another embodiment, is provided a cell composition comprising APCs expressing at least an EVIR along with a protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9).

According to an embodiment, is provided a cell composition of the invention, wherein expression of the EVIR persists for at least several hours after delivery with a vector of the invention.

According to an embodiment, is provided a cell composition of the invention, wherein at least 1% of the cell population expresses at least one EVIR of the invention and said expression persists for at least several hours after delivery with a vector of the invention.

According to an embodiment, is provided a cell composition of the invention, wherein expression of a protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9), persists for at least several hours after delivery with a vector of the invention.

According to one embodiment, the expression level and time of EVIRs can be measured by methods such as flow cytometry, protein analysis, or nucleic acidic amplification.

According to another embodiment, the invention provides a cell according to the invention, wherein said cells is a hematopoietic cell with the ability to differentiate into monocytes, macrophages or dendritic cells, including hematopoietic stem/progenitor cells.

According to another embodiment, the invention provides a cell according to the invention, wherein said cell is selected from hematopoietic stem cell and progenitor cell.

According to another embodiment, the invention provides a cell according to the invention, wherein said cell is an antigen-presenting cell (APC).

According to another embodiment, the invention provides a cell according to the invention, wherein said cell is an APC selected from a monocyte, a macrophage or a dendritic cell.

In another embodiment, the invention provides a cell expressing at least one EVIR, wherein said cell further expresses at least one protein capable of inducing APC differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9).

It is understood that, when co-expressed in a cell expressing at least one EVIR of the invention, CD40 can act to enhance antigen-presenting cell and T-cell activation; Type I and II interferon (e.g. IFNγ) can act to enhance antigen-presenting cell and T-cell maturation and activation; LIN28 blocks the maturation of the microRNA Let-7, promoting activation and antigen presentation by macrophages and DCs (Baer et al., 2016, *Nat Cell Biol.*, 18(7):790-802); Rab34 can act to enhance antigen cross-presentation; GM-CSF (CSF2) can act to increase antigen-presenting cell and dendritic cell differentiation, maturation and activation; IL-2 can act to increase T-cell proliferation; CXCL9 can act to increase T-cell recruitment.

In another embodiment, the invention provides EVIR-expressing cells that are able to internalize EVs to the cell cytoplasm.

In another embodiment, the invention provides EVIR-expressing cells with enhanced internalization capabilities of cancer-cell derived EVs, as compared to the same cells not expressing an EVIR of the invention, which property is independent of a contact with the cancer cells.

In another embodiment, the invention provides EVIR-expressing cells with faster internalization of cancer-cell derived EVs, as compared to cells not expressing EVIR, which property is independent of contact with cancer cells.

According to one embodiment, the internalization level and kinetics of EVs by EVIR-expressing cells can be measured by methods such as flow cytometry and protein analysis.

In another embodiment, the invention provides EVIR-expressing cells that are able to uptake, process, and present to T-cells tumor associated antigens (TAAs) without the need of a pre-identification of those TAAs.

In another embodiment, the invention provides EVIR-expressing cells that facilitate TAAs cross-presentation to $CD8^+$ T cells.

In another embodiment, the invention provides EVIR-expressing cells with enhanced presentation (in terms of repertoire of TAAs and in terms of quantity of each TAA) to T-cells of EV-associated TAAs as compared to cells not expressing EVIR.

According to one embodiment, the level of presentation of TAAs to T cells achieved by cells of the invention can be measured by methods such as flow cytometry, protein analysis, and T-cell proliferation/activation assays.

In another embodiment, the invention provides cells according to the invention that induce T-cells proliferation.

In another embodiment, the invention provides cells according to the invention with enhanced ability to induce T-cell proliferation as compared to cells not expressing EVIR.

According to one embodiment, T-cell proliferation can be measured by methods such as flow cytometry, cell cycle analysis, T-cell suppression, and mixed leukocyte reactions (MLR).

Methods and Uses According to the Invention

The invention provides a method of inducing expression of EVIRs, optionally along with a protein capable of inducing differentiation, survival, activation and/or cross-presentation (for example CD40, GM-CSF (CSF2), Type I and II interferon (e.g. IFNγ), LIN28, or Rab34), or attracting and/or activating T cells (for example IL-2 or CXCL9), in an antigen-presenting cell (APC) or a stem or progenitor cell thereof according to the invention.

In one particular method of the invention, APC differentiation can be conducted according to methods involving exposing APC precursors such as monocytes under cell culture conditions well-known to those skilled in the art.

In a particular embodiment, the invention provides a method of inducing expression of EVIRs in APCs, said method comprising the step of transfecting or transducing said cells with a vector according to the invention.

In another embodiment, is provided an ex vivo method of preparing EVIR-expressing, TAA-presenting cells according to the invention, wherein the provided EVs are tumor-derived particles, such as exosomes and other vesicles, isolated from either a tumor or blood sample.

In another embodiment, is provided an ex vivo method of preparing EVIR-expressing, TAA-presenting cells according to the invention, wherein the APC and cancer cells or EVs are co-cultured and the EVs derive from the ex-vivo cultured cancer cells.

According to a particular embodiment, the EVIR-expressing, TAAs-presenting cells according to the invention can be injected to cancer subject, while and optionally inducing APC differentiation, maturation or activation in vivo and can be useful in a method of treatment according to the invention.

In one embodiment, is provided an in vivo method of inducing presentation of TAAs in an EVIR-expressing cell of the invention, comprising the step of delivering an EVIR-expressing vector via systemic (e.g., intravenous) or local (e.g., intra-tumoral, peri-tumoral, lymphnodal, etc.) routes to a cancer subject.

In another embodiment, is provided a method of inducing an immune response to cancer cells in a subject, comprising the step of administering EVIR-expressing vectors or cells according to the invention in a patient in need thereof, wherein said EVIR-expressing vectors or cells are administered alone, or pre-treated in a co-culture with cancer cells, or pre-treated in a co-culture with cancer-cell derived EVs, in particular exosomes, or in combination with another anti-cancer therapy. Standard procedures used in DC vaccination procedures might be used.

In a particular embodiment, the cancer cells or cancer-cell derived EVs are autologous, i.e. originating from the patient to be treated.

In a particular embodiment, the APCs or stem/progenitor cells are autologous, i.e. originating from the patient to be treated.

In a particular embodiment, the invention provides a method of identifying new TAAs loaded on MHCI or MHCII molecules according to the invention wherein the identification of the new TAAs is performed by proteomics methods.

In another aspect, the invention provides a use of cells according to the invention for the preparation of a vaccine for treating and/or preventing a cancer.

According to a particular aspect, the EVIRs of the invention are useful for uptaking cancer cell-derived EVs that contain free (unloaded) TAAs.

According to another particular aspect, the EVIRs of the invention are useful for uptaking cancer cell-derived EVs that contain TAAs already loaded on MHCI or MHCII molecules.

Another aspect of the invention relates to an isolated cell expressing at least one EVIR of the invention and capable of presenting unloaded TAAs via MHCI or MHCII molecules.

Another aspect of the invention provides an isolated cell expressing at least one EVIR of the invention and capable of presenting TAAs already loaded on MHCI or MHCII molecules.

It is worth pointing that currently existing approaches using APC-TAA are not designed to instruct the APC to uptake and present TAAs endogenously, i.e., in the body of the patient and from the tumor of the patient, but instead rely on the ex vivo exposure to tumor-derived material. Therefore, the EVIR-expressing vectors or cells according to the invention and methods using thereof are particularly advantageous over the existing approaches in immunotherapy and/or in the prevention and/or treatment of cancers.

Compositions According to the Invention

Pharmaceutical compositions or formulations according to the invention may be administered as a pharmaceutical formulation, which contains EVIR-expressing vectors or cells as described herewith.

Another aspect of the invention provides a pharmaceutical composition comprising cells of the invention and at least one pharmaceutically acceptable agent able to promote APC differentiation, maturation and/or activation in vivo.

The invention provides pharmaceutical or therapeutic cells as compositions and methods for treating a subject, preferably a mammalian subject, and most preferably a human patient who is suffering from a cancer.

Cells of the invention or formulations thereof may be administered as a pharmaceutical formulation, which can contain one or more co-agents according to the invention in any form described herein. The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended dosage range to be employed.

Compositions of this invention may be liquid formulations including, but not limited to aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methylcellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions of this invention may also be formulated as a depot preparation, which may be administered by implantation or by intramuscular injection.

The compounds of this invention can also be administered in sustained release forms or from sustained release drug delivery systems.

According to a particular embodiment, compositions according to the invention are for intravenous use.

According to a particular embodiment, compositions according to the invention are for intratumoral use.

According to a particular embodiment, compositions according to the invention are for subcutaneous use.

According to a particular embodiment, compositions according to the invention are for intralymphnodal use.

According to a particular aspect, compositions of the invention are vaccine compositions.

According to a particular aspect, vaccine compositions may comprise one or more co-agents selected among CpG oligonucleotides (short single-stranded synthetic DNA molecules that contain a cytosine triphosphate deoxynucleotide ("C") followed by a guanine triphosphate deoxynucleotide ("G"), "p" refers to the phosphodiester link between consecutive nucleotides) diphtheria toxin, growth factors (non-limiting examples are: M-CSF (macrophage colony-stimulating factor), GM-CSF, granulocyte-macrophage colony-stimulating factor), FLT3 (FMS-like tyrosine kinase-3),) and/or cytokines (non-limiting examples are: IFNγ (Interferon gamma), CXCL9 (Chemokine (C—X—C motif) ligand 9), IL12 (interleukin 12), IL2 (interleukin 2), IL-4 (interleukin 4)).

In another particular aspect, compositions according to the invention are adapted for delivery by single administration.

According to a particular embodiment, compositions of the invention are veterinary compositions.

Further materials as well as formulation processing techniques and the like are set out in Part 5 of Remington's "*The Science and Practice of Pharmacy*", 22$^{nd}$ Edition, 2012, University of the Sciences in Philadelphia, Lippincott Williams & Wilkins, which is incorporated herein by reference.

In another aspect, the invention provides compositions comprising vectors according to the invention.

In another aspect, the invention provides compositions comprising EVIR-expressing cells according to the invention.

Mode of Administration

Cells and formulations thereof according to this invention may be administered in any manner including parenterally, intravenously, intratumorally, subcutaneously, intra-dermally, rectally, direct tissue perfusion during surgery, or combinations thereof. Parenteral administration includes, but is not limited to, intravenous, intra-arterial, intra-peritoneal, subcutaneous and intramuscular. The compositions of this invention may also be administered in the form of an implant, which allows slow release of the compositions as well as a slow controlled i.v. infusion.

Combination

According to the invention, the vectors and cells according to the invention, and pharmaceutical formulations thereof, can be administered alone or in combination with a co-agent useful in the prevention and/or treatment of a cancer such as therapeutic antibodies that enhance the adaptive immune system's activity against the tumor (such as anti-PD1, anti-PDL1, anti-CTLA4 antibodies), therapeutic antibodies or TLR agonists that enhance the innate immune system's activity against the tumor (such as anti-CD40 antibodies), therapeutic antibodies or small molecule inhibitors that deplete endogenous monocytes, macrophages or dendritic cells (for example anti-CSF1R inhibitors), thus favoring the engraftment of and uptake of EVs by EVIR expressing cells of the invention.

The cells according to the invention might also be combined with known chemo-, radio-therapeutics that enhance cancer cell killing and release of cancer-cell derived EVs, as defined in the application.

The invention encompasses the administration of vectors or cells, pharmaceutical formulations thereof, or composition according to the invention, wherein said vectors or cells or compositions are administered to an individual prior to, simultaneously or sequentially with other therapeutic regimens, co-agents useful in the prevention and/or treatment of a cancer, in a therapeutically effective amount.

Cells or composition according to the invention, or the pharmaceutical formulation thereof, that are administered simultaneously with said co-agents can be administered in the same or different composition(s) and by the same or different route(s) of administration.

Kits

According to another aspect of the invention, is provided a kit comprising at least one recombinant expression vector and/or at least one cell according to the invention, and optionally instructional material.

According to another further embodiment, the kit according to the invention comprises at least one recombinant expression vector and further comprises at least one agent for transducing an antigen-presenting cell or a stem/progenitor cell thereof with said recombinant expression vector.

According to another further embodiment, the kit according to the invention comprises at least one cell according to the invention and further comprises at least one agent for the preservation of said cells and/or culture of said cells with cancer cells of cancer derived EVs.

Patients

In an embodiment, patients according to the invention are suffering from any type of cancer.

In an embodiment, patients according to the invention are suffering from any type of cancer at any stage, including non-metastatic and metastatic.

In a particular embodiment, patients according to the invention are suffering from carcinomas, sarcomas, melanomas, brain tumors, hematological cancers, or any pre-malignant or malignant neoplasm.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention.

EXAMPLES

The following abbreviations refer respectively to the definitions below:

293T cells (human embryonic kidney cells); B4GALNT1 (Beta-1,4-N-Acetyl-Galactosaminyltransferase 1, GD2 synthase); B16 cells (murine melanoma tumor cell line); BM (bone marrow); BMDC (bone marrow derived dendritic cell); BMDM (bone marrow derived macrophage); CCR1 (chemokine receptor type 1); CCR2 (C—C chemokine receptor type 2); CCR5 (chemokine receptor type 5); CSF2 (colony stimulating factor 2); CSF2RB (colony-stimulating factor-2 receptor B); CXCR4 (chemokine receptor CXCR4); CD40 (cluster of differentiation 40); DC (dendritic cell); CXCL9 (chemokine (C—X—C motif) ligand 9); EC (extracellular domain); EV (extracellular vesicle); dLNGFR (truncated low-affinity human nerve growth factor receptor); EVIR (extra-cellular vesicle internalizing receptor); FLT3 (receptor tyrosine kinase); GD2 (ganglioside GD2); GFP (green fluorescent protein); iBMM (immortalized murine bone marrow derived macrophages); IC (intracellular domain); IFNγ (interferon gamma); ITGB2 (integrin beta chain beta 2 receptor); LIN28 (protein encoded by the LIN28 gene); LV (lentiviral vector); MC38 (a colon carcinoma cell line); mTq (turquoise fluorescent protein); OVA (ovalbumin); MFI (mean fluorescence intensity); P388D1 (murine monocytic cell line isolated from lymphoma); PM (Peritoneal macrophages); SELPLG (P-selectin glycoprotein-1 ligand receptor); SFFV (spleen forming focus virus); ST8SIA1 (ST8 Alpha-N-Acetyl-Neuraminide Alpha-2,8-Sialyltransferase 1, GD3 synthase); TLR4 (toll-like receptor 4); TM (transmembrane domain); TYRP1 (tyrosinase-related protein-1); UT (untransduced).

Example 1

Design of Extra-Cellular Vesicle Internalizing Receptor 11 different EVIR molecules were designed as follows.

Cloning Design of EVIRs 11 transmembrane receptors were selected and their intracellular (IC) domain, transmembrane (TM) domain, and a short extracellular (EC) domain were cloned in combination with the DNA coding sequence for the HER2-specific scFv termed CHA21 (SEQ ID NO: 128) (extracellular antibody domain specific for a surface molecule of a cancer cell).

DNA coding sequences from the selected transmembrane receptors were: the human nerve growth factor receptor (dLNGFR, SEQ ID NO: 43), FcγRIIIA receptor (a member of the Fcγ receptor family expressed by cells of the innate immune system, SEQ ID NO: 44), the receptor tyrosine kinase (FLT3, SEQ ID NO: 45), the toll-like receptor 4 (TLR4, SEQ ID NO: 46), the C—C chemokine receptor type 2 (CCR2, SEQ ID NO: 47), the integrin beta chain beta 2 receptor (ITGB2, SEQ ID NO: 48), the colony-stimulating factor-2 receptor B (CSF2RB, SEQ ID NO: 49), the chemokine receptor CCR1 (SEQ ID NO: 50), the chemokine receptor CCR5 (SEQ ID NO: 51), the chemokine receptor CXCR4 (SEQ ID NO: 52), the P-selectin glycoprotein-1 ligand receptor (SELPLG, SEQ ID NO: 53).

A mouse-optimized CHA21 coding DNA sequence (SEQ ID NO: 128) was obtained from GeneArt® (LifeTechnologies). A coding DNA sequence of IgK signal domain (SEQ ID NO: 129) was incorporated to increase the export of a receptor to membrane. A linker sequence containing a high efficiency Kozak sequence and restriction sites for cloning (SEQ ID NO: 3) was incorporated at the 5' end of the EVIR coding sequence. Restriction enzyme sites and a stop codon (SEQ ID NO: 4) were incorporated at the 3'end of the scFv sequence for cloning, before the STOP codon, the DNA sequence of the transmembrane and intracellular domains of the EVIR.

The DNA coding sequence of FcγRIIIa was obtained from GeneArt® (Life Technologies).

The linker sequences were added to the sequence at the 5' (SEQ ID NO: 5) and 3' (SEQ ID NO: 6) end of the FcγRIIIa coding sequence.

The DNA coding sequence of dLNGFR was obtained by PCR from a lentiviral vector (LV) that expresses the dLNGFR and GFP (Amendola et al., 2005, *Nat biotechnol*, 23(1): 108-16). Primers that contain restriction sites for AgeI and MluI were used as specified in Table 1. The DNA coding sequence of FLT3 was obtained by PCR from cDNA of BM-derived DCs as described in Example 2 and primers that contain restriction sites for AgeI and XhoI were used. The DNA coding sequences of the mouse Tlr4, Ccr2, Itgb2, Csf2rb, Ccr1, Ccr5, Cxcr4, Selplg receptors were obtained by PCR from cDNA of peritoneal macrophages as described in Example 2 and primers that contain restriction sites for AgeI, XmaI, MluI and SalI were used.

TABLE 1

| Gene name | Forward primer | Reverse Primer |
|---|---|---|
| dLNGFR | AAAAAACCGGTCTTCTGGGGGTGTCCCTTG (SEQ ID NO: 7) | AAAAAACGCGTAGTTAGCCTCCCCCAT CTCC (SEQ ID NO: 8) |
| Flt3 | AAAAAACCGGTCCAGGCCCCTTCCCTTTCA TC (SEQ ID NO: 9) | AAAAACTCGAGAGAGGCGAGGCTAATC TTGG (SEQ ID NO: 10) |
| Tlr4 | AAAAAACCGGTCAGCTGTATTCCCTCAGC ACT (SEQ ID NO: 11) | AAAAAGTCGACTGGGTTTAGGCCCCAG AGTT (SEQ ID NO: 12) |
| Ccr2 | AAAAAACCGGTATGGAAGACAATAATATG TTACCTC (SEQ ID NO: 13) | AAAAAACGCGTATGTACAAACTGCTCC CTCC (SEQ ID NO: 14) |
| Itgb2 | AAAAAACCGGTAATGCACGGCTGGTAGAG TG (SEQ ID NO: 15) | AAAAAACGCGTGGGGGTCACATCTGCT TGAT (SEQ ID NO: 16) |
| Csf2rb | AAAAAACCGGTACTCAGAAGATGGCTTAC TCATTCA (SEQ ID NO: 17) | AAAAAACGCGTTGGTGAGATTGGGAGG AGAC (SEQ ID NO: 18) |
| Ccr1 | AAAAAACCGGTACTCCATGCCAAAAGACT GCT (SEQ ID NO: 19) | AAAAAACGCGTACCTTCCTTGGTTGAC ACCTATG (SEQ ID NO: 20) |
| Ccr5 | AAAAAACCGGTATGTCAGCACCCTGCCAA AAA (SEQ ID NO: 21) | AAAAAACGCGTCATTCCTACTCCCAAG CTGCAT (SEQ ID NO: 22) |
| Cxcr4 | AAAAACCCGGGTTCCGGGATGAAAACGTC CA (SEQ ID NO: 23) | AAAAAACGCGTTGCATAAGTGTTAGCT GGAGTG (SEQ ID NO: 24) |
| Selplg | AAAAAACCGGTATTGCCACCACTGACCCT A (SEQ ID NO: 25) | AAAAAACGCGTGCAAAGGTCTCGCTTA GGTG (SEQ ID NO: 26) |

The synthetic DNA sequence encoding for CHA21 was inserted in an LV containing the spleen forming focus virus (SFFV) promoter and the WPRE stabilizing sequence (Squadrito et al., 2012, Cell Rep, 1(2): 141-54). To this aim, the plasmid containing CHA21 with BamHI and XhoI, and the plasmid containing the SFFV.miR-511-3p.OFP.WPRE (Squadrito et al., 2012, supra), were digested with BamHI and SalI. The IC, TM and EC domains of the selected receptors were then inserted by digesting the PCR products indicated above with the restriction enzymes present in the corresponding primers.

In order to trace EVIR expression, the resulting SFFV.E-VIR.WPRE sequence was cloned into a bidirectional LV (Amendola et al., 2005, supra) by replacing the hPGK.dLNGFR cassette with the SFFV.EVIR cassette with EcoRV and AvrII restriction sites. In this bidirectional LV, the GFP is expressed under the transcriptional control of the minimal cytomegalovirus promoter (mCMV).

Total RNA obtained from either bone marrow derived macrophages (BMDMs) or peritoneal macrophages was isolated by using the miRNeasy RNA kit (Qiagen) as indicated by the manufacturer. cDNA was then obtained by using Vilo reverse transcriptase (Life Technologies) as indicated by the manufacture. cDNA or plasmids were then amplified by PCR using the Pfu ultra II (Agilent Technologies) polymerase as indicated by the manufacture. Primers are described above. PCR was run in SensoQuest GmbH labcycler and purified using High Pure PCR product purification kit (Roche). After running the amplicons in 1% agarose gel, they were extracted using Jetquick gel extraction spin kit (Genomed). MiniPrep were performed using NucleoSpin Plasmid kit (Macherey-Nagel).

To express the EVIRs, a bidirectional lentiviral vector (LV) was used that was expressing a GFP sequence in antisense orientation, under the transcriptional control of a minimal cytomegalovirus (mCMV) promoter, and the anti-HER2 EVIR in sense orientation, under the transcriptional control of the spleen focus forming virus (SFFV) promoter (FIG. 1). The resulting LVs were identified and named according to the intracellular component of the EVIR (being the extracellular domain, CHA21, constant), as follows: EVIR-N (dLNGFR-CHA21), EVIR-G (FcγRIIIa-CHA21), EVIR-F (FLT3-CHA21), EVIR-T (TLR4-CHA2), EVIR-C2 (CCR2-CHA21), EVIR-I (ITGB2-CHA21), EVIR-C (CSF2RB-CHA21), EVIR-C1 (CCR1-CHA21), EVIR-C5 (CCR5-CHA21), EVIR-CX (CXCR4-CHA21), EVIR-S (SELPLG-CHA21).

Example 2

Expression and Stability of an Anti-HER2 EVIRs

The stability and expression profile of EVIRs in different cells was tested.

Immortalized murine bone marrow (BM) derived macrophages (iBMM) were described previously (Squadrito et al., 2014, Cell Rep., 8(5):1432-46).

Briefly, the cells were obtained by transducing mouse BM cells with a LV expressing the proto-oncogene SV40 large T-antigen. iBMMs were cultured in macrophage serum free medium (SFM medium, Life Technologies), supplemented with macrophage colony-stimulating factor (M-CSF, 50 ng/ml). iBMMs were then cultured in Iscove's Modified Dulbecco's Medium (IMDM, Sigma-Aldrich), supplemented with M-CSF (50 ng/ml), 20% fetal bovine serum (FBS, EuroClone Group), 5.5 mL L-glutamine (Life Technologies) and 5.5 ml penicillin-streptomycin (Life Technologies).

Murine monocytes cell line (P388D1) and colon carcinoma cell line (MC38) were cultured in IMDM supplemented with 10% FBS, glutamine and penicillin-streptomycin, as described above.

Peritoneal macrophages (PMs), bone marrow derived dendritic cells (BMDCs) and bone marrow derived macrophages (BMDM) were isolated from 5-6 weeks BL6C57 mice.

PMs were obtained by flushing the peritoneum of euthanized mice with phosphate-buffered saline (PBS). Cells were then seeded in plates with IMDM supplemented with M-CSF (50 ng/ml), after 1 h non-adherent cells were discarded. BMDMs and BMDCs were obtained by flashing femurs and tibias with PBS. BM cells were then cultured for 8 days in IMDM or Roswell Park Memorial Institute (RPMI) medium respectively supplemented with M-CSF (50 ng Preprotech) for the BMDMs or GM-CSF (100 ng, Preprotech) for the BMDCs.

Lentiviral Vector Production by Transfection of 293T Cells and Cell Transduction Vesicular stomatitis virus (VSV)-pseudotyped, third-generation lentiviruses were produced by transient four-plasmid co-transfection into human embryonic kidney cells (293T) as described previously (De Palma et al., 2002, *Methods in enzymology*, 346: 514-529). Briefly, 9 million 293T cells were seeded in a 15 cm dish 24 h before transfection in 20 ml of medium. 2 h before transfection, medium was changed. Per plate, the plasmid DNA mix was prepared with envelope ENV plasmid (VSV-G, 9 µg), pMDLg/pRRE plasmid (12.5 µg), REV plasmid (6.25 µg), pADVANTAGE (15 µg) and transfer plasmid (32 µg). 125 µl of 2.5M $CaCl_2$ were added to the plasmid mix and 0.1 TE/dH20 (2:1) was used to have a final volume of 1125 µl. While vortexing at full speed this solution, 1125 µl of 2× HBS solution (pH 7.12) was added drop-wise. The final HBS and plasmid solution was rapidly transferred on the cells. The medium was changed 12-14 h later and 16 ml of fresh media was added per dish. The cell supernatant was collected and filtered (0.22 µm) 30 hours after and concentrated by ultracentrifugation using a Beckman ultracentrifuge equipped with a SW31Ti rotor, at 22'000 rpm for 2 h, at 20° C. Reagent compositions were as follows: 2× HBS (281 mM NaCl, 100 mM of 4-(2-hydroxyethyl)-1-piperazineethanesulfonic acid (HEPES buffer), 1.5 mM $Na_2HPO_4$), 0.1× TE buffer (10 mM Tris (pH 8.0), 1 mM EDTA (pH 8.0) diluted 1:10 with distilled $H_2O$). The stocks of LVs were kept at −80° C.

LVs (all expressing fluorescent proteins) were titered cells by dilutions ranging from 10-3 to 10-7 on 100'000 293T cells seeded in a 6-well plate the day before transduction. The percentage of positive cells was measured by flow cytometry 4-7 days after transduction. The titer was calculated applying the formula: TU/ml='number of cells'*'percentage positive cells'/100/'dilution'. The 'percentage positive cells' used in the formula was always the lowest dilution with a value lower than 15%. 293T, P388D1 and iBMMs were transduced with LV doses ranging from $10^6$ to $10^7$ transducing units (TU)/ml. In experiments with double transduction (HER2-expressing LV and mCherry-expressing LV for instance), sequential transduction was performed i) transducing the cells with HER2-expressing LV, ii) washing and replating the cells and iii) transducing the cells with mCherry-expressing LV) 5-7 days after the first transduction.

Immunofluorescence Analysis of iBMMs

EVIR/Control-transduced iBMMMs were seeded in a glass cover slide coated with fibronectin (200 µg/ml, Preprotech). The day after the medium was removed, the cells were washed 3 times for 1 min with PBS. iBMMs were then fixed in 4% paraformaldehyde (PFA) for 15 min at room temperature in the dark. After removing the PFA, 3 washes with PBS for 1 min were performed. The cells were then incubated for 30 min in blocking solution (0.1% Triton and 10% normal goat serum (NGS) in PBS). Then, a staining solution containing an anti-F(ab')2 antibody conjugated with Alexa Fluor 647 (Jackson ImmunoResearch) was prepared in blocking solution. 200 µl of staining solution were added per well for 4 h. The staining solution was removed and the slides were washed with PBS 3× for 3 min. Phalloidin-Alexa Fluor 546 (Life Technologies) in blocking solution was added for 20 min. Then slides were washed 3× with PBS and finally 4',6-diamidino-2-phenylindole (DAPI) was added for 10 min and washed 5× for 3 min. DAKO mounting medium was added and samples were dried overnight at RT. Images were acquired by confocal microscopy (Zeiss LSM 700 INVERT).

Flow Cytometry Analysis

After transduction and cell culture, cells were detached by trypsin and stained with the appropriate antibodies before flow cytometry analysis.

Figure 2:
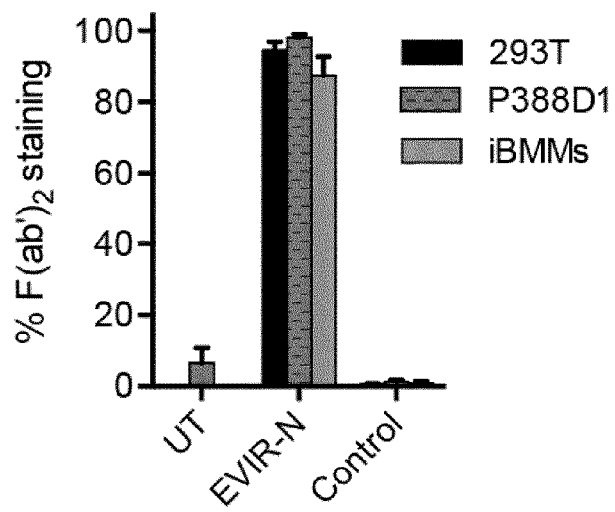
FIG. 2. Expression of EVIRs after cell transduction. Anti-HER2 EVIR-N expression measured as the percentage of F(ab')2-positive cells (mean±SEM, n=5) analyzed by flow cytometry (anti-F(ab')2 staining) in 293T, P388D1 and iBMMs, either untransduced (UT; F(ab')2-positive cells are undetectable, and signal from P388D1 cells represents noise) or transduced with control or EVIR-N LVs (design described in Example 1).

To validate the expression of EVIR-N, human kidney cells (293T cells), immortalized bone-marrow macrophages (iBMMs) and monocytes (P388D1 cells) were transduced with the EVIR-N LV or, as a control LV, a bidirectional LV that expresses GFP and dLNGFR (without the extracellular scFv domain). To measure EVIR-N expression, transduced cells were stained with an anti-F(ab')2 antibody, which recognizes the scFv domain of the EVIR. A robust surface expression of EVIR-N in all cell types was observed (FIG. 2).

Figure 3:
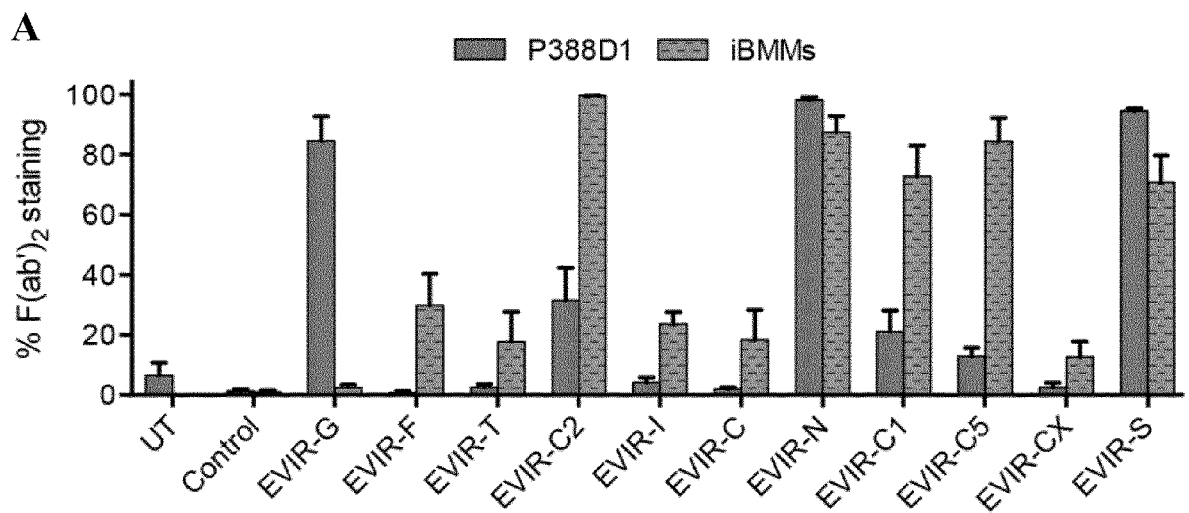
FIG. 3. Expression of EVIRs with different signal domains after cell transduction. A: Anti-HER2 EVIR expression measured as the percentage of F(ab')2-positive cells (mean±SEM, n=5) analysed by flow cytometry (anti-F(ab')2 staining) in P388D1 and iBMMs. B: Representative images of immunofluorescence analysis of iBMMs transduced with control, EVIR-N, EVIR-T or EVIR-G LVs, stained with anti-F(ab')$_2$ antibody, as described in Example 2.
Figure 3:
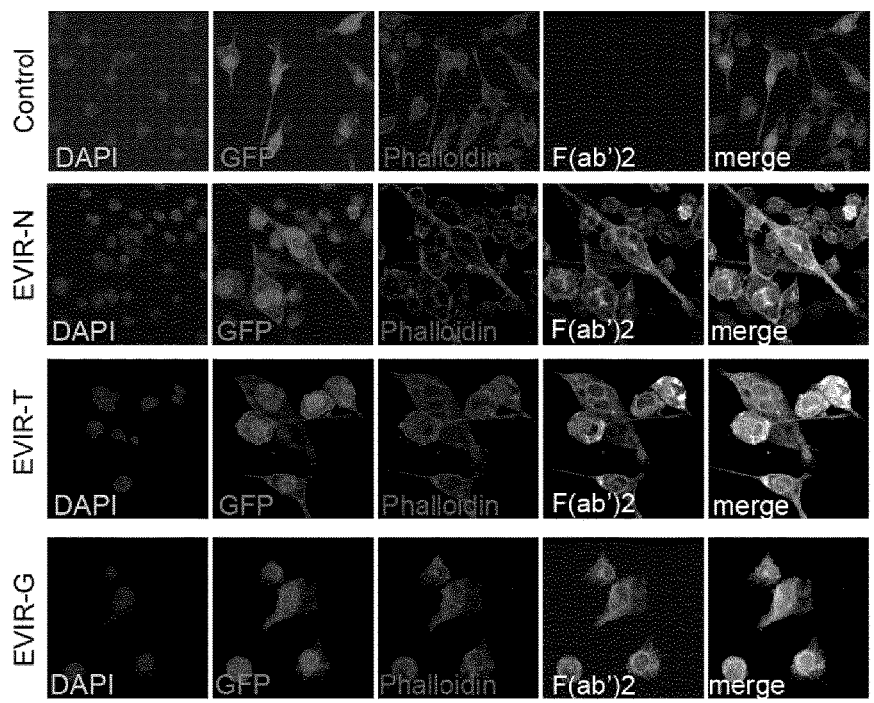

Immunofluorescence staining analysis of iBMMs confirmed robust EVIR-N expression at the cell surface (FIG. 3B).

Figure 4:
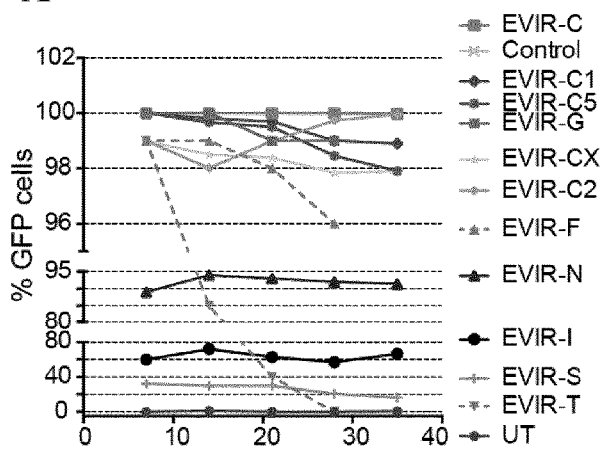
FIG. 4. Persistence of EVIR-expressing cells. Data show the percentage of GFP-positive cells (A: iBMMs, B: P388D1) over a period of 36 days from transduction with control or anti-HER2 EVIR LVs, measured by flow cytometry as described in Example 2.
Figure 4:
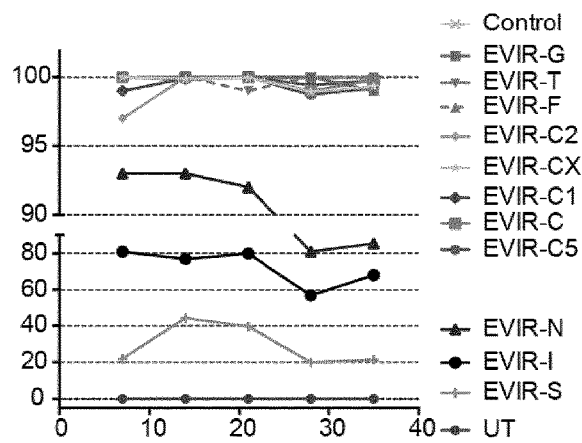

The stability of EVIR-N-expressing monocytes/iBMMs over an extended period of time (5 weeks post-transduction) was analysed. GFP expression, which is indicative of the persistence of transduced cells, was stable in both P388D1 and iBMMs cells during the 5-week time window (FIG. 4).

Additional EVIRs (as listed above) featuring a repertoire of distinct proteinic domains comprising transmembrane and intracellular signaling domains were tested. To investigate whether anti-HER2 EVIRs can be expressed in a sustained manner, we transduced iBMMs and P388D1 monocytes were transduced with the various GFP/EVIR and the control GFP/dLNGFR LVs. Flow cytometry showed heterogeneous expression of the different EVIRs at the cellular membrane, which was dependent on the EVIR or cell type tested (FIG. 3A). Whereas EVIR-N was robustly expressed by either cell type, other EVIRs, such as EVIR-C, EVIR-CX and EVIR-I, were expressed less efficiently. Some EVIRs displayed differential expression among the two cell types, e.g., EVIR-G was highly expressed in P388D1 cells but much less so in iBMMs. Immunofluorescence analysis of iBMMs transduced with EVIR-N, EVIR-G, EVIR-T or control LVs further indicated that these EVIRs were detectably expressed, albeit to varying levels (FIG. 3B). The stability of EVIR-expression over an extended period of time (5 weeks post-transduction) was investigated. For most EVIRs, GFP expression was stable in the iBMM and P388D1 cell lines during the 5-week time window (FIG. 4). It is noted that a good expression of EVIRs is achieved when at least 1% of population of any cell type, preferentially monocytes, macrophage or dendritic cell (DC) expresses EVIRs and when this expression is detectable for a few weeks post-transduction.

Together, these results indicate that LVs can be used to stably express the anti-HER2 EVIRs on membranes of several cell types, including monocyte and macrophage-lineage cells.

Example 3

Anti-HER2 EVIRs Enhance Monocyte/Macrophage Binding to Cancer Cells

EVIRs expression in cells on binding to monocytes/macrophages was tested.

Binding Assay in Co-Culture

Turquoise fluorescent protein (mTq) positive MC38 either expressing HER2 were obtained by transducing mTq$^-$ MC38 with a HER2 expressing LV, which was obtained by substituting the GFP coding sequence of a PGK. GFP LV as described in Amendola et al., 2005 (*Nat biotechnol,* 23(1): 108-16) with a HER2 coding sequence as described in Leto et al., 2015 (*Clin Cancer Res.* 21(24):5519-31). mTq+ MC38, HER2 transduced or untransduced, were detached according to standard protocol and seeded in 24-well plates (Corning Costar), 20,000 cells/well. After 24 h, iBMMs, transduced with either mCherry or GFP (EVIR)-expressing LVs, were detached according to standard protocols. 20,000 mCherry+ and GFP+ cells were mixed to a 1:1 ratio approx. and seeded on top of the mTq+ MC38 cells. After 24 h of co-culture, both cell types were detached with trypsin, stained with 7-AAD and analyzed by flow cytometry (LSRII, BD).

Binding Assay in Suspension

P388D1 transduced with either control or EVIR-N LVs and mCherry MC38 (transduced with HER2-LV or UT) were detached and washed according to standard protocol and re-suspended in IMDM to a concentration of 5'000 cells/µl in a final volume of 30 µl. In a 0.5 ml tube (Eppendorf), the cells were mixed at different ratios (1:10, 1:1 and 10:1) and put on a rotating wheel for 3 hours at 20 rpm. The mix of cells was kept at 4° C. in the dark to avoid internalization of the receptors and fluorescence squelching. After the incubation time, 30 µl 7-AAD 2× was added and cell suspensions were analyzed by flow cytometry (LSRII, BD).

It was tested whether EVIR-N expression facilitates monocyte/macrophage binding to HER2-expressing cancer cells. To this aim, colon cancer MC38 cells were transduced with a turquoise fluorescent protein (mTq)-expressing LV, with or without a HER2-expressing LV.

Figure 5:
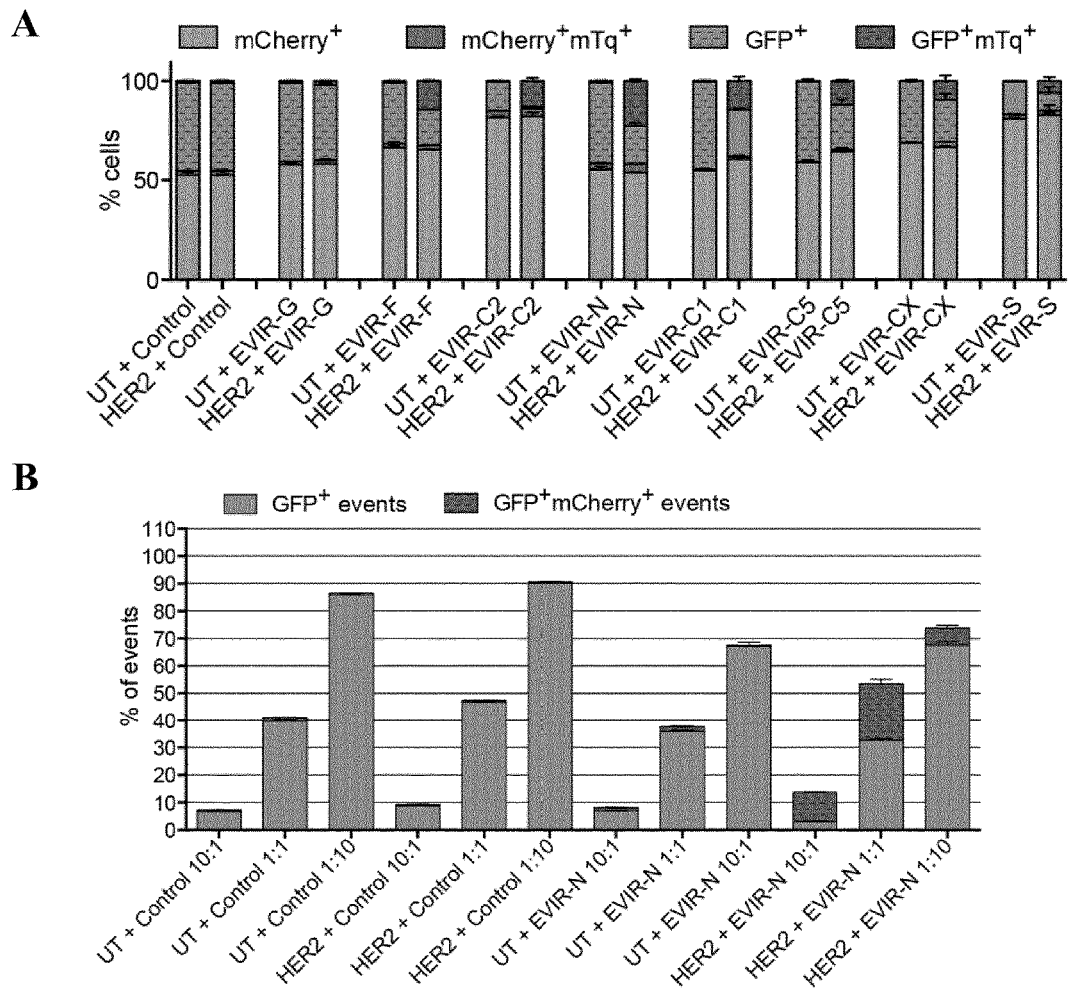
FIG. 5. Co-culture assays. A: Percentage (mean±SEM, n=3) of mCherry$^+$, GFP$^+$, GFP$^+$mTq$^+$ or mCherry$^+$mTq$^+$ iBMMs within total iBMMs (indicated as 100%), measured by flow cytometry analysis of co-cultures of HER2$^+$ or HER2$^-$ (untransduced, UT) mTq+ MC38 cells. iBMMs were either transduced (EVIR) or not (control) with the anti-HER2 EVIR-expressing LVs, as described in Example 3. mCherry+mTq+ and GFP+mTq+ indicate events positive for mCherry and mTq, or GFP and mTq, which represent iBMMs binding to MC38 cells. B: Percentage (mean±SEM, n=3) of binding events between EVIR-N or Control-transduced P388D1 cells and HER2-transduced or UT mCherry+ MC38 cells, at different ratios (10:1, 1:1 or 1:10).

Double-transduced MC38 cells, hereon termed HER2$^+$ mTq$^+$ MC38 cells, were 69% HER2/mTq double-positive, whereas control mTq+ MC38 cells were 79% mTq-positive. In parallel, iBMMs were transduced with either EVIR-N/GFP or mCherry-expressing LVs (hereon termed EVIR$^+$ GFP$^+$ and mCherry+ iBMMs, respectively). The transduction efficiency of iBMMs was 78% and 97% for the EVIR-N/GFP and mCherry-expressing LVs, respectively. Next, a mixed population of EVIR-N GFP$^+$ and mCherry$^+$ iBMMs (1:1) with either HER2$^+$ mTq$^+$ or mTq$^+$ MC38 cells at high density was co-cultured. In this assay, the presence of mTq+GFP+ or mTq+mCherry+ double-positive cells is indicative of binding/aggregation between iBMMs and MC38 cancer cells. It was found that EVIR-N$^+$GFP$^+$ iBMMs could bind efficiently to HER2$^-$mTq$^+$ MC38 cells. The occurrence of mTq$^+$GFP$^+$ events was only present when EVIR-N-expressing iBMMs and HER2$^+$ MC38 cancer cells were present in the co-culture (FIG. 5A). Conversely, mCherry+ iBMMs did not bind to either mTq$^+$ or HER2$^+$mTq$^+$ MC38 cells, indicating that macrophages bind MC38 cancer cells specifically through the anti-HER2 EVIR-N. Furthermore, EVIR-N$^+$ GFP$^+$ iBMMs did not bind to HER2-negative MC38 cells, indicating that binding occurs only when HER2 is expressed on the surface of the cancer cells. Retro-gating of the mTq$^+$GFP$^+$ double-positive events showed that they fell in the non-singlet cell region of the physical parameter plot, thus proving binding/aggregation and excluding cell phagocytosis as a source of double fluorescence.

Next, it was investigated whether EVIR-N-expressing P388D1 cells could rapidly bind to HER2$^+$ MC38 cells also in a cell suspension assay. To this aim, first HER2$^-$ or HER2$^-$ MC38 cells were transduced with an LV expressing mCherry. Next, P388D1 cells were transduced with the EVIR-N or control LV (which both express GFP). Several days after transduction mCheery$^+$ MC38 cells either expressing HER2 or not, were co-incubated with the GFP+ P388D1 cells, either expressing EVIR-N or dLNGFR, for 2 h at 4° C. to avoid phagocytosis or nonspecific binding. In agreement with data obtained with iBMMs in co-culture, it was found that expression of the EVIR-N greatly enhanced the binding of P388D1 cells to HER2-positive cancer cells, both at low and high monocyte concentration (FIG. 5B). Confocal analysis of the cells reveled that most of the double-positive events measured by flow cytometry were indeed aggregates containing both cell types.

Next, the co-culture experiments were performed to assay the binding of EVIR-expressing iBMMs to HER2-expressing MC38 cells, as described above. It was found that EVIR$^+$GFP$^+$ iBMMs could efficiently bind to HER2+mTq+ MC38 cells, in particular when EVIR-N, EVIR-C2, EVIR-F, EVIR-C1 or EVIR-C5 were used (FIG. 5A).

These results show that anti-HER2 EVIRs expressed by monocytes/macrophages promote their binding to HER2-cancer cells.

Example 4

Anti-HER2 EVIRs Enhance Tumor Antigen Uptake Via EV Internalization

Next it was tested if anti-HER2 EVIRs expressed by monocytes, macrophages or other APCs, could specifically enhance the uptake of tumor-associated antigens (TAAs) contained in cancer-cell derived extracellular vesicles (EVs), independent of contact with cancer cells.

EV Purification, Measurement, and Cell Treatment

Five million HER2$^+$/UT mCherry$^+$ MC38 cells or HER2$^+$/UT ovalbumin (OVA)$^+$ MC38 were seeded in 15 cm plates in 16 ml of IMDM medium supplemented with 10% FBS (LifeTechnologies) previously ultracentrifuged for 16 h at 4° C. at 28,000 rpm in a Beckman ultracentrifuge equipped with a SW32Ti rotor. After 72 h medium was collected, debris were discarded by three steps differential centrifugation at 500 g for 5 min, 2000 g for 5 min and finally 4600 g×20 min. Supernatants were then ultracentrifuged as described above, but for 1 to 10 h. Pellets were re-suspended in 80 µl of PBS for 36 ml medium. EVs were then diluted 1:1000 in PBS and quantified by using a NanoSight apparatus (Malvern Instrument) using the standard protocol. Concentration of EVs ranged from 0.8×10$^7$ to 6×10$^9$ particles/µl.

In experiments to measure mCherry transfer, 20,000 iBMMs or BMDCs per well were seeded in 24 wells plate (Corning) in 500 µl their respective culture medium. 2×10$^9$ EV-particles/500 µl were then added to the cells in the medium. After incubation (ranging from 5 min to 48 h) cells were analysed by flow cytometry (LSRII, BD). In experiments to measure mCherry by immunofluorescence, iBMMs were seeded as described in the methods and treated with 1×10$^9$ EV-particles/250 µl. In experiments that measure EV uptake at increasing EV concentrations, BMDCs were seeded in flat-bottom 96 well plates (10,000 cells/200 µl medium/well) and treated with $0.8 \times 10^7$, $4 \times 10^7$, $2 \times 10^8$, $1 \times 10^9$, $3 \times 10^9$, or $6 \times 10^9$ mCherry+ EVs.

It is increasingly appreciated that cancer cells release EVs, encompassing exosomes or microvesicles, which may contain immunogenic TAAs (Zeelenberg et al., 2011, *Journal of Immunology* (Baltimore, Md.: 1950), 187: 1281-1288). Based on the ability of the anti-HER2 EVIR-N to bind efficiently to HER2-positive cancer cells, it was hypothesized that EVIR-N-expressing APCs would also bind to cancer cell-derived EVs, internalize them, and present EV-derived TAAs. EVs released from mCheery+, HER2-positive or negative MC38 cells were isolated. Nanosight analysis using a NS3000 device (Malvern) confirmed the presence of EVs (diameter: 100-400 nm, mean ~150 nm) in medium conditioned by MC38 cells.

Figure 6:
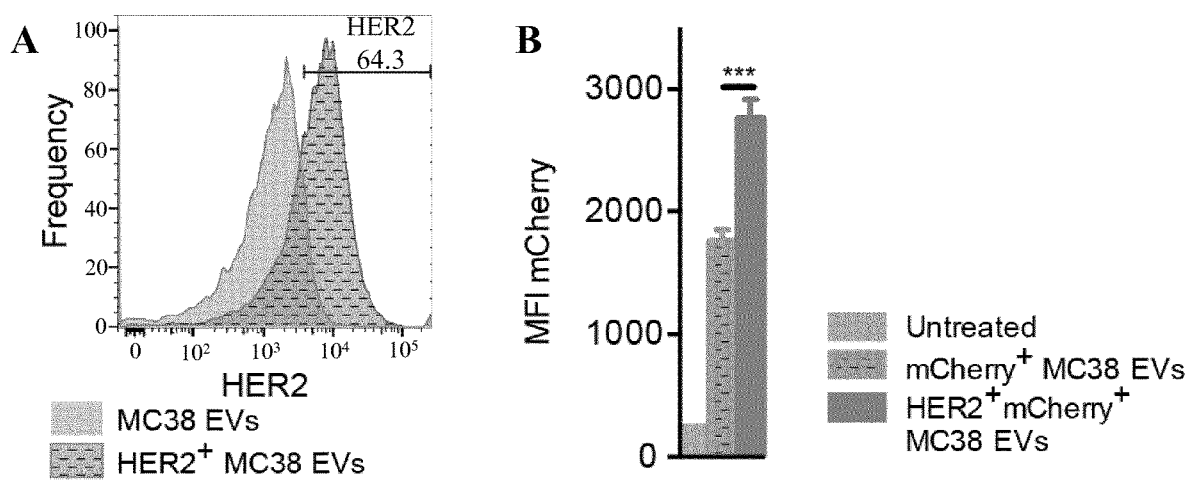
FIG. 6. EV uptake by anti-HER2 EVIRs. A: Representative histogram of flow cytometry analysis of EVs derived from HER2$^+$ MC38 cells stained with an anti-HER2 antibody, as described in Example 4. B: Flow cytometry analysis of mCherry expression in anti-HER2 EVIR-N$^+$ iBMMs untreated or treated with EVs isolated from HER2$^+$ or HER2$^-$ (UT) mCherry+ MC38 cells (median fluorescence intensity, MFI; mean±SEM, n=2). Statistical analysis by one-way ANOVA with Tukey's multiple comparison test. C: Time course analysis of the MFI of mCherry in iBMMs expressing an anti-HER2 EVIR and treated with HER2$^+$/mCherry$^+$ MC38-derived EVs (1) or EVs isolated from HER2$^-$/mCherry+ MC38 cells (2); p<0.001, by two-way ANOVA statistical analysis; D: Immunofluorescence imaging of anti-HER2 EVIR-N$^+$ iBMMs treated with EVs isolated from HER2$^+$/mCherry$^+$ MC38 cells. E: mCherry MFI of BMDCs, either expressing a control EVIR (Control$^+$ BMDCs) or an anti-HER2 EVIR (EVIR-N$^+$ BMDCs), untreated or treated with EVs from HER2+/mCherry+ or HER2$^-$/mCherry+ (indicated as mCherry+) MC38 cells. Statistical analysis by two-way ANOVA with Tukey's multiple comparison test. F: Flow cytometry analysis of mCherry fluorescence in anti-HER2 EVIR-N$^+$ or Control EVIR$^+$ BMDCs treated with increasing concentrations of EVs isolated from HER2$^-$ mCherry+ MC38 cells (mean±SEM, n=3).
Figure 6:
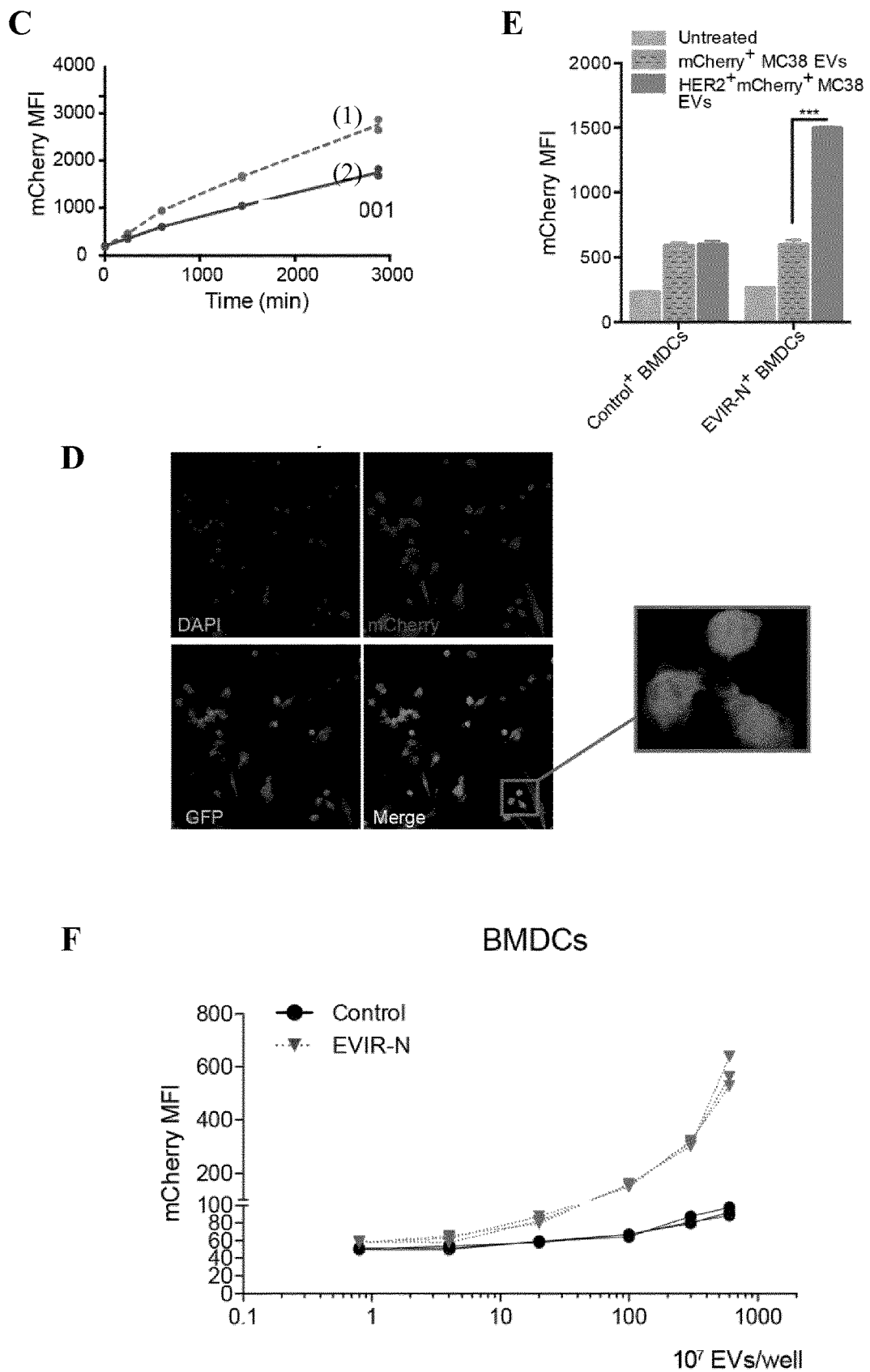

Furthermore, flow cytometry analysis of the EVs showed well detectable expression of HER2 in EVs derived from HER2+ MC38 cells (FIG. 6A). Next EVIR-N+GFP− iBMMs were treated with matched amounts of EVs isolated from HER2+mCheery+ or HER2 mCheery+ MC38 cells. Twenty-four hours after treatment, the EVIR-N+GFP+ iBMMs displayed higher mCherry mean fluorescence intensity (MFI) when they had been exposed to HER2+mCheery+ MC38 cell-derived EVs as compared to HER2−mCheery+ EVs (FIG. 6B). It was also found that EVIR-N-expressing iBMMs did uptake HER2+mCheery+ MC38 cell-derived EVs more rapidly than control (EVIR-N−) iBMMs, without evidence for saturation within 48 hours (FIG. 6C). In order to investigate whether the EVs were internalized or remained associated with the iBMM's cell surface, the EV-treated iBMMs were analyzed by confocal microscopy.

It was found that the mCherry signal largely co-localized with the cell cytoplasm, indicating internalization of HER2+ EVs by the EVIR-N-expressing iBMMs (FIG. 6D). Of note, EV internalization was also observed in co-culture experiments using mTq+ MC38 cells.

Figure 7:
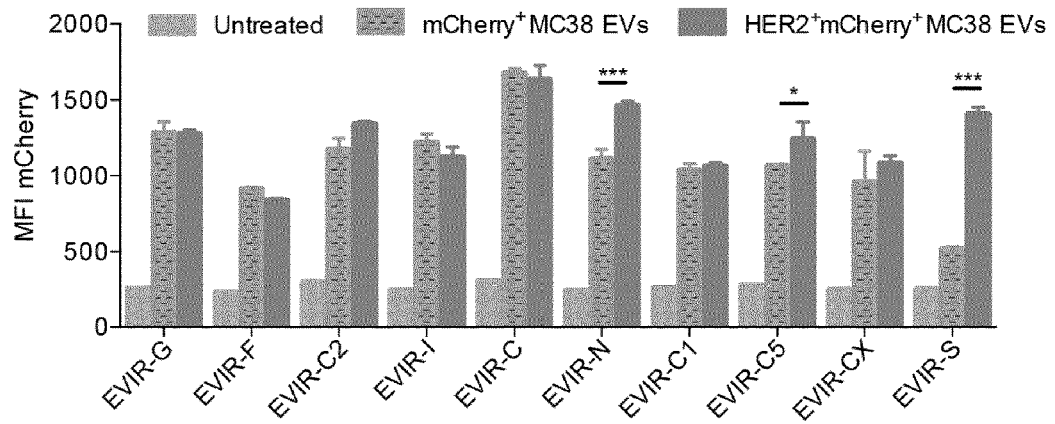
FIG. 7. EVIRs with different intracellular signaling domains. Cytometry analysis of mCherry MFI (mean±SEM, n=2) of anti-HER2 EVIR-transduced iBMMs untreated or treated with EVs isolated from HER2+ or HER2$^-$ (UT) mCherry+ MC38 cells as described in Example 4. Statistical analysis by two-way ANOVA with Tukey's multiple comparison test.

Next, it was investigated whether EVIR-N could enhance the internalization of cancer cell-derived EVs by dendritic cells (DCs). BMDCs were transduced with either the EVIR-N or the control LV. The transduced BMDCs were then treated with EVs isolated from either mCheery+HER2+ or mCheery+HER2− MC38 cells. In agreement with findings in iBMMs, EVIR-N+ BMDCs internalized greater amounts of cancer-cell derived HER2+ EVs than control cells (FIG. 6E), across a broad range of EV doses (FIG. 6F). Furthermore, other EVIR-expressing iBMMs internalized EVs derived from HER2+mCheery+ MC38 cells more rapidly than EVs derived from control HER−mCheery− MC38 cells, in particular when the EVIR-N, EVIR-C5 and EVIR-S were used (FIG. 7).

Taken together, these results indicate that anti-HER2 EVIRs enhance the uptake of cancer-cell derived EVs by macrophages or DCs.

Example 5

Anti-HER2 EVIRs Enhance TAA Presentation by APCs

It was tested whether enhanced EV internalization by EVIR-N-expressing DCs was associated with increased presentation of an unrelated TAA.

OT-I T Cell Proliferation Assay

OT-I CD8+ T cells were obtained from OT-I TCR transgenic mouse line, which produces MHC class I-restricted, ovalbumin-specific, CD8+ T cells (OT-I cells) (Hogquist, et al., 1994, supra). CD8+ OT-I T cells were purified from spleens obtained from OT-I BL6/C57 mice.

First, we depleted CD11c+ cells by using an automatic MACS-separator with anti-CD11c microbeads (Miltenyi biotech). Subsequently, we positively selected CD8+ T cells using anti-CD8 microbeads (Miltenyi biotech). OT-I CD8+ T cells were stained with Cell Tracer-violet (Life Technologies) following the manufacturer's instructions. $2 \times 10^5$ purified OT-I T cells were co-cultured in flat-bottom 96-well plate together with $2 \times 10^4$ EVIR/Control-transduced BMDCs. EVs isolated from OVA MC38 cells transduced with HER2 or UT were added to the wells together with BMDCs and T cells at day zero and kept for 3 days. In the pre-incubation experiments BMDCs were incubated for 24 h with the EVs isolated from MC38 cells, then washed with PBS and added to the OT-I T cells. Proliferation of CD8 T cells was measured at day 3 by flow cytometry (LSRII, BD) gating on CD8+ CD11b−7AAD− T cells. Used antibodies were as follows: goat anti-F(ab')2-Alexa Fluor 647 (Jackson ImmunoResearch), anti-HER2-Alexa Fluor 647 (BioLegend, 24B2), anti-CD8-PE (BioLegend, 53-6.7), anti-CD11b-APC-Cy7 (BioLegend, M1/70), anti-Fc(BD, 2.4G2). In the experiments to measure OT-I CD8 T cell proliferation, $8 \times 10^9$/ml EV-particles were added to the BMDCs or BMDCs+T cells as described in the methods of Example 4. In experiments that measure OT-I CD8 T cell proliferation at different concentrations of EVs, the EVs were added as described in Example 4.

Figure 8:
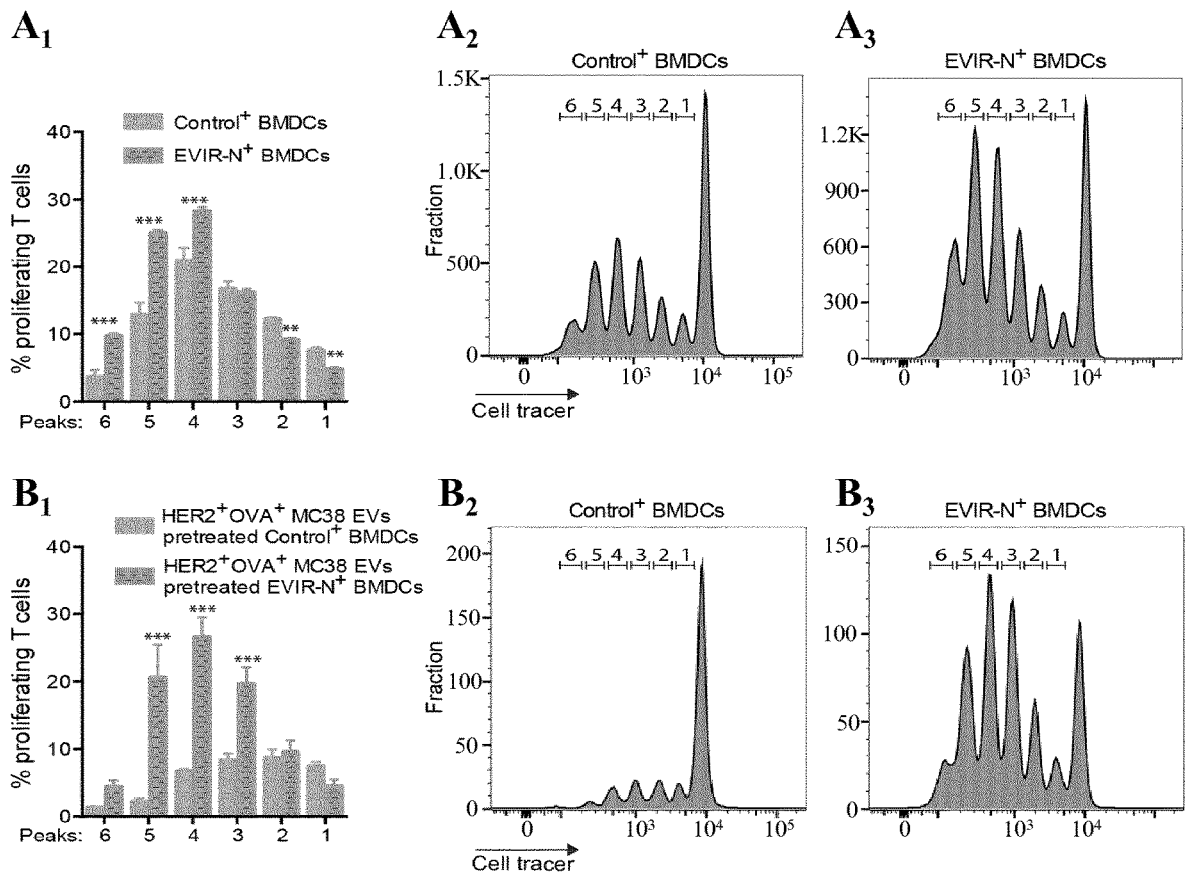
FIG. 8. T cell proliferation assays as described in Example 5. A$_1$: percentage of proliferating OT-I T cells labeled with cell tracer to measure the number of proliferation cycles ("peaks" in A$_{2-3}$), after culture with BMDCs either expressing a control EVIR (control$^+$) or an anti-HER2 EVIR-N (EVIR-N$^+$), in the presence of EVs isolated from HER2$^+$ OVA$^+$ MC38 cells. The percentage of proliferating T cells was obtained by analyzing each "peak" (1-6) in Figures A$_{2-3}$, wherein each peak is indicative of one cell division. B$_1$: percentage of proliferating OT-I T cells labeled with cell tracer and cultured with BMDCs either expressing a control EVIR (control$^+$) or an anti-HER2 EVIR-N (EVIR-N$^-$), pre-treated for 24 h with EVs isolated from HER2$^+$OVA$^+$ MC38 cells (A$_1$-B$_1$: two-way ANOVA statistical analysis with Sidak post-test correction for multiple comparisons (mean±SEM, n=3). A$_{2-3}$: representative histograms showing T cell proliferation cycles after culture with control+ (A$_2$) or anti-HER2 EVIR-N+ (A$_3$) BMDCs together with EVs; B$_{2-3}$: representative histograms showing T cell proliferation cycles after culture with control+ (B$_2$) or anti-HER2 EVIR-N+ (B$_3$) BMDCs pre-treated with EVs; Statistical analysis in A$_1$ and B$_1$ by two-way ANOVA with Sidak's multiple comparison test. C$_{1-3}$: representative histograms showing T cell proliferation after their exposure to HER2$^+$OVA$^+$ EVs (C$_1$), control+ BMDCs (C$_2$) or anti-HER2 EVIR-N+ BMDMs (C$_3$) without EVs. D: Proliferation of CD8$^+$ OT-I T cells labeled with cell tracer after culture with BMDCs either expressing a control or an anti-HER2 EVIR-N, and treated with increasing concentrations of EVs isolated from HER2$^-$ OVA$^+$ MC38 cells. Data-points indicate 3 independent biological replicates.
Figure 8:
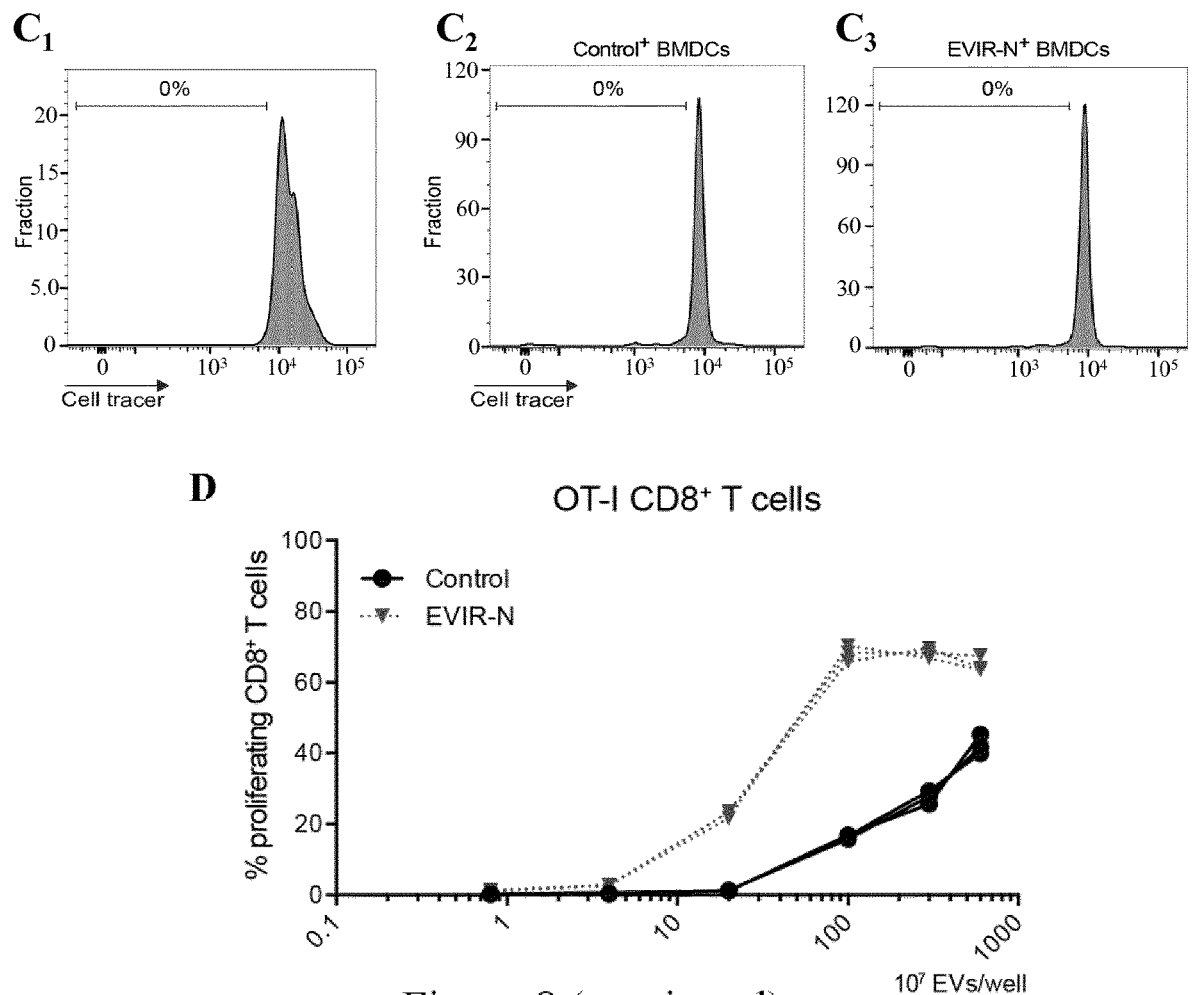

MC38 cells expressing OVA were transduced with a HER2-expressing LV. In parallel, CD8+ T cells from OT-I mice were isolated, which express an MHCI-restricted, anti-OVA TCR. HER2+OVA+ EVs isolated from MC38 were co-cultured for 72 h in the presence of, (i) GFP+ BMDCs, either expressing EVIR-N or dLNGFR and (ii) cell tracer-stained OT-I CD8+ T cells. Remarkably, significantly greater T cell proliferation was observed when the OT-I T cells were co-cultured together with EVIR-N-expressing BMDCs and HER2−OVA+ EVs, compared to other co-culture conditions (FIG. 8A).

In order to understand whether EVIR-N+ BMDCs acquire the OVA antigen from cancer cell-derived EVs, the following cells were co-cultured for 72 h (i) GFP+ BMDCs, either expressing EVIR-N or dLNGFR, pretreated with HER2+ OVA+ EVs, and (ii) tracer-stained OT-I CD8+ T cells. Greater OT-I CD8+ T-cell proliferation in the presence of pretreated-EVIR-N+ BMDMs, compared to other conditions was observed (FIG. 8B). Remarkably, OT-I CD8+ T-cell proliferation was not observed when OT-I CD8+ T cells were treated with HER2+OVA+ EVs in the absence of BMDCs, or when OT-I CD8+ T cells were co-cultured with GFP+ BMDCs, either expressing EVIR-N or dLNGFR (FIG. 8C). Furthermore, EVIR-expressing BMDCs stimulated OT-I CD8+ T proliferation was observed also when low EV doses were employed in a dose-response assay (FIG. 8D).

These results indicate that EVIR-N expression by DCs and BMDCs greatly enhances their ability to uptake, process, and present to T-cells, EV-associated TAAs.

Example 6

EVIR-N2 and EVIR-N1 Enhance EV Uptake by APCs and Promote Cancer-Specific T Cell Proliferation Further EVIRs directed against two distinct melanoma-specific surface antigens, DG2 and TYRP1 were designed. An EVIR-N2 was designed, which is specific to the ganglioside GD2 expressed on melanoma cells. GD2 has been previously employed as a target of melanoma immunotherapy, for example, for the design of GD2-specific CAR-T cells (Yvon et al., *Clin Cancer Res.* 2009, 15(18):5852-60). Next, an EVIR-N1 was designed, which is specific to the melanoma antigen TYRP1 expressed on melanoma cells (Saenger et al., 2008, *Cancer Res,* 68(23); 9884-91). It was tested whether EVIR-N1 and EVIR-N2 enhance EV uptake by APCs and promote cancer-specific T cell proliferation.

Cloning Design of EVIR-N1 and EVIR-N2

Mouse-optimized TA99 scFv (SEQ ID NO: 111; anti-TYRP1) and mouse-optimized 14G2a scFv (SEQ ID NO: 112; anti-GD2) coding DNA sequences were obtained from GeneArt® (LifeTechnologies). For both scFv sequences, a coding DNA sequence of IgK signal domain (SEQ ID NO: 109 for EVIR-N1 and SEQ ID NO: 110 for EVIR-N2) was incorporated to increase the export of the chimeric receptor to the cell membrane. A linker sequence containing a high efficiency Kozak sequence and restriction sites (SEQ ID NO: 3) was incorporated at the 5' end of the EVIR coding sequence. A restriction enzyme site for AgeI was incorporated at the 3'end of the scFv sequence for cloning (in frame with the rest of the DNA sequence) the transmembrane and intracellular domains of the EVIR. The IgK-anti-HER2 scFv CHA21 sequence was then replaced in the EVIR-N lentiviral with the IgK-anti-TYRP1 scFv TA99 or the IgK-anti-GD2 scFv 14G2a sequences, respectively and the DNA coding sequences from the truncated human nerve growth factor receptor (dLNGFR, SEQ ID NO: 43), as described in Example 1, was used in both constructs.

Preparation of TYRP1$^+$ Cells and GD2$^+$ Cells

TYRP1$^+$ B16 were obtained by transducing B16 cells (murine melanoma tumor cell line) with a mouse TYRP1-expressing LV. TYRP1 sequence was obtained by PCR using cDNA from B16 cells as template and the specific primers (TYRP1 Fw of SEQ ID NO: 134 and TYRP1 Rv of SEQ ID NO: 135). GD2$^-$ mCherry$^+$ MC38 cells were obtained by transducing mCherry$^-$ MC38 cells with LVs expressing B4GALNT1 (Beta-1,4-N-Acetyl-Galactosaminyltransferase 1, GD2 synthase) and ST8SIA1 (ST8 Alpha-N-Acetyl-Neuraminide Alpha-2,8-Sialyltransferase 1, GD3 synthase), enzymes involved in GD2 synthesis (Dall'Olio et al., 2014, *Biochim Biophys Acta,* 1840(9):2752-64). Mouse optimized GD2 and GD3 synthase DNA sequences were obtained from GeneArt® (LifeTechnologies). EVs derived from GD2$^+$ mCherry$^-$ MC38 and TYRP1$^+$ B16 were obtained as described in the Example 4.

Measurements and cell treatment as described in the Example 4.

OT-I T cell proliferation assay as described in the Example 5.

Figure 9:
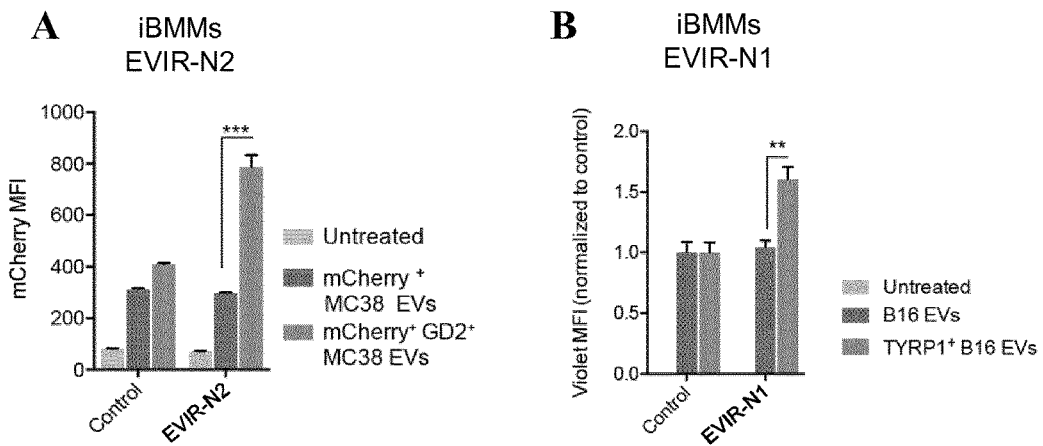
FIG. 9. EVIRs directed against two distinct melanoma-specific surface antigens, DG2 and TYRP1 as described in Example 6. A: mCherry MFI of Control$^+$ or EVIR-N2$^+$ iBMMs (mean±SEM, n=3) untreated or treated with EVs from GD2$^+$/mCherry$^+$ or GD2$^-$/mCherry$^+$ MC38 cells. B: MFI of CellTracker™ Blue in Control$^+$ or EVIR-N1 iBMMs (mean±SEM, n=3) untreated or treated with EVs isolated from TYRP1$^+$ or TYRP1$^-$ B16 melanoma cells. Statistical analysis by two-way ANOVA with Tukey's multiple comparison test. C: Number of proliferating CD8$^+$ OT-I T cells labeled with cell tracer after culture with BMDCs either expressing a Control or an EVIR-N1 and treated with EVs isolated from TYRP1$^+$ OVA$^+$ B16 melanoma cells (mean±SEM, n=3). Statistical analysis by Student's t test.
Figure 9:
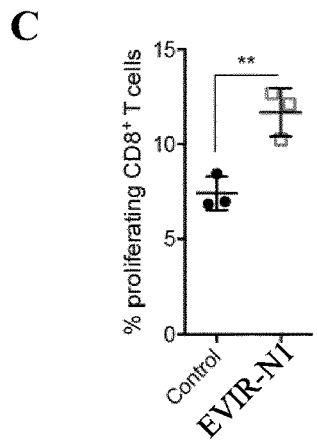

As shown in FIG. 9A-B, the GD2 and TYRP1-specific EVIRs (EVIR-N2 and EVIR-N1, respectively) enhanced the uptake by engineered iBMMs of EVs expressing the respective bait antigens since EVIR-N2$^+$ and EVIR-N1$^+$ iBMMs internalized greater amounts of cancer-cell derived GD2$^-$ EVs and TYRP1$^+$ EVs than control cells (FIG. 9A, B). Furthermore, BMDCs engineered to express an EVIR-N1 increased the proliferation of OT-I CD8$^+$ T cells when co-incubated with EVs obtained from OVA$^+$TYRP1$^-$ melanoma cells (OVA$^+$TYRP1$^+$ B16), compared to BMDCs engineered to express a control EVIR (FIG. 9C).

These data indicate that EVIRs can be designed against a variety of surface antigens expressed by cancer cells, including melanoma cells.

Example 7

EVIRs can be Co-Delivered to APCs Along with APC-Stimulating Factors

The co-expression of EVIRS with APC-stimulating factors has been tested as follows.

The DNA coding sequences of the APC-stimulating factors: Cxcl9 (SEQ ID NO: 117), Csf2 (SEQ ID NO: 120) and IFNγ (SEQ ID NO: 123) were obtained by PCR from cDNA of peritoneal macrophages as described in Example 2, and primers that contain restriction sites for XmaI, SaI and NheI were used (Table 2). The DNA-coding sequence for Lin28 (SEQ ID NO: 126) was obtained by PCR from cDNA from mouse trophoblasts (Baer et al., 2016, supra), and primers that contain restriction sites for XmaI, SaI and NheI were used (Table 2).

The DNA-coding sequence for CD40 (SEQ ID NO: 127) was obtained from GeneArt® (LifeTechnologies). The DNA coding sequences of these APC-stimulating factors were then cloned under the transcriptional control of a minimal CMV promoter by replacing the GFP coding sequence in the bidirectional LV (Amendola et al., 2005, supra) described in the Example 1.

EV purification, measurement, and cell treatment as described in the Example 4.

Measurement of EVIR expression as described in the Example 2.

Flow cytometry analysis of expression of surface molecules CD86 and CCR7 as described in the Example 2.

TABLE 2

| Gene name | Forward primer | Reverse Primer |
| --- | --- | --- |
| Cxcl9 | AAAACCCGGGTCACTCCAACACAGT GACTC (SEQ ID NO: 115) | AAAAAGTCGACGCTAGCCAGGGTGCTTGTTG GTAAAGT (SEQ ID NO: 116) |
| Csf2 | AAAAACCCGGGCAGAGAGAAAGGCTA AGGTCC (SEQ ID NO: 118) | AAAAAGTCGACGCTAGCAGTCTGAGAAGCTG GATT (SEQ ID NO: 119) |
| IFNγ | AAAAACCCGGGAGTTCTGGGCTTCTCC TCCT (SEQ ID NO: 121) | AAAAAGTCGACGCTAGCGACAATCTCTTCCC CACCCC (SEQ ID NO: 122) |
| Lin28 | AAAAAGGATCCCTTTGCCTCCGGACTT CTCTGG (SEQ ID NO: 124) | AAAAAGTCGACAAAGACAGGGTGACACTGG GA (SEQ ID NO: 125) |

Figure 10:
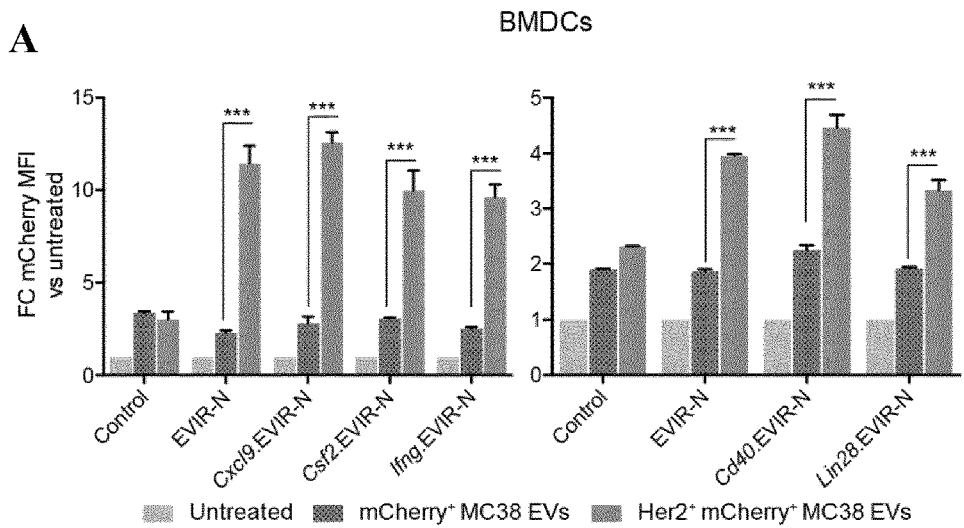
FIG. 10. Transduction by bidirectional LVs of EVIRs together with a factor favoring APC differentiation, activation, and presentation, and/or T-cell recruitment as described in Example 7. A: mCherry uptake of EVs isolated from HER2$^+$ or HER2$^-$ mCherry$^+$ MC38 cells by EVIR$^+$ BMDCs after cell transduction with LVs encoding a Control EVIR alone, an EVIR-N alone, or a bidirectional LV encoding both the EVIR-N and one of the indicated proteins (CXCL9, CSF2, IFNγ, CD40, LIN28). Data represent the mean of 3 transduction replicates per EVIR (biological replicates; mean±SEM, n=3). Statistical analysis by one-way ANOVA with Tukey's multiple comparison test. B: Expression of EVIR$^-$ in BMDCs after transduction of cells with LVs encoding a Control EVIR alone, an EVIR-N alone, or EVIR-N along with one of the indicated proteins (CXCL9, CSF2, IFNγ, CD40, LIN28). Data represent technical replicate (mean±SEM, n=3). C-D: Expression of CCR7 (C) or CD86 (D) in BMDCs (mean±SEM, n=3) transduced with Control EVIR alone, EVIR-N alone, or EVIR-N with LIN28. Data represent the mean of 3 transduction replicates per EVIR (biological replicates; mean±SEM, n=3). Statistical analysis by one-way ANOVA with Tukey's multiple comparison test.
Figure 10:
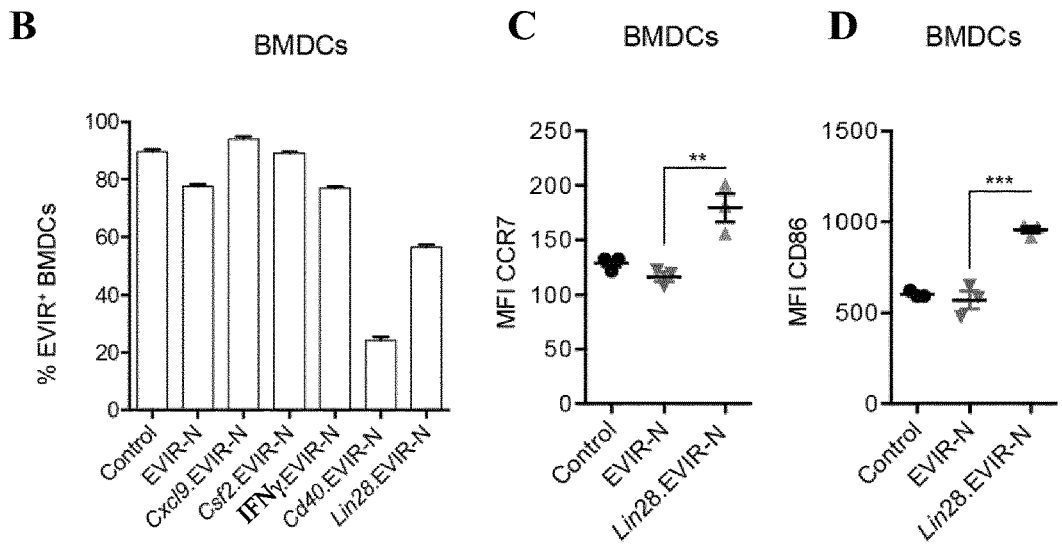

As shown in FIG. 10A-B, the co-expression of proteins that potentiate APC differentiation, activation, and presentation, and/or T-cell recruitment, did not compromise the expression of the EVIR or its ability to promote EV uptake in BMDCs. Further (FIG. 10C-D), it was found that the co-transduction of LIN28, a protein that blocks Let-7 miRNA activity, increased the expression in the BMDCs of surface molecules indicative of APC activation, e.g., CD86 (cluster of differentiation 86) and CCR7 (C—C chemokine receptor type 7).

Together, these data indicate that the co-delivery of accessory proteins along with the EVIR not only does not impair their EV-internalizing activity, but can also help enhance APC functions.

Example 8

EVIRs can Promote the Transfer of MHC-Antigen Complexes from the Cancer Cells to the APCs Potential EVIR-mediated transfer of MHCI-antigen complexes from cancer cells to APCs was tested as follows.

Disruption of MHCI Expression in Cancer Cells

In order to disrupt B2m and abrogate MHCI expression in cancer cells, we generated a self-inducible LV based on the CRISPR/Cas9 system. We obtained a TetO-CAS9 LV also expressing a reverse tTA (rtTA) and a selection marker (puromycin). This LV was further modified to include a U6 promoter-driven anti-B2m single guide RNA (sgRNA) sequence (SEQ ID NO: 136), which was cloned upstream to the TetO-CAS9 expression cassette to obtain the doxycycline-self-inducible LV: U6-sgRNA.TetO-CAS9.Pgk-PURO/2A/rtTA LV.

Figure 11:
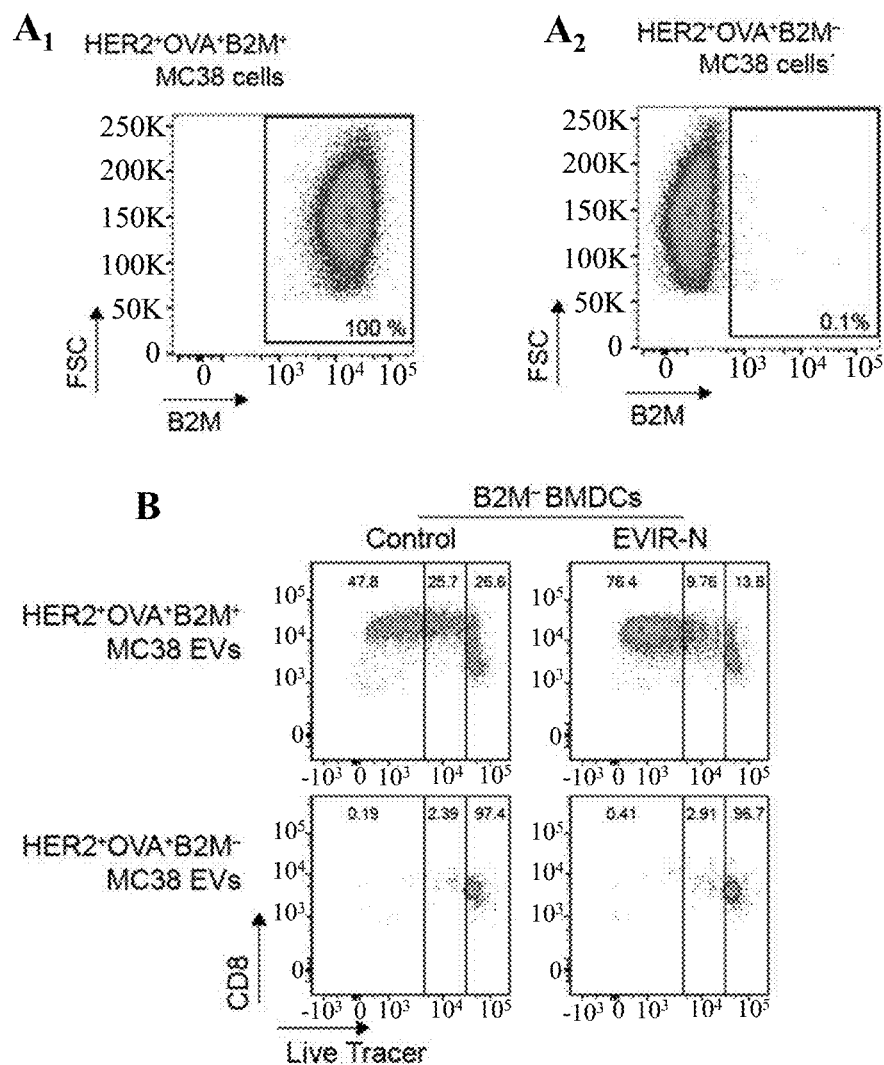
FIG. 11. T-cell proliferation assays as described in Example 11. $A_{1-2}$: Data show flow cytometry analysis of the indicated MC38 cells in which the B2M gene was either intact ($A_1$) or disrupted by CRISPR transduction ($A_2$). B: Data show flow cytometry analysis of $CD8^+$ OT-I T cells labeled with cell tracer after culture with BMDCs isolated from MHCI-deficient B2M$^-$ mice and expressing either a Control EVIR or EVIR-N. Cultures were treated with EVs isolated from either B2M-proficient (B2M$^+$) or deficient (B2M$^-$) HER2$^+$ OVA$^+$ MC38 cancer cells.

B2M-deficient EVs were obtained by transducing HER2$^+$OVA$^+$MC38 cancer cells with the above LV. Transduced HER2$^+$OVA$^+$MC38 cells were cultured in a cell medium containing puromycin (2 μg/ml) and doxycycline (10 μg/ml) for 3 days, in order to activate the CRISPR/Cas9 system and select a clonal population of cells with disrupted B2m gene (FIG. 11A). EVs were then purified as described in the Example 4.

In the experiment, the BMDCs were isolated from the BM of B2M$^{-/-}$ mice, which lack the ability of presenting MHCI/antigen complexes (Koller et al., 1990, *Science*, 248(4960): 1227-30). The MHCI-deficient B2M$^-$ BMDCs were then transduced with either a control EVIR or an EVIR-N and assayed in T-cell proliferation assays as those described in Example 5.

Under specific experimental conditions whereby the APCs are genetically modified to lack the ability of cross-presenting, the direct transfer of MHC complexes from cancer cell-derived EVs to EVIR-expressing APCs was sufficient to promote T-cell proliferation (FIG. 11B).

The co-incubation of the MHCI-deficient BMDCs and OT-I T cells with OVA+HER2+ EVs led to increased T cell proliferation in the presence of the EVIR-N (versus control EVIR), suggesting enhanced MHCI cross-dressing (FIG. 11B, top panels). On the other hand, disruption of B2M in the cancer cells using the LV described above (U6-sgRNA-.TetO-CAS9.Pgk-PURO/2A/rtTA) completely blocked cross-dressing from purified EVs, proving the specificity of this phenomenon (FIG. 11B, bottom panels).

These results support that direct transfer of MHC complexes from cancer cell-derived EVs to EVIR-expressing APCs may be sufficient to promote T-cell proliferation in the absence of endogenous MHCI in the APCs.

Example 9

EVIR-Engineered APCs Inhibit Tumor Growth in Mice

The action of EVIR was tested in in vivo with EVIR-N DC-based vaccination experiment.

The DCs were obtained from the BM of syngeneic mice, transduced with LVs, and activated with LPS (lipopolysaccharides, 10 ng/ml) prior to their inoculation (two sequential DC doses of 10$^7$cells, one week apart) in mice carrying small, established tumors (n=4 in no DCs, 7 in CTRL-DCs and 9 in EVIR DCs mice/group).

Figure 12:
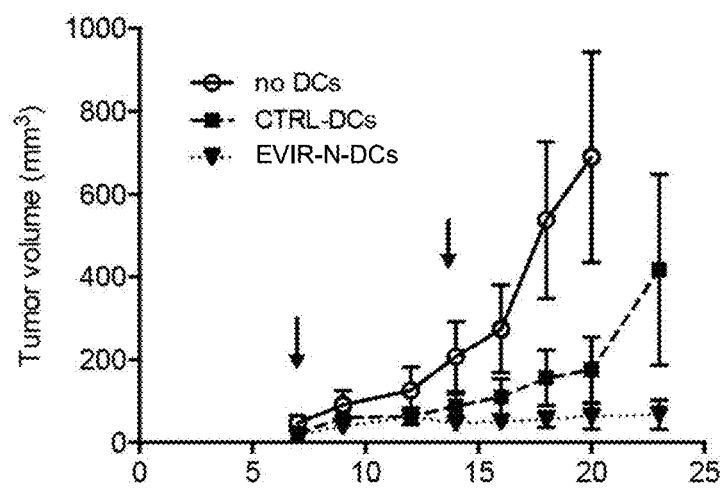
FIG. 12. Tumor vaccination study as described in Example 12. HER2$^+$ MC38 tumor growth in syngeneic mice injected subcutaneously with PBS (no DCs; n=4) or vaccinated with either DCs expressing a Control EVIR (CTRL DCs; n=7) or an anti-HER2 EVIR (EVIR-DCs; n=9) at day 7 and 14 post-MC38 tumor injection.

It was found that the subcutaneous, peri-tumoral deployment of EVIR-N transduced DCs inhibited the growth of MC38-HER2 tumors, compared to control EVIR-transduced DCs (FIG. 12). Although the control EVIR-transduced DCs also delayed tumor growth, the EVIR-N-transduced DCs significantly improved tumor control, demonstrating the superior anti-tumoral activity of the EVIR engineered DCs.

Those data demonstrate that EVIR-engineered APCs can enhance inhibition of tumour growth in vivo.

---

Sequence listing

Nucleic acid sequence of anti-HER2 scFv CHA21
SEQ ID NO: 1:
GGGGATATTGTCCTCACACAGACTCCCAGCTCCCTGCCTGTGTCCGTCGGAGAGAAAGTGACCATGAC
ATGCAAGTCTAGTCAGACACTGCTCTACTCTAACAATCAGAAGAACTACCTCGCATGGTATCAGCAGA
AACCAGGACAGAGCCCCAAGCTGCTCATCTCCTGGGCTTTCACCCGGAAATCCGGGGTGCCTGACCGC
TTCACAGGTAGCGGCTCCGGAACTGATTTTACTCTGACCATTGGATCTGTGAAGGCAGAGGACCTCGC
CGTCTACTATTGCCAGCAGTACAGTAATTATCCATGGACTTTTGGCGGAGGGACCAGGCTGGAAATCA
AGAGAGGTGGAGGAGGGTCCGGTGGAGGAGGGTCTGGTGGAGGAGGGAGTGGTGGAGGAGGGTCAGAG
GTGCAGCTGCAGCAGTCTGGCCCCGAAGTGGTCAAAACTGGAGCTTCAGTCAAAATCAGCTGTAAGGC
ATCTGGGTACAGCTTCACCGGCTACTTCATCAACTGGGTGAAGAAAATTCAGGGAAGAGCCCTGAGT
GGATCGGCCACATTTCAAGCTCCTACGCCACAAGCACTTACAACCAGAAGTTCAAAAATAAGGCCGCT
TTTACCGTGGACACATCTAGTTCAACCGCCTTCATGCAGCTGAACTCCCTCACATCTGAAGATAGTGC
TGTGTACTATTGTGTCAGGAGCGGCAACTACGAAGAATATGCTATGGATTACTGGGGCAGGGGACCT
CCGTGACTGTCTCAAGC Nucleic acid sequence of IgK domain
SEQ ID NO: 2:
ATGGATTTTCAGGTCCAGATTTTCTCCTTCCTCCTCATTTCAGCCAGCGTCATTATGTCTCGG Nucleic acid sequence of S5_BamHI_Kozak
SEQ ID NO: 3: GGATCCGCCACC Sequence listing Nucleic acid sequence of S3_BamHI_AgeI_MluI_SalI_stop_XhoI
SEQ ID NO: 4: ACCGGTACGCGTGTCGACTGACTCGAG Nucleic acid sequence of S5_FCgRIIIa_BamHI_Kozak.start_AgeI
SEQ ID NO: 5: GGATCCGCCACCATGACCGGT Nucleic acid sequence of S3_FCgRIIIa_MluI_SalI_stop_XhoI
SEQ ID NO: 6: ACGCGTGTCGACTGACTCGAG Nucleic acid sequence of dLNGFR_Fw_AgeI
SEQ ID NO: 7: AAAAACCGGTCTTCTGGGGGTGTCCCTTG Nucleic acid sequence of dLNGFR_Rv_MluI
SEQ ID NO: 8: AAAAACGCGTAGTTAGCCTCCCCCATCTCC Nucleic acid sequence of FLT3_Fw_AgeI
SEQ ID NO: 9: AAAAACCGGTCCAGGCCCCTTCCCTTTCATC Nucleic acid sequence of FLT3_Rv_XhoI
SEQ ID NO: 10: AAAAACTCGAGAGAGGCGAGGCTAATCTTGG Nucleic acid sequence of Tlr4_Fw_AgeI
SEQ ID NO: 11: AAAAACCGGTCAGCTGTATTCCCTCAGCACT Nucleic acid sequence of Tlr4_Rv_SalI
SEQ ID NO: 12: AAAAAGTCGACTGGGTTTAGGCCCCAGAGTT Nucleic acid sequence of Ccr2_Fw_AgeI
SEQ ID NO: 13: AAAAACCGGTATGGAAGACAATAATATGTTACCTC Nucleic acid sequence of Ccr2_Rv_MluI
SEQ ID NO: 14: AAAAACGCGTATGTACAAACTGCTCCCTCC Nucleic acid sequence of Itgb2_Fw_AgeI
SEQ ID NO: 15: AAAAACCGGTAATGCACGGCTGGTAGAGTG Nucleic acid sequence of Itgb2_Rv_MluI
SEQ ID NO: 16: AAAAACGCGTGGGGGTCACATCTGCTTGAT Nucleic acid sequence of Csf2rb_Fw_AgeI
SEQ ID NO: 17: AAAAACCGGTACTCAGAAGATGGCTTACTCATTCA Nucleic acid sequence of Csf2rb_Rv_MluI
SEQ ID NO: 18: AAAAACGCGTTGGTGAGATTGGGAGGAGAC Nucleic acid sequence of Ccr1_Fw_AgeI
SEQ ID NO: 19: AAAAACCGGTACTCCATGCCAAAAGACTGCT Nucleic acid sequence of Ccr1_Rv_MluI
SEQ ID NO: 20: AAAAACGCGTACCTTCCTTGGTTGACACCTATG Nucleic acid sequence of Ccr5_Fw_AgeI
SEQ ID NO: 21: AAAAACCGGTATGTCAGCACCCTGCCAAAAA Nucleic acid sequence of Ccr5_Rv_MluI
SEQ ID NO: 22: AAAAACGCGTCATTCCTACTCCCAAGCTGCAT Nucleic acid sequence of Cxcr4_Fw_XmaI
SEQ ID NO: 23: AAAAACCCGGGTTCCGGGATGAAAACGTCCA Nucleic acid sequence of Cxcr4_Rv_MluI
SEQ ID NO: 24: AAAAACGCGTTGCATAAGTGTTAGCTGGAGTG Nucleic acid sequence of Selplg_Fw_AgeI
SEQ ID NO: 25: AAAAACCGGTATTGCCACCACTGACCCTA Nucleic acid sequence of Selplg_Rv_MluI
SEQ ID NO: 26: AAAAACGCGTGCAAAGGTCTCGCTTAGGTG Amino acid sequence of anti-HER2 CHA21
SEQ ID NO: 27:
DIVLTQTPSSLPVSVGEKVTMTCKSSQTLLYSNNQKNYLAWYQQKPGQSPKLLISWAFTRKSGVPDRF
TGSGSGTDFTLTIGSVKAEDLAVYYCQQYSNYPWTFGGGTRLEIKRGGGGSGGGGSGGGGSGGGGSEV
QLQQSGPEVVKTGASVKISCKASGYSFTGYFINWVKKNSGKSPEWIGHISSSYATSTYNQKFKNKAAF
TVDTSSSTAFMQLNSLTSEDSAVYYCVRSGNYEEYAMDYWGQGTSVTVSS Amino acid sequence of anti-HER2 trastuzumab-based scFv-
SEQ ID NO: 28:
DIQMTQSPSSLSASVGDRVTITCRASQDVNTAVAWYQQKPGKAPKLLIYSASFLYSGVPSRFSGSRSG
TDFTLTISSLQPEDFATYYCQQHYTTPPTFGQGTKVEIKRTGSTSGSGKPGSGEGSEVQLVESGGGLV
QPGGSLRLSCAASGFNIKDTYIHWVRQAPGKGLEWVARTYPTNGYTRYADSVKGRFTISADTSKNTAY
LQMNSLRAEDTAVYYCSRWGGDGFYAMDVWGQGTLVTVSSGTGTRX Amino acid sequence of anti-HER2 pertuzumab-based scFv-
SEQ ID NO: 29:
DIQMTQSPSSLSASVGDRVTITCKASQDVSIGVAWYQQKPGKAPKLLIYSASYRYTGVPSRFSGSGSG
TDFTLTISSLQPEDFATYYCQQYYIYPYTFGQGTKVEIKRTVAAPGGGGSGGGGSGGGGSGGGGSEVQ
LVESGGGLVQPGGSLRLSCAASGFTFTDYTMDWVRQAPGKGLEWVADVNPNSGGSIYNQRFKGRFTLS
VDRSKNTLYLQMNSLRAEDTAVYYCARNLGPSFYFDYW Amino acid sequence of anti-HER2 FRP5-based scFv
SEQ ID NO: 30:
QVQLQQSGPELKKPGETVKISCKASGYPFTNYGMNWVKQAPGQGLKWMGWINTSTGESTFADDFKGRF
DFSLETSANTAYLQINNLKSEDMATYFCARWEVYHGYVPYWGQGTTVTVSSGGGGSGGGGSGGGGSDI
QLTQSHKFLSTSVGDRVSITCKASQDVYNAVAWYQQKPGQSPKLLIYSASSRYTGVPSRFTGSGSGPD
FTFTISSVQAEDLAVYFCQQHFRTPFTFGSGTKLEIKRX Amino acid sequence of proteinic domain derived from dLNGFR
SEQ ID NO: 31:
LLGVSLGGAKEACPTGLYTHSGECCKACNLGEGVAQPCGANQTVCEPCLDSVTFSDVVSATEPCKPCT
ECVGLQSMSAPCVEADDAVCRCAYGYYQDETTGRCEACRVCEAGSGLVFSCQDKQNTVCEECPDGTYS
DEANHVDPCLPCTVCEDTERQLRECTRWADAECEEIPGRWITRSTPPEGSDSTAPSTQEPEAPPEQDL
IASTVAGVVTTVMGSSQPVVTRGTTDNLIPVYCSILAAVVVGLVAYIAFKRWNRGIL Amino acid sequence of proteinic domain derived from FcγRIIIA
SEQ ID NO: 32:
HENSELLIPKATHNDSGSYFCRGLIGHNNKSSASFRISLGDPGSPSMFPPWHQITFCLLIGLLFAIDT
VLYFSVRRGLQSPVADYEEPKIQWSKEPQDKTRVD Amino acid sequence of proteinic domain derived from FLT3
SEQ ID NO: 33:
PGPFPFIQDNISFYATIGLCLPFIVVLIVLICHKYKKQFRYESQLQMIQVTGPLDNEYFYVDFRDYEY
DLKWEFPRENLEFGKVLGSGAFGRVMNATAYGISKTGVSIQVAVKMLKEKADSCEKEALMSELKMMTH
LGHHDNIVNLLGACTLSGPVYLIFEYCCYGDLLNYLRSKREKFHRTWTEIFKEHNFSFYPTQAHSNS
SMPGSREVQLHPPLDQLSGFNGNLIHSEDEIEYENQKRLAEEEEEDLNVLTFEDLLCFAYQVAKGMEF
LEFKSCVHRDLAARNVLVTHGKVVKICDFGLARDILSDSSYVVRGNARLPVKWMAPESLFEGIYTIKS
DVWSYGILLWEIFSLGVNPYPGIPVDANFYKLIQSGFKMEQPFYATEGIYFVMQSCWAFDSRKRPSFP
NLTSFLGCQLAEAEEEAMYQNMGGNVPEHPSIYQNRRPLSREAGSEPPSPQAQVKIHGERS Amino acid sequence of proteinic domain derived from TLR4
SEQ ID NO: 34:
QLYSLSTLDCSFNRIETSKGILQHFPKSLAFFNLTNNSVACICEHQKFLQWVKEQKQFLVNVEQMTCA
TPVEMNTSLVLDFNNSTCYMYKTIISVSVVSVIVVSTVAFLIYHFYFHLILIAGCKKYSRGESIYDAF
VIYSSQNEDWVRNELVKNLEEGVPRFHLCLHYRDFIPGVAIAANIIQEGFHKSRKVIVVVSRHFIQSR
WCIFEYEIAQTWQFLSSRSGIIFIVLEKVEKSLLRQQVELYRLLSRNTYLEWEDNPLGRHIFWRRLKN
ALLDGKASNPEQTAEEEQETATWT Amino acid sequence of proteinic domain derived from CCR2
SEQ ID NO: 35:
MEDNNMLPQFIHGILSTSHSLFTRSIQELDEGATTPYDYDDGEPCHKTSVKQIGAWILPPLYSLVFIF
GFVGNMLVIIILIGCKKLKSMTDIYLLNLAISDLLFLLTLPFWAHYAANEWVFGNIMCKVFTGLYHIG
YFGGIFFIILLTIDRYLAIVHAVFALKARTVTFGVITSVVTWVVAVFASLPGIIFTKSKQDDHHYTCG
PYFTQLWKNFQTIMRNILSLILPLLVMVICYSGILHTLFRCRNEKKRHRAVRLIFAIMIVYFLFWTPY
NIVLFLTTFQESLGMSNCVIDKHLDQAMQVTETLGMTHCCINPVIYAFVGEKFRRYLSIFFRKHIAKR
LCKQCPVFYRETADRVSSTFTPSTGEQEVSVGL Amino acid sequence of proteinic domain derived from ITGB2
SEQ ID NO: 36:
NARLVECSGRGHCQCNRCICDEGYQPPMCEDCPSCGSHCRDNHTSCAECLKFDKGPFEKNCSVQCAGM
TLQTIPLKKKPCKERDSEGCWITYTLQQKDGRNIYNIHVEDSLECVKGPNVAAIVGGTVVGVVLIGVL
LLVIWKALTHLTDLREYRRFEKEKLKSQWNNDNPLFKSATTTVMNPKFAES Amino acid sequence of proteinic domain derived from CSF2RB
SEQ ID NO: 37:
TQKMAYSFIEHTFQVQYKKKSDSWEDSKTENLDRAHSMDLSQLEPDTSYCARVRVKPISNYDGIWSKW
SEEYTWKTDWVMPTLWIVLILVFLILTLLLILRFGCVSVYRTYRKWKEKIPNPSKSLLFQDGGKGLWP
PGSMAAFATKNPALQGPQSRLLAEQQGESYAHLEDNNVSPLTIEDPNIIRVPPSGPDTTPAASSESTE
QLPNVQVEGPTPNRPRKQLPSFDFNGPYLGPPQSHSLPDLPDQLGSPQVGGSLKPALPGSLEYMCLPP
GGQAQLVPLSQVMGQGQAMDVQCGSSLETSGSPSVEPKENPPVELSMEEQEARDNPVTLPISSGGPEG
SMMASDYVTPGDPVLTLPTGPLSTSLGPSLGLPSAQSPRLCLKLPRVPSGSPALGPPGFEDYVELPPS
VSQAAKSPPGHPAPPVASSPTVIPGEPREEVGPASPHPEGLLVLQQVGDYCFLPGLGPGSLSPHSKPP
SPSLCSETEDLVQDLSVKKFPYQPMPQAPAIQFFKSLKHQDYLSLPPWDNSQSGKVC Amino acid sequence of proteinic domain derived from CCR1
SEQ ID NO: 38:
TPCQKTAVRAFGAGLLPPLYSLVFIIGVVGNVLVILVLMQHRRLQSMTSIYLFNLAVSDLVFLFTLPF
WIDYKLKDDWIFGDAMCKLLSGFYYLGLYSEIFFIILLTIDRYLAIVHAVFALRARTVTFGIITSIIT
WALAILASMPALYFFKAQWEFTHRTCSPHFPYKSLKQWKRFQALKLNLLGLILPLLVMIICYAGIIRI
LLRRPSEKKVKAVRLIFAITLLFFLLWTPYNLSVFVSAFQDVLFTNQCEQSKQLDLAMQVTEVIAYTH
CCVNPIIYVFVGERFWKYLRQLFQRHVAIPLAKWLPFLSVDQLERTSSISPSTGEHELSAGF Amino acid sequence of proteinic domain derived from CCR5
SEQ ID NO: 39:
MSAPCQKINVKQIAAQLLPPLYSLVFIFGFVGNMMVFLILISCKKLKSVTDIYLLNLAISDLLFLLTL
PFWAHYAANEWVFGNIMCKVFTGLYHIGYFGGIFFIILLTIDRYLAIVHAVFALKVRTVNFGVITSVV
TWAVAVFASLPEIIFTRSQKEGFHYTCSPHFPHTQYHFWKSFQTLKMVILSLILPLLVMVICYSGILH
TLFRCRNEKKRHRAVRLIFAIMIVYFLFWTPYNIVLLLTTFQEFFGLNNCSSSNRLDQAMQATETLGM
THCCLNPVIYAFVGEKFRSYLSVFFRKHIVKRFCKRCSIFQQDNPDRASSVYTRSTGEHEVSTGL Amino acid sequence of proteinic domain derived from CXCR4
SEQ ID NO: 40:
FRDENVHFNRIFLPTIYFIIFLTGIVGNGLVILVMGYQKKLRSMTDKYRLHLSVADLLFVITLPFWAV
DAMADWYFGKFLCKAVHIIYTVNLYSSVLILAFISLDRYLAIVHATNSQRPKLLAEKAVYVGVWIPA
LLLTIPDFIFADVSQGDISQGDDRYICDRLYPDSLWMVVFQPQHIMVGLVLPGIVILSCYCIIISKLS
HSKGHQKRKALKTTVILILAFFACWLPYYVGISIDSFILLGVIKQGCDFESIVHKWISITEALAFFHC
CLNPILYAFLGAKFKSSAQHALNSMSRGSSLKILSKGKRGGHSSVSTESESSSFHSS Amino acid sequence of proteinic domain derived from SELPLG
SEQ ID NO: 41:
IATTDPTAPGTGGTAVGMLSTDSATQWSLTSVETVQPASTEVETSQPAPMEAETSQPAPMEAETSQPA
PMEADTSKPAPTEAETSKPAPTEAETSQPAPNEAETSKPAPTEAETTQLPRIQAVKTL
FTTSAATEVPSTEPTTMETASTESNESTIFLGPSVTHLPDSGLKKGLIVTPGNSPAPTLPGSSDLIPV
KQCLLIILILASLATIFLVCTVVLAVRLSRKTHMYPVRNYSPTEMICISSLLPEGGDGAPVTANGGLP
KVQDLKTEPSGDRDGDDLTLHSFLP Amino acid sequence of IgK domain
SEQ ID NO: 42: MDFQVQIFSFLLISASVIMSRG Nucleic acid sequence of proteinic domain derived from dLNGFR
SEQ ID NO: 43:
CTTCTGGGGGTGTCCCTTGGAGGTGCCAAGGAGGCATGCCCCACAGGCCTGTACACACACAGCGGTGA
GTGCTGCAAAGCCTGCAACCTGGGCGAGGGTGTGGCCCAGCCTTGTGGAGCCAACCAGACCGTGTGTG
AGCCCTGCCTGGACAGCGTGACGTTCTCCGACGTGGTGAGCGCGACCGAGCCGTGCAAGCCGTGCACC
GAGTGCGTGGGGCTCCAGAGCATGTCGGCGCCGTGCGTGGAGGCCGACGAGCCGTGCCGCTGCGC
CTACGGCTACTACCAGGATGAGACGACTGGGCGCTGCGAGGCGTGCCGCGTGTGCGAGGCGGGCTCGG
GCCTCGTGTTCTCCTGCCAGGACAAGCAGAACACCGTGTGCGAGGAGTGCCCCGACGGCACGTATTCC
GACGAGGCCAACCACGTGGACCCGTGCCTGCCCTGCACCGTGTGCGAGGACACCGAGCGCCAGCTCCG
CGAGTGCACACGCTGGGCCGACGCCGAGTGCGAGGAGATCCCTGGCCGTTGGATTACACGGTCCACAC
CCCCAGAGGGCTCGGACAGCACAGCCCCCAGCACCCAGGAGCCTGAGGCACCTCCAGAACAAGACCTC
ATAGCCAGCACGGTGGCAGGTGTGGTGACCACAGTGATGGGCAGCTCCCAGCCCGTGGTGACCCGAGG
CACCACCGACAACCTCATCCCTGTCTATTGCTCCATCCTGGCTGCTGTGGTTGTGGGCCTTGTGGCCT
ACATAGCCTTCAAGAGGTGGAACAGGGGGATCCTCTAG Nucleic acid sequence of proteinic domain derived from FcγRIIIA
SEQ ID NO: 44:
CACGAGAACTCCGAACTGCTGATTCCTAAGGCAACTCACAACGACTCCGGCTCCTATTTCTGTAGAGG
GCTGATTGGACATAACAACAAGAGCTCCGCCTCATTCAGGATTAGCCTGGGCGACCCAGGGTCTCCCA
GTATGTTCCCCCCTTGGCACCAGATCACCTTTTGCCTGCTGATTGGACTGCTGTTCGCTATCGATACA
GTGCTGTACTTTTCTGTCCGGAGAGGCCTGCAGTCACCCGTGGCAGATTACGAAGAACCCAAGATTCA
GTGGAGCAAGGAGCCCCAGGATAAGACGCGTGTCGACTGA Nucleic acid sequence of proteinic domain derived from FLT3
SEQ ID NO: 45:
CCAGGCCCCTTCCCTTTCATCCAAGACAACATCTCCTTCTATGCGACCATTGGGCTCTGTCTCCCCTT
CATTGTTGTTCTCATTGTGTTGATCTGCCACAAATACAAAAAGCAATTTAGGTACGAGAGTCAGCTGC
AGATGATCCAGGTGACTGGCCCCCTGGATAACGAGTACTTCTACGTTGACTTCAGGGACTATGAATAT
GACCTTAAGTGGGAGTTCCCGAGAGAGAACTTAGAGTTTGGGAAGGTCCTGGGGTCTGGCGCTTTCGG
GAGGGTGATGAACGCCACGGCCTATGGCATTAGTAAAACGGGAGTCTCAATTCAGGTGGCGGTGAAGA
TGCTAAAAGAGAAAGCTGACAGCTGTGAAAAAGAAGCTCTCATGTCGGAGCTCAAAATGATGACCCAC
CTGGGACACCATGACAACATCGTGAATCTGCTGGGGCATGCACACTGTCAGGGCCAGTGTACTTGAT
TTTTGAATATTGTTGCTATGGTGACCTCCTCAACTACCTAAGAAGTAAAAGAGAGAAGTTTCACAGGA
CATGGACAGAGATTTTTAAGGAACATAATTTCAGTTTTTACCCTACTTTCCAGGCACATTCAAATTCC
AGCATGCCTGGTTCACGAGAAGTTCAGTTACACCCGCCCTTGGATCAGCTCTCAGGGTTCAATGGGAA
TTTAATTCATTCTGAAGATGAGATTGAATATGAAAACAGAGAAGGCTGGCAGAAGAAGAGGAGGAAG
ATTTGAACGTGCTGACGTTTGAAGACCTCCTTTGCTTTGCGTACCAAGTGGCCAAAGGCATGAATTC
CTGGAGTTCAAGTCGTGTGTCCACAGAGACCTGGCAGCCAGGAATGTGTTGGTCACCCACGGGAAGGT
GGTGAAGATCTGTGACTTTGGACTGGCCCGAGACATCCTGAGCGACTCCAGCTACGTCGTCAGGGGCA
ACGCACGGCTGCCGGTGAAGTGGATGGCACCTGAGAGCTTATTTGAAGGGATCTACACAATCAAGAGT
GACGTCTGGTCCTACGGCATCCTTCTCTGGGAGATATTTTCACTGGGTGTGAACCCTTACCCTGGCAT
TCCTGTCGACGCTAACTTCTATAAACTGATTCAGAGTGGATTTAAATGGAGCAGCCATTCTATGCCA

```
CAGAAGGGATATACTTTGTAATGCAATCCTGCTGGGCTTTTGACTCAAGGAAGCGGCCATCCTTCCCC
AACCTGACTTCATTTTTAGGATGTCAGCTGGCAGAGGCAGAAGAAGCGATGTATCAGAACATGGGTGG
CAACGTCCCAGAACATCCATCCATCTACCAAAACAGGCGGCCCCTCAGCAGAGAGGCAGGCTCAGAGC
CGCCATCGCCACAGGCCCAGGTGAAGATTCACGGAGAAAGAAGTTAG
```

Nucleic acid sequence of proteinic domain derived from TLR4
SEQ ID NO: 46:
```
CAGCTGTATTCCCTCAGCACTCTTGATTGCAGTTTCAATCGCATAGAGACATCTAAAGGAATACTGCA
ACATTTTCCAAAGAGTCTAGCCTTCTTCAATCTTACTAACAATTCTGTTGCTTGTATATGTGAACATC
AGAAATTCCTGCAGTGGGTCAAGGAACAGAAGCAGTTCTTGGTGAATGTTGAACAAATGACATGTGCA
ACACCTGTAGAGATGAATACCTCCTTAGTGTTGGATTTTAATAATTCTACCTGTTATATGTACAAGAC
AATCATCAGTGTGTCAGTGGTCAGTGTGATTGTGGTATCCACTGTAGCATTTCTGATATACCACTTCT
ATTTTCACCTGATACTTATTGCTGGCTGTAAAAAGTACAGCAGAGGAGAAAGCATCTATGATGCATTT
GTGATCTACTCGAGTCAGAATGAGGACTGGGTGAGAAATGAGCTGGTAAAGAATTTAGAAGAAGGAGT
GCCCCGCTTTCACCTCTGCCTTCACTACAGAGACTTTATTCCTGGTGTAGCCATTGCTGCCAACATCA
TCCAGGAAGGCTTCCACAAGAGCCGGAAGGTTATTGTGGTAGTGTCTAGACACTTTATTCAGAGCCGT
TGGTGTATCTTTGAATATGAGATTGCTCAAACATGGCAGTTTCTGAGCAGCCGCTCTGGCATCATCTT
CATTGTCCTTGAGAAGGTTGAGAAGTCCCTGCTGAGGCAGCAGGTGGAATTGTATCGCCTTCTTAGCA
GAAACACCTACCTGGAATGGGAGGACAATCCTCTGGGGAGGCACATCTTCTGGAAGAGCTTAAAAAT
GCCCTATTGGATGGAAAAGCCTCGAATCCTGAGCAAACAGCAGAGGAAGAACAAGAAACGGCAACTTG
GACCTGA
```

Nucleic acid sequence of proteinic domain derived from CCR2
SEQ ID NO: 47:
```
ATGGAAGACAATAATATGTTACCTCAGTTCATCCATGGCATACTATCAACATCTCATTCTCTATTTAC
ACGAAGTATCCAAGAGCTTGATGAAGGGGCCACCACACCGTATGACTACGATGATGGTGAGCCTTGTC
ATAAAACCAGTGTGAAGCAAATTGGAGCTTGGATCCTGCCTCCACTCTACTCCCTGGTATTCATCTTT
GGTTTTGTGGGCAACATGTTGGTCATTATAATTCTGATAGGCTGTAAAAAGCTGAAGAGCATGACTGA
TATCTATCTGCTCAACCTGGCCATCTCTGACCTGCTCTTCCTGCTCACATTACCATTCTGGGCTCACT
ATGCTGCAAATGAGTGGGTCTTTGGGAATATAATGTGTAAAGTATTCACAGGGCTCTATCACATTGGT
TATTTTGGTGGAATCTTTTTCATTATCCTCCTGACAATTGATAGGTACTTGGCTATTGTTCATGCTGT
GTTTGCTTTAAAAGCCAGGACAGTTACCTTTGGGGTGATAACAAGTGTAGTCACTTGGTGGTGGCTG
TGTTTGCCTCTCTACCAGGAATCATATTTACTAAATCCAAACAAGATGATCACCATTACACCTGTGGC
CCTTATTTTACACAACTATGGAAGAATTTCCAAACAATAATGAGAAATATCTTGAGCCTGATCCTGCC
TCTACTTGTCATGGTCATCTGCTACTCAGGAATTCTCCACACCCTGTTTCGCTGTAGGAATGAGAAGA
AGAGGCACAGGGCTGTGAGGCTCATCTTTGCCATCATGATTGTCTACTTTCTCTTCTGGACTCCATAC
AATATTGTTCTCTTCTTGACCACCTTCCAGGAATCCTTGGGAATGAGTAACTGTGTGATTGACAAGCA
CTTAGACCAGGCCATGCAGGTGACAGAGACTCTTGGAATGACACACTGCTGCATTAATCCTGTCATTT
ATGCCTTTGTTGGAGAGAAGTTCCGAAGGTATCTCTCCATATTTTTCAGAAAGCACATTGCTAAACGT
CTCTGCAAACAGTGCCCAGTTTTCTATAGGGAGACAGCAGATCGAGTGAGCTCTACATTCACTCCTTC
CACTGGGGAGCAAGAGGTCTCGGTTGGGTTGTAA
```

Nucleic acid sequence of proteinic domain derived from ITGB2
SEQ ID NO: 48:
```
AATGCACGGCTGGTAGAGTGCAGTGGCCGTGGCCACTGCCAATGCAACAGGTGCATATGTGACGAAGG
CTACCAGCCACCGATGTGTGAGGATTGTCCCAGCTGTGGCTCGCACTGCAGGGACAACCACACCTCTT
GTGCCGAGTGCCTGAAGTTTGATAAGGGCCCTTTTGAGAAGAACTGTAGTGTTCAGTGTGCTGGTATG
ACGCTGCAGACTATCCCTTTGAAGAAAAAGCCCTGCAAGGAGAGGGACTCGGAAGGCTGTTGGATAAC
TTACACTTTGCAGCAGAAGGACGGAAGGAACATTTACAACATCCATGTGGAGGACAGTCTAGAGTGTG
TGAAGGGCCCCAATGTGGCTGCCATCGTAGGGGGCACCGTGGTAGGTGTCGTACTGATTGGTGTCCTC
CTCCTGGTCATCTGGAAGGCCCTGACCCACCTGACTGACCTCAGGGAGTACAGGCGCTTTGAGAAGGA
GAAACTCAAGTCCCAATGGAACAATGACAACCCCCTCTTCAAGAGTGCTACGACAACGGTCATGAACC
CCAAGTTTGCTGAAAGCTAG
```

Nucleic acid sequence of proteinic domain derived from CSF2RB
SEQ ID NO: 49:
```
ACTCAGAAGATGGCTTACTCATTCATTGAGCACACATTCCAGGTCCAGTACAAGAAGAAATCGGACAG
CTGGGAGGACAGCAAGACAGAGAACCTAGATCGAGCCCATAGCATGGACCTCTCCCAGCTGGAGCCAG
ACACCTCATACTGCGCCAGGGTGAGGGTCAAGCCCATCTCTAACTACGATGGGATCTGGAGCAAGTGG
AGCGAAGAGTACACTTGGAAGACTGACTGGGTGATGCCCACGCTGTGGATAGTCCTCATCCTGGTCTT
TCTCATCCTTGCTCCTGATCCTTCGCTTTGGCTGTGTCTCTGTATACAGGACGTACAGGAAGT
GGAAGGAAAAGATCCCCAACCCCAGCAAGAGCCTCCTGTTCCAGGATGGAGGTAAAGGTCTCTGGCCT
CCTGGCAGCATGGCAGCCTTCGCCACTAAGAACCCCGCTCTCCAGGGGCCACAGAGCAGGCTTCTTGC
TGAGCAACAGGGGGAGTCATATGCACATTTGGAAGACAACAACGTGTCACCTCTCACTATAGAGGACC
CTAATATAATTCGAGTTCCACCATCCGGGCCTGATACAACCCCAGCTGCCTCATCCGAATCCACAGAG
CAACTTCCCAATGTTCAAGTAGAGGGACCAACTCCTAACAGACTCAGGAAGCAATTACCCAGCTTTGA
CTTCAATGGGCCCTACCTGGGGCCTCCCCAATCCCACTCTCTGCCTGATCTCCCAGACCAGCTGGGTT
CCCCCCAGGTGGGTGGGAGCCTGAAGCCAGCACTGCCAGGCTCCTTGGAGTACATGTGTCTGCCCCCT
GGAGGTCAAGCGCAACTGGTTCCATTGTCCCAGGTGATGGGCAGGGCCAGGCTATGGATGTGCAGTG
TGGGTCCAGCCTGGAGACCTCAGGGAGCCCTTCTGTGGAGCAAAGGAGAACCCTCCAGTTGAGCTGA
GCATGGGGAACAGGAGGCACGGGACAACCCAGTGACTCTGCCCATAAGCTCTGGGGGCCCTGAGGGC
AGTATGATGGCCTCTGATTATGTCACTCCTGGAGATCCGGTGCTCACTCTGCCCCACAGGGCCCCTGTC
TACCTCTCTGGGCCCCTCTCTAGGGTTGCCCTCAGCCCAAAGCCCCCGTCTCTGTCTTAAGCTGCCCA
GGGTCCCCTCTGGAAGCCCAGCTCTAGGGCCACCAGGGTTTGAGGACTATGTGGAGCTGCCTCCAAGT
GTGAGCCAGGCTGCCAAGTCCCCTCCAGGCCATCCTGCTCCTCCTGTGGCAAGCAGCCCCACAGTGAT
CCCAGGAGAGCCCAGGGAGGAAGTGGGCCCAGCATCCCCACATCCCGAAGGCCTCCTTGTTCTTCAGC
AGGTTGGGGACTACTGCTTCCTCCCTGGCCTGGGACCTGGCTCCCTCTCACCACACAGTAAGCCACCC
```

TCTCCAAGTCTGTGTTCTGAGACTGAGGACCTAGTCCAGGACTTGTCTGTCAAAAAGTTTCCCTATCA
GCCCATGCCCCAGGCGCCAGCCATTCAGTTTTTCAAGTCCCTAAAGCATCAGGACTACCTGTCCCTGC
CCCCTTGGGACAATAGCCAGTCTGGGAAGGTGTGCTGA

Nucleic acid sequence of proteinic domain derived from CCR1
SEQ ID NO: 50:
ACTCCATGCCAAAAGACTGCTGTAAGAGCCTTTGGGGCTGGACTCCTGCCCCCCCTGTATTCTCTAGT
GTTCATCATTGGAGTGGTGGGCAATGTCCTAGTGATTCTGGTGCTCATGCAGCATAGGAGGCTTCAAA
GCATGACCAGCATCTACCTGTTCAACCTGGCTGTCTCTGATCTGGTCTTCCTTTTCACTTTACCTTTC
TGGATTGACTACAAGTTGAAAGACGACTGGATTTTTGGTGATGCCATGTGCAAGCTTCTCTCTGGGTT
TTATTACCTGGGTTTATACAGTGAGATCTTCTTTATCATCCTGTTGACGATTGACAGATACCTGGCCA
TTGTCCATGCTGTGTTTGCCCTGAGGGCCCGAACTGTTACTTTTGGCATCATCACCAGTATTATCACC
TGGGCCCTAGCCATCTTAGCTTCCATGCCTGCCTTATACTTTTTTAAGGCCCAGTGGGAGTTCACTCA
CCGTACCTGTAGCCCTCATTTCCCCTACAAGAGCCTGAAGCAGTGGAAGAGGTTTCAAGCTCTAAAGC
TAAACCTTCTTGGACTAATTTTGCCTCTGTTAGTCATGATAATCTGCTATGCAGGGATCATCAGAATT
CTGCTCAGAAGACCCAGTGAGAAGAAGGTCAAAGCCGTGCGTCTGATATTTGCTATTACTCTTCTATT
CTTCCTCCTCTGGACCCCCTACAATCTGAGTGTATTTGTTTCTGCTTTCCAAGATGTTCTATTCACCA
ATCAGTGTGAGCAGAGTAAGCAACTGGACCTGGCCATGCAGGTGACTGAGGTGATTGCCTACACCCAC
TGTTGTGTCAACCCAATCATTTATGTTTTTGTGGGTAACGGTTCTGGAAGTACCTTCGGCAGCTGTT
TCAAAGGCATGTGGCTATACCACTGGCAAAATGGCTGCCCTTCCTCTCTGTGGACCAACTAGAAAGGA
CCAGTTCTATATCTCCATCCACAGGAGAACATGAGCTCTCTGCTGGCTTCTGA Nucleic acid sequence of proteinic domain derived from CCR5
SEQ ID NO: 51:
ATGTCAGCACCCTGCCAAAAAATCAATGTGAAACAAATTGCGGCTCAGCTCCTGCCCCCACTCTACTC
CCTGGTATTCATCTTTGGTTTTGTGGGTAACATGATGGTCTTCCTCATCTTGATAAGCTGCAAAAAGC
TGAAGAGCGTGACTGATATCTACCTGCTCAACCTGGCCATCTCTGACCTGCTCTTCCTGCTCACACTA
CCATTCTGGGCTCACTATGCTGCAAATGAGTGGGTCTTTGGGAACATAATGTGTAAAGTATTCACAGG
GCTCTATCACATTGGTTATTTTGGTGGAATCTTCTTCATTATCCTCCTGACAATTGATAGGTACTTGG
CTATTGTCCATGCTGTGTTTGCTTTAAAAGTCAGAACGGTCAACTTTGGGGTGATAACAAGTGTAGTC
ACTTGGGCGGTGGCTGTGTTTGCCTCTCTCCCAGAAATAATCTTTACCAGATCTCAGAAAGAAGGTTT
TCATTATACATGCAGTCCTCATTTTCCACACACTCAGTAGAAGTTTGGAAGAGTTTCAAACATTAA
AGATGGTCATCTTGAGCCTGATCCTGCCTCTACTTGTCATGGTCATCTGCTACTCAGGAATTCTCCAC
ACCCTGTTTCGCTGTAGGAATGAGAAGAAGAGGCACAGGGCTGTGAGGCTCATCTTTGCCATCATGAT
TGTCTACTTTCTCTTCTGGACTCCCTACAACATTGTCCTCCTCCTGACCACCTTCCAGGAATTCTTTG
GACTGAATAACTGCAGTAGTTCTAATAGACTAGACCAGGCCATGCAGGCAACAGAGACTCTTGGAATG
ACACACTGCTGCCTAAACCCTGTCATCTATGCCTTTGTTGGAGAGAAGTTCCGGAGTTATCTCTCAGT
GTTCTTCCGAAAACACATTGTCAAACGCTTTTGCAAACGGTGTTCAATTTTCCAGCAAGACAATCCTG
ATCGTGCAAGCTCAGTCTATACCCGATCCACAGGAGAACATGAAGTTTCTACTGGTTTATGA Nucleic acid sequence of proteinic domain derived from CXCR4
SEQ ID NO: 52:
TTCCGGGATGAAAACGTCCATTTCAATAGGATCTTCCTGCCCACCATCTACTTCATCATCTTCTTGAC
TGGCATAGTCGGCAATGGATTGGTGATCCTGGTCATGGGTTACCAGAAGAAGCTAAGGAGCATGACGG
ACAAGTACCGGCTGCACCTGTCAGTGGCTGACCTCCTCTTTGTCATCACACTCCCCTTCTGGGCAGTT
GATGCCATGGCTGACTGGTACTTTGGGAAATTTTTGTGTAAGGCTGTCCATATCATCTACACTGTCAA
CCTCTACAGCAGCGTTCTCATCCTGGCCTTCATCAGCCTGGACCGGTACCTCGCTATTGTCCACGCCA
CCAACAGTCAGAGGCCAAGGAAACTGCTGGCTGAAAAGGCAGTCTATGTGGGCGTCTGGATCCCAGCC
CTCCTCCTGACTATACCTGACTTCATCTTTGCCGACGTCAGCCAGGGGGACATCAGTCAGGGGGATGA
CAGGTACATCTGTGACCGCTTTTACCCCGATAGCCTGTGGATGGTGGTGTTTCAATTCCAGCATATAA
TGGTGGGTCTCGTCCTGCCCGGCATCGTCATCCTCTCCTGTTACTGCATCATCATCTCTAAGCTGTCA
CACTCCAAGGGCCACCAGAAGCGCAAGGCCCTCAAGACGACAGTCATCCTCATCCTAGCTTTCTTTGC
CTGCTGGCTGCCATATTATGTGGGGATCAGCATCGACTCCTTCATCCTTTTGGGGGTCATCAAGCAAG
GATGTGACTTCGAGAGCATCGTGCACAAGTGGATCTCCATCACAGAGGCCCTCGCCTTCTTCCACTGT
TGCCTGAACCCCATCCTCTATGCCTTCCTCGGGGCCAAGTTCAAAAGCTCTGCCCAGCATGCACTCAA
CTCCATGAGCAGAGGCTCCAGCCTCAAGATCCTTTCCAAAGGAAAGCGGGGTGGACACTCTTCCGTCT
CCACGGAGTCAGAATCCTCCAGTTTTCACTCCAGCTAA Nucleic acid sequence of proteinic domain derived from SELPLG
SEQ ID NO: 53:
ATTGCCACCACTGACCCTACTGCCCCAGGTACAGGAGGGACAGCTGTTGGGATGCTGAGCACAGACTC
TGCCACACAGTGGAGTCTAACCTCAGTAGAGACCGTCCAACCAGCATCCACAGAGGTAGAGACCTCGC
AGCCAGCACCCATGGAGGCAGAGACCTCGCAGCCAGCACCCATGGAGGCAGAGACCTCGCAGCCAGCA
CCCATGGAGGCAGACACCTCAAAGCCAGCACCCACGGAGGCAGAGACCTCAAAGCCAGCACCCACGGA
GGCAGAGACCTCTCAGCCAGCACCCAACGAGGCAGAGACCTCAAAACCAGCACCCACGGAGGCAGAGA
CCTCAAAACCAGCACCCACGGAGGCAGAGACCACCCAGCTTCCCAGGATTCAGGCTGTAAAAACTCTG
TTTACAACGTCTGCAGCCACCGAAGTCCCTTCCACAGAACCTACCACCATGGAGACGGCGTCCACAGA
GTCTAACGAGTCTACCATCTTCCTTGGGCATCCGTGACTTGACTCATTTACCTGACAGGCCTGAAGAAAG
GGCTGATTGTGACCCCTGGGAATTCACCTGCCCCAACCCTGCCAGGGAGTTCAGATCTCATCCCGGTG
AAGCAATGTCTGCTGATTATCCTCATCTTGGCTTCTCTGGCCACCATTCCTCGTGTGCACAGTGGT
GCTGGCCGGTCCGTCTGCCCGTAAGACCCACATGTACCCAGTGCGGAACTACTCCCCACGGAGATGA
TCTGCATCTCGTCCCTGCTACCTGAGGGGGGAGCGGGGCCCCTGTCACAGCCAATGGGGCCTGCCC
AAGGTCCAGGACCTGAAGACAGAGCCCAGTGGGACCGGGATGGGGACGACCTCACCCTGCACAGCTT
CCTCCCTTAG

```
Amino acid sequence of EVIR-N
SEQ ID NO: 54:
MDFQVQIFSFLLISASVI

-continued

Sequence listing

```
GIWSKWSEEYTWKTDWVMPTLWIVLILVFLILTLLLILRFGCVSVYRTYRKWKEKIPNPSKSLLFQDG
GKGLWPPGSMAAFATKNPALQGPQSRLLAEQQGESYAHLEDNNVSPLTIEDPNIIRVPPSGPDTTPAA
SSESTEQLPNVQVEGPTPNRPRKQLPSFDFNGPYLGPPQSHSLPDLPDQLGSPQVGGSLKPALPGSLE
YMCLPPGGQAQLVPLSQVMGQGQAMDVQCGSSLETSGSPSVEPKENPPVELSMEEQEARDNPVTLPIS
SGGPEGSMMASDYVTPGDPVLTLPTGPLSTSLGPSLGLPSAQSPRLCLKLPRVPSGSPALGPPGFEDY
VELPPSVSQAAKSPPGHPAPPVASSPTVIPGEPREEVGPASPHPEGLLVLQQVGDYCFLPGLGPGSLS
PHSKPPSPSLCSETEDLVQDLSVKKFPYQPMPQAPAIQFFKSLKHQDYLSLPPWDNSQSGKVC

Amino acid sequence of EVIR-C1
SEQ ID NO: 61:
MDFQVQIFSFLLISASVIMSRGDIVLTQTPSSLPVSVGEKVTMTCKSSQTLLYSNNQKNYLAWYQQKP
GQSPKLLISWAFTRKSGVPDRFTGSGSGTDFTLTIGSVKAEDLAVYYCQQYSNYPWTFGGGTRLEIKR
GGGGSGGGGSGGGGSGGGGSEVQLQQSGPEVVKTGASVKISCKASGYSFTGYFINWVKKNSGKSPEWI
GHISSSYATSTYNQKFKNKAAFTVDTSSSTAFMQLNSLTSEDSAVYYCVRSGNYEEYAMDYWGQGTSV
TVSSTGTPCQKTAVRAFGAGLLPPLYSLVFIIGVVGNVLVILVLMQHRRLQSMTSIYLFNLAVSDLVF
LFTLPFWIDYKLKDDWIFGDAMCKLLSGFYYLGLYSEIFFIILLTIDRYLAIVHAVFALRARTVTFGI
ITSIITWALAILASMPALYFFKAQWEFTHRTCSPHFPYKSLKQWKRFQALKLNLLGLILPLLVMIICY
AGIIRILLRRPSEKKVKAVRLIFAITLLFFLLWTPYNLSVFVSAFQDVLFTNQCEQSKQLDLAMQVTE
VIAYTHCCVNPIIYVFVGERFWKYLRQLFQRHVAIPLAKWLPFLSVDQLERTSSISPSTGEHELSAGF Amino acid sequence of EVIR-C5
SEQ ID NO: 62:
MDFQVQIFSFLLISASVIMSRGDIVLTQTPSSLPVSVGEKVTMTCKSSQTLLYSNNQKNYLAWYQQKP
GQSPKLLISWAFTRKSGVPDRFTGSGSGTDFTLTIGSVKAEDLAVYYCQQYSNYPWTFGGGTRLEIKR
GGGGSGGGGSGGGGSGGGGSEVQLQQSGPEVVKTGASVKISCKASGYSFTGYFINWVKKNSGKSPEWI
GHISSSYATSTYNQKFKNKAAFTVDTSSSTAFMQLNSLTSEDSAVYYCVRSGNYEEYAMDYWGQGTSV
TVSSTGMSAPCQKINVKQIAAQLLPPLYSLVFIFGFVGNMMVFLILISCKKLKSVTDIYLLNLAISDL
LFLLLTLPFWAHYAANEWVFGNIMCKVPTGLYHIGYFGGIFFIILTIDRYLAIVHAVFALKVRTVNPG
VITSVVTWAVAVFASLPEIIFTRSQKEGFHYTCSPHFPHTQYHFWKSFQTLKMVILSLILPLLVMVIC
YSGILHTLFRCRNEKKRHRAVRLIFAIMIVYPLFWTPYNIVLLLTTFQEFFGLNNCSSSNRLDQAMQA
TETLGMTHCCLNPVIYAFVGEKFRSYLSVFFRKHIVKRFCKRCSIFQQDNPDRASSVYTRSTGEHEVS
TGL Amino acid sequence of EVIR-CX
SEQ ID NO: 63:
MDFQVQIFSFLLISASVIMSRGDIVLTQTPSSLPVSVGEKVTMTCKSSQTLLYSNNQKNYLAWYQQKP
GQSPKLLISWAFTRKSGVPDRFTGSGSGTDFTLTIGSVKAEDLAVYYCQQYSNYPWTFGGGTRLEIKR
GGGGSGGGGSGGGGSGGGGSEVQLQQSGPEVVKTGASVKISCKASGYSFTGYFINWVKKNSGKSPEWI
GHISSSYATSTYNQKFKNKAAFTVDTSSSTAFMQLNSLTSEDSAVYYCVRSGNYEEYAMDYWGQGTSV
TVSSTGFRDENVHFNRIFLPTIYFIIFLTGIVGNGLVILVMGYQKKLRSMTDKYRLHLSVADLLFVIT
LPFWAVDAMADWYFGKFLCKAVHIIYTVNLYSSVLILAFISLDRYLAIVHATNSQRPRKLLAEKAVYV
GVWIPALLLTIPDFIFADVSQGDISQGDDRYICDRLYPDSLWMVVFQFQHIMVGLVLPGIVILSCYCI
IISKLSHSKGHQKRKALKTTVILILAFFACWLPYYVGISIDSFILLGVIKQGCDFESIVHKWISITEA
LAFFHCCLNPILYAFLGAKFKSSAQHALNSMSRGSSLKILSKGKRGGHSSVSTESESSSFHSS Amino acid sequence of EVIR-S
SEQ ID NO: 64:
MDFQVQIFSFLLISASVIMSRGDIVLTQTPSSLPVSVGEKVTMTCKSSQTLLYSNNQKNYLAWYQQKP
GQSPKLLISWAFTRKSGVPDRFTGSGSGTDFTLTIGSVKAEDLAVYYCQQYSNYPWTFGGGTRLEIKR
GGGGSGGGGSGGGGSGGGGSEVQLQQSGPEVVKTGASVKISCKASGYSFTGYFINWVKKNSGKSPEWI
GHISSSYATSTYNQKFKNKAAFTVDTSSSTAFMQLNSLTSEDSAVYYCVRSGNYEEYAMDYWGQGTSV
TVSSTGIATTDPTAPGTGGTAVGMLSTDSATQWSLTSVETVQPASTEVETSQPAPMEAETSQPAPMEA
ETSQPAPMEADTSKPAPTEAETSKPAPTEAETSQPAPNEAETSKPAPTEAETSKPAPTEAETTQLPRI
QAVKTLFTTSAATEVPSTEPTTMETASTESNESTIFLGPSVTHLPDSGLKKGLIVTPGNSPAPTLPGS
SDLIPVKQCLLIILILASLATIFLVCTVVLAVRLSRKTHMYPVRNYSPTEMICISSLLPEGGDGAPVT
ANGGLPKVQDLKTEPSGDRDGDDLTLHSFLP Nucleic acid sequence of EVIR-N
SEQ ID NO: 65:
ATGGATTTTCAGGTCCAGATTTTCTCCTTCCTCCTCATTTCAGCCAGCGTCATTATGTCTCGGGGGA
TATTGTCCTCACACAGACTCCCAGCTCCCTGCCTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGAACCTCCGTG
ACTGTCTCAAGCACCGGTCTTCTGGGGGTGTCCCTTGGAGGTGCCAAGGAGGCATGCCCCACAGGCCT
GTACACACACAGCGGTGAGTGCTGCAAAGCCTGCAACCTGGGCGAGGGTGTGGCCCAGCCTTGTGGAG
CCAACCAGACCGTGTGTGAGCCCTGCCTGGACAGCGTGACGTTCTCCGACGTGGTGAGCGCGACCGAG
CCGTGCAAGCCGTGCACCGAGTGCGTGGGGCTCCAGAGCATGTCGGCGCCGTGCGTGGAGGCCGACGA
CGCCGTGTGCCGCTGCGCCTACGGCTACTACCAGGATGAGACGACTGGGCGCTGCGAGGCGTGCCGCG
TGTGCGAGGCGGGCTCGGGCCTCGTGTTCTCCTGCCAGGACAAGCAGAACACCGTGTGCGAGGAGTGC
```

CCCGACGGCACGTATTCCGACGAGGCCAACCACGTGGACCCGTGCCTGCCCTGCACCGTGTGCGAGGA
CACCGAGCGCCAGCTCCGCGAGTGCACACGCTGGGCCGACGCCGAGTGCGAGGAGATCCCTGGCCGTT
GGATTACACGGTCCACACCCCCAGAGGGCTCGGACAGCACAGCCCCCAGCACCCAGGAGCCTGAGGCA
CCTCCAGAACAAGACCTCATAGCCAGCACGGTGGCAGGTGTGGTGACCACAGTGATGGGCAGCTCCCA
GCCCGTGGTGACCCGAGGCACCACCGACAACCTCATCCCTGTCTATTGCTCCATCCTGGCTGCTGTGG
TTGTGGGCCTTGTGGCCTACATAGCCTTCAAGAGGTGGAACAGGGGGATCCTCTAG

Nucleic acid sequence of EVIR-G
SEQ ID NO: 66:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGGACCTCCGTG
ACTGTCTCAAGCACCGGTCACGAGAACTCCGAACTGCTGATTCCTAAGGCAACTCACAACGACTCCGG
CTCCTATTTCTGTAGAGGGCTGATTGGACATAACAACAAGAGCTCCGCCTCATTCAGGATTAGCCTGG
GCGACCCAGGGTCTCCCAGTATGTTCCCCCCTTGGCACCAGATCACCTTTTGCCTGCTGATTGGACTG
CTGTTCGCTATCGATACAGTGCTGTACTTTTCTGTCCGGAGAGGCCTGCAGTCACCCGTGGCAGATTA
CGAAGAACCCAAGATTCAGTGGAGCAAGGAGCCCCAGGATAAGACGCGTGTCGACTGA Nucleic acid sequence of EVIR-F
SEQ ID NO: 67:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGGACCTCCGTG
ACTGTCTCAAGCACCGGTCCAGGCCCCTTCCCTTTCATCCAAGACAACATCTCCTTCTATGCGACCAT
TGGGCTCTGTCTCCCCTTCATTGTTGTTCTCATTGTGTTGATCTGCCACAAATACAAAAAGCAATTTA
GGTACGAGAGTCAGCTGCAGATGATCCAGGTGACTGGCCCCCTGGATAACGAGTACTTCTACGTTGAC
TTCAGGGACTATGAATATGACCTTAAGTGGGAGTTCCCGAGAGAGAACTTAGAGTTTGGGAAGGTCCT
GGGGTCTGGCGCTTTCGGGAGGGTGATGAACGCCACGGCCTATGGCATTAGTAAAACGGGAGTCTCAA
TTCAGGTGGCGGTGAAGATGCTAAAAGAGAAAGCTGACAGCTGTGAAAAAGAAGCTCTCATGTCGGAG
CTCAAAATGATGACCCACCTGGGACACCATGACAACATCGTGAATCTGCTGGGGGCATGCACACTGTC
AGGGCCAGTGTACTTGATTTTTGAATATTGTTGCTATGGTGACCTCCTCAACTACCTAAGAAGTAAAA
GAGAGAAGTTTCACAGGACATGGACAGAGATTTTTAAGGAACATAATTTCAGTTTTTACCCTACTTTC
CAGGCACATTCAAATTCCAGCATGCCTGGTTCACGAGAAGTTCAGTTACACCCGCCCTTGGATCAGCT
CTCAGGGTTCAATGGGAATTTAATTCATTCTGAAGATGAGATTGAATATGAAAACCAGAAGAGGCTGG
CAGAAGAAGAGGAGGAAGATTTGAACGTGCTGACGTTTGAAGACCTCCTTTGCTTTGCGTACCAAGTG
GCCAAAGGCATGGAATTCCTGGAGTTCAAGTCGTGTGTCCACAGAGACCTGGCAGCCAGGAATGTGTT
GGTCACCCACGGGAAGGTGGTGAAGATCTGTGACTTTGGACTGGCCCGAGACATCCTGAGCGACTCCA
GCTACGTCGTCAGGGGCAACGCACGGCTGCCGGTGAAGTGGATGGCACCTGAGAGCTTATTTGAAGGG
ATCTACACAATCAAGAGTGACGTCTGGTCCTACGGCATCCTTCTCTGGGAGATATTTTCACTGGGTGT
GAACCCTTACCCTGGCATTCCTGTCGACGCTAACTTCTATAAACTGATTCAGAGTGGATTTAAAATGG
AGCAGCCATTCTATGCCACAGAAGGGATATACTTTGTAATGCAATCCTGCTGGGCTTTTGACTCAAGG
AAGCGGCCATCCTTCCCCAACCTGACTTCATTTTTAGGATGTCAGCTGGCAGAGGCAGAAGAAGCGAT
GTATCAGAACATGGGTGGCAACGTCCCAGAACATCCATCCATCTACCAAAACAGGCGGCCCCTCAGCA
GAGAGGCAGGCTCAGAGCCGCCATCGCCACAGGCCCAGGTGAAGATTCACGGAGAAAGAAGTTAG Nucleic acid sequence of EVIR-T
SEQ ID NO: 68:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGGACCTCCGTG

```
Sequence listing
```

ACTGTCTCAAGCACCGGTCAGCTGTATTCCCTCAGCACTCTTGATTGCAGTTTCAATCGCATAGAGAC
ATCTAAAGGAATACTGCAACATTTTCCAAAGAGTCTAGCCTTCTTCAATCTTACTAACAATTCTGTTG
CTTGTATATGTGAACATCAGAAATTCCTGCAGTGGGTCAAGGAACAGAAGCAGTTCTTGGTGAATGTT
GAACAAATGACATGTGCAACACCTGTAGAGATGAATACCTCCTTAGTGTTGGATTTTAATAATTCTAC
CTGTTATATGTACAAGACAATCATCAGTGTGTCAGTGGTCAGTGTGATTGTGGTATCCACTGTAGCAT
TTCTGATATACCACTTCTATTTTCACCTGATACTTATTGCTGGCTGTAAAAAGTACAGCAGAGGAGAA
AGCATCTATGATGCATTTGTGATCTACTCGAGTCAGAATGAGGACTGGGTGAGAAATGAGCTGGTAAA
GAATTTAGAAGAAGGAGTGCCCCGCTTTCACCTCTGCCTTCACTACAGAGACTTTATTCCTGGTGTAG
CCATTGCTGCCAACATCATCCAGGAAGGCTTCCACAAGAGCCGGAAGGTTATTGTGGTAGTGTCTAGA
CACTTTATTCAGAGCCGTTGGTGTATCTTTGAATATGAGATTGCTCAAACATGGCAGTTTCTGAGCAG
CCGCTCTGGCATCATCTTCATTGTCCTTGAGAAGGTTGAGAAGTCCCTGCTGAGGCAGCAGGTGGAAT
TGTATCGCCTTCTTAGCAGAAACACCTACCTGGAATGGGAGGACAATCCTCTGGGGAGGCACATCTTC
TGGAGAAGACTTAAAAATGCCCTATTGGATGGAAAAGCCTCGAATCCTGAGCAAACAGCAGAGGAAGA
ACAAGAAACGGCAACTTGGACCTGA

Nucleic acid sequence of EVIR-C2
SEQ ID NO: 69:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGGACCTCCGTG
ACTGTCTCAAGCACCGGTATGGAAGACAATAATATGTTACCTCAGTTCATCCATGGCATACTATCAAC
ATCTCATTCTCTATTTACACGAAGTATCCAAGAGCTTGATGAAGGGGCCACCACACCGTATGACTACG
ATGATGGTGAGCCTTGTCATAAAACCAGTGTGAAGCAAATTGGAGGTTGGATCCTGCCTCCACTCTAC
TCCCTGGTATTCATCTTTGGTTTTGTGGGCAACATGTTGGTCATTATAATTCTGATAGGCTGTAAAAA
GCTGAAGAGCATGACTGATATCTATCTGCTCAACCTGGCCATCTCTGACCTGCTCTTCCTGCTCACAT
TACCATTCTGGGCTCACTATGCTGCAAATGAGTGGGTCTTTGGGAATATAATGTGTAAAGTATTCACA
GGGCTCTATCACATTGGTTATTTTGGTGGAATCTTTTTCATTATCCTCCTGACAATTGATAGGTACTT
GGCTATTGTTCATGCTGTGTTTGCTTTAAAAGCCAGGACAGTTACCTTTGGGGTGATAACAAGTGTAG
TCACTTGGGTGGTGGCTGTGTTTGCCTCTCTACCAGGAATCATATTTACTAAATCCAAACAAGATGAT
CACCATTACACCTGTGGCCCTTATTTTACACAACTATGGAAGAATTTCCAAACAATAATGAGAAATAT
CTTGAGCCTGAATCCTGCCTCTACTTGTCATGGTCATCTGCTACTCAGGAATTCTCCACACCCTGTTTC
GCTGTAGGAATGAGAAGAAGAGGCACAGGGCTGTGAGGCTCATCTTTGCCATCATGATTGTCTACTTT
CTCTTCTGGACTCCATACAATATTGTTCTCTTCTTGACCACCTTCCAGGAATCCTTGGGAATGAGTAA
CTGTGTGATTGACAAGCACTTAGACCAGGCCATGCAGGTGACAGAGACTCTTGGAATGACACACTGCT
GCATTAATCCTGTCATTTATGCCTTTGTTGGAGAGAAGTTCCGAAGGTATCTCTCCATATTTTTCAGA
AAGCACATTGCTAAACGTCTCTGCAAACAGTGCCCAGTTTTCTATAGGGAGACAGCAGATCGAGTGAG
CTCTACATTCACTCCTTCCACTGGGGAGCAAGAGGTCTCGGTTGGGTTGTAA Nucleic acid sequence of EVIR-I
SEQ ID NO: 70:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGGACCTCCGTG
ACTGTCTCAAGCACCGGTAATGCACGGCTGGTAGAGTGCAGTGGCCGTGGCCACTGCCAATGCAACAG
GTGCATATGTGACGAAGGCTACCAGCCACCGATGTGTGAGGATTGTCCCAGCTGTGGCTCGCACTGCA
GGGACAACCACACCTCTTGTGCCGAGTGCCTGAAGTTTGATAAGGGCCCTTTTGAGAAGAACTGTAGT
GTTCAGTGTGCTGGTATGACGCTGCAGACTATCCCTTTGAAGAAAAAGCCCTGCAAGGAGAGGGACTC
GGAAGGCTGTTGGATAACTTACACTTTGCAGCAGAAGGACGGAGGGAACATTTACAACATCCATGTGG
AGGACACTCTAGAGTGTGTGAAGGGCCCCAATGTGGCTGCCATCGTAGGGGGCACCGTGGTAGGTGTC
GTACTGATTGGTGTCCTCCTCCTGGTCATCTGGAAGGCCCTGACCCACCTGACTGACCTCAGGGAGTA
CAGGCGCTTTGAGAAGGAGAAACTCAAGTCCCAATGGAACAATGACAACCCCCTCTTCAAGAGTGCTA
CGACAACGGTCATGAACCCCAAGTTTGCTGAAAGCTAG Nucleic acid sequence of EVIR-C
SEQ ID NO: 71:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC -continued Sequence listing AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGGACCTCCGTG
ACTGTCTCAAGCACCGGTACTCAGAAGATGGCTTACTCATTCATTGAGCACACATTCCAGGTCCAGTA
CAAGAAGAAATCGGACAGCTGGGAGGACAGCAAGACAGAGAACCTAGATCGAGCCCATAGCATGGACC
TCTCCCAGCTGGAGCCAGACACCTCATACTGCGCCAGGGTGAGGGTCAAGCCCATCTCTAACTACGAT
GGGATCTGGAGCAAGTGGAGCGAAGAGTACACTTGGAAGACTGACTGGGTGATGCCCACGCTGTGGAT
AGTCCTCATCCTGGTCTTTCTCATCCTCACCTTGCTCCTGATCCTTCGCTTTGGCTGTGTCTCTGTAT
ACAGGACGTACAGGAAGTGGAAGGAAAAGATCCCCAACCCCAGCAAGAGCCTCCTGTTCCAGGATGGA
GGTAAAGGTCTCTGGCCTCCTGGCAGCATGGCAGCCTTCGCCACTAAGAACCCCGCTCTCCAGGGGCC
ACAGAGCAGGCTTCTTGCTGAGCAACAGGGGGAGTCATATGCACATTTGGAAGACAACAACGTGTCAC
CTCTCACTATAGAGGACCCTAATATAATTCGAGTTCCACCATCCGGGCCTGATACAACCCCAGCTGCC
TCATCCGAATCCACAGAGCAACTTCCCAATGTTCAAGTAGAGGGACCAACTCCTAACAGACCTAGGAA
GCAATTACCCAGCTTTGACTTCAATGGGCCCTACCTGGGGCCTCCCCAATCCCACTCTCTGCCTGATC
TCCCAGACCAGCTGGGTTCCCCCCAGGTGGGTGGGAGCCTGAAGCCAGCACTGCCAGGCTCCTTGGAG
TACATGTGTCTGCCCCCTGGAGGTCAAGCGCAACTGGTTCCATTGTCCCAGGTGATGGGGCAGGGCCA
GGCTATGGATGTGCAGTGTGGGTCCAGCCTGGAGACCTCAGGGAGCCCTTCTGTGGAGCCAAAGGAGA
ACCCTCCAGTTGAGCTGAGCATGGAGGAACAGGAGGCACGGGACAACCCAGTGACTCTGCCCATAAGC
TCTGGGGGCCCTGAGGGCAGTATGATGGCCTCTGATTATGTCACTCCTGGAGATCCGGTGCTCACTCT
GCCCACAGGGCCCCTGTCTACCTCTCTGGGCCCCTCTCTAGGGTTGCCCTCAGCCCAAAGCCCCCGTC
TCTGTCTTAAGCTGCCCAGGGTCCCCTCTGGAAGCCCAGCTCTAGGGCCACCAGGGTTTGAGGACTAT
GTGGAGCTGCCTCCAAGTGTGAGCCAGGCTGCCAAGTCCCCTCCAGGCCATCCTGCTCCTCCTGTGGC
AAGCAGCCCCACAGTGATCCCAGGAGAGCCCAGGGAGGAAGTGGGCCCAGCATCCCCACATCCCGAAG
GCCTCCTTGTTCTTCAGCAGGTTGGGGACTACTGCTTCCTCCCTGGCCTGGGACCTGGCTCCCTCTCA
CCACACAGTAAGCCACCCTCTCCAAGTCTGTGTTCTGAGACTGAGGACCTAGTCCAGGACTTGTCTGT
CAAAAAGTTTCCCTATCAGCCCATGCCCCAGGCGCCAGCCATTCAGTTTTTCAAGTCCCTAAAGCATC
AGGACTACCTGTCCCTGCCCCCTTGGGACAATAGCCAGTCTGGGAAGGTGTGCTGA Nucleic acid sequence of EVIR-C1
SEQ ID NO: 72:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGGACCTCCGTG
ACTGTCTCAAGCACCGGTACTCCATGCCAAAAGACTGCTGTAAGAGCCTTTGGGGCTGGACTCCTGCC
CCCCCTGTATTCTCTAGTGTTCATCATTGGAGTGGTGGGCAATGTCCTAGTGATTCTGGTGCTCATGC
AGCATAGGAGGCTTCAAAGCATGACCAGCATCTACCTGTTCAACCTGGCTGTCTCTGATCTGGTCTTC
CTTTTCACTTTACCTTTCTGGATTGACTACAAGTTGAAAGACGACTGGATTTTTGGTGATGCCATGTG
CAAGCTTCTCTCTGGGTTTTATTACCTGGGTTTATACAGTGAGATCTTCTTTATCATCCTGTTGACGA
TTGACAGATACCTGGCCATTGTCCATGCTGTGTTTGCCCTGAGGGCCCGAACTGTTACTTTTGGCATC
ATCACCAGTATTATCACCTGGGCCCTAGCCATCTTAGCTTCCATGCCTGCCTTATACTTTTTTAAGGC
CCAGTGGGAGTTCACTCACCGTACCTGTAGCCCTCATTTCCCCTACAAGAGCCTGAAGCAGTGGAAGA
GGTTTCAAGCTCTAAAGCTAAACCTTCTTGGACTAATTTTGCCTCTGTTAGTCATGATAATCTGCTAT
GCAGGGATCATCAGAATTCTGCTCAGAAGACCCAGTGAGAAGAAGGTCAAAGCCGTGCGTCTGATATT
TGCTATTACTCTTCTATTCTTCCTCCTCTGGACCCCCTACAATCTGAGTGTATTTGTTTCTGCTTTCC
AAGATGTTCTATTCACCAATCAGTGTGAGCAGAGTAAGCAACTGGACCTGGCCATGCAGGTGACTGAG
GTGATTGCCTACACCCACTGTTGTGTCAACCCAATCATTTATGTTTTTGTGGGTGAACGGTTCTGGAA
GTACCTTCGGCAGCTGTTTCAAAGGCATGTGGCTATACCACTGGCAAAATGGCTGCCCTTCCTCTCTG
TGGACCAACTAGAAAGGACCAGTTCTATATCTCCATCCACAGGAGAACATGAGCTCTCTGCTGGCTTC
TGA Nucleic acid sequence of EVIR-C5
SEQ ID NO: 73:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT -continued

| Sequence listing |
|---|

ACTATTGTGTCAGGAGCGGCAACTACGAAGAATATGCTATGGATTACTGGGGGCAGGGGACCTCCGTG
ACTGTCTCAAGCACCGGTATGTCAGCACCCTGCCAAAAAATCAATGTGAAACAAATTGCGGCTCAGCT
CCTGCCCCCACTCTACTCCCTGGTATTCATCTTTGGTTTTGTGGGTAACATGATGGTCTTCCTCATCT
TGATAAGCTGCAAAAAGCTGAAGAGCGTGACTGATATCTACCTGCTCAACCTGGCCATCTCTGACCTG
CTCTTCCTGCTCACACTACCATTCTGGGCTCACTATGCTGCAAATGAGTGGGTCTTTGGGAACATAAT
GTGTAAAGTATTCACAGGGCTCTATCACATTGGTTATTTTGGTGGAATCTTCTTCATTATCCTCCTGA
CAATTGATAGGTACTTGGCTATTGTCCATGCTGTGTTTGCTTTAAAAGTCAGAACGGTCAACTTTGGG
GTGATAACAAGTGTAGTCACTTGGGCGGTGGCTGTGTTTGCCTCTCTCCCAGAAATAATCTTTACCAG
ATCTCAGAAAGAAGGTTTTCATTATACATGCAGTCCTCATTTTCCACACACTCAGTATCATTTCTGGA
AGAGTTTCCAAACATTAAAGATGGTCATCTTGAGCCTGATCCTGCCTCTACTTGTCATGGTCATCTGC
TACTCAGGAATTCTCCACACCCTGTTTCGCTGTAGGAATGAGAAGAAGAGGCACAGGGCTGTGAGGCT
CATCTTTGCCATCATGATTGTCTACTTTCTCTTCTGGACTCCCTACAACATTGTCCTCCTCCTGACCA
CCTTCCAGGAATTCTTTGGACTGAATAACTGCAGTAGTTCTAATAGACTAGACCAGGCCATGCAGGCA
ACAGAGACTCTTGGAATGACACACTGCTGCCTAAACCCTGTCATCTATGCCTTTGTTGGAGAGAAGTT
CCGGAGTTATCTCTCAGTGTTCTTCCGAAAACACATTGTCAAACGCTTTTGCAAACGGTGTTCAATTT
TCCAGCAAGACAATCCTGATCGTGCAAGCTCAGTCTATACCCGATCCACAGGAGAACATGAAGTTTCT
ACTGGTTTATGA

Nucleic acid sequence of EVIR-CX
SEQ ID NO: 74:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGGACCTCCGTG
ACTGTCTCAAGCACCGGGTTCCGGGATGAAAACGTCCATTTCAATAGGATCTTCCTGCCCACCATCTA
CTTCATCATCTTCTTGACTGGCATAGTCGGCAATGGATTGGTGATCCTGGTCATGGGTTACCAGAAGA
AGCTAAGGAGCATGACGGACAAGTACCGGCTGCACCTGTCAGTGGCTGACCTCCTCTTTGTCATCACA
CTCCCCTTCTGGGCAGTTGATGCCATGGCTGACTGGTACTTTGGGAAATTTTTGTGTAAGGCTGTCCA
TATCATCTACACTGTCAACCTCTACAGCAGCGTTCTCATCCTGGCCTTCATCAGCCTGGACCGGTACC
TCGCTATTGTCCACGCCACCAACAGTCAGAGGCCAAGGAAACTGCTGGCTGAAAAGGCAGTCTATGTG
GGCGTCTGGATCCCAGCCCTCCTCCTGACTATACCTGACTTCATCTTTGCCGACGTCAGCCAGGGGGA
CATCAGTCAGGGGGATGACAGGTACATCTGTGACCGCCTTTACCCCGATAGCCTGTGGATGGTGGTGT
TTCAATTCCAGCATATAATGGTGGGTCTCGTCCTGCCCGGCATCGTCATCCTCTCCTGTTACTGCATC
ATCATCTCTAAGCTGTCACACTCCAAGGGCCACCAGAAGCGCAAGGCCCTCAAGACGACAGTCATCCT
CATCCTAGCTTTCTTTGCCTGCTGGCTGCCATATTATGTGGGGATCAGCATCGACTCCTTCATCCTTT
TGGGGGTCATCAAGCAAGGATGTGACTTCGAGAGCATCGTGCACAAGTGGATCTCCATCACAGAGGCC
CTCGCCTTCTTCCACTGTTGCCTGAACCCCATCCTCTATGCCTTCCTCGGGGCCAAGTTCAAAAGCTC
TGCCCAGCATGCACTCAACTCCATGAGCAGAGGCTCCAGCCTCAAGATCCTTTCCAAAGGAAAGCGGG
GTGGACACTCTTCCGTCTCCACGGAGTCAGAATCCTCCAGTTTTCACTCCAGCTAA Nucleic acid sequence of EVIR-S
SEQ ID NO: 75:
ATGGATTTTCAGGTCCAGATTTTCTCCTTCCTCCTCATTTCAGCCAGCGTCATTATGTCTCGGGGGGA
TATTGTCCTCACACAGACTCCCAGCTCCCTGCCTGTGTCCGTCGGAGAGAAAGTGACCATGACATGCA
AGTCTAGTCAGACACTGCTCTACTCTAACAATCAGAAGAACTACCTCGCATGGTATCAGCAGAAACCA
GGACAGAGCCCCAAGCTGCTCATCTCCTGGGCTTTCACCCGGAAATCCGGGGTGCCTGACCGCTTCAC
AGGTAGCGGCTCCGGAACTGATTTTACTCTGACCATTGGATCTGTGAAGGCAGAGGACCTCGCCGTCT
ACTATTGCCAGCAGTACAGTAATTATCCATGGACTTTTGGCGGAGGGACCAGGCTGGAAATCAAGAGA
GGTGGAGGAGGGTCCGGTGGAGGAGGGTCTGGTGGAGGAGGGAGTGGTGGAGGAGGGTCAGAGGTGCA
GCTGCAGCAGTCTGGCCCCGAAGTGGTCAAAACTGGAGCTTCAGTCAAAATCAGCTGTAAGGCATCTG
GGTACAGCTTCACCGGCTACTTCATCAACTGGGTGAAGAAAAATTCAGGGAAGAGCCCTGAGTGGATC
GGCCACATTTCAAGCTCCTACGCCACAAGCACTTACAACCAGAAGTTCAAAAATAAGGCCGCTTTTAC
CGTGGACACATCTAGTTCAACCGCCTTCATGCAGCTGAACTCCCTCACATCTGAAGATAGTGCTGTGT
ACTATTGTGTCAGGAGCGGCAACTACGAAGAATATGCTATGGATTACTGGGGGCAGGGGACCTCCGTG
ACTGTCTCAAGCACCGGTATTGCCACCACTGACCCTACTGCCCCAGGTACAGGAGGGACAGCTGTTGG
GATGCTGAGCACAGACTCTGCCACACAGTGGAGTCTAACCTCAGTAGAGACCGTCCAACCAGCATCCA
CAGAGGTAGAGACCTCGCAGCCAGCACCCATGGAGGCAGAGACCTCGCAGCCAGCACCCATGGAGGCA
GAGACCTCGCAGCCAGCACCCATGGAGGCAGACACCTCAAAGCCAGCACCCACGGAGGCAGAGACCTC
AAAGCCAGCACCCACGGAGGCAGAGACCTCTCAGCCAGCACCCAACGAGGCAGAGACCTCAAAACCAG
CACCCACGGAGGCAGAGACCTCAAAACCAGCACCCACGGAGGCAGAGACCACCCAGCTTCCCAGGATT
CAGGCTGTAAAAACTCTGTTTACAACGTCTGCAGCCACCGAAGTCCCTTCCACAGAACCTACCACCAT
GGAGACGGCGTCCACAGAGTCTAACGAGTCTACCATCTTCCTTGGGCCATCCGTGACTCACTTACCTG
ACAGCGGCCTGAAGAAAGGGCTGATTGTGACCCCTGGGAATTCACCTGCCCCAACCCTGCCAGGGAGT
TCAGATCTCATCCCGGTGAAGCAATGTCTGCTGATTATCCTCATCTTGGCTTCTCTGGCCACCATCTT
CCTCGTGTGCACAGTGGTGCTGGCGGTCCGTCTGTCCCGTAAGACCCACATGTACCCAGTGCGGAACT
ACTCCCCCACGGAGATGATCTGCATCTCGTCCCTGCTACCTGAGGGGGGAGACGGGGCCCCTGTCACA
GCCAATGGGGGCCTGCCCAAGGTCCAGGACCTGAAGACAGAGCCCAGTGGGGACCGGGATGGGGACGA
CCTCACCCTGCACAGCTTCCTCCCTTAG

| Sequence listing |
|---|

Nucleic acid sequence of anti-HER2 scPv Trastuzumab
SEQ ID NO: 76:
GATATTCAGATGACCCAGTCCCCCAGCTCCCTGTCAGCAAGCGTGGGCGACCGAGTCACTATCACCTG
CCGAGCTAGCCAGGATGTGAACACCGCAGTCGCCTGGTACCAGCAGAAGCCAGGGAAAGCACCCAAGC
TGCTCATCTACTCCGCCTCTTTCCTGTATTCAGGAGTGCCAAGCAGGTTTAGTGGCTCAAGAAGCGGA
ACTGACTTCACACTGACTATCTCTAGTCTCCAGCCCGAGGATTTTGCAACCTACTATTGCCAGCAGCA
CTATACCACACCCCTACCTTCGGTCAGGGCACAAAAGTGGAAATTAAGCGGACCGGCTCCACATCTG
GAAGTGGGAAGCCCGGTTCCGGCGAGGGATCTGAAGTGCAGCTGGTCGAGTCCGGAGGAGGACTCGTG
CAGCCTGGTGGCAGTCTGAGGCTCTCATGTGCCGCTAGCGGCTTCAACATCAAAGACACATACATTCA
TTGGGTGCGCCAGGCTCCTGGGAAGGGTCTGGAATGGGTCGCACGAATCTATCCAACTAATGGGTACA
CCCGATATGCTGACTCTGTGAAAGGCAGGTTCACAATTTCCGCCGATACATCTAAGAACACTGCTTAC
CTGCAGATGAATAGTCTCAGAGCTGAGGATACTGCAGTCTACTATTGTAGCCGGTGGGGAGGGGATGG
CTTCTATGCTATGGATGTCTGGGGGCAGGGGACTCTGGTGACTGTCTCAAGTGGTACCGGTACGCGTG Nucleic acid sequence of anti-HER2 scPv Pertuzumab
SEQ ID NO: 77:
GATATTCAGATGACCCAGAGCCCAAGCTCCCTGTCAGCTAGCGTGGGCGACCGAGTCACCATCACATG
CAAAGCCAGTCAGGATGTGTCAATTGGCGTCGCTTGGTACCAGCAGAAGCCCGGAAAAGCTCCTAAGC
TGCTCATCTATTCCGCATCTTACAGGTACACAGGCGTGCCCTCTCGCTTCAGTGGTTCAGGCAGCGGA
ACTGACTTTACTCTGACCATTTCTAGTCTCCAGCCTGAGGATTTCGCAACCTACTATTGTCAGCAGTA
CTATATCTACCCATATACCTTTGGGCAGGGTACAAAAGTGGAAATTAAGAGAACAGTCGCAGCTCCAG
GAGGAGGAGGTAGCGGAGGAGGGGGTTCCGGCGGAGGGGGTTCTGGCGGAGGGGGTAGTGAGGTGCAG
CTGGTCGAAAGCGGAGGAGGACTCGTGCAGCCTGGTGGCAGCCTGAGACTCTCCTGCGCAGCCTCTGG
CTTCACCTTCACCGACTACACCATGGATTGGGTGCGGCAGGCACCAGGAAAGGGACTGGAGTGGGTGG
CAGACGTCAACCCCAATTCCGGAGGGTCTATCTACAACCAGAGGTTCAAAGGAAGGTTCACCCTGAGT
GTGGATCGATCAAAGAACACCCTGTATCTCCAGATGAATTCCCTGAGGGCCGAAGATACAGCCGTCTA
TTATTGTGCAAGAAACCTGGGTCCATCATTTTATTTTGACTATTGG Nucleic acid sequence of anti-HER2 scFv FRP5
SEQ ID NO: 78:
CAGGTCCAGCTCCAGCAGTCAGGTCCAGAACTCAAGAAGCCAGGGGAAACAGTCAAAATCTCATGTAA
AGCCTCAGGATACCCATTCACTAACTATGGGATGAATTGGGTGAAGCAGGCACCTGGCCAGGGACTGA
AATGGATGGGTTGGATCAACACTAGCACCGGGGAGTCCACATTCGCCGACGATTTTAAGGGCCGGTTC
GACTTTTCTCTCGAAACCAGTGCAAATACAGCCTATCTGCAGATTAACAATCTCAAATCCGAGGATAT
GGCCACCTACTTCTGCGCTCGCTGGGAAGTGTACCACGGATATGTCCCATACTGGGGGCAGGGTACCA
CAGTGACAGTCAGCTCCGGAGGAGGAGGTTCAGGAGGAGGAGGTAGCGGAGGAGGAGGTTCCGACATC
CAGCTGACACAGTCTCATAAGTTTCTCTCCACTTCTGTGGGCGACAGGGTCTCTATTACCTGTAAAGC
TAGTCAGGATGTGTATAACGCCGTCGCTTGGTACCAGCAGAAGCCCGGCCAGAGCCCTAAACTGCTCA
TCTATAGCGCCTCTAGTAGGTACACTGGAGTGCCAAGCAGATTCACCGGCAGTGGATCAGGGCCCGAC
TTCACCTTCACCATTTCAAGCGTGCAGGCTGAGGATCTGGCAGTCTACTTTTGCCAGCAGCATTTTCG
CACCCCTTTCACCTTTGGAAGCGGGACTAAACTGGAGATTAAGAGGA Amino acid sequence of hinge domain derived from dLNGFR
SEQ ID NO: 79:
LLGVSLGGAKEACPTGLYTHSGECCKACNLGEGVAQPCGANQTVCEPCLDSVTFSDVVSATEPCKPCT
ECVGLQSMSAPCVEADDAVCRCAYGYYQDETTGRCEACRVCEAGSGLVFSCQDKQNTVCEECPDGTYS
DEANHVDPCLPCTVCEDTERQLRECTRWADAECEEIPGRWITRSTPPEGSDSTAPSTQEPEAPPEQDL
IASTVAGVVTTVMGSSQPVVTRGTTDN Amino acid sequence of a transmembrane domain derived from dLNGFR
SEQ ID NO: 80:
LIPVYCSILAAVVVGLVAYIAF Amino acid sequence of an intracellular domain derived from dLNGFR
SEQ ID NO: 81:
KRWNRGIL Amino acid sequence of hinge domain derived from FcγRIIIA
SEQ ID NO: 82:
HENSELLIPKATHNDSGSYFCRGLIGHNNKSSASFRISLGDPGSPSMFPP Amino acid sequence of a transmembrane domain derived from FcγRIIIA
SEQ ID NO: 83:
WHQITFCLLIGLLFAIDTVLYF Amino acid sequence of an intracellular domain derived from FcγRIIIA
SEQ ID NO: 84:
SVRRGLQSPVADYEEPKIQWSKEPQDKTRVD Amino acid sequence of hinge domain derived from FLT3
SEQ ID NO: 85:
PGPFPFIQDN Amino acid sequence of a transmembrane domain derived from FLT3
SEQ ID NO: 86:
ISFYATIGLCLPFIVVLIVLIC

```
Sequence listing
```

Amino acid sequence of an intracellular domain derived from FLT3
SEQ ID NO: 87:
HKYKKQFRYESQLQMIQVTGPLDNEYFYVDFRDYEYDLKWEFPRENLEFGKVLGSGAFGRVMNATAYG
ISKTGVSIQVAVKMLKEKADSCEKEALMSELKMMTHLGHHDNIVNLLGACTLSGPVYLIFEYCCYGDL
LNYLRSKREKFHRTWTEIFKEHNFSFYPTFQAHSNSSMPGSREVQLHPPLDQLSGFNGNLIHSEDEIE
YENQKRLAEEEEEDLNVLTFEDLLCFAYQVAKGMEFLEFKSCVHRDLAARNVLVTHGKVVKICDFGLA
RDILSDSSYVVRGNARLPVKWMAPESLFEGIYTIKSDVWSYGILLWEIFSLGVNPYPGIPVDANFYKL
IQSGFKMEQPFYATEGIYFVMQSCWAFDSRKRPSFPNLTSFLGCQLAEAEEAMYQNMGGNVPEHPSIY
QNRRPLSREAGSEPPSPQAQVKIHGERS Amino acid sequence of hinge domain derived from TLR4
SEQ ID NO: 88:
QLYSLSTLDCSFNRIETSKGILQHFPKSLAFFNLTNNSVACICEHQKFLQWVKEQKQFLVNVEQMTCA
TPVEMNTSLVLDFNNSTCYMYKTIISVSVVS Amino acid sequence of a transmembrane domain derived from TLR4
SEQ ID NO: 89:
VIVVSTVAFLIYHFYFHLILI Amino acid sequence of an intracellular domain derived from TLR4
SEQ ID NO: 90:
AGCKKYSRGESIYDAFVIYSSQNEDWVRNELVKNLEEGVPRFHLCLHYRDFIPGVAIAANIIQEGFHK
SRKVIVVVSRHFIQSRWCIFEYEIAQTWQFLSSRSGIIFIVLEKVEKSLLRQQVELYRLLSRNTYLEW
EDNPLGRHIFWRRLKNALLDGKASNPEQTAEEEQETATWT Amino acid sequence of hinge domain derived from CCR2
SEQ ID NO: 91:
MEDNNMLPQFIHGILSTSHSLFTRSIQELDEGATTPYDYDDGEPCHKTSVKQIGA Amino acid sequence of hinge domain derived from ITGB2
SEQ ID NO: 92:
NARLVECSGRGHCQCNRCICDEGYQPPMCEDCPSCGSHCRDNHTSCAECLKFDKGPFEKNCSVQCAGM
TLQTIPLKKKPCKERDSEGCWITYTLQQKDGRNIYNIHVEDSLECVKGPN Amino acid sequence of a transmembrane domain derived from ITGB2
SEQ ID NO: 93:
VAAIVGGTVVGVVLIGVLLLVIW Amino acid sequence of an intracellular domain derived from ITGB2
SEQ ID NO: 94:
KALTHLTDLREYRRFEKEKLKSQWNNDNPLFKSATTTVMNPKFAES Amino acid sequence of hinge domain derived from CSF2RB
SEQ ID NO: 95:
TQKMAYSFIEHTFQVQYKKKSDSWEDSKTENLDRAHSMDLSQLEPDTSYCARVRVKPISNYDGIWSKW
SEEYTWKTDW Amino acid sequence of a transmembrane domain derived from CSF2RB
SEQ ID NO: 96:
VMPTLWIVLILVFLILTLLLIL Amino acid sequence of an intracellular domain derived from CSF2RB
SEQ ID NO: 97:
RFGCVSVYRTYRKWKEKIPNPSKSLLFQDGGKGLWPPGSMAAFATKNPALQGPQSRLLAEQQGESYAH
LEDNNVSPLTIEDPNIIRVPPSGPDTTPAASSESTEQLPNVQVEGPTPNRPRKQLPSFDFNGPYLGPP
QSHSLPDLPDQLGSPQVGGSLKPALPGSLEYMCLPPGGQAQLVPLSQVMGQGQAMDVQCGSSLETSGS
PSVEPKENPPVELSMEEQEARDNPVTLPISSGGPEGSMMASDYVTPGDPVLTLPTGPLSTSLGPSLGL
PSAQSPRLCLKLPRVPSGSPALGPPGFEDYVELPPSVSQAAKSPPGHPAPPVASSPTVIPGEPREEVG
PASPHPEGLLVLQQVGDYCFLPGLGPGSLSPHSKPPSPSLCSETEDLVQDLSVKKFPYQPMPQAPAIQ
FFKSLKHQDYLSLPPWDNSQSGKVC Amino acid sequence of hinge domain derived from CCR1
SEQ ID NO: 98:
TPCQKTAVRAFGA Amino acid sequence of hinge domain derived from CCR5
SEQ ID NO: 99:
MSAPCQKINVKQIAA Amino acid sequence of hinge domain derived from CXCR4
SEQ ID NO: 100:
FRDENVHFNR Amino acid sequence of hinge domain derived from SELPLG
SEQ ID NO: 101:
IATTDPTAPGTGGTAVGMLSTDSATQWSLTSVETVQPASTEVETSQPAPMEAETSQPAPMEAETSQPA
PMEADTSKPAPTEAETSKPAPTEAETSQPAPNEAETSKPAPTEAETSKPAPTEAETTQLPRIQAVKTL

```
Sequence listing
```

FTTSAATEVPSTEPTTMETASTESNESTIFLGPSVTHLPDSGLKKGLIVTPGNSPAPTLPGSSDLIPV
KQC

Amino acid sequence of a transmembrane domain derived from SELPLG
SEQ ID NO: 102:
LLIILILASLATIFLVCTVVL Amino acid sequence of an intracellular domain derived from SELPLG
SEQ ID NO: 103:
AVRLSRKTHMYPVRNYSPTEMICISSLLPEGGDGAPVTANGGLPKVQDLKTEPSGDRDGDDLTLHSFL
P Amino acid sequence of peptide that facilitates DNA engineering
SEQ ID NO: 104:
TG Nucleic acid sequence of IgK domain (for FRP5 and trastuzumab)
SEQ ID NO: 105:
ATGGATTTTCAGGTGCAGATTTTCTCTTTCCTCCTCATTTCCGCCTCAGTGATTATGTCAAGGGGG Nucleic acid sequence of IgK domain (for pertuzumab)
SEQ ID NO: 106:
ATGGATTTTCAGGTGCAGATTTTCTCCTTTCTCCTCATTTCAGCCAGCGTGATTATGTCTCGGGGG Nucleic acid sequence of a peptide that facilitates DNA engineering
SEQ ID NO: 107:
ACCGGT Nucleic acid sequence of a peptide that facilitates DNA engineering
SEQ ID NO: 108:
ACCGGG Nucleic acid sequence of IgK domain (for EVIR-N1)
SEQ ID NO: 109:
ATGGACTTCCAGGTGCAGATCTTCAGCTTCCTGCTGATCTCCGCCAGCGTGATCATGAGCAGAGGC Nucleic acid sequence of IgK domain (for EVIR-N2)
SEQ ID NO: 110:
ATGGATTTTCAGGTGCAGATCTTCAGCTTCCTGCTGATCTCCGCCAGCGTGATCATGAGCAGAGGC Nucleic acid sequence of anti-TYRP1 scFv TA99
SEQ ID NO: 111:
GACATCCAGATGAGCCAGAGCCCTGCCAGCCTGTCTGCCTCTGTGGGCGAGACAGTGACCATCACCTG
TAGAGCCAGCGGCAACATCTACAACTACCTGGCCTGGTATCAGCAGAAGCAGGGCAAGAGCCCCCATC
TGCTGGTGTACGACGCCAAGACACTGGCCGACGGCGTGCCCTCTAGATTCTCTGGCAGCGGCTCCGGC
ACCCAGTACAGCCTGAAGATCAGCTCCCTGCAGACCGAGGACTCCGGCAACTACTACTGCCAGCACTT
CTGGTCCCTGCCCTTCACCTTCGGCAGCGGCACCAAGCTGGAAATCAAGAGAGGCGGCGGAGGCTCTG
GCGGAGGCGGATCTGGGGGCGGAGGAAGTGGCGGGGGAGGATCTGAAGTGCAGCTGCAGCAGTCTGGC
GCTGAGCTCGTGCGACCTGGCGCTCTCGTGAAGCTGAGCTGCAAGACCAGCGGCTTCAATATCAAGGA
CTACTTCCTGCACTGGGTGCGACAGAGGCCTGACCAGGGCCTGGAATGGATCGGCTGGATCAACCCCG
ACAACGGCAACACCGTGTACGACCCTAAGTTCCAGGGCACCGCCAGCCTGACAGCCGACACAAGCTCC
AACACAGTGTACCTGCAGCTGAGCGGCCTGACCTCCGAGGATACCGCCGTGTACTTCTGCACCAGAAG
AGACTACACCTACGAGAAGGCCGCCCTGGACTACTGGGGCCAGGGAACAACCGTGACCGTGTCC Nucleic acid sequence of anti-GD2 scFv 14G2a
SEQ ID NO: 112:
GAAGTTCAGCTGCTGCAGAGCGGACCCGAACTGGAAAAACCTGGCGCCTCCGTGATGATCAGCTGCAA
GGCCTCTGGCAGCTCCTTCACCGGCTACAACATGAACTGGGTCCGACAGAACATCGGCAAGAGCCTGG
AATGGATCGGCGCCATCGATCCTTACTACGGCGGCACCAGCTACAACCAGAAGTTCAAGGGCAGAGCC
ACACTGACCGTGGACAAGAGCAGCAGCACAGCCTACATGCATCTGAAGTCCCTGACCAGCGAGGACAG
CGCCGTGTACTACTGTGTGTCCGGCATGGAATACTGGGGCCAGGGCACAAGCGTGACAGTCTCTTCTG
GCGGCGGTGGATCTGGCGGAGGCGGAAGTGGTGGCGGCGGATCTGATGTGGTCATGACACAGACCCCT
CTGAGCCTGCCTGTGTCTCTGGGAGATCAGGCCAGCATCAGCTGTAGAAGCAGCCAGAGCCTGGTGCA
CAGAAACGGCAACACCTACCTGCACTGGTATCTGCAGAAGCCCGGCCAGTCTCCTAAGCTGCTGATCC
ACAAGGTGTCCAACAGATTCAGCGGCGTGCCCGACAGATTCTCTGGCTCTGGAAGCGGCACCGACTTC
ACCCTGAAGATTAGCAGAGTGGAAGCCGAGGACCTGGGCGTGTACTTCTGTAGCCAGAGCACACACGT
GCCACCTCTGACATTTGGCGCTGGCACCAAGCTGGAACTG Amino acid sequence of TA99-based anti-TYRP1 scFv
SEQ ID NO: 113:
DIQMSQSPASLSASVGETVTITCRASGNIYNYLAWYQQKQGKSPHLLVYDAKTLADGVPSRFSGSGSG
TQYSLKISSLQTEDSGNYYCQHFWSLPFTFGSGTKLEIKRGGGGSGGGGSGGGGSGGGGSEVQLQQSG
AELVRPGALVKLSCKTSGFNIKDYFLHWVRQRPDQGLEWIGWINPDNGNTVYDPKFQGTASLTADTSS
NTVYLQLSGLTSEDTAVYFCTRRDYTYEKAALDYWGQGTTVTVS

Sequence listing

Amino acid sequence of 14G2a-based anti-GD2 scFv
SEQ ID NO: 114:
EVQLLQSGPELEKPGASVMISCKASGSSFTGYNMNWVRQNIGKSLEWIGAIDPYYGGTSYNQKFKGRA
TLTVDKSSSTAYMHLKSLTSEDSAVYYCVSGMEYWGQGTSVTVSSGGGGSGGGGSGGGGSDVVMTQTP
LSLPVSLGDQASISCRSSQSLVHRNGNTYLHWYLQKPGQSPKLLIHKVSNRFSGVPDRFSGSGSGTDF
TLKISRVEAEDLGVYFCSQSTHVPPLTFGAGTKLEL Nucleic acid sequence of Cxcl9_Fw_XmaI
SEQ ID NO: 115: AAAACCCGGGTCACTCCAACACAGTGACTC Nucleic acid sequence of Cxcl9_Rv_SalI/NheI
SEQ ID NO: 116: AAAAGTCGACGCTAGCCAGGGTGCTTGTTGGTAAAGT Nucleic acid sequence of Cxcl9
SEQ ID NO: 117:
tcactccaacacagtgactcaatagaactcagctctgccatgaagtccgctgttcttttcctcttggg
catcatcttcctggagcagtgtggagttcgaggaaccctagtgataaggaatgcacgatgctcctgca
tcagcaccagccgaggcacgatccactacaaatccctcaaagacctcaaacagtttgccccaagcccc
aattgcaacaaaactgaaatcattgctacactgaagaacggagatcaaacctgcctagatccggactc
ggcaaatgtgaagaagctgatgaaagaatgggaaaagaagatcagccaaaagaaaaagcaaaagaggg
ggaaaaaacatcaaaagaacatgaaaaacagaaaacccaaaacaccccaaagtcgtcgtcgttcaagg
aagactacataagagaccattactttaccaacaagcaccctg Nucleic acid sequence of GM-CSF_Fw_XmaI
SEQ ID NO: 118: AAAACCCGGGCAGAGAGAAAGGCTAAGGTCC Nucleic acid sequence of GM-CSF_Rv_SalI/NheI
SEQ ID NO: 119: AAAAGTCGACGCTAGCAGTCTGAGAAGCTGGATT Nucleic acid sequence of GM-CSF
SEQ ID NO: 120:
CAGAGAGAAAGGCTAAGGTCCTGAGGAGGATGTGGCTGCAGAATTTACTTTTCCTGGGCATTGTGGTC
TACAGCCTCTCAGCACCCACCCGCTCACCCATCACTGTCACCCGGCCTTGGAAGCATGTAGAGGCCAT
CAAAGAAGCCCTGAACCTCCTGGATGACATGCCTGTCACGTTGAATGAAGAGGTAGAAGTCGTCTCTA
ACGAGTTCTCCTTCAAGAAGCTAACATGTGTGCAGACCCGCCTGAAGATATTCGAAGCAGGGTCTACGG
GGCAATTTCACCAAACTCAAGGGCGCCTTGAACATGACAGCCAGCTACTACCAGACATACTGCCCCCC
AACTCCGGAAACGGACTGTGAAACACAAGTTACCACCTATGCGGATTTCATAGACAGCCTTAAAACCT
TTCTGACTGATATCCCCTTTGAATGCAAAAAACCAGGCCAAAAATGAGGAAGCCCAGGCCAGCTCTGA
ATCCAGCTTCTCAGACT Nucleic acid sequence of IFNγ_Fw_XmaI
SEQ ID NO: 121: AAAACCCGGGAGTTCTGGGCTTCTCCTCCT Nucleic acid sequence of IFNγ_Rv_SalI/NheI
SEQ ID NO: 122: AAAAGTCGACGCTAGCGACAATCTCTTCCCCACCCC Nucleic acid sequence of IFNγ
SEQ ID NO: 123:
AGTTCTGGGCTTCTCCTCCTGCGGCCTAGCTCTGAGACAATGAACGCTACACACTGCATCTTGGCTTT
GCAGCTCTTCCTCATGGCTGTTTCTGGCTGTTACTGCCACGGCACAGTCATTGAAAGCCTAGAAAGTC
TGAATAACTATTTTAACTCAAGTGGCATAGATGTGGAAGAAAAGAGTCTCTTCTTGGATATCTGGAGG
AACTGGCAAAAGGATGGTGACATGAAAATCCTGCAGAGCCAGATTATCTCTTTCTACCTCAGACTCTT
TGAAGTCTTGAAAGACAATCAGGCCATCAGCAACAACATAAGCGTCATTGAATCACACCTGATTACTA
CCTTCTTCAGCAACAGCAAGGCGAAAAGGATGCATTCATGAGTATTGCCAAGTTTGAGGTCAACAAC
CCACAGGTCCAGCGCCAAGCATTCAATGAGCTCATCCGAGTGGTCCACCAGCTGTTGCCGGAATCCAG
CCTCAGGAAGCGGAAAAGGAGTCGCTGCTGATTCGGGGTGGGAAGAGATTGTC Nucleic acid sequence of LIN28_Fw_BamHI
SEQ ID NO: 124: AAAAGGATCCCTTTGCCTCCGGACTTCTCTGG Nucleic acid sequence of LIN28_Rv_SalI
SEQ ID NO: 125: AAAAGTCGACAAAGACAGGGTGACACTGGGA Nucleic acid sequence of LIN28 (PstI and SmaI-mouse trophoblast cells)
SEQ ID NO: 126:
CTTTGCCTCCGGACTTCTCTGGGGCCAGCAGCCGCCCGACCTGGGGCCCGGGGCCACGGGCTCAGCAG
ACGACCATGGGCTCGGTGTCCAACCAGCAGTTTGCAGGTGGCTGCGCCAAGGCAGCGGAGAAGGCGCC
AGAGGAGGCGCCGCCTGACGCGGCCCGAGCGGCAGACGAGCCGCAGCTGCTGCACGGGGCCGGCATCT
GTAAGTGGTTCAACGTGCGCATGGGGTTCGGCTTCCTGTCTATGACCGCCCGCGCTGGGGTCGCGCTC
GACCCCCGGTGGACGTCTTTGTGCACCAGAGCAAGCTGCACATGGAAGGGTTCCGAAGCCTCAAGGA
GGGTGAGGCGGTGGAGTTCACCTTTAAGAAGTCTGCCAAGGGTCTGGAATCCATCCGTGTCACTGGCC
CTGGTGGTGTGTTCTGTATTGGAAGTGAGCGGCGGCCAAAGGGGAAGAACATGCAGAAGCGAAGATCC
AAAGGAGACAGGTGCTACAACTGCGGTGGGCTAGACCATCATGCCAAGGAATGCAAGCTGCCACCCCA
GCCCAAGAAGTGCCACTTTTGCCAAAGCATCAACCATATGGTGGCCTCGTGTCCACTGAAGGCCCAGC
AGGGCCCCAGTTCTCAGGGAAAGCCTGCCTACTTCCGGGAGGAAGAGGAAGAGATCCACAGCCCTGCC CTGCTCCCAGAAGCCCAGAATTGAGGCCCAGGAGTCAGGGTTATTCTTTGGCTAATGGGGAGTTTAAG
GAAAGAGGCATCAATCTGCAGAGTGGAGAAAGTGGGGGTAAGGGTGGGTTGCGTGGGTAGCTTGCACT
GCCGTGTCTCAGGCCGGGGTTCCCAGTGTCACCCTGTCTTT Nucleic acid sequence of CD40 (GeneArt CD40 Blunt sites (SmaI-AgeI-
blunted) in AfeI/NheI-blunted bidirectional)
SEQ ID NO: 127:
GCCACCATGGTCTCTCTCCCTCGGCTGTGTGCTCTGTGGGGTTGTCTGCTCACCGCTGTGCATCTCGG
CCAGTGTGTGACTTGTTCTGATAAACAGTACCTGCATGACGGGCAGTGCTGTGATCTGTGCCAGCCCG
GTTCTAGGCTCACCAGTCATTGTACAGCCCTGGAGAAGACTCAGTGCCACCCTTGTGACTCAGGGGAG
TTCAGCGCTCAGTGGAACCGAGAAATTAGGTGCCACCAGCATAGACACTGTGAGCCTAATCAGGGGCT
GCGGGTGAAGAAAGAGGGTACCGCAGAAAGTGACACTGTCTGCACCTGTAAGGAGGGCCAGCATTGCA
CCTCAAAAGATTGCGAAGCTTGTGCACAGCACACACCTTGTATCCCAGGCTTCGGAGTGATGGAGATG
GCTACTGAAACCACAGACACCGTGTGCCACCCATGTCCCGTCGGATTCTTTTCTAACCAGAGCTCCCT
CTTTGAGAAGTGCTATCCATGGACAAGCTGTGAGGATAAGAACCTGGAAGTGCTCCAGAAAGGCACAT
CCCAGACTAATGTCATTTGCGGACTGAAATCTCGGATGCGCGCCCTGCTCGTGATCCCAGTGGTCATG
GGCATCCTCATTACTATCTTCGGAGTGTTTCTGTACATTAAGAAAGTGGTCAAGAAACCCAAGGACAA
CGAGATCCTCCCACCTGCAGCTAGGAGACAGGACCCCCAGGAGATGGAAGATTATCCTGGACATAATA
CAGCAGCCCCAGTGCAGGAAACTCTGCACGGGTGTCAGCCCGTCACCCAGGAGGATGGCAAGGAAAGC
AGAATCTCCGTCCAGGAAAGGCAGGTCACTGATAGCATCGCACTCCGCCCACTCGTCTGA Nucleic acid sequence of anti-HER2 scFv CHA21 (1)
SEQ ID NO: 128:
GATATTGTCCTCACACAGACTCCCAGCTCCCTGCCTGTGTCCGTCGGAGAGAAAGTGACCATGACATG
CAAGTCTAGTCAGACACTGCTCTACTCTAACAATCAGAAGAACTACCTCGCATGGTATCAGCAGAAAC
CAGGACAGAGCCCCAAGCTGCTCATCTCCTGGGCTTTCACCCGGAAATCCGGGGTGCCTGACCGCTTC
ACAGGTAGCGGCTCCGGAACTGATTTTACTCTGACCATTGGATCTGTGAAGGCAGAGGACCTCGCCGT
CTACTATTGCCAGCAGTACAGTAATTATCCATGGACTTTTGGCGGAGGGACCAGGCTGGAAATCAAGA
GAGGTGGAGGAGGGTCCGGTGGAGGAGGGTCTGGTGGAGGAGGGAGTGGTGGAGGAGGGTCAGAGGTG
CAGCTGCAGCAGTCTGGCCCCGAAGTGGTCAAAACTGGAGCTTCAGTCAAAATCAGCTGTAAGGCATC
TGGGTACAGCTTCACCGGCTACTTCATCAACTGGGTGAAGAAAAATTCAGGGAAGAGCCCTGAGTGGA
TCGGCCACATTTCAAGCTCCTACGCCACAAGCACTTACAACCAGAAGTTCAAAAATAAGGCCGCTTTT
ACCGTGGACACATCTAGTTCAACCGCCTTCATGCAGCTGAACTCCCTCACATCTGAAGATAGTGCTGT
GTACTATTGTGTCAGGAGCGGCAACTACGAAGAATATGCTATGGATTACTGGGGGCAGGGGACCTCCG
TGACTGTCTCAAGC Nucleic acid sequence of IgK domain (1)
SEQ ID NO: 129:
ATGGATTTTCAGGTCCAGATTTTCTCCTTCCTCCTCATTTCAGCCAGCGTCATTATGTCTCGGGGG Nucleic acid sequence of EVIR-N1
SEQ ID NO: 130:
ATGGACTTCCAGGTGCAGATCTTCAGCTTCCTGCTGATCTCCGCCAGCGTGATCATGAGCAGAGGCGA
CATCCAGATGAGCCAGAGCCCTGCCAGCCTGTCTGCCTCTGTGGGCGAGACAGTGACCATCACCTGTA
GAGCCAGCGGCAACATCTACAACTACCTGGCCTGGTATCAGCAGAAGCAGGGCAAGAGCCCCCATCTG
CTGGTGTACGACGCCAAGACACTGGCCGACGGCGTGCCCTCTAGATTCTCTGGCAGCGGCTCCGGCAC
CCAGTACAGCCTGAAGATCAGCTCCCTGCAGACCGAGGACTCCGGCAACTACTACTGCCAGCACTTCT
GGTCCCTGCCCTTCACCTTCGGCAGCGGCACCAAGCTGGAAATCAAGAGAGGCGGCGGAGGCTCTGGC
GGAGGCGGATCTGGGGGCGGAGGAAGTGGCGGGGGAGGATCTGAAGTGCAGCTGCAGCAGTCTGGCGC
TGAGCTCGTGCGACCTGGCGCTCTCGTGAAGCTGAGCTGCAAGACCAGCGGCTTCAATATCAAGGACT
ACTTCCTGCACTGGGTGCGACAGAGGCCTGACCAGGGCCTGGAATGGATCGGCTGGATCAACCCCGAC
AACGGCAACACCGTGTACGACCCTAAGTTCCAGGGCACCGCCAGCCTGACAGCCGACACAAGCTCCAA
CACAGTGTACCTGCAGCTGAGCGGCCTGACCTCCGAGGATACCGCCGTGTACTTCTGCACCAGAAGAG
ACTACACCTACGAGAAGGCCGCCCTGGACTACTGGGGCCAGGGAACAACCGTGACCGTGTCCACCGGT
CTTCTGGGGGTGTCCCTTGGAGGTGCCAAGGAGGCATGCCCCACAGGCCTGTACACACACAGCGGTGA
GTGCTGCAAAGCCTGCAACCTGGGCGAGGGTGTGGCCCAGCCTTGTGGAGCCAACCAGACCGTGTGTG
AGCCCTGCCTGGACAGCGTGACGTTCCCGACGTGGTGAGCGCCACAGAGGCCGTGCAAGCCGTGCACC
GAGTGCGTGGGGCTCCAGAGCATGTCGGCGCCGTGCGTGGAGGCCGACGACGCCGTGTGCCGCTGCGC
CTACGGCTACTACCAGGATGAGACGACTGGGCGCTGCAGGCGTGCCGCGTGTGCGAGGCGGGCTCGG
GCCTCGTGTTCTCCTGCCAGGACAAGCAGAACACCGTGTGCGAGGAGTGCCCCGACGGCACGTATTCC
GACGAGGCCAACCACGTGGACCCGTGCCTGCCCTGCACCGTGTGCGAGGACACCGAGCGCCAGCTCCG
CGAGTGCACACGCTGGGCCGACGCCGAGTGCGAGGAGATCCCTGGCCGTTGGATTACACGGTCCACAC
CCCCAGAGGGCTCGGACAGCACAGCCCCAGCACCCAGGAGCCTGAGGCACCTCCAGAACAAGACCTC
ATAGCCAGCACGGTGGCAGGTGTGGTGACCACAGTGATGGGCAGCTCCCAGCCCGTGGTGACCCGAGG
CACCACCGACAACCTCATCCCTGTCTATTGCTCCATCCTGGCTGCTGTGGTTGTGGGCCTTGTGGCCT
ACATAGCCTTCAAGAGGTGGAACAGGGGGATCCTCTAG Nucleic acid sequence of EVIR-N2
SEQ ID NO: 131:
ATGGATTTTCAGGTGCAGATCTTCAGCTTCCTGCTGATCTCCGCCAGCGTGATCATGAGCAGAGGCGA
AGTTCAGCTGCTGCAGAGCGGACCCGAACTGGAAAAACCTGGCGCCTCCGTGATGATCAGCTGCAAGG
CCTCTGGCAGCTCCTTCACCGGCTACAACATGAACTGGGTCCGACAGAACATCGGCAAGAGCCTGGAA
TGGATCGGCGCCATCGATCCTTACTACGGCGGCACCAGCTACAACCAGAAGTTCAAGGGCAGAGCCAC
ACTGACCGTGGACAAGAGCAGCAGCACAGCCTACATGCATCTGAAGTCCCTGACCAGCGAGGACAGCG
CCGTGTACTACTGTGTGTCCGGCATGGAATACTGGGGCCAGGGCACAAGCGTGACAGTCTCTTCTGGC
GGCGGTGGATCTGGCGGAGGCGGAAGTGGTGGCGGCGGATCTGATGTGGTCATGACACAGACCCCTCT
GAGCCTGCCTGTGTCTCTGGGAGATCAGGCCAGCATCAGCTGTAGAAGCAGCCAGAGCCTGGTGCACA

```
GAAACGGCAACACCTACCTGCACTGGTATCTGCAGAAGCCCGGCCAGTCTCCTAAGCTGCTGATCCAC
AAGGTGTCCAACAGATTCAGCGGCGTGCCCGACAGATTCTCTGGCTCTGGAAGCGGCACCGACTTCAC
CCTGAAGATTAGCAGAGTGGAAGCCGAGGACCTGGGCGTGTACTTCTGTAGCCAGAGCACACACGTGC
CACCTCTGACATTTGGCGCTGGCACCAAGCTGGAACTGACCGGTCTTCTGGGGGTGTCCCTTGGAGGT
GCCAAGGAGGCATGCCCCACAGGCCTGTACACACACAGCGGTGAGTGCTGCAAAGCCTGCAACCTGGG
CGAGGGTGTGGCCCAGCCTTGTGGAGCCAACCAGACCGTGTGTGAGCCCTGCCTGGACAGCGTGACGT
TCTCCGACGTGGTGAGCGCGACCGAGCCGTGCAAGCCGTGCACCGAGTGCGTGGGGCTCCAGAGCATG
TCGGCGCCGTGCGTGGAGGCCGACGACGCCGTGTGCCGCTGCGCCTACGGCTACTACCAGGATGAGAC
GACTGGGCGCTGCGAGGCGTGCCGCGTGTGCGAGGCGGGCTCGGGCCTCGTGTTCTCCTGCCAGGACA
AGCAGAACACCGTGTGCGAGGAGTGCCCCGACGGCACGTATTCCGACGAGGCCAACCACGTGGACCCG
TGCCTGCCCTGCACCGTGTGCGAGGACACCGAGCGCCAGCTCCGCGAGTGCACACGCTGGGCCGACGC
CGAGTGCGAGGAGATCCCTGGCCGTTGGATTACACGGTCCACACCCCCAGAGGGCTCGGACAGCACAG
CCCCCAGCACCCAGGAGCCTGAGGCACCTCCAGAACAAGACCTCATAGCCAGCACGGTGGCAGGTGTG
GTGACCACAGTGATGGGCAGCTCCCAGCCCGTGGTGACCCGAGGCACCACCGACAACCTCATCCCTGT
CTATTGCTCCATCCTGGCTGCTGTGGTTGTGGGCCTTGTGGCCTACATAGCCTTCAAGAGGTGGAACA
GGGGGATCCTCTAG

Amino acid sequence of EVIR-N1
SEQ ID NO: 132:
MDFQVQIFSFLLISASVIMSRGDIQMSQSPASLSASVGETVTITCRASGNIYNYLAWYQQKQGKSPHL
LVYDAKTLADGVPSRFSGSGSGTQYSLKISSLQTEDSGNYYCQHFWSLPFTFGSGTKLEIKRGGGGSG
GGGSGGGGSGGGGSEVQLQQSGAELVRPGALVKLSCKTSGFNIKDYFLHWVRQRPDQGLEWIGWINPD
NGNTVYDPKFQGTASLTADTSSNTVYLQLSGLTSEDTAVYFCTRRDYTYEKAALDYWGQGTTVTVSTG
LLGVSLGGAKEACPTGLYTHSGECCKACNLGEGVAQPCGANQTVCEPCLDSVTFSDVVSATEPCKPCT
ECVGLQSMSAPCVEADDAVCRCAYGYYQDETTGRCEACRVCEAGSGLVFSCQDKQNTVCEECPDGTYS
DEANHVDPCLPCTVCEDTERQLRECTRWADAECEEIPGRWITRSTPPEGSDSTAPSTQEPEAPPEQDL
IASTVAGVVTTVMGSSQPVVTRGTTDNLIPVYCSILAAVVVGLVAYIAFKRWNRGIL Amino acid sequence of EVIR-N2
SEQ ID NO: 133:
MDFQVQIFSFLLISASVIMSRGEVQLLQSGPELEKPGASVMISCKASGSSFTGYNMNWVRQNIGKSLE
WIGAIDPYYGGTSYNQKFKGRATLTVDKSSSTAYMHLKSLTSEDSAVYYCVSGMEYWGQGTSVTVSSG
GGGSGGGGSGGGGSDVVMTQTPLSLPVSLGDQASISCRSSQSLVHRNGNTYLHWYLQKPGQSPKLLIH
KVSNRFSGVPDRFSGSGSGTDFTLKISRVEAEDLGVYFCSQSTHVPPLTFGAGTKLELTGLLGVSLGG
AKEACPTGLYTHSGECCKACNLGEGVAQPCGANQTVCEPCLDSVTFSDVVSATEPCKPCTECVGLQSM
SAPCVEADDAVCRCAYGYYQDETTGRCEACRVCEAGSGLVFSCQDKQNTVCEECPDGTYSDEANHVDP
CLPCTVCEDTERQLRECTRWADAECEEIPGRWITRSTPPEGSDSTAPSTQEPEAPPEQDLIASTVAGV
VTTVMGSSQPVVTRGTTDNLIPVYCSILAAVVVGLVAYIAFKRWNRGIL Nucleic acid sequence of TYRP1 Fw
SEQ ID NO: 134: AAAAAAACCGGTGACCTGTGTTCTGAACTCTTGC Nucleic acid sequence of TYRP1 Rv
SEQ ID NO: 135: AAAAAAGTCGACACTGTCATCACTGGAGAGCA Nucleic acid sequence of the anti-B2m gRNA
SEQ ID NO: 136:
GGTCGTCAGCATGGCTCGCTGTTTTAGAGCTAGAAATAGCAAGTTAAAATAAGGCTAGTCCGTTATCA
ACTTGAAAAAGTGGCACCGAGTCGGTGCTTTTTTT

The invention claimed is:

1. A recombinant extra-cellular vesicle internalizing receptor (EVIR) comprising:
   (i) an extracellular antibody domain specific for a membrane molecule of a cancer cell, wherein said membrane molecule is a tumor-associated antigen;
   (ii) a proteinic domain to anchor the EVIR to the membrane of an antigen-presenting cell when expressed in said cell; and
   (iii) optionally, a cell membrane export domain increasing the export of the EVIR to the cellular membrane of an antigen-presenting cell when expressed in said cell, wherein:
   said EVIR comprises an amino acid sequence selected from SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 132 and SEQ ID NO: 133 or a variant thereof, wherein said variant has an amino acid sequence which is at least 90% identical to the original amino acid sequence and which binds to and has specificity for said tumor-associated antigen.

2. The EVIR according to claim 1, comprising an amino acid sequence selected from SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63 and SEQ ID NO: 64 or a variant thereof, wherein said variant has an amino acid sequence which is at least 90% identical to the original amino acid sequence and which binds to and has specificity for said tumor-associated antigen.

3. The EVIR according to claim 1, comprising an amino acid sequence selected from SEQ ID NO: 132 and SEQ ID NO: 133 or a variant thereof, wherein said variant has an amino acid sequence which is at least 90% identical to the original amino acid sequence and which binds to and has specificity for said tumor-associated antigen.

4. An isolated nucleic acid sequence encoding an EVIR according to claim 1.

5. The isolated nucleic acid according to claim 4, said nucleic acid comprising a sequence selected from SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74 and SEQ ID NO: 75 or a variant thereof.

6. The isolated nucleic acid according to claim 4, said nucleic acid comprising a sequence selected from SEQ ID NO: 130 and SEQ ID NO: 131 or a variant thereof.

7. A vector comprising at least one nucleic acid sequence of claim 4.

8. The vector according to claim 7 further comprising at least one nucleic acid encoding for a functional protein that promotes survival, differentiation, proliferation, activation, maturation, phagocytosis, endocytosis, antigen-processing and presentation, T-cell recruitment in monocyte, macrophage and/or dendritic cells or a protein capable of inducing antigen presenting cell (APC) differentiation, survival, activation and/or cross-presentation or attracting and/or activating T cells.

9. A method of inducing expression of at least one EVIR in an antigen-presenting cell (APC) or a stem/progenitor cell thereof ex vivo or in subject in need thereof, comprising the steps of:
   (i) ex vivo transducing said cell with a vector encoding at least one EVIR according to claim 1 or administering a vector comprising a nucleic acid sequence encoding said EVIR to said subject under suitable conditions for inducing transduction of the subject's APCs or stem/progenitor cell thereof in vivo with said vector; and
   (ii) optionally inducing cell differentiation, maturation or activation either ex vivo and\or in vivo.

10. An isolated antigen presenting cell (APC) or a stem or progenitor cell thereof expressing at least one EVIR according to claim 1.

11. An ex vivo method of preparing EVIR-expressing, tumor associated antigens (TAAs)-presenting cells, comprising the steps of:
   (i) providing at least one cancer cell or at least one cancer cell-derived extracellular vesicle (EV) obtained from a cancer subject;
   (ii) providing an EVIR-expressing cell according to claim 10;
   (iii) contacting, ex vivo, an EVIR-expressing cell provided under (ii) with said at least one cancer cell or EV provided under (i); and
   (iv) collecting EVIR-expressing, tumor associated antigens (TAAs)-presenting cells obtained in step (iii).

12. A pharmaceutical composition comprising at least one vector encoding at least one EVIR according to claim 1 or antigen presenting cells (APC) or stem cells or progenitor cell thereof transduced with said at least one vector and at least one pharmaceutically acceptable carrier, diluent or excipient thereof.

13. The pharmaceutical composition according to claim 12, wherein said composition is a vaccine composition.

14. A kit comprising at least one EVIR according to claim 1, or at least one recombinant expression vector comprising a nucleic acid encoding said EVIR or an antigen presenting cell (APC) or a stem cell or progenitor cell thereof expressing said EVIR.

15. A method of treating a cancer, said method comprising administering to a subject in need of treatment:
   a) an effective amount of an isolated antigen presenting cell (APC) or a stem or progenitor cell thereof expressing at least one EVIR according to claim 1; or
   b) at least one recombinant vector comprising a nucleic acid sequence encoding said EVIR.

16. The method according to claim 15, wherein said cancer is a carcinoma, sarcoma, melanoma, brain tumor, hematological cancer, or a pre-malignant or malignant neoplasm.

17. The pharmaceutical composition according to claim 12, said pharmaceutical composition comprising at least one vector encoding at least one EVIR comprising an amino acid sequence selected from SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 132 and SEQ ID NO: 133 or a variant thereof, wherein said variant has an amino acid sequence which is at least 90% identical to the original amino acid sequence and which binds to and has specificity for said tumor-associated antigen and at least one pharmaceutically acceptable carrier, diluent or excipient thereof.

18. The pharmaceutical composition according to claim 12, said pharmaceutical composition comprising an antigen presenting cell (APC) or a stem cell or progenitor cell thereof expressing at least one EVIR, said at least one EVIR comprising an amino acid sequence selected from SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 132, SEQ ID NO: 133 and variants thereof, wherein said variant has an amino acid sequence which is at least 90% identical to the original amino acid sequence and which binds to and has specificity for said tumor-associated antigen and at least one pharmaceutically acceptable carrier, diluent or excipient thereof.

\* \* \* \* \*

```

SEQUENCE LISTING

<160> NUMBER OF SEQ ID NOS: 136

<210> SEQ ID NO 1
<211> LENGTH: 765
<212> TYPE: DNA
<213> ORGANISM: Artificial Sequence
<220> FEATURE:
<223> OTHER INFORMATION: Nucleic acid sequence of anti-HER2 scFv CHA21

<400> SEQUENCE: 1

```
ggggatattg tcctcacaca gactcccagc tccctgcctg tgtccgtcgg agagaaagtg      60
accatgacat gcaagtctag tcagacactg ctctactcta acaatcagaa gaactacctc     120
gcatggtatc agcagaaacc aggacagagc cccaagctgc tcatctcctg ggctttcacc     180
cggaaatccg gggtgcctga ccgcttcaca ggtagcggct ccggaactga ttttactctg     240
accattggat ctgtgaaggc agaggacctc gccgtctact attgccagca gtacagtaat     300
```

```
tatccatgga cttttggcgg agggaccagg ctggaaatca agagaggtgg aggagggtcc      360
ggtggaggag ggtctggtgg aggagggagt ggtggaggag ggtcagaggt gcagctgcag      420
cagtctggcc ccgaagtggt caaaactgga gcttcagtca aaatcagctg taaggcatct      480
gggtacagct tcaccggcta cttcatcaac tgggtgaaga aaaattcagg gaagagccct      540
gagtggatcg gccacatttc aagctcctac gccacaagca cttacaacca gaagttcaaa      600
aataaggccg cttttaccgt ggacacatct agttcaaccg ccttcatgca gctgaactcc      660
ctcacatctg aagatagtgc tgtgtactat tgtgtcagga gcggcaacta cgaagaatat      720
gctatggatt actgggggca ggggacctcc gtgactgtct caagc                     765

<210> SEQ ID NO 2
<211> LENGTH: 63
<212> TYPE: DNA
<213> ORGANISM: Artificial Sequence
<220> FEATURE:
<223> OTHER INFORMATION: Nucleic acid sequence of IgK domain

<400> SEQUENCE: 2
atggattttc aggtccagat tttctccttc ctcctcattt cagccagcgt cattatgtct      60
cgg                                                                    63

<210> SEQ ID NO 3
<211> LENGTH: 12
<212> TYPE: DNA
<213> ORGANISM: Artificial Sequence
<220> FEATURE:
<223> OTHER INFORMATION: Nucleic acid sequence of S5_BamHI_Kozak

<400> SEQUENCE: 3
ggatccgcca cc                                                          12

<210> SEQ ID NO 4
<211> LENGTH: 27
<212> TYPE: DNA
<213> ORGANISM: Artificial Sequence
<220> FEATURE:
<223> OTHER INFORMATION: Nucleic acid sequence of
      S3_BamHI_AgeI_MluI_SalI_stop_XhoI

<400> SEQUENCE: 4
accggtacgc gtgtcgactg actcgag                                          27

<210> SEQ ID NO 5
<211> LENGTH: 21
<212> TYPE: DNA
<213> ORGANISM: Artificial Sequence
<220> FEATURE:
<223> OTHER INFORMATION: Nucleic acid sequence of
      S5_FCgRIIIa_BamHI_Kozak.start_AgeI

<400> SEQUENCE: 5
ggatccgcca ccatgaccgg t                                                21

<210> SEQ ID NO 6
<211> LENGTH: 21
<212> TYPE: DNA
<213> ORGANISM: Artificial Sequence
<220> FEATURE:
<223> OTHER INFORMATION: Nucleic acid sequence of
      S3_FCgRIIIa_MluI_SalI_stop_XhoI

<400> SEQUENCE: 6
```
acgcgtgtcg actgactcga g                                              21

<210> SEQ ID NO 7
<211> LENGTH: 30
<212> TYPE: DNA
<213> ORGANISM: Artificial Sequence
<220> FEATURE:
<223> OTHER INFORMATION: Nucleic acid sequence of dLNGFR_Fw_AgeI

<400> SEQUENCE: 7
aaaaaaccgg tcttctgggg gtgtcccttg                                     30

<210> SEQ ID NO 8
<211> LENGTH: 31
<212> TYPE: DNA
<213> ORGANISM: Artificial Sequence
<220> FEATURE:
<223> OTHER INFORMATION: Nucleic acid sequence of dLNGFR_Rv_MluI

<400> SEQUENCE: 8
aaaaaacgcg tagttagcct cccccatctc c                                   31

<210> SEQ ID NO 9
<211> LENGTH: 32
<212> TYPE: DNA
<213> ORGANISM: Artificial Sequence
<220> FEATURE:
<223> OTHER INFORMATION: Nucleic acid sequence of FLT3_Fw_AgeI

<400> SEQUENCE: 9
aaaaaaccgg tccaggcccc ttcccttcca tc                                  32

<210> SEQ ID NO 10
<211> LENGTH: 31
<212> TYPE: DNA
<213> ORGANISM: Artificial Sequence
<220> FEATURE:
<223> OTHER INFORMATION: Nucleic acid sequence of FLT3_Rv_XhoI

<400> SEQUENCE: 10
aaaaactcga gagaggcgag gctaatcttg g                                   31

<210> SEQ ID NO 11
<211> LENGTH: 32
<212> TYPE: DNA
<213> ORGANISM: Artificial Sequence
<220> FEATURE:
<223> OTHER INFORMATION: Nucleic acid sequence of Tlr4_Fw_AgeI

<400> SEQUENCE: 11
aaaaaaccgg tcagctgtat tccctcagca ct                                  32

<210> SEQ ID NO 12
<211> LENGTH: 31
<212> TYPE: DNA
<213> ORGANISM: Artificial Sequence
<220> FEATURE:
<223> OTHER INFORMATION: Nucleic acid sequence of Tlr4_Rv_SalI

<400> SEQUENCE: 12
aaaaagtcga ctgggtttag gccccagagt t                                   31

<210> SEQ ID NO 13
<211> LENGTH: 36
<212> TYPE: DNA
<213> ORGANISM: Artificial Sequence

```
<220> FEATURE:
<223> OTHER INFORMATION: Nucleic acid sequence of Ccr2_Fw_AgeI

<400> SEQUENCE: 13
aaaaaaccgg tatggaagac aataatatgt tacctc                                36

<210> SEQ ID NO 14
<211> LENGTH: 31
<212> TYPE: DNA
<213> ORGANISM: Artificial Sequence
<220> FEATURE:
<223> OTHER INFORMATION: Nucleic acid sequence of Ccr2_Rv_MluI

<400> SEQUENCE: 14
aaaaaacgcg tatgtacaaa ctgctccctc c                                     31

<210> SEQ ID NO 15
<211> LENGTH: 31
<212> TYPE: DNA
<213> ORGANISM: Artificial Sequence
<220> FEATURE:
<223> OTHER INFORMATION: Nucleic acid sequence of Itgb2_Fw_AgeI

<400> SEQUENCE: 15
aaaaaaccgg taatgcacgg ctggtagagt g                                     31

<210> SEQ ID NO 16
<211> LENGTH: 31
<212> TYPE: DNA
<213> ORGANISM: Artificial Sequence
<220> FEATURE:
<223> OTHER INFORMATION: Nucleic acid sequence of Itgb2_Rv_MluI

<400> SEQUENCE: 16
aaaaaacgcg tgggggtcac atctgcttga t                                     31

<210> SEQ ID NO 17
<211> LENGTH: 36
<212> TYPE: DNA
<213> ORGANISM: Artificial Sequence
<220> FEATURE:
<223> OTHER INFORMATION: Nucleic acid sequence of Csf2rb_Fw_AgeI

<400> SEQUENCE: 17
aaaaaaccgg tactcagaag atggcttact cattca                                36

<210> SEQ ID NO 18
<211> LENGTH: 31
<212> TYPE: DNA
<213> ORGANISM: Artificial Sequence
<220> FEATURE:
<223> OTHER INFORMATION: Nucleic acid sequence of Csf2rb_Rv_MluI

<400> SEQUENCE: 18
aaaaaacgcg ttggtgagat tgggaggaga c                                     31

<210> SEQ ID NO 19
<211> LENGTH: 32
<212> TYPE: DNA
<213> ORGANISM: Artificial Sequence
<220> FEATURE:
<223> OTHER INFORMATION: Nucleic acid sequence of Ccr1_Fw_AgeI

<400> SEQUENCE: 19
aaaaaaccgg tactccatgc caaaagactg ct                                    32
```

```
<210> SEQ ID NO 20
<211> LENGTH: 34
<212> TYPE: DNA
<213> ORGANISM: Artificial Sequence
<220> FEATURE:
<223> OTHER INFORMATION: Nucleic acid sequence of Ccr1_Rv_MluI

<400> SEQUENCE: 20
aaaaaacgcg taccttcctt ggttgacacc tatg                              34

<210> SEQ ID NO 21
<211> LENGTH: 32
<212> TYPE: DNA
<213> ORGANISM: Artificial Sequence
<220> FEATURE:
<223> OTHER INFORMATION: Nucleic acid sequence of Ccr5_Fw_AgeI

<400> SEQUENCE: 21
aaaaaaccgg tatgtcagca ccctgccaaa aa                                32

<210> SEQ ID NO 22
<211> LENGTH: 33
<212> TYPE: DNA
<213> ORGANISM: Artificial Sequence
<220> FEATURE:
<223> OTHER INFORMATION: Nucleic acid sequence of Ccr5_Rv_MluI

<400> SEQUENCE: 22
aaaaaacgcg tcattcctac tcccaagctg cat                               33

<210> SEQ ID NO 23
<211> LENGTH: 31
<212> TYPE: DNA
<213> ORGANISM: Artificial Sequence
<220> FEATURE:
<223> OTHER INFORMATION: Nucleic acid sequence of Cxcr4_Fw_XmaI

<400> SEQUENCE: 23
aaaaacccgg gttccgggat gaaaacgtcc a                                 31

<210> SEQ ID NO 24
<211> LENGTH: 33
<212> TYPE: DNA
<213> ORGANISM: Artificial Sequence
<220> FEATURE:
<223> OTHER INFORMATION: Nucleic acid sequence of Cxcr4_Rv_MluI

<400> SEQUENCE: 24
aaaaaacgcg ttgcataagt gttagctgga gtg                               33

<210> SEQ ID NO 25
<211> LENGTH: 30
<212> TYPE: DNA
<213> ORGANISM: Artificial Sequence
<220> FEATURE:
<223> OTHER INFORMATION: Nucleic acid sequence of Selplg_Fw_AgeI

<400> SEQUENCE: 25
aaaaaaccgg tattgccacc actgacccta                                   30

<210> SEQ ID NO 26
<211> LENGTH: 31
<212> TYPE: DNA
<213> ORGANISM: Artificial Sequence
<220> FEATURE:
<223> OTHER INFORMATION: Nucleic acid sequence of Selplg_Rv_MluI
```

<400> SEQUENCE: 26
aaaaaacgcg tgcaaaggtc tcgcttaggt g                                31

<210> SEQ ID NO 27
<211> LENGTH: 254
<212> TYPE: PRT
<213> ORGANISM: Artificial Sequence
<220> FEATURE:
<223> OTHER INFORMATION: Amino acid sequence of anti-HER2 CHA21

<400> SEQUENCE: 27

```
Asp Ile Val Leu Thr Gln Thr Pro Ser Ser Leu Pro Val Ser Val Gly
1               5                   10                  15

Glu Lys Val Thr Met Thr Cys Lys Ser Ser Gln Thr Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Ser Trp Ala Phe Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Gly Ser Val Lys Ala Glu Asp Leu Ala Val Tyr Tyr Cys Gln Gln
                85                  90                  95

Tyr Ser Asn Tyr Pro Trp Thr Phe Gly Gly Thr Arg Leu Glu Ile
            100                 105                 110

Lys Arg Gly Gly Gly Gly Ser Gly Gly Gly Gly Ser Gly Gly Gly Gly
            115                 120                 125

Ser Gly Gly Gly Gly Ser Glu Val Gln Leu Gln Gln Ser Gly Pro Glu
        130                 135                 140

Val Val Lys Thr Gly Ala Ser Val Lys Ile Ser Cys Lys Ala Ser Gly
145                 150                 155                 160

Tyr Ser Phe Thr Gly Tyr Phe Ile Asn Trp Val Lys Lys Asn Ser Gly
                165                 170                 175

Lys Ser Pro Glu Trp Ile Gly His Ile Ser Ser Ser Tyr Ala Thr Ser
            180                 185                 190

Thr Tyr Asn Gln Lys Phe Lys Asn Lys Ala Ala Phe Thr Val Asp Thr
        195                 200                 205

Ser Ser Ser Thr Ala Phe Met Gln Leu Asn Ser Leu Thr Ser Glu Asp
    210                 215                 220

Ser Ala Val Tyr Tyr Cys Val Arg Ser Gly Asn Tyr Glu Glu Tyr Ala
225                 230                 235                 240

Met Asp Tyr Trp Gly Gln Gly Thr Ser Val Thr Val Ser Ser
                245                 250
```

<210> SEQ ID NO 28
<211> LENGTH: 250
<212> TYPE: PRT
<213> ORGANISM: Artificial Sequence
<220> FEATURE:
<223> OTHER INFORMATION: Amino acid sequence of anti-HER2 trastuzumab-
      based scFv
<220> FEATURE:
<221> NAME/KEY: misc_feature
<222> LOCATION: (250)..(250)
<223> OTHER INFORMATION: Xaa can be any naturally occurring amino acid

<400> SEQUENCE: 28

Asp Ile Gln Met Thr Gln Ser Pro Ser Ser Leu Ser Ala Ser Val Gly

```
              1               5                   10                  15
Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Ser Thr
                100                 105                 110

Ser Gly Ser Gly Lys Pro Gly Ser Gly Glu Gly Ser Glu Val Gln Leu
                115                 120                 125

Val Glu Ser Gly Gly Gly Leu Val Gln Pro Gly Gly Ser Leu Arg Leu
130                 135                 140

Ser Cys Ala Ala Ser Gly Phe Asn Ile Lys Asp Thr Tyr Ile His Trp
145                 150                 155                 160

Val Arg Gln Ala Pro Gly Lys Gly Leu Glu Trp Val Ala Arg Ile Tyr
                165                 170                 175

Pro Thr Asn Gly Tyr Thr Arg Tyr Ala Asp Ser Val Lys Gly Arg Phe
                180                 185                 190

Thr Ile Ser Ala Asp Thr Ser Lys Asn Thr Ala Tyr Leu Gln Met Asn
                195                 200                 205

Ser Leu Arg Ala Glu Asp Thr Ala Val Tyr Tyr Cys Ser Arg Trp Gly
                210                 215                 220

Gly Asp Gly Phe Tyr Ala Met Asp Val Trp Gly Gln Gly Thr Leu Val
225                 230                 235                 240

Thr Val Ser Ser Gly Thr Gly Thr Arg Xaa
                245                 250

<210> SEQ ID NO 29
<211> LENGTH: 242
<212> TYPE: PRT
<213> ORGANISM: Artificial Sequence
<220> FEATURE:
<223> OTHER INFORMATION: Amino acid sequence of anti-HER2 pertuzumab-
      based scFv

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
                35                  40                  45

Tyr Ser Ala Ser Tyr Arg Tyr Thr Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
                100                 105                 110
```

```
Pro Gly Gly Gly Gly Ser Gly Gly Gly Ser Gly Gly Gly Ser
            115                 120                 125

Gly Gly Gly Gly Ser Glu Val Gln Leu Val Glu Ser Gly Gly Gly Leu
            130                 135                 140

Val Gln Pro Gly Gly Ser Leu Arg Leu Ser Cys Ala Ala Ser Gly Phe
145                 150                 155                 160

Thr Phe Thr Asp Tyr Thr Met Asp Trp Val Arg Gln Ala Pro Gly Lys
                165                 170                 175

Gly Leu Glu Trp Val Ala Asp Val Asn Pro Asn Ser Gly Gly Ser Ile
                180                 185                 190

Tyr Asn Gln Arg Phe Lys Gly Arg Phe Thr Leu Ser Val Asp Arg Ser
            195                 200                 205

Lys Asn Thr Leu Tyr Leu Gln Met Asn Ser Leu Arg Ala Glu Asp Thr
210                 215                 220

Ala Val Tyr Tyr Cys Ala Arg Asn Leu Gly Pro Ser Phe Tyr Phe Asp
225                 230                 235                 240

Tyr Trp

<210> SEQ ID NO 30
<211> LENGTH: 243
<212> TYPE: PRT
<213> ORGANISM: Artificial Sequence
<220> FEATURE:
<223> OTHER INFORMATION: Amino acid sequence of anti-HER2 FRP5-based
      scFv
<220> FEATURE:
<221> NAME/KEY: misc_feature
<222> LOCATION: (243)..(243)
<223> OTHER INFORMATION: Xaa can be any naturally occurring amino acid

<400> SEQUENCE: 30

Gln Val Gln Leu Gln Gln Ser Gly Pro Glu Leu Lys Lys Pro Gly Glu
1               5                   10                  15

Thr Val Lys Ile Ser Cys Lys Ala Ser Gly Tyr Pro Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Ser Thr Gly Glu Ser Thr Phe Ala Asp Asp Phe
    50                  55                  60

Lys Gly Arg Phe Asp Phe Ser Leu Glu Thr Ser Ala Asn Thr Ala Tyr
65                  70                  75                  80

Leu Gln Ile Asn Asn Leu Lys Ser Glu Asp Met Ala Thr Tyr Phe Cys
                85                  90                  95

Ala Arg Trp Glu Val Tyr His Gly Tyr Val Pro Tyr Trp Gly Gln Gly
            100                 105                 110

Thr Thr Val Thr Val Ser Ser Gly Gly Gly Gly Ser Gly Gly Gly Gly
            115                 120                 125

Ser Gly Gly Gly Gly Ser Asp Ile Gln Leu Thr Gln Ser His Lys Phe
        130                 135                 140

Leu Ser Thr Ser Val Gly Asp Arg Val Ser Ile Thr Cys Lys Ala Ser
145                 150                 155                 160

Gln Asp Val Tyr Asn Ala Val Ala Trp Tyr Gln Gln Lys Pro Gly Gln
                165                 170                 175

Ser Pro Lys Leu Leu Ile Tyr Ser Ala Ser Ser Arg Tyr Thr Gly Val
            180                 185                 190

Pro Ser Arg Phe Thr Gly Ser Gly Ser Gly Pro Asp Phe Thr Phe Thr
        195                 200                 205
```

```
Ile Ser Ser Val Gln Ala Glu Asp Leu Ala Val Tyr Phe Cys Gln Gln
    210                 215                 220
His Phe Arg Thr Pro Phe Thr Phe Gly Ser Gly Thr Lys Leu Glu Ile
225                 230                 235                 240

Lys Arg Xaa

<210> SEQ ID NO 31
<211> LENGTH: 261
<212> TYPE: PRT
<213> ORGANISM: Artificial Sequence
<220> FEATURE:
<223> OTHER INFORMATION: Amino acid sequence of proteinic domain derived
      from dLNGFR

<400> SEQUENCE: 31

Leu Leu Gly Val Ser Leu Gly Gly Ala Lys Glu Ala Cys Pro Thr Gly
1               5                   10                  15
Leu Tyr Thr His Ser Gly Glu Cys Cys Lys Ala Cys Asn Leu Gly Glu
                20                  25                  30
Gly Val Ala Gln Pro Cys Gly Ala Asn Gln Thr Val Cys Glu Pro Cys
            35                  40                  45
Leu Asp Ser Val Thr Phe Ser Asp Val Val Ser Ala Thr Glu Pro Cys
    50                  55                  60
Lys Pro Cys Thr Glu Cys Val Gly Leu Gln Ser Met Ser Ala Pro Cys
65                  70                  75                  80
Val Glu Ala Asp Asp Ala Val Cys Arg Cys Ala Tyr Gly Tyr Tyr Gln
                85                  90                  95
Asp Glu Thr Thr Gly Arg Cys Glu Ala Cys Arg Val Cys Glu Ala Gly
            100                 105                 110
Ser Gly Leu Val Phe Ser Cys Gln Asp Lys Gln Asn Thr Val Cys Glu
        115                 120                 125
Glu Cys Pro Asp Gly Thr Tyr Ser Asp Glu Ala Asn His Val Asp Pro
130                 135                 140
Cys Leu Pro Cys Thr Val Cys Glu Asp Thr Glu Arg Gln Leu Arg Glu
145                 150                 155                 160
Cys Thr Arg Trp Ala Asp Ala Glu Cys Glu Glu Ile Pro Gly Arg Trp
                165                 170                 175
Ile Thr Arg Ser Thr Pro Pro Glu Gly Ser Asp Ser Thr Ala Pro Ser
            180                 185                 190
Thr Gln Glu Pro Glu Ala Pro Pro Glu Gln Asp Leu Ile Ala Ser Thr
        195                 200                 205
Val Ala Gly Val Val Thr Thr Val Met Gly Ser Ser Gln Pro Val Val
    210                 215                 220
Thr Arg Gly Thr Thr Asp Asn Leu Ile Pro Val Tyr Cys Ser Ile Leu
225                 230                 235                 240
Ala Ala Val Val Val Gly Leu Val Ala Tyr Ile Ala Phe Lys Arg Trp
                245                 250                 255
Asn Arg Gly Ile Leu
            260

<210> SEQ ID NO 32
<211> LENGTH: 103
<212> TYPE: PRT
<213> ORGANISM: Artificial Sequence
<220> FEATURE:
<223> OTHER INFORMATION: Amino acid sequence of proteinic domain derived
      from FcgRIIIA
```

<400> SEQUENCE: 32

```
His Glu Asn Ser Glu Leu Leu Ile Pro Lys Ala Thr His Asn Asp Ser
1               5                   10                  15

Gly Ser Tyr Phe Cys Arg Gly Leu Ile Gly His Asn Asn Lys Ser Ser
            20                  25                  30

Ala Ser Phe Arg Ile Ser Leu Gly Asp Pro Gly Ser Pro Ser Met Phe
        35                  40                  45

Pro Pro Trp His Gln Ile Thr Phe Cys Leu Leu Ile Gly Leu Leu Phe
50                  55                  60

Ala Ile Asp Thr Val Leu Tyr Phe Ser Val Arg Arg Gly Leu Gln Ser
65                  70                  75                  80

Pro Val Ala Asp Tyr Glu Glu Pro Lys Ile Gln Trp Ser Lys Glu Pro
                85                  90                  95

Gln Asp Lys Thr Arg Val Asp
            100
```

<210> SEQ ID NO 33
<211> LENGTH: 468
<212> TYPE: PRT
<213> ORGANISM: Artificial Sequence
<220> FEATURE:
<223> OTHER INFORMATION: Amino acid sequence of proteinic domain derived from FLT3

<400> SEQUENCE: 33

```
Pro Gly Pro Phe Pro Phe Ile Gln Asp Asn Ile Ser Phe Tyr Ala Thr
1               5                   10                  15

Ile Gly Leu Cys Leu Pro Phe Ile Val Val Leu Ile Val Leu Ile Cys
            20                  25                  30

His Lys Tyr Lys Lys Gln Phe Arg Tyr Glu Ser Gln Leu Gln Met Ile
        35                  40                  45

Gln Val Thr Gly Pro Leu Asp Asn Glu Tyr Phe Tyr Val Asp Phe Arg
    50                  55                  60

Asp Tyr Glu Tyr Asp Leu Lys Trp Glu Phe Pro Arg Glu Asn Leu Glu
65                  70                  75                  80

Phe Gly Lys Val Leu Gly Ser Gly Ala Phe Gly Arg Val Met Asn Ala
                85                  90                  95

Thr Ala Tyr Gly Ile Ser Lys Thr Gly Val Ser Ile Gln Val Ala Val
            100                 105                 110

Lys Met Leu Lys Glu Lys Ala Asp Ser Cys Glu Lys Glu Ala Leu Met
        115                 120                 125

Ser Glu Leu Lys Met Met Thr His Leu Gly His His Asp Asn Ile Val
    130                 135                 140

Asn Leu Leu Gly Ala Cys Thr Leu Ser Gly Pro Val Tyr Leu Ile Phe
145                 150                 155                 160

Glu Tyr Cys Cys Tyr Gly Asp Leu Leu Asn Tyr Leu Arg Ser Lys Arg
                165                 170                 175

Glu Lys Phe His Arg Thr Trp Thr Glu Ile Phe Lys Glu His Asn Phe
            180                 185                 190

Ser Phe Tyr Pro Thr Phe Gln Ala His Ser Asn Ser Ser Met Pro Gly
        195                 200                 205

Ser Arg Glu Val Gln Leu His Pro Pro Leu Asp Gln Leu Ser Gly Phe
    210                 215                 220

Asn Gly Asn Leu Ile His Ser Glu Asp Glu Ile Glu Tyr Glu Asn Gln
225                 230                 235                 240
```

Lys Arg Leu Ala Glu Glu Glu Glu Asp Leu Asn Val Leu Thr Phe
            245                 250                 255

Glu Asp Leu Leu Cys Phe Ala Tyr Gln Val Ala Lys Gly Met Glu Phe
        260                 265                 270

Leu Glu Phe Lys Ser Cys Val His Arg Asp Leu Ala Ala Arg Asn Val
        275                 280                 285

Leu Val Thr His Gly Lys Val Val Lys Ile Cys Asp Phe Gly Leu Ala
        290                 295                 300

Arg Asp Ile Leu Ser Asp Ser Ser Tyr Val Val Arg Gly Asn Ala Arg
305                 310                 315                 320

Leu Pro Val Lys Trp Met Ala Pro Glu Ser Leu Phe Glu Gly Ile Tyr
                325                 330                 335

Thr Ile Lys Ser Asp Val Trp Ser Tyr Gly Ile Leu Leu Trp Glu Ile
            340                 345                 350

Phe Ser Leu Gly Val Asn Pro Tyr Pro Gly Ile Pro Val Asp Ala Asn
        355                 360                 365

Phe Tyr Lys Leu Ile Gln Ser Gly Phe Lys Met Glu Gln Pro Phe Tyr
    370                 375                 380

Ala Thr Glu Gly Ile Tyr Phe Val Met Gln Ser Cys Trp Ala Phe Asp
385                 390                 395                 400

Ser Arg Lys Arg Pro Ser Phe Pro Asn Leu Thr Ser Phe Leu Gly Cys
                405                 410                 415

Gln Leu Ala Glu Ala Glu Glu Ala Met Tyr Gln Asn Met Gly Gly Asn
            420                 425                 430

Val Pro Glu His Pro Ser Ile Tyr Gln Asn Arg Arg Pro Leu Ser Arg
        435                 440                 445

Glu Ala Gly Ser Glu Pro Pro Ser Pro Gln Ala Gln Val Lys Ile His
    450                 455                 460

Gly Glu Arg Ser
465

<210> SEQ ID NO 34
<211> LENGTH: 296
<212> TYPE: PRT
<213> ORGANISM: Artificial Sequence
<220> FEATURE:
<223> OTHER INFORMATION: Amino acid sequence of proteinic domain derived
      from TLR4

<400> SEQUENCE: 34

Gln Leu Tyr Ser Leu Ser Thr Leu Asp Cys Ser Phe Asn Arg Ile Glu
1               5                   10                  15

Thr Ser Lys Gly Ile Leu Gln His Phe Pro Lys Ser Leu Ala Phe Phe
            20                  25                  30

Asn Leu Thr Asn Asn Ser Val Ala Cys Ile Cys Glu His Gln Lys Phe
        35                  40                  45

Leu Gln Trp Val Lys Glu Gln Lys Gln Phe Leu Val Asn Val Glu Gln
    50                  55                  60

Met Thr Cys Ala Thr Pro Val Glu Met Asn Thr Ser Leu Val Leu Asp
65                  70                  75                  80

Phe Asn Asn Ser Thr Cys Tyr Met Tyr Lys Thr Ile Ile Ser Val Ser
                85                  90                  95

Val Val Ser Val Ile Val Val Ser Thr Val Ala Phe Leu Ile Tyr His
            100                 105                 110

Phe Tyr Phe His Leu Ile Leu Ile Ala Gly Cys Lys Lys Tyr Ser Arg

```
            115                 120                 125
Gly Glu Ser Ile Tyr Asp Ala Phe Val Ile Tyr Ser Ser Gln Asn Glu
    130                 135                 140

Asp Trp Val Arg Asn Glu Leu Val Lys Asn Leu Glu Glu Gly Val Pro
145                 150                 155                 160

Arg Phe His Leu Cys Leu His Tyr Arg Asp Phe Ile Pro Gly Val Ala
                165                 170                 175

Ile Ala Ala Asn Ile Ile Gln Glu Gly Phe His Lys Ser Arg Lys Val
            180                 185                 190

Ile Val Val Ser Arg His Phe Ile Gln Ser Arg Trp Cys Ile Phe
        195                 200                 205

Glu Tyr Glu Ile Ala Gln Thr Trp Gln Phe Leu Ser Ser Arg Ser Gly
    210                 215                 220

Ile Ile Phe Ile Val Leu Glu Lys Val Glu Lys Ser Leu Leu Arg Gln
225                 230                 235                 240

Gln Val Glu Leu Tyr Arg Leu Leu Ser Arg Asn Thr Tyr Leu Glu Trp
                245                 250                 255

Glu Asp Asn Pro Leu Gly Arg His Ile Phe Trp Arg Arg Leu Lys Asn
            260                 265                 270

Ala Leu Leu Asp Gly Lys Ala Ser Asn Pro Glu Gln Thr Ala Glu Glu
        275                 280                 285

Glu Gln Glu Thr Ala Thr Trp Thr
    290                 295

<210> SEQ ID NO 35
<211> LENGTH: 373
<212> TYPE: PRT
<213> ORGANISM: Artificial Sequence
<220> FEATURE:
<223> OTHER INFORMATION: Amino acid sequence of proteinic domain derived
      from CCR2

<400> SEQUENCE: 35

Met Glu Asp Asn Asn Met Leu Pro Gln Phe Ile His Gly Ile Leu Ser
1               5                   10                  15

Thr Ser His Ser Leu Phe Thr Arg Ser Ile Gln Glu Leu Asp Glu Gly
            20                  25                  30

Ala Thr Thr Pro Tyr Asp Tyr Asp Asp Gly Glu Pro Cys His Lys Thr
        35                  40                  45

Ser Val Lys Gln Ile Gly Ala Trp Ile Leu Pro Pro Leu Tyr Ser Leu
    50                  55                  60

Val Phe Ile Phe Gly Phe Val Gly Asn Met Leu Val Ile Ile Ile Leu
65                  70                  75                  80

Ile Gly Cys Lys Lys Leu Lys Ser Met Thr Asp Ile Tyr Leu Leu Asn
                85                  90                  95

Leu Ala Ile Ser Asp Leu Leu Phe Leu Thr Leu Pro Phe Trp Ala
            100                 105                 110

His Tyr Ala Ala Asn Glu Trp Val Phe Gly Asn Ile Met Cys Lys Val
        115                 120                 125

Phe Thr Gly Leu Tyr His Ile Gly Tyr Phe Gly Gly Ile Phe Phe Ile
    130                 135                 140

Ile Leu Leu Thr Ile Asp Arg Tyr Leu Ala Ile Val His Ala Val Phe
145                 150                 155                 160

Ala Leu Lys Ala Arg Thr Val Thr Phe Gly Val Ile Thr Ser Val Val
                165                 170                 175
```

Thr Trp Val Val Ala Val Phe Ala Ser Leu Pro Gly Ile Ile Phe Thr
            180                 185                 190

Lys Ser Lys Gln Asp Asp His His Tyr Thr Cys Gly Pro Tyr Phe Thr
        195                 200                 205

Gln Leu Trp Lys Asn Phe Gln Thr Ile Met Arg Asn Ile Leu Ser Leu
    210                 215                 220

Ile Leu Pro Leu Leu Val Met Val Ile Cys Tyr Ser Gly Ile Leu His
225                 230                 235                 240

Thr Leu Phe Arg Cys Arg Asn Glu Lys Lys Arg His Arg Ala Val Arg
            245                 250                 255

Leu Ile Phe Ala Ile Met Ile Val Tyr Phe Leu Phe Trp Thr Pro Tyr
        260                 265                 270

Asn Ile Val Leu Phe Leu Thr Thr Phe Gln Glu Ser Leu Gly Met Ser
    275                 280                 285

Asn Cys Val Ile Asp Lys His Leu Asp Gln Ala Met Gln Val Thr Glu
    290                 295                 300

Thr Leu Gly Met Thr His Cys Cys Ile Asn Pro Val Ile Tyr Ala Phe
305                 310                 315                 320

Val Gly Glu Lys Phe Arg Arg Tyr Leu Ser Ile Phe Phe Arg Lys His
            325                 330                 335

Ile Ala Lys Arg Leu Cys Lys Gln Cys Pro Val Phe Tyr Arg Glu Thr
        340                 345                 350

Ala Asp Arg Val Ser Ser Thr Phe Thr Pro Ser Thr Gly Glu Gln Glu
            355                 360                 365

Val Ser Val Gly Leu
        370

<210> SEQ ID NO 36
<211> LENGTH: 187
<212> TYPE: PRT
<213> ORGANISM: Artificial Sequence
<220> FEATURE:
<223> OTHER INFORMATION: Amino acid sequence of proteinic domain derived
      from ITGB2

<400> SEQUENCE: 36

Asn Ala Arg Leu Val Glu Cys Ser Gly Arg Gly His Cys Gln Cys Asn
1               5                   10                  15

Arg Cys Ile Cys Asp Glu Gly Tyr Gln Pro Pro Met Cys Glu Asp Cys
            20                  25                  30

Pro Ser Cys Gly Ser His Cys Arg Asp Asn His Thr Ser Cys Ala Glu
        35                  40                  45

Cys Leu Lys Phe Asp Lys Gly Pro Phe Glu Lys Asn Cys Ser Val Gln
    50                  55                  60

Cys Ala Gly Met Thr Leu Gln Thr Ile Pro Leu Lys Lys Lys Pro Cys
65                  70                  75                  80

Lys Glu Arg Asp Ser Glu Gly Cys Trp Ile Thr Tyr Thr Leu Gln Gln
            85                  90                  95

Lys Asp Gly Arg Asn Ile Tyr Asn Ile His Val Glu Asp Ser Leu Glu
        100                 105                 110

Cys Val Lys Gly Pro Asn Val Ala Ala Ile Val Gly Gly Thr Val Val
    115                 120                 125

Gly Val Val Leu Ile Gly Val Leu Leu Leu Val Ile Trp Lys Ala Leu
130                 135                 140

Thr His Leu Thr Asp Leu Arg Glu Tyr Arg Arg Phe Glu Lys Glu Lys
145                 150                 155                 160

Leu Lys Ser Gln Trp Asn Asn Asp Asn Pro Leu Phe Lys Ser Ala Thr
            165                 170                 175

Thr Thr Val Met Asn Pro Lys Phe Ala Glu Ser
            180                 185

<210> SEQ ID NO 37
<211> LENGTH: 533
<212> TYPE: PRT
<213> ORGANISM: Artificial Sequence
<220> FEATURE:
<223> OTHER INFORMATION: Amino acid sequence of proteinic domain derived
      from CSF2RB

<400> SEQUENCE: 37

Thr Gln Lys Met Ala Tyr Ser Phe Ile Glu His Thr Phe Gln Val Gln
1               5                   10                  15

Tyr Lys Lys Lys Ser Asp Ser Trp Glu Asp Ser Lys Thr Glu Asn Leu
            20                  25                  30

Asp Arg Ala His Ser Met Asp Leu Ser Gln Leu Glu Pro Asp Thr Ser
        35                  40                  45

Tyr Cys Ala Arg Val Arg Val Lys Pro Ile Ser Asn Tyr Asp Gly Ile
    50                  55                  60

Trp Ser Lys Trp Ser Glu Glu Tyr Thr Trp Lys Thr Asp Trp Val Met
65                  70                  75                  80

Pro Thr Leu Trp Ile Val Leu Ile Leu Val Phe Leu Ile Leu Thr Leu
                85                  90                  95

Leu Leu Ile Leu Arg Phe Gly Cys Val Ser Val Tyr Arg Thr Tyr Arg
            100                 105                 110

Lys Trp Lys Glu Lys Ile Pro Asn Pro Ser Lys Ser Leu Leu Phe Gln
        115                 120                 125

Asp Gly Gly Lys Gly Leu Trp Pro Pro Gly Ser Met Ala Ala Phe Ala
    130                 135                 140

Thr Lys Asn Pro Ala Leu Gln Gly Pro Gln Ser Arg Leu Leu Ala Glu
145                 150                 155                 160

Gln Gln Gly Glu Ser Tyr Ala His Leu Glu Asp Asn Asn Val Ser Pro
                165                 170                 175

Leu Thr Ile Glu Asp Pro Asn Ile Ile Arg Val Pro Pro Ser Gly Pro
            180                 185                 190

Asp Thr Thr Pro Ala Ala Ser Ser Glu Ser Thr Gln Leu Pro Asn
        195                 200                 205

Val Gln Val Glu Gly Pro Thr Pro Asn Arg Pro Arg Lys Gln Leu Pro
    210                 215                 220

Ser Phe Asp Phe Asn Gly Pro Tyr Leu Gly Pro Pro Gln Ser His Ser
225                 230                 235                 240

Leu Pro Asp Leu Pro Asp Gln Leu Gly Ser Pro Gln Val Gly Gly Ser
                245                 250                 255

Leu Lys Pro Ala Leu Pro Gly Ser Leu Glu Tyr Met Cys Leu Pro Pro
            260                 265                 270

Gly Gly Gln Ala Gln Leu Val Pro Leu Ser Gln Val Met Gly Gln Gly
        275                 280                 285

Gln Ala Met Asp Val Gln Cys Gly Ser Ser Leu Glu Thr Ser Gly Ser
    290                 295                 300

Pro Ser Val Glu Pro Lys Glu Asn Pro Val Glu Leu Ser Met Glu
305                 310                 315                 320

Glu Gln Glu Ala Arg Asp Asn Pro Val Thr Leu Pro Ile Ser Ser Gly

```
                    325                 330                 335
Gly Pro Glu Gly Ser Met Met Ala Ser Asp Tyr Val Thr Pro Gly Asp
            340                 345                 350
Pro Val Leu Thr Leu Pro Thr Gly Pro Leu Ser Thr Ser Leu Gly Pro
            355                 360                 365
Ser Leu Gly Leu Pro Ser Ala Gln Ser Pro Arg Leu Cys Leu Lys Leu
            370                 375                 380
Pro Arg Val Pro Ser Gly Ser Pro Ala Leu Gly Pro Pro Gly Phe Glu
385                 390                 395                 400
Asp Tyr Val Glu Leu Pro Pro Ser Val Ser Gln Ala Ala Lys Ser Pro
                    405                 410                 415
Pro Gly His Pro Ala Pro Pro Val Ala Ser Ser Pro Thr Val Ile Pro
                    420                 425                 430
Gly Glu Pro Arg Glu Glu Val Gly Pro Ala Ser Pro His Pro Glu Gly
                    435                 440                 445
Leu Leu Val Leu Gln Gln Val Gly Asp Tyr Cys Phe Leu Pro Gly Leu
            450                 455                 460
Gly Pro Gly Ser Leu Ser Pro His Ser Lys Pro Pro Ser Pro Ser Leu
465                 470                 475                 480
Cys Ser Glu Thr Glu Asp Leu Val Gln Asp Leu Ser Val Lys Lys Phe
                    485                 490                 495
Pro Tyr Gln Pro Met Pro Gln Ala Pro Ala Ile Gln Phe Phe Lys Ser
                    500                 505                 510
Leu Lys His Gln Asp Tyr Leu Ser Leu Pro Pro Trp Asp Asn Ser Gln
                    515                 520                 525
Ser Gly Lys Val Cys
            530

<210> SEQ ID NO 38
<211> LENGTH: 334
<212> TYPE: PRT
<213> ORGANISM: Artificial Sequence
<220> FEATURE:
<223> OTHER INFORMATION: Amino acid sequence of proteinic domain derived
      from CCR1

<400> SEQUENCE: 38

Thr Pro Cys Gln Lys Thr Ala Val Arg Ala Phe Gly Ala Gly Leu Leu
1               5                   10                  15
Pro Pro Leu Tyr Ser Leu Val Phe Ile Ile Gly Val Val Gly Asn Val
                    20                  25                  30
Leu Val Ile Leu Val Leu Met Gln His Arg Arg Leu Gln Ser Met Thr
            35                  40                  45
Ser Ile Tyr Leu Phe Asn Leu Ala Val Ser Asp Leu Val Phe Leu Phe
    50                  55                  60
Thr Leu Pro Phe Trp Ile Asp Tyr Lys Leu Lys Asp Asp Trp Ile Phe
65                  70                  75                  80
Gly Asp Ala Met Cys Lys Leu Leu Ser Gly Phe Tyr Tyr Leu Gly Leu
                85                  90                  95
Tyr Ser Glu Ile Phe Phe Ile Ile Leu Leu Thr Ile Asp Arg Tyr Leu
                    100                 105                 110
Ala Ile Val His Ala Val Phe Ala Leu Arg Ala Arg Thr Val Thr Phe
            115                 120                 125
Gly Ile Ile Thr Ser Ile Ile Thr Trp Ala Leu Ala Ile Leu Ala Ser
    130                 135                 140
```

```
Met Pro Ala Leu Tyr Phe Lys Ala Gln Trp Glu Phe Thr His Arg
145                 150                 155                 160

Thr Cys Ser Pro His Phe Pro Tyr Lys Ser Leu Lys Gln Trp Lys Arg
                165                 170                 175

Phe Gln Ala Leu Lys Leu Asn Leu Leu Gly Leu Ile Leu Pro Leu Leu
                180                 185                 190

Val Met Ile Ile Cys Tyr Ala Gly Ile Ile Arg Ile Leu Leu Arg Arg
                195                 200                 205

Pro Ser Glu Lys Lys Val Lys Ala Val Arg Leu Ile Phe Ala Ile Thr
210                 215                 220

Leu Leu Phe Phe Leu Leu Trp Thr Pro Tyr Asn Leu Ser Val Phe Val
225                 230                 235                 240

Ser Ala Phe Gln Asp Val Leu Phe Thr Asn Gln Cys Glu Gln Ser Lys
                245                 250                 255

Gln Leu Asp Leu Ala Met Gln Val Thr Glu Val Ile Ala Tyr Thr His
                260                 265                 270

Cys Cys Val Asn Pro Ile Ile Tyr Val Phe Val Gly Glu Arg Phe Trp
                275                 280                 285

Lys Tyr Leu Arg Gln Leu Phe Gln Arg His Val Ala Ile Pro Leu Ala
                290                 295                 300

Lys Trp Leu Pro Phe Leu Ser Val Asp Gln Leu Glu Arg Thr Ser Ser
305                 310                 315                 320

Ile Ser Pro Ser Thr Gly Glu His Glu Leu Ser Ala Gly Phe
                325                 330

<210> SEQ ID NO 39
<211> LENGTH: 337
<212> TYPE: PRT
<213> ORGANISM: Artificial Sequence
<220> FEATURE:
<223> OTHER INFORMATION: Amino acid sequence of proteinic domain derived
      from CCR5

<400> SEQUENCE: 39

Met Ser Ala Pro Cys Gln Lys Ile Asn Val Lys Gln Ile Ala Ala Gln
1               5                   10                  15

Leu Leu Pro Pro Leu Tyr Ser Leu Val Phe Ile Phe Gly Phe Val Gly
                20                  25                  30

Asn Met Met Val Phe Leu Ile Leu Ile Ser Cys Lys Lys Leu Lys Ser
                35                  40                  45

Val Thr Asp Ile Tyr Leu Leu Asn Leu Ala Ile Ser Asp Leu Leu Phe
50                  55                  60

Leu Leu Thr Leu Pro Phe Trp Ala His Tyr Ala Ala Asn Glu Trp Val
65                  70                  75                  80

Phe Gly Asn Ile Met Cys Lys Val Phe Thr Gly Leu Tyr His Ile Gly
                85                  90                  95

Tyr Phe Gly Gly Ile Phe Phe Ile Ile Leu Leu Thr Ile Asp Arg Tyr
                100                 105                 110

Leu Ala Ile Val His Ala Val Phe Ala Leu Lys Val Arg Thr Val Asn
                115                 120                 125

Phe Gly Val Ile Thr Ser Val Val Thr Trp Ala Val Ala Val Phe Ala
                130                 135                 140

Ser Leu Pro Glu Ile Ile Phe Thr Arg Ser Gln Lys Glu Gly Phe His
145                 150                 155                 160

Tyr Thr Cys Ser Pro His Phe Pro His Thr Gln Tyr His Phe Trp Lys
                165                 170                 175
```

```
Ser Phe Gln Thr Leu Lys Met Val Ile Leu Ser Leu Ile Leu Pro Leu
            180                 185                 190

Leu Val Met Val Ile Cys Tyr Ser Gly Ile Leu His Thr Leu Phe Arg
            195                 200                 205

Cys Arg Asn Glu Lys Lys Arg His Arg Ala Val Arg Leu Ile Phe Ala
210                 215                 220

Ile Met Ile Val Tyr Phe Leu Phe Trp Thr Pro Tyr Asn Ile Val Leu
225                 230                 235                 240

Leu Leu Thr Thr Phe Gln Glu Phe Phe Gly Leu Asn Asn Cys Ser Ser
            245                 250                 255

Ser Asn Arg Leu Asp Gln Ala Met Gln Ala Thr Glu Thr Leu Gly Met
            260                 265                 270

Thr His Cys Cys Leu Asn Pro Val Ile Tyr Ala Phe Val Gly Glu Lys
            275                 280                 285

Phe Arg Ser Tyr Leu Ser Val Phe Arg Lys His Ile Val Lys Arg
            290                 295                 300

Phe Cys Lys Arg Cys Ser Ile Phe Gln Gln Asp Asn Pro Asp Arg Ala
305                 310                 315                 320

Ser Ser Val Tyr Thr Arg Ser Thr Gly Glu His Glu Val Ser Thr Gly
            325                 330                 335

Leu

<210> SEQ ID NO 40
<211> LENGTH: 329
<212> TYPE: PRT
<213> ORGANISM: Artificial Sequence
<220> FEATURE:
<223> OTHER INFORMATION: Amino acid sequence of proteinic domain derived
      from CXCR4

<400> SEQUENCE: 40

Phe Arg Asp Glu Asn Val His Phe Asn Arg Ile Phe Leu Pro Thr Ile
1               5                   10                  15

Tyr Phe Ile Ile Phe Leu Thr Gly Ile Val Gly Asn Gly Leu Val Ile
            20                  25                  30

Leu Val Met Gly Tyr Gln Lys Lys Leu Arg Ser Met Thr Asp Lys Tyr
            35                  40                  45

Arg Leu His Leu Ser Val Ala Asp Leu Leu Phe Val Ile Thr Leu Pro
50                  55                  60

Phe Trp Ala Val Asp Ala Met Ala Asp Trp Tyr Phe Gly Lys Phe Leu
65                  70                  75                  80

Cys Lys Ala Val His Ile Ile Tyr Thr Val Asn Leu Tyr Ser Ser Val
            85                  90                  95

Leu Ile Leu Ala Phe Ile Ser Leu Asp Arg Tyr Leu Ala Ile Val His
            100                 105                 110

Ala Thr Asn Ser Gln Arg Pro Arg Lys Leu Leu Ala Glu Lys Ala Val
            115                 120                 125

Tyr Val Gly Val Trp Ile Pro Ala Leu Leu Leu Thr Ile Pro Asp Phe
            130                 135                 140

Ile Phe Ala Asp Val Ser Gln Gly Asp Ile Ser Gln Gly Asp Asp Arg
145                 150                 155                 160

Tyr Ile Cys Asp Arg Leu Tyr Pro Asp Ser Leu Trp Met Val Val Phe
            165                 170                 175

Gln Phe Gln His Ile Met Val Gly Leu Val Leu Pro Gly Ile Val Ile
            180                 185                 190
```

```
Leu Ser Cys Tyr Cys Ile Ile Ile Ser Lys Leu Ser His Ser Lys Gly
        195                 200                 205

His Gln Lys Arg Lys Ala Leu Lys Thr Thr Val Ile Leu Ile Leu Ala
        210                 215                 220

Phe Phe Ala Cys Trp Leu Pro Tyr Tyr Val Gly Ile Ser Ile Asp Ser
225                 230                 235                 240

Phe Ile Leu Leu Gly Val Ile Lys Gln Gly Cys Asp Phe Glu Ser Ile
                245                 250                 255

Val His Lys Trp Ile Ser Ile Thr Glu Ala Leu Ala Phe Phe His Cys
                260                 265                 270

Cys Leu Asn Pro Ile Leu Tyr Ala Phe Leu Gly Ala Lys Phe Lys Ser
                275                 280                 285

Ser Ala Gln His Ala Leu Asn Ser Met Ser Arg Gly Ser Ser Leu Lys
                290                 295                 300

Ile Leu Ser Lys Gly Lys Arg Gly Gly His Ser Ser Val Ser Thr Glu
305                 310                 315                 320

Ser Glu Ser Ser Ser Phe His Ser Ser
                325

<210> SEQ ID NO 41
<211> LENGTH: 297
<212> TYPE: PRT
<213> ORGANISM: Artificial Sequence
<220> FEATURE:
<223> OTHER INFORMATION: Amino acid sequence of proteinic domain derived
      from SELPLG

<400> SEQUENCE: 41

Ile Ala Thr Thr Asp Pro Thr Ala Pro Gly Thr Gly Gly Thr Ala Val
1               5                   10                  15

Gly Met Leu Ser Thr Asp Ser Ala Thr Gln Trp Ser Leu Thr Ser Val
                20                  25                  30

Glu Thr Val Gln Pro Ala Ser Thr Glu Val Glu Thr Ser Gln Pro Ala
            35                  40                  45

Pro Met Glu Ala Glu Thr Ser Gln Pro Ala Pro Met Glu Ala Glu Thr
        50                  55                  60

Ser Gln Pro Ala Pro Met Glu Ala Asp Thr Ser Lys Pro Ala Pro Thr
65                  70                  75                  80

Glu Ala Glu Thr Ser Lys Pro Ala Pro Thr Glu Ala Glu Thr Ser Gln
                85                  90                  95

Pro Ala Pro Asn Glu Ala Glu Thr Ser Lys Pro Ala Pro Thr Glu Ala
            100                 105                 110

Glu Thr Ser Lys Pro Ala Pro Thr Glu Ala Glu Thr Thr Gln Leu Pro
        115                 120                 125

Arg Ile Gln Ala Val Lys Thr Leu Phe Thr Thr Ser Ala Ala Thr Glu
    130                 135                 140

Val Pro Ser Thr Glu Pro Thr Thr Met Glu Thr Ala Ser Thr Glu Ser
145                 150                 155                 160

Asn Glu Ser Thr Ile Phe Leu Gly Pro Ser Val Thr His Leu Pro Asp
                165                 170                 175

Ser Gly Leu Lys Lys Gly Leu Ile Val Thr Pro Gly Asn Ser Pro Ala
            180                 185                 190

Pro Thr Leu Pro Gly Ser Ser Asp Leu Ile Pro Val Lys Gln Cys Leu
        195                 200                 205

Leu Ile Ile Leu Ile Leu Ala Ser Leu Ala Thr Ile Phe Leu Val Cys
```

```
                    210                 215                 220
Thr Val Val Leu Ala Val Arg Leu Ser Arg Lys Thr His Met Tyr Pro
225                 230                 235                 240

Val Arg Asn Tyr Ser Pro Thr Glu Met Ile Cys Ile Ser Ser Leu Leu
                245                 250                 255

Pro Glu Gly Gly Asp Gly Ala Pro Val Thr Ala Asn Gly Gly Leu Pro
            260                 265                 270

Lys Val Gln Asp Leu Lys Thr Glu Pro Ser Gly Asp Arg Asp Gly Asp
        275                 280                 285

Asp Leu Thr Leu His Ser Phe Leu Pro
    290                 295

<210> SEQ ID NO 42
<211> LENGTH: 22
<212> TYPE: PRT
<213> ORGANISM: Artificial Sequence
<220> FEATURE:
<223> OTHER INFORMATION: Amino acid sequence of IgK domain

<400> SEQUENCE: 42

Met Asp Phe Gln Val Gln Ile Phe Ser Phe Leu Leu Ile Ser Ala Ser
1               5                   10                  15

Val Ile Met Ser Arg Gly
            20

<210> SEQ ID NO 43
<211> LENGTH: 786
<212> TYPE: DNA
<213> ORGANISM: Artificial Sequence
<220> FEATURE:
<223> OTHER INFORMATION: Nucleic acid sequence of proteinic domain
      derived from dLNGFR

<400> SEQUENCE: 43
cttctggggg tgtcccttgg aggtgccaag gaggcatgcc ccacaggcct gtacacacac      60
agcggtgagt gctgcaaagc ctgcaacctg ggcgagggtg tggcccagcc ttgtggagcc     120
aaccagaccg tgtgtgagcc ctgcctggac agcgtgacgt tctccgacgt ggtgagcgcg     180
accgagccgt gcaagccgtg caccgagtgc gtggggctcc agagcatgtc ggcgccgtgc     240
gtggaggccg acgacgccgt gtgccgctgc gcctacggct actaccagga tgagacgact     300
gggcgctgcg aggcgtgccg cgtgtgcgag gcgggctcgg gcctcgtgtt ctcctgccag     360
gacaagcaga acaccgtgtg cgaggagtgc cccgacggca cgtattccga cgaggccaac     420
cacgtggacc cgtgcctgcc ctgcaccgtg tgcgaggaca ccgagcgcca gctccgcgag     480
tgcacacgct gggccgacgc cgagtgcgag gagatccctg gccgttggat tacacggtcc     540 acaccccccag agggctcgga cagcacagcc cccagcaccc aggagcctga ggcacctcca     600
gaacaagacc tcatagccag cacggtggca ggtgtggtga ccacagtgat gggcagctcc     660
cagcccgtgg tgacccgagg caccaccgac aacctcatcc ctgtctattg ctccatcctg     720
gctgctgtgg ttgtgggcct tgtggcctac atagccttca gaggtggaa caggggatc      780 ctctag                                                                786

<210> SEQ ID NO 44
<211> LENGTH: 312
<212> TYPE: DNA
<213> ORGANISM: Artificial Sequence
<220> FEATURE:
<223> OTHER INFORMATION: Nucleic acid sequence of proteinic domain
``` derived from FcgRIIIA

<400> SEQUENCE: 44

| cacgagaact ccgaactgct gattcctaag gcaactcaca acgactccgg ctcctatttc | 60 |
| tgtagagggc tgattggaca taacaacaag agctccgcct cattcaggat tagcctgggc | 120 |
| gacccagggt ctcccagtat gttccccct tggcaccaga tcaccttttg cctgctgatt | 180 |
| ggactgctgt tcgctatcga tacagtgctg tacttttctg tccggagagg cctgcagtca | 240 |
| cccgtggcag attacgaaga acccaagatt cagtggagca aggagcccca ggataagacg | 300 |
| cgtgtcgact ga | 312 |

<210> SEQ ID NO 45
<211> LENGTH: 1407
<212> TYPE: DNA
<213> ORGANISM: Artificial Sequence
<220> FEATURE:
<223> OTHER INFORMATION: Nucleic acid sequence of proteinic domain derived from FLT3

<400> SEQUENCE: 45

| ccaggcccct tccctttcat ccaagacaac atctccttct atgcgaccat tgggctctgt | 60 |
| ctccccttca ttgttgttct cattgtgttg atctgccaca atacaaaaa gcaatttagg | 120 |
| tacgagagtc agctgcagat gatccaggtg actggccccc tggataacga gtacttctac | 180 |
| gttgacttca gggactatga atatgacctt aagtgggagt cccgagaga aacttagag | 240 |
| tttgggaagg tcctggggtc tggcgctttc ggagggtga tgaacgccac ggcctatggc | 300 |
| attagtaaaa cgggagtctc aattcaggtg gcggtgaaga tgctaaaaga aaagctgac | 360 |
| agctgtgaaa agaagctct catgtcggag ctcaaaatga tgacccacct gggacaccat | 420 |
| gacaacatcg tgaatctgct gggggcatgc acactgtcag gccagtgta cttgattttt | 480 |
| gaatattgtt gctatggtga cctcctcaac tacctaagaa gtaaaagaga aagtttcac | 540 |
| aggacatgga cagagatttt taaggaacat aatttcagtt tttaccctac tttccaggca | 600 |
| cattcaaatt ccagcatgcc tggttcacga aagttcagt tacacccgcc cttggatcag | 660 |
| ctctcagggt tcaatgggaa tttaattcat tctgaagatg agattgaata tgaaaaccag | 720 |
| aagaggctgg cagaagaaga ggaggaagat ttgaacgtgc tgacgtttga agacctcctt | 780 |
| tgctttgcgt tccaagtggc caaaggcatg gaattcctgg agttcaagtc gtgtgtccac | 840 |
| agagacctgg cagccaggaa tgtgttggtc acccacggga aggtggtgaa gatctgtgac | 900 |
| tttggactgg cccgagacat cctgagcgac tccagctacg tcgtcagggg caacgcacgg | 960 |
| ctgccggtga agtggatggc acctgagagc ttatttgaag gatctacac aatcaagagt | 1020 |
| gacgtctggt cctacggcat ccttctctgg gagatatttt cactgggtgt gaaccccttac | 1080 |
| cctggcattc ctgtcgacgc taacttctat aaactgattc agagtggatt taaaatggag | 1140 |
| cagccattct atgccacaga agggatatac tttgtaatgc aatcctgctg gcttttgac | 1200 |
| tcaaggaagc ggccatcctt ccccaacctg acttcatttt taggatgtca gctggcagag | 1260 |
| gcagaagaag cgatgtatca gaacatgggt ggcaacgtcc cagaacatcc atccatctac | 1320 |
| caaaacaggc ggcccctcag cagagaggca ggctcagagc cgccatcgcc acaggcccag | 1380 |
| gtgaagattc acggagaaag aagttag | 1407 |

<210> SEQ ID NO 46
<211> LENGTH: 891
<212> TYPE: DNA

<213> ORGANISM: Artificial Sequence
<220> FEATURE:
<223> OTHER INFORMATION: Nucleic acid sequence of proteinic domain
      derived from TLR4

<400> SEQUENCE: 46

| | |
|---|---|
| cagctgtatt ccctcagcac tcttgattgc agtttcaatc gcatagagac atctaaagga | 60 |
| atactgcaac attttccaaa gagtctagcc ttcttcaatc ttactaacaa ttctgttgct | 120 |
| tgtatatgtg aacatcagaa attcctgcag tgggtcaagg aacagaagca gttcttggtg | 180 |
| aatgttgaac aaatgacatg tgcaacacct gtagagatga atacctcctt agtgttggat | 240 |
| tttaataatt ctacctgtta tatgtacaag acaatcatca gtgtgtcagt ggtcagtgtg | 300 |
| attgtggtat ccactgtagc atttctgata taccacttct attttcacct gatacttatt | 360 |
| gctggctgta aaaagtacag cagaggagaa agcatctatg atgcatttgt gatctactcg | 420 |
| agtcagaatg aggactgggt gagaaatgag ctggtaaaga atttagaaga aggagtgccc | 480 |
| cgctttcacc tctgccttca ctacagagac tttattcctg gtgtagccat tgctgccaac | 540 |
| atcatccagg aaggcttcca caagagccgg aaggttattg tggtagtgtc tagacacttt | 600 |
| attcagagcc gttggtgtat ctttgaatat gagattgctc aaacatggca gtttctgagc | 660 |
| agccgctctg gcatcatctt cattgtcctt gagaaggttg agaagtccct gctgaggcag | 720 |
| caggtggaat tgtatcgcct tcttagcaga aacacctacc tggaatggga ggacaatcct | 780 |
| ctggggaggc acatcttctg gagaagactt aaaaatgccc tattggatgg aaaagcctcg | 840 |
| aatcctgagc aaacagcaga ggaagaacaa gaaacggcaa cttggacctg a | 891 |

<210> SEQ ID NO 47
<211> LENGTH: 1122
<212> TYPE: DNA
<213> ORGANISM: Artificial Sequence
<220> FEATURE:
<223> OTHER INFORMATION: Nucleic acid sequence of proteinic domain
      derived from CCR2

<400> SEQUENCE: 47

| | |
|---|---|
| atggaagaca ataatatgtt acctcagttc atccatggca tactatcaac atctcattct | 60 |
| ctatttacac gaagtatcca agagcttgat gaaggggcca ccacccgta tgactacgat | 120 |
| gatggtgagc cttgtcataa aaccagtgtg aagcaaattg agcttggat cctgcctcca | 180 |
| ctctactccc tggtattcat ctttggtttt gtgggcaaca tgttggtcat tataattctg | 240 |
| ataggctgta aaaagctgaa gagcatgact gatatctatc tgctcaacct ggccatctct | 300 |
| gacctgctct tcctgctcac attaccattc tgggctcact atgctgcaaa tgagtgggtc | 360 |
| tttgggaata atgtgtaa agtattcaca gggctctatc acattggtta ttttggtgga | 420 |
| atcttttttca ttatcctcct gacaattgat aggtacttgg ctattgttca tgctgtgttt | 480 |
| gctttaaaag ccaggacagt tacctttggg gtgataacaa gtgtagtcac ttgggtggtg | 540 |
| gctgtgtttg cctctctacc aggaatcata tttactaaat ccaaacaaga tgatcaccat | 600 |
| tacacctgtg gcccttattt tacacaacta tggaagaatt ccaaacaat aatgagaaat | 660 |
| atcttgagcc tgatcctgcc tctacttgtc atggtcatct gctactcagg aattctccac | 720 |
| accctgtttc gctgtaggaa tgagaagaag aggcacaggg ctgtgaggct catctttgcc | 780 |
| atcatgattg tctactttct cttctggact ccatacaata ttgttctctt cttgaccacc | 840 |
| ttccaggaat ccttgggaat gagtaactgt gtgattgaca gcacttaga ccaggccatg | 900 |
| caggtgacag agactcttgg aatgacacac tgctgcatta atcctgtcat ttatgccttt | 960 |

```
gttggagaga agttccgaag gtatctctcc atattttca gaaagcacat tgctaaacgt   1020
ctctgcaaac agtgcccagt tttctatagg gagacagcag atcgagtgag ctctacattc   1080
actccttcca ctggggagca agaggtctcg gttgggttgt aa                     1122
```

<210> SEQ ID NO 48
<211> LENGTH: 564
<212> TYPE: DNA
<213> ORGANISM: Artificial Sequence
<220> FEATURE:
<223> OTHER INFORMATION: Nucleic acid sequence of proteinic domain derived from ITGB2

<400> SEQUENCE: 48

```
aatgcacggc tggtagagtg cagtggccgt ggccactgcc aatgcaacag gtgcatatgt    60
gacgaaggct accagccacc gatgtgtgag gattgtccca gctgtggctc gcactgcagg   120
gacaaccaca cctcttgtgc cgagtgcctg aagtttgata agggcccttt tgagaagaac   180
tgtagtgttc agtgtgctgg tatgacgctg cagactatcc ctttgaagaa aaagccctgc   240
aaggagaggg actcggaagg ctgttggata acttacactt tgcagcagaa ggacggaagg   300
aacatttaca acatccatgt ggaggacagt ctagagtgtg tgaagggccc caatgtggct   360
gccatcgtag ggggcaccgt ggtaggtgtc gtactgattg gtgtcctcct cctggtcatc   420
tggaaggccc tgacccacct gactgacctc agggagtaca ggcgctttga aaggagaaa   480 ctcaagtccc aatggaacaa tgacaacccc ctcttcaaga gtgctacgac aacggtcatg   540 aacccccaagt ttgctgaaag ctag                                         564
```

<210> SEQ ID NO 49
<211> LENGTH: 1602
<212> TYPE: DNA
<213> ORGANISM: Artificial Sequence
<220> FEATURE:
<223> OTHER INFORMATION: Nucleic acid sequence of proteinic domain derived from CSF2RB

<400> SEQUENCE: 49

```
actcagaaga tggcttactc attcattgag cacacattcc aggtccagta caagaagaaa    60
tcggacagct gggaggacag caagacagag aacctagatc gagcccatag catggacctc   120
tcccagctgg agccagacac ctcatactgc gccagggtga gggtcaagcc catctctaac   180
tacgatggga tctggagcaa gtggagcgaa gagtacactt ggaagactga ctgggtgatg   240
cccacgctgt ggatagtcct catcctggtc tttctcatcc tcaccttgct cctgatcctt   300
cgctttggct gtgtctctgt atacaggacg tacaggaagt ggaaggaaaa gatccccaac   360
cccagcaaga gcctcctgtt ccaggatgga ggtaaaggtc tctggcctcc tggcagcatg   420
gcagccttcg ccactaagaa ccccgctctc caggggccac agagcaggct tcttgctgag   480 caacagggg agtcatatgc acatttggaa gacaacaacg tgtcacctct cactatagag   540
gaccctaata taattcgagt tccaccatcc gggcctgata aaccccagc tgcctcatcc   600 gaatccacag agcaacttcc caatgttcaa gtagagggac caactcctaa cagacctagg   660
aagcaattac ccagctttga cttcaatggg ccctacctgg ggcctcccca atcccactct   720
ctgcctgatc tcccagacca gctgggttcc ccccaggtgg gtgggagcct gaagccagca   780
ctgccaggct ccttggagta catgtgtctg ccccctggg gtcaagcgca actggttcca   840
ttgtcccagg tgatggggca gggccaggct atggatgtgc agtgtgggtc cagcctggag   900
```

| | |
|---|---|
| acctcaggga gcccttctgt ggagccaaag gagaaccctc cagttgagct gagcatggag | 960 |
| gaacaggagg cacgggacaa cccagtgact ctgcccataa gctctggggg ccctgagggc | 1020 |
| agtatgatgg cctctgatta tgtcactcct ggagatccgg tgctcactct gcccacaggg | 1080 |
| cccctgtcta cctctctggg cccctctcta gggttgccct cagcccaaag ccccgtctc | 1140 |
| tgtcttaagc tgcccagggt cccctctgga agcccagctc tagggccacc agggtttgag | 1200 |
| gactatgtgg agctgcctcc aagtgtgagc caggctgcca agtcccctcc aggccatcct | 1260 |
| gctcctcctg tggcaagcag ccccacagtg atcccaggag agcccaggga ggaagtgggc | 1320 |
| ccagcatccc cacatcccga aggcctcctt gttcttcagc aggttgggga ctactgcttc | 1380 |
| ctccctggcc tgggacctgg ctccctctca ccacacagta agccaccctc tccaagtctg | 1440 |
| tgttctgaga ctgaggacct agtccaggac ttgtctgtca aaagtttcc ctatcagccc | 1500 |
| atgccccagg cgccagccat tcagtttttc aagtccctaa agcatcagga ctacctgtcc | 1560 |
| ctgccccctt gggacaatag ccagtctggg aaggtgtgct ga | 1602 |

<210> SEQ ID NO 50
<211> LENGTH: 1005
<212> TYPE: DNA
<213> ORGANISM: Artificial Sequence
<220> FEATURE:
<223> OTHER INFORMATION: Nucleic acid sequence of proteinic domain derived from CCR1

<400> SEQUENCE: 50

| | |
|---|---|
| actccatgcc aaaagactgc tgtaagagcc tttggggctg gactcctgcc ccccctgtat | 60 |
| tctctagtgt tcatcattgg agtggtgggc aatgtcctag tgattctggt gctcatgcag | 120 |
| cataggaggc ttcaaagcat gaccagcatc tacctgttca acctggctgt ctctgatctg | 180 |
| gtcttccttt tcactttacc tttctggatt gactacaagt tgaaagacga ctggattttt | 240 |
| ggtgatgcca tgtgcaagct ctctctgggt ttttattacc tgggtttata cagtgagatc | 300 |
| ttctttatca tcctgttgac gattgacaga tacctggcca ttgtccatgc tgtgtttgcc | 360 |
| ctgagggccc gaactgttac ttttggcatc atcaccagta ttatcacctg ggccctagcc | 420 |
| atcttagctt ccatgcctgc cttatacttt tttaaggccc agtgggagtt cactcaccgt | 480 |
| acctgtagcc tcattttccc ctacaagagc ctgaagcagt ggaagaggtt caagctcta | 540 |
| aagctaaacc ttcttggact aattttgcct ctgttagtca tgataatctg ctatgcaggg | 600 |
| atcatcagaa ttctgctcag aagacccagt gagaagaagg tcaaagccgt gcgtctgata | 660 |
| tttgctatta ctcttctatt cttcctcctc tggaccccct acaatctgag tgtatttgtt | 720 |
| tctgctttcc aagatgttct attcaccaat cagtgtgagc agagtaagca actggacctg | 780 |
| gccatgcagg tgactgaggt gattgcctac acccactgtt gtgtcaaccc aatcatttat | 840 |
| gttttgtgg gtgaacggtt ctggaagtac cttcggcagc tgtttcaaag gcatgtggct | 900 |
| ataccactgg caaatggct gcccttcctc tctgtggacc aactagaaag gaccagttct | 960 |
| atatctccat ccacaggaga acatgagctc tctgctggct tctga | 1005 |

<210> SEQ ID NO 51
<211> LENGTH: 1014
<212> TYPE: DNA
<213> ORGANISM: Artificial Sequence
<220> FEATURE:
<223> OTHER INFORMATION: Nucleic acid sequence of proteinic domain derived from CCR5

<400> SEQUENCE: 51

```
atgtcagcac cctgccaaaa aatcaatgtg aaacaaattg cggctcagct cctgccccca    60
ctctactccc tggtattcat ctttggtttt gtgggtaaca tgatggtctt cctcatcttg   120
ataagctgca aaaagctgaa gagcgtgact gatatctacc tgctcaacct ggccatctct   180
gacctgctct tcctgctcac actaccattc tgggctcact atgctgcaaa tgagtgggtc   240
tttgggaaca taatgtgtaa agtattcaca gggctctatc acattggtta ttttggtgga   300
atcttcttca ttatcctcct gacaattgat aggtacttgg ctattgtcca tgctgtgttt   360
gctttaaaag tcagaacggt caactttggg gtgataacaa gtgtagtcac ttgggcggtg   420
gctgtgtttg cctctctccc agaaataatc tttaccagat ctcagaaaga aggttttcat   480
tatacatgca gtcctcattt tccacacact cagtatcatt tctggaagag tttccaaaca   540
ttaaagatgg tcatcttgag cctgatcctg cctctacttg tcatggtcat ctgctactca   600
ggaattctcc acaccctgtt tcgctgtagg aatgagaaga gaggcacag ggctgtgagg   660 ctcatctttg ccatcatgat tgtctacttt tctcttctgga ctccctacaa cattgtcctc   720
ctcctgacca ccttccagga attctttgga ctgaataact gcagtagttc taatagacta   780
gaccaggcca tgcaggcaac agagactctt ggaatgacac actgctgcct aaaccctgtc   840
atctatgcct ttgttggaga aagttccgg agttatctct cagtgttctt ccgaaaacac   900
attgtcaaac gcttttgcaa acggtgttca attttccagc aagacaatcc tgatcgtgca   960
agctcagtct ataccgatc cacaggagaa catgaagttt ctactggttt atga         1014

<210> SEQ ID NO 52
<211> LENGTH: 990
<212> TYPE: DNA
<213> ORGANISM: Artificial Sequence
<220> FEATURE:
<223> OTHER INFORMATION: Nucleic acid sequence of proteinic domain
      derived from CXCR4

<400> SEQUENCE: 52
ttccgggatg aaaacgtcca tttcaatagg atcttcctgc ccaccatcta cttcatcatc    60
ttcttgactg gcatagtcgg caatggattg tgatcctgg tcatgggtta ccagaagaag   120
ctaaggagca tgacggacaa gtaccggctg cacctgtcag tggctgacct cctctttgtc   180
atcacactcc ccttctgggc agttgatgcc atggctgact ggtactttgg gaatttttg   240 tgtaaggctg tccatatcat ctacactgtc aacctctaca gcagcgttct catcctggcc   300
ttcatcagcc tggaccggta cctcgctatt gtccacgcca ccaacagtca gaggccaagg   360
aaactgctgg ctgaaaaggc agtctatgtg ggcgtctgga tcccagcccct cctcctgact   420 atacctgact tcatctttgc cgacgtcagc caggggggaca tcagtcaggg ggatgacagg   480
tacatctgtg accgccttta ccccgatagc ctgtggatgg tggtgttca attccagcat   540 ataatggtgg gtctcgtcct gcccggcatc gtcatcctct cctgttactg catcatcatc   600
tctaagctgt cacactccaa gggccaccag aagcgcaagg ccctcaagac gacagtcatc   660
ctcatcctag ctttcttgc ctgctggctg ccatattatg tggggatcag catcgactcc   720
ttcatccttt tggggtcat caagcaagga tgtgacttcg agagcatcgt gcacaagtgg   780
atctccatca cagaggccct cgccttcttc cactgttgcc tgaaccccat cctctatgcc   840
ttcctcgggg ccaagttcaa aagctctgcc cagcatgcac tcaactccat gagcagaggc   900
tccagcctca agatcctttc caaaggaaag cggggtggac actcttccgt ctccacggag   960
tcagaatcct ccagttttca ctccagctaa                                    990
```

<210> SEQ ID NO 53
<211> LENGTH: 894
<212> TYPE: DNA
<213> ORGANISM: Artificial Sequence
<220> FEATURE:
<223> OTHER INFORMATION: Nucleic acid sequence of proteinic domain derived from SELPLG

<400> SEQUENCE: 53

```
attgccacca ctgaccctac tgccccaggt acaggaggga cagctgttgg gatgctgagc      60
acagactctg ccacacagtg gagtctaacc tcagtagaga ccgtccaacc agcatccaca     120
gaggtagaga cctcgcagcc agcacccatg gaggcagaga cctcgcagcc agcacccatg     180
gaggcagaga cctcgcagcc agcacccatg gaggcagaca cctcaaagcc agcacccacg     240
gaggcagaga cctcaaagcc agcacccacg gaggcagaga cctctcagcc agcacccaac     300
gaggcagaga cctcaaaacc agcacccacg gaggcagaga cctcaaaacc agcacccacg     360
gaggcagaga ccacccagct tcccaggatt caggctgtaa aaactctgtt tacaacgtct     420
gcagccaccg aagtcccttc cacagaacct accaccatgg agacggcgtc cacagagtct     480
aacgagtcta ccatcttcct tgggccatcc gtgactcact acctgacag cggcctgaag      540
aaagggctga ttgtgacccc tgggaattca cctgccccaa ccctgccagg gagttcagat     600
ctcatcccgg tgaagcaatg tctgctgatt atcctcatct tggcttctct ggccaccatc     660
ttcctcgtgt gcacagtggt gctggcggtc cgtctgtccc gtaagaccca catgtaccca     720
gtgcggaact actcccccac ggagatgatc tgcatctcgt ccctgctacc tgaggggga     780
gacggggccc ctgtcacagc caatgggggc ctgcccaagg tccaggacct gaagacagag     840
cccagtgggg accggatgg ggacgacctc accctgcaca gcttcctccc ttag            894
```

<210> SEQ ID NO 54
<211> LENGTH: 539
<212> TYPE: PRT
<213> ORGANISM: Artificial Sequence
<220> FEATURE:
<223> OTHER INFORMATION: Amino acid sequence of EVIR-N

<400> SEQUENCE: 54

```
Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Thr Pro Ser Ser
            20                  25                  30

Leu Pro Val Ser Val Gly Glu Lys Val Thr Met Thr Cys Lys Ser Ser
        35                  40                  45

Gln Thr Leu Leu Tyr Ser Asn Asn Gln Lys Asn Tyr Leu Ala Trp Tyr
    50                  55                  60

Gln Gln Lys Pro Gly Gln Ser Pro Lys Leu Leu Ile Ser Trp Ala Phe
65                  70                  75                  80

Thr Arg Lys Ser Gly Val Pro Asp Arg Phe Thr Gly Ser Gly Ser Gly
            85                  90                  95

Thr Asp Phe Thr Leu Thr Ile Gly Ser Val Lys Ala Glu Asp Leu Ala
        100                 105                 110

Val Tyr Tyr Cys Gln Gln Tyr Ser Asn Tyr Pro Trp Thr Phe Gly Gly
    115                 120                 125

Gly Thr Arg Leu Glu Ile Lys Arg Gly Gly Gly Gly Ser Gly Gly Gly
130                 135                 140
```

-continued

```
Gly Ser Gly Gly Gly Ser Gly Gly Gly Ser Glu Val Gln Leu
145                 150                 155                 160

Gln Gln Ser Gly Pro Glu Val Val Lys Thr Gly Ala Ser Val Lys Ile
            165                 170                 175

Ser Cys Lys Ala Ser Gly Tyr Ser Phe Thr Gly Tyr Phe Ile Asn Trp
            180                 185                 190

Val Lys Lys Asn Ser Gly Lys Ser Pro Glu Trp Ile Gly His Ile Ser
            195                 200                 205

Ser Ser Tyr Ala Thr Ser Thr Tyr Asn Gln Lys Phe Lys Asn Lys Ala
            210                 215                 220

Ala Phe Thr Val Asp Thr Ser Ser Thr Ala Phe Met Gln Leu Asn
225                 230                 235                 240

Ser Leu Thr Ser Glu Asp Ser Ala Val Tyr Tyr Cys Val Arg Ser Gly
                245                 250                 255

Asn Tyr Glu Glu Tyr Ala Met Asp Tyr Trp Gly Gln Gly Thr Ser Val
            260                 265                 270

Thr Val Ser Ser Thr Gly Leu Leu Gly Val Ser Leu Gly Gly Ala Lys
            275                 280                 285

Glu Ala Cys Pro Thr Gly Leu Tyr Thr His Ser Gly Glu Cys Cys Lys
            290                 295                 300

Ala Cys Asn Leu Gly Glu Gly Val Ala Gln Pro Cys Gly Ala Asn Gln
305                 310                 315                 320

Thr Val Cys Glu Pro Cys Leu Asp Ser Val Thr Phe Ser Asp Val Val
                325                 330                 335

Ser Ala Thr Glu Pro Cys Lys Pro Cys Thr Glu Cys Val Gly Leu Gln
            340                 345                 350

Ser Met Ser Ala Pro Cys Val Glu Ala Asp Asp Ala Val Cys Arg Cys
            355                 360                 365

Ala Tyr Gly Tyr Tyr Gln Asp Glu Thr Thr Gly Arg Cys Glu Ala Cys
            370                 375                 380

Arg Val Cys Glu Ala Gly Ser Gly Leu Val Phe Ser Cys Gln Asp Lys
385                 390                 395                 400

Gln Asn Thr Val Cys Glu Glu Cys Pro Asp Gly Thr Tyr Ser Asp Glu
                405                 410                 415

Ala Asn His Val Asp Pro Cys Leu Pro Cys Thr Val Cys Glu Asp Thr
            420                 425                 430

Glu Arg Gln Leu Arg Glu Cys Thr Arg Trp Ala Asp Ala Glu Cys Glu
            435                 440                 445

Glu Ile Pro Gly Arg Trp Ile Thr Arg Ser Thr Pro Pro Glu Gly Ser
450                 455                 460

Asp Ser Thr Ala Pro Ser Thr Gln Glu Pro Glu Ala Pro Pro Glu Gln
465                 470                 475                 480

Asp Leu Ile Ala Ser Thr Val Ala Gly Val Val Thr Thr Val Met Gly
                485                 490                 495

Ser Ser Gln Pro Val Val Thr Arg Gly Thr Thr Asp Asn Leu Ile Pro
            500                 505                 510

Val Tyr Cys Ser Ile Leu Ala Ala Val Val Val Gly Leu Val Ala Tyr
            515                 520                 525

Ile Ala Phe Lys Arg Trp Asn Arg Gly Ile Leu
            530                 535
```

<210> SEQ ID NO 55
<211> LENGTH: 381
<212> TYPE: PRT

<213> ORGANISM: Artificial Sequence
<220> FEATURE:
<223> OTHER INFORMATION: Amino acid sequence of EVIR-G

<400> SEQUENCE: 55

```
Met Asp Phe Gln Val Gln Ile Phe Ser Phe Leu Leu Ile Ser Ala Ser
1               5                   10                  15

Val Ile Met Ser Arg Gly Asp

<210> SEQ ID NO 56
<211> LENGTH: 746
<212> TYPE: PRT
<213> ORGANISM: Artificial Sequence
<220> FEATURE:
<223> OTHER INFORMATION: Amino acid sequence of EVIR-F

<400> SEQUENCE: 56

```
Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Thr Pro Ser Ser
            20                  25                  30

Leu Pro Val Ser Val Gly Glu Lys Val Thr Met Thr Cys Lys Ser Ser
        35                  40                  45

Gln Thr Leu Leu Tyr Ser Asn Asn Gln Lys Asn Tyr Leu Ala Trp Tyr
    50                  55                  60

Gln Gln Lys Pro Gly Gln Ser Pro Lys Leu Leu Ile Ser Trp Ala Phe
65                  70                  75                  80

Thr Arg Lys Ser Gly Val Pro Asp Arg Phe Thr Gly Ser Gly Ser Gly
                85                  90                  95

Thr Asp Phe Thr Leu Thr Ile Gly Ser Val Lys Ala Glu Asp Leu Ala
            100                 105                 110

Val Tyr Tyr Cys Gln Gln Tyr Ser Asn Tyr Pro Trp Thr Phe Gly Gly
        115                 120                 125

Gly Thr Arg Leu Glu Ile Lys Arg Gly Gly Gly Ser Gly Gly Gly
    130                 135                 140

Gly Ser Gly Gly Gly Gly Ser Gly Gly Gly Gly Ser Glu Val Gln Leu
145                 150                 155                 160

Gln Gln Ser Gly Pro Glu Val Val Lys Thr Gly Ala Ser Val Lys Ile
                165                 170                 175

Ser Cys Lys Ala Ser Gly Tyr Ser Phe Thr Gly Tyr Phe Ile Asn Trp
            180                 185                 190

Val Lys Lys Asn Ser Gly Lys Ser Pro Glu Trp Ile Gly His Ile Ser
        195                 200                 205

Ser Ser Tyr Ala Thr Ser Thr Tyr Asn Gln Lys Phe Lys Asn Lys Ala
    210                 215                 220

Ala Phe Thr Val Asp Thr Ser Ser Ser Thr Ala Phe Met Gln Leu Asn
225                 230                 235                 240

Ser Leu Thr Ser Glu Asp Ser Ala Val Tyr Tyr Cys Val Arg Ser Gly
                245                 250                 255

Asn Tyr Glu Glu Tyr Ala Met Asp Tyr Trp Gly Gln Gly Thr Ser Val
            260                 265                 270

Thr Val Ser Ser Thr Gly Pro Gly Pro Phe Pro Phe Ile Gln Asp Asn
        275                 280                 285

Ile Ser Phe Tyr Ala Thr Ile Gly Leu Cys Leu Pro Phe Ile Val Val
    290                 295                 300

Leu Ile Val Leu Ile Cys His Lys Tyr Lys Lys Gln Phe Arg Tyr Glu
305                 310                 315                 320

Ser Gln Leu Gln Met Ile Gln Val Thr Gly Pro Leu Asp Asn Glu Tyr
                325                 330                 335

Phe Tyr Val Asp Phe Arg Asp Tyr Glu Tyr Asp Leu Lys Trp Glu Phe
            340                 345                 350

Pro Arg Glu Asn Leu Glu Phe Gly Lys Val Leu Gly Ser Gly Ala Phe
        355                 360                 365

Gly Arg Val Met Asn Ala Thr Ala Tyr Gly Ile Ser Lys Thr Gly Val
```

```
        370                 375                 380
Ser Ile Gln Val Ala Val Lys Met Leu Lys Glu Lys Ala Asp Ser Cys
385                 390                 395                 400

Glu Lys Glu Ala Leu Met Ser Glu Leu Lys Met Met Thr His Leu Gly
                405                 410                 415

His His Asp Asn Ile Val Asn Leu Leu Gly Ala Cys Thr Leu Ser Gly
                420                 425                 430

Pro Val Tyr Leu Ile Phe Glu Tyr Cys Cys Tyr Gly Asp Leu Leu Asn
            435                 440                 445

Tyr Leu Arg Ser Lys Arg Glu Lys Phe His Arg Thr Trp Thr Glu Ile
        450                 455                 460

Phe Lys Glu His Asn Phe Ser Phe Tyr Pro Thr Phe Gln Ala His Ser
465                 470                 475                 480

Asn Ser Ser Met Pro Gly Ser Arg Glu Val Gln Leu His Pro Pro Leu
                485                 490                 495

Asp Gln Leu Ser Gly Phe Asn Gly Asn Leu Ile His Ser Glu Asp Glu
            500                 505                 510

Ile Glu Tyr Glu Asn Gln Lys Arg Leu Ala Glu Glu Glu Glu Glu Asp
        515                 520                 525

Leu Asn Val Leu Thr Phe Glu Asp Leu Leu Cys Phe Ala Tyr Gln Val
530                 535                 540

Ala Lys Gly Met Glu Phe Leu Glu Phe Lys Ser Cys Val His Arg Asp
545                 550                 555                 560

Leu Ala Ala Arg Asn Val Leu Val Thr His Gly Lys Val Val Lys Ile
                565                 570                 575

Cys Asp Phe Gly Leu Ala Arg Asp Ile Leu Ser Asp Ser Ser Tyr Val
            580                 585                 590

Val Arg Gly Asn Ala Arg Leu Pro Val Lys Trp Met Ala Pro Glu Ser
        595                 600                 605

Leu Phe Glu Gly Ile Tyr Thr Ile Lys Ser Asp Val Trp Ser Tyr Gly
610                 615                 620

Ile Leu Leu Trp Glu Ile Phe Ser Leu Gly Val Asn Pro Tyr Pro Gly
625                 630                 635                 640

Ile Pro Val Asp Ala Asn Phe Tyr Lys Leu Ile Gln Ser Gly Phe Lys
                645                 650                 655

Met Glu Gln Pro Phe Tyr Ala Thr Glu Gly Ile Tyr Phe Val Met Gln
            660                 665                 670

Ser Cys Trp Ala Phe Asp Ser Arg Lys Arg Pro Ser Phe Pro Asn Leu
        675                 680                 685

Thr Ser Phe Leu Gly Cys Gln Leu Ala Glu Ala Glu Glu Ala Met Tyr
690                 695                 700

Gln Asn Met Gly Gly Asn Val Pro Glu His Pro Ser Ile Tyr Gln Asn
705                 710                 715                 720

Arg Arg Pro Leu Ser Arg Glu Ala Gly Ser Glu Pro Pro Ser Pro Gln
                725                 730                 735

Ala Gln Val Lys Ile His Gly Glu Arg Ser
            740                 745

<210> SEQ ID NO 57
<211> LENGTH: 574
<212> TYPE: PRT
<213> ORGANISM: Artificial Sequence
<220> FEATURE:
<223> OTHER INFORMATION: Amino acid sequence of EVIR-T
```

<400> SEQUENCE: 57

```
Met Asp Phe Gln Val Gln Ile Phe Ser Phe Leu Leu Ile Ser Ala Ser
1               5                   10                  15
Val Ile Met Ser Arg Gly Asp Ile Val Leu Thr Gln Thr Pro Ser Ser
            20                  25                  30
Leu Pro Val Ser Val Gly Glu Lys Val Thr Met Thr Cys Lys Ser Ser
        35                  40                  45
Gln Thr Leu Leu Tyr Ser Asn Asn Gln Lys Asn Tyr Leu Ala Trp Tyr
    50                  55                  60
Gln Gln Lys Pro Gly Gln Ser Pro Lys Leu Leu Ile Ser Trp Ala Phe
65                  70                  75                  80
Thr Arg Lys Ser Gly Val Pro Asp Arg Phe Thr Gly Ser Gly Ser Gly
                85                  90                  95
Thr Asp Phe Thr Leu Thr Ile Gly Ser Val Lys Ala Glu Asp Leu Ala
            100                 105                 110
Val Tyr Tyr Cys Gln Gln Tyr Ser Asn Tyr Pro Trp Thr Phe Gly Gly
        115                 120                 125
Gly Thr Arg Leu Glu Ile Lys Arg Gly Gly Gly Gly Ser Gly Gly Gly
    130                 135                 140
Gly Ser Gly Gly Gly Gly Ser Gly Gly Gly Gly Ser Glu Val Gln Leu
145                 150                 155                 160
Gln Gln Ser Gly Pro Glu Val Val Lys Thr Gly Ala Ser Val Lys Ile
                165                 170                 175
Ser Cys Lys Ala Ser Gly Tyr Ser Phe Thr Gly Tyr Phe Ile Asn Trp
            180                 185                 190
Val Lys Lys Asn Ser Gly Lys Ser Pro Glu Trp Ile Gly His Ile Ser
        195                 200                 205
Ser Ser Tyr Ala Thr Ser Thr Tyr Asn Gln Lys Phe Lys Asn Lys Ala
    210                 215                 220
Ala Phe Thr Val Asp Thr Ser Ser Ser Thr Ala Phe Met Gln Leu Asn
225                 230                 235                 240
Ser Leu Thr Ser Glu Asp Ser Ala Val Tyr Tyr Cys Val Arg Ser Gly
                245                 250                 255
Asn Tyr Glu Glu Tyr Ala Met Asp Tyr Trp Gly Gln Gly Thr Ser Val
            260                 265                 270
Thr Val Ser Ser Thr Gly Gln Leu Tyr Ser Leu Ser Thr Leu Asp Cys
        275                 280                 285
Ser Phe Asn Arg Ile Glu Thr Ser Lys Gly Ile Leu Gln His Phe Pro
    290                 295                 300
Lys Ser Leu Ala Phe Phe Asn Leu Thr Asn Asn Ser Val Ala Cys Ile
305                 310                 315                 320
Cys Glu His Gln Lys Phe Leu Gln Trp Val Lys Glu Gln Lys Gln Phe
                325                 330                 335
Leu Val Asn Val Glu Gln Met Thr Cys Ala Thr Pro Val Glu Met Asn
            340                 345                 350
Thr Ser Leu Val Leu Asp Phe Asn Asn Ser Thr Cys Tyr Met Tyr Lys
        355                 360                 365
Thr Ile Ile Ser Val Ser Val Ser Val Ile Val Ser Thr Val
    370                 375                 380
Ala Phe Leu Ile Tyr His Phe Tyr Phe His Leu Ile Leu Ile Ala Gly
385                 390                 395                 400
Cys Lys Lys Tyr Ser Arg Gly Glu Ser Ile Tyr Asp Ala Phe Val Ile
                405                 410                 415
```

```
Tyr Ser Ser Gln Asn Glu Asp Trp Val Arg Asn Glu Leu Val Lys Asn
                420                 425                 430

Leu Glu Glu Gly Val Pro Arg Phe His Leu Cys Leu His Tyr Arg Asp
            435                 440                 445

Phe Ile Pro Gly Val Ala Ile Ala Ala Asn Ile Gln Glu Gly Phe
450                 455                 460

His Lys Ser Arg Lys Val Ile Val Val Ser Arg His Phe Ile Gln
465                 470                 475                 480

Ser Arg Trp Cys Ile Phe Glu Tyr Glu Ile Ala Gln Thr Trp Gln Phe
                485                 490                 495

Leu Ser Ser Arg Ser Gly Ile Ile Phe Ile Val Leu Glu Lys Val Glu
                500                 505                 510

Lys Ser Leu Leu Arg Gln Gln Val Glu Leu Tyr Arg Leu Leu Ser Arg
                515                 520                 525

Asn Thr Tyr Leu Glu Trp Glu Asp Asn Pro Leu Gly Arg His Ile Phe
                530                 535                 540

Trp Arg Arg Leu Lys Asn Ala Leu Leu Asp Gly Lys Ala Ser Asn Pro
545                 550                 555                 560

Glu Gln Thr Ala Glu Glu Gln Glu Thr Ala Thr Trp Thr
                565                 570
```

<210> SEQ ID NO 58
<211> LENGTH: 651
<212> TYPE: PRT
<213> ORGANISM: Artificial Sequence
<220> FEATURE:
<223> OTHER INFORMATION: Amino acid sequence of EVIR-C2

<400> SEQUENCE: 58

```
Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Thr Pro Ser Ser
                20                  25                  30

Leu Pro Val Ser Val Gly Glu Lys Val Thr Met Thr Cys Lys Ser Ser
            35                  40                  45

Gln Thr Leu Leu Tyr Ser Asn Asn Gln Lys Asn Tyr Leu Ala Trp Tyr
    50                  55                  60

Gln Gln Lys Pro Gly Gln Ser Pro Lys Leu Leu Ile Ser Trp Ala Phe
65                  70                  75                  80

Thr Arg Lys Ser Gly Val Pro Asp Arg Phe Thr Gly Ser Gly Ser Gly
                85                  90                  95

Thr Asp Phe Thr Leu Thr Ile Gly Ser Val Lys Ala Glu Asp Leu Ala
            100                 105                 110

Val Tyr Tyr Cys Gln Gln Tyr Ser Asn Tyr Pro Trp Thr Phe Gly Gly
        115                 120                 125

Gly Thr Arg Leu Glu Ile Lys Arg Gly Gly Gly Ser Gly Gly Gly
    130                 135                 140

Gly Ser Gly Gly Gly Ser Gly Gly Gly Ser Glu Val Gln Leu
145                 150                 155                 160

Gln Gln Ser Gly Pro Glu Val Val Lys Thr Gly Ala Ser Val Lys Ile
                165                 170                 175

Ser Cys Lys Ala Ser Gly Tyr Ser Phe Thr Gly Tyr Phe Ile Asn Trp
            180                 185                 190

Val Lys Lys Asn Ser Gly Lys Ser Pro Glu Trp Ile Gly His Ile Ser
        195                 200                 205
```

```
Ser Ser Tyr Ala Thr Ser Thr Tyr Asn Gln Lys Phe Lys Asn Lys Ala
    210                 215                 220
Ala Phe Thr Val Asp Thr Ser Ser Thr Ala Phe Met Gln Leu Asn
225                 230                 235                 240
Ser Leu Thr Ser Glu Asp Ser Ala Val Tyr Tyr Cys Val Arg Ser Gly
                245                 250                 255
Asn Tyr Glu Glu Tyr Ala Met Asp Tyr Trp Gly Gln Gly Thr Ser Val
            260                 265                 270
Thr Val Ser Ser Thr Gly Met Glu Asp Asn Asn Met Leu Pro Gln Phe
        275                 280                 285
Ile His Gly Ile Leu Ser Thr Ser His Ser Leu Phe Thr Arg Ser Ile
    290                 295                 300
Gln Glu Leu Asp Glu Gly Ala Thr Thr Pro Tyr Asp Tyr Asp Asp Gly
305                 310                 315                 320
Glu Pro Cys His Lys Thr Ser Val Lys Gln Ile Gly Ala Trp Ile Leu
                325                 330                 335
Pro Pro Leu Tyr Ser Leu Val Phe Ile Phe Gly Phe Val Gly Asn Met
            340                 345                 350
Leu Val Ile Ile Ile Leu Ile Gly Cys Lys Lys Leu Lys Ser Met Thr
        355                 360                 365
Asp Ile Tyr Leu Leu Asn Leu Ala Ile Ser Asp Leu Leu Phe Leu Leu
    370                 375                 380
Thr Leu Pro Phe Trp Ala His Tyr Ala Ala Asn Glu Trp Val Phe Gly
385                 390                 395                 400
Asn Ile Met Cys Lys Val Phe Thr Gly Leu Tyr His Ile Gly Tyr Phe
                405                 410                 415
Gly Gly Ile Phe Phe Ile Ile Leu Leu Thr Ile Asp Arg Tyr Leu Ala
            420                 425                 430
Ile Val His Ala Val Phe Ala Leu Lys Ala Arg Thr Val Thr Phe Gly
        435                 440                 445
Val Ile Thr Ser Val Val Thr Trp Val Val Ala Val Phe Ala Ser Leu
    450                 455                 460
Pro Gly Ile Ile Phe Thr Lys Ser Lys Gln Asp Asp His His Tyr Thr
465                 470                 475                 480
Cys Gly Pro Tyr Phe Thr Gln Leu Trp Lys Asn Phe Gln Thr Ile Met
                485                 490                 495
Arg Asn Ile Leu Ser Leu Ile Leu Pro Leu Leu Val Met Val Ile Cys
            500                 505                 510
Tyr Ser Gly Ile Leu His Thr Leu Phe Arg Cys Arg Asn Glu Lys Lys
        515                 520                 525
Arg His Arg Ala Val Arg Leu Ile Phe Ala Ile Met Ile Val Tyr Phe
    530                 535                 540
Leu Phe Trp Thr Pro Tyr Asn Ile Val Leu Phe Leu Thr Thr Phe Gln
545                 550                 555                 560
Glu Ser Leu Gly Met Ser Asn Cys Val Ile Asp Lys His Leu Asp Gln
                565                 570                 575
Ala Met Gln Val Thr Glu Thr Leu Gly Met Thr His Cys Cys Ile Asn
            580                 585                 590
Pro Val Ile Tyr Ala Phe Val Gly Glu Lys Phe Arg Arg Tyr Leu Ser
        595                 600                 605
Ile Phe Phe Arg Lys His Ile Ala Lys Arg Leu Cys Lys Gln Cys Pro
    610                 615                 620
```

-continued

```
Val Phe Tyr Arg Glu Thr Ala Asp Arg Val Ser Ser Thr Phe Thr Pro
625                 630                 635                 640

Ser Thr Gly Glu Gln Glu Val Ser Val Gly Leu
            645                 650

<210> SEQ ID NO 59
<211> LENGTH: 465
<212> TYPE: PRT
<213> ORGANISM: Artificial Sequence
<220> FEATURE:
<223> OTHER INFORMATION: Amino acid sequence of EVIR-I

<400> SEQUENCE: 59

Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Thr Pro Ser Ser
            20                  25                  30

Leu Pro Val Ser Val Gly Glu Lys Val Thr Met Thr Cys Lys Ser Ser
            35                  40                  45

Gln Thr Leu Leu Tyr Ser Asn Asn Gln Lys Asn Tyr Leu Ala Trp Tyr
    50                  55                  60

Gln Gln Lys Pro Gly Gln Ser Pro Lys Leu Leu Ile Ser Trp Ala Phe
65                  70                  75                  80

Thr Arg Lys Ser Gly Val Pro Asp Arg Phe Thr Gly Ser Gly Ser Gly
                85                  90                  95

Thr Asp Phe Thr Leu Thr Ile Gly Ser Val Lys Ala Glu Asp Leu Ala
            100                 105                 110

Val Tyr Tyr Cys Gln Gln Tyr Ser Asn Tyr Pro Trp Thr Phe Gly Gly
        115                 120                 125

Gly Thr Arg Leu Glu Ile Lys Arg Gly Gly Gly Ser Gly Gly Gly
    130                 135                 140

Gly Ser Gly Gly Gly Gly Ser Gly Gly Gly Gly Ser Glu Val Gln Leu
145                 150                 155                 160

Gln Gln Ser Gly Pro Glu Val Val Lys Thr Gly Ala Ser Val Lys Ile
                165                 170                 175

Ser Cys Lys Ala Ser Gly Tyr Ser Phe Thr Gly Tyr Phe Ile Asn Trp
            180                 185                 190

Val Lys Lys Asn Ser Gly Lys Ser Pro Glu Trp Ile Gly His Ile Ser
        195                 200                 205

Ser Ser Tyr Ala Thr Thr Tyr Asn Gln Lys Phe Lys Asn Lys Ala
    210                 215                 220

Ala Phe Thr Val Asp Thr Ser Ser Ser Thr Ala Phe Met Gln Leu Asn
225                 230                 235                 240

Ser Leu Thr Ser Glu Asp Ser Ala Val Tyr Tyr Cys Val Arg Ser Gly
                245                 250                 255

Asn Tyr Glu Glu Tyr Ala Met Asp Tyr Trp Gly Gln Gly Thr Ser Val
            260                 265                 270

Thr Val Ser Ser Thr Gly Asn Ala Arg Leu Val Glu Cys Ser Gly Arg
        275                 280                 285

Gly His Cys Gln Cys Asn Arg Cys Ile Cys Asp Glu Gly Tyr Gln Pro
    290                 295                 300

Pro Met Cys Glu Asp Cys Pro Ser Cys Gly Ser His Cys Arg Asp Asn
305                 310                 315                 320

His Thr Ser Cys Ala Glu Cys Leu Lys Phe Asp Lys Gly Pro Phe Glu
                325                 330                 335
```

Lys Asn Cys Ser Val Gln Cys Ala Gly Met Thr Leu Gln Thr Ile Pro
            340                 345                 350

Leu Lys Lys Lys Pro Cys Lys Glu Arg Asp Ser Glu Gly Cys Trp Ile
            355                 360                 365

Thr Tyr Thr Leu Gln Gln Lys Asp Gly Arg Asn Ile Tyr Asn Ile His
            370                 375                 380

Val Glu Asp Ser Leu Glu Cys Val Lys Gly Pro Asn Val Ala Ala Ile
385                 390                 395                 400

Val Gly Gly Thr Val Gly Val Val Leu Ile Gly Val Leu Leu Leu
            405                 410                 415

Val Ile Trp Lys Ala Leu Thr His Leu Thr Asp Leu Arg Glu Tyr Arg
            420                 425                 430

Arg Phe Glu Lys Glu Lys Leu Lys Ser Gln Trp Asn Asn Asp Asn Pro
            435                 440                 445

Leu Phe Lys Ser Ala Thr Thr Thr Val Met Asn Pro Lys Phe Ala Glu
            450                 455                 460

Ser
465

<210> SEQ ID NO 60
<211> LENGTH: 811
<212> TYPE: PRT
<213> ORGANISM: Artificial Sequence
<220> FEATURE:
<223> OTHER INFORMATION: Amino acid sequence of EVIR-C

<400> SEQUENCE: 60

Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Thr Pro Ser Ser
            20                  25                  30

Leu Pro Val Ser Val Gly Glu Lys Val Thr Met Thr Cys Lys Ser Ser
            35                  40                  45

Gln Thr Leu Leu Tyr Ser Asn Asn Gln Lys Asn Tyr Leu Ala Trp Tyr
        50                  55                  60

Gln Gln Lys Pro Gly Gln Ser Pro Lys Leu Leu Ile Ser Trp Ala Phe
65                  70                  75                  80

Thr Arg Lys Ser Gly Val Pro Asp Arg Phe Thr Gly Ser Gly Ser Gly
            85                  90                  95

Thr Asp Phe Thr Leu Thr Ile Gly Ser Val Lys Ala Glu Asp Leu Ala
            100                 105                 110

Val Tyr Tyr Cys Gln Gln Tyr Ser Asn Tyr Pro Trp Thr Phe Gly Gly
            115                 120                 125

Gly Thr Arg Leu Glu Ile Lys Arg Gly Gly Gly Ser Gly Gly Gly
            130                 135                 140

Gly Ser Gly Gly Gly Gly Ser Gly Gly Gly Ser Glu Val Gln Leu
145                 150                 155                 160

Gln Gln Ser Gly Pro Glu Val Val Lys Thr Gly Ala Ser Val Lys Ile
            165                 170                 175

Ser Cys Lys Ala Ser Gly Tyr Ser Phe Thr Gly Tyr Phe Ile Asn Trp
            180                 185                 190

Val Lys Lys Asn Ser Gly Lys Ser Pro Glu Trp Ile Gly His Ile Ser
            195                 200                 205

Ser Ser Tyr Ala Thr Ser Thr Tyr Asn Gln Lys Phe Lys Asn Lys Ala
            210                 215                 220

```
Ala Phe Thr Val Asp Thr Ser Ser Thr Ala Phe Met Gln Leu Asn
225                 230                 235                 240

Ser Leu Thr Ser Glu Asp Ser Ala Val Tyr Tyr Cys Val Arg Ser Gly
            245                 250                 255

Asn Tyr Glu Glu Tyr Ala Met Asp Tyr Trp Gly Gln Gly Thr Ser Val
        260                 265                 270

Thr Val Ser Ser Thr Gly Thr Gln Lys Met Ala Tyr Ser Phe Ile Glu
    275                 280                 285

His Thr Phe Gln Val Gln Tyr Lys Lys Ser Asp Ser Trp Glu Asp
    290                 295                 300

Ser Lys Thr Glu Asn Leu Asp Arg Ala His Ser Met Asp Leu Ser Gln
305                 310                 315                 320

Leu Glu Pro Asp Thr Ser Tyr Cys Ala Arg Val Arg Val Lys Pro Ile
                325                 330                 335

Ser Asn Tyr Asp Gly Ile Trp Ser Lys Trp Ser Glu Glu Tyr Thr Trp
                340                 345                 350

Lys Thr Asp Trp Val Met Pro Thr Leu Trp Ile Val Leu Ile Leu Val
                355                 360                 365

Phe Leu Ile Leu Thr Leu Leu Leu Ile Leu Arg Phe Gly Cys Val Ser
    370                 375                 380

Val Tyr Arg Thr Tyr Arg Lys Trp Lys Glu Lys Ile Pro Asn Pro Ser
385                 390                 395                 400

Lys Ser Leu Leu Phe Gln Asp Gly Gly Lys Gly Leu Trp Pro Pro Gly
                405                 410                 415

Ser Met Ala Ala Phe Ala Thr Lys Asn Pro Ala Leu Gln Gly Pro Gln
                420                 425                 430

Ser Arg Leu Leu Ala Glu Gln Gln Gly Glu Ser Tyr Ala His Leu Glu
            435                 440                 445

Asp Asn Asn Val Ser Pro Leu Thr Ile Glu Asp Pro Asn Ile Ile Arg
            450                 455                 460

Val Pro Pro Ser Gly Pro Asp Thr Thr Pro Ala Ala Ser Ser Glu Ser
465                 470                 475                 480

Thr Glu Gln Leu Pro Asn Val Gln Val Glu Gly Pro Thr Pro Asn Arg
                485                 490                 495

Pro Arg Lys Gln Leu Pro Ser Phe Asp Phe Asn Gly Pro Tyr Leu Gly
                500                 505                 510

Pro Pro Gln Ser His Ser Leu Pro Asp Leu Pro Asp Gln Leu Gly Ser
            515                 520                 525

Pro Gln Val Gly Gly Ser Leu Lys Pro Ala Leu Pro Gly Ser Leu Glu
            530                 535                 540

Tyr Met Cys Leu Pro Pro Gly Gly Gln Ala Gln Leu Val Pro Leu Ser
545                 550                 555                 560

Gln Val Met Gly Gln Gly Gln Ala Met Asp Val Gln Cys Gly Ser Ser
                565                 570                 575

Leu Glu Thr Ser Gly Ser Pro Ser Val Glu Pro Lys Glu Asn Pro Pro
            580                 585                 590

Val Glu Leu Ser Met Glu Glu Gln Ala Arg Asp Asn Pro Val Thr
            595                 600                 605

Leu Pro Ile Ser Ser Gly Gly Pro Glu Gly Ser Met Met Ala Ser Asp
            610                 615                 620

Tyr Val Thr Pro Gly Asp Pro Val Leu Thr Leu Pro Thr Gly Pro Leu
625                 630                 635                 640

Ser Thr Ser Leu Gly Pro Ser Leu Gly Leu Pro Ser Ala Gln Ser Pro
```

```
                    645                 650                 655
Arg Leu Cys Leu Lys Leu Pro Arg Val Pro Ser Gly Ser Pro Ala Leu
                660                 665                 670

Gly Pro Pro Gly Phe Glu Asp Tyr Val Glu Leu Pro Pro Ser Val Ser
            675                 680                 685

Gln Ala Ala Lys Ser Pro Pro Gly His Pro Ala Pro Pro Val Ala Ser
        690                 695                 700

Ser Pro Thr Val Ile Pro Gly Glu Pro Arg Glu Glu Val Gly Pro Ala
705                 710                 715                 720

Ser Pro His Pro Glu Gly Leu Leu Val Leu Gln Gln Val Gly Asp Tyr
                725                 730                 735

Cys Phe Leu Pro Gly Leu Gly Pro Gly Ser Leu Ser Pro His Ser Lys
            740                 745                 750

Pro Pro Ser Pro Ser Leu Cys Ser Glu Thr Glu Asp Leu Val Gln Asp
        755                 760                 765

Leu Ser Val Lys Lys Phe Pro Tyr Gln Pro Met Pro Gln Ala Pro Ala
770                 775                 780

Ile Gln Phe Phe Lys Ser Leu Lys His Gln Asp Tyr Leu Ser Leu Pro
785                 790                 795                 800

Pro Trp Asp Asn Ser Gln Ser Gly Lys Val Cys
                805                 810

<210> SEQ ID NO 61
<211> LENGTH: 612
<212> TYPE: PRT
<213> ORGANISM: Artificial Sequence
<220> FEATURE:
<223> OTHER INFORMATION: Amino acid sequence of EVIR-C1

<400> SEQUENCE: 61

Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Thr Pro Ser Ser
            20                  25                  30

Leu

```
            195                 200                 205
Ser Ser Tyr Ala Thr Ser Thr Tyr Asn Gln Lys Phe Lys Asn Lys Ala
    210                 215                 220

Ala Phe Thr Val Asp Thr Ser Ser Thr Ala Phe Met Gln Leu Asn
225                 230                 235                 240

Ser Leu Thr Ser Glu Asp Ser Ala Val Tyr Tyr Cys Val Arg Ser Gly
                245                 250                 255

Asn Tyr Glu Glu Tyr Ala Met Asp Tyr Trp Gly Gln Gly Thr Ser Val
            260                 265                 270

Thr Val Ser Ser Thr Gly Thr Pro Cys Gln Lys Thr Ala Val Arg Ala
        275                 280                 285

Phe Gly Ala Gly Leu Leu Pro Pro Leu Tyr Ser Leu Val Phe Ile Ile
290                 295                 300

Gly Val Val Gly Asn Val Leu Val Ile Leu Val Leu Met Gln His Arg
305                 310                 315                 320

Arg Leu Gln Ser Met Thr Ser Ile Tyr Leu Phe Asn Leu Ala Val Ser
                325                 330                 335

Asp Leu Val Phe Leu Phe Thr Leu Pro Phe Trp Ile Asp Tyr Lys Leu
            340                 345                 350

Lys Asp Asp Trp Ile Phe Gly Asp Ala Met Cys Lys Leu Leu Ser Gly
        355                 360                 365

Phe Tyr Tyr Leu Gly Leu Tyr Ser Glu Ile Phe Phe Ile Ile Leu Leu
370                 375                 380

Thr Ile Asp Arg Tyr Leu Ala Ile Val His Ala Val Phe Ala Leu Arg
385                 390                 395                 400

Ala Arg Thr Val Thr Phe Gly Ile Ile Thr Ser Ile Ile Thr Trp Ala
                405                 410                 415

Leu Ala Ile Leu Ala Ser Met Pro Ala Leu Tyr Phe Phe Lys Ala Gln
            420                 425                 430

Trp Glu Phe Thr His Arg Thr Cys Ser Pro His Phe Pro Tyr Lys Ser
        435                 440                 445

Leu Lys Gln Trp Lys Arg Phe Gln Ala Leu Lys Leu Asn Leu Leu Gly
450                 455                 460

Leu Ile Leu Pro Leu Leu Val Met Ile Ile Cys Tyr Ala Gly Ile Ile
465                 470                 475                 480

Arg Ile Leu Leu Arg Arg Pro Ser Glu Lys Lys Val Lys Ala Val Arg
                485                 490                 495

Leu Ile Phe Ala Ile Thr Leu Leu Phe Phe Leu Leu Trp Thr Pro Tyr
            500                 505                 510

Asn Leu Ser Val Phe Val Ser Ala Phe Gln Asp Val Leu Phe Thr Asn
        515                 520                 525

Gln Cys Glu Gln Ser Lys Gln Leu Asp Leu Ala Met Gln Val Thr Glu
530                 535                 540

Val Ile Ala Tyr Thr His Cys Cys Val Asn Pro Ile Ile Tyr Val Phe
545                 550                 555                 560

Val Gly Glu Arg Phe Trp Lys Tyr Leu Arg Gln Leu Phe Gln Arg His
                565                 570                 575

Val Ala Ile Pro Leu Ala Lys Trp Leu Pro Phe Leu Ser Val Asp Gln
            580                 585                 590

Leu Glu Arg Thr Ser Ser Ile Ser Pro Ser Thr Gly Glu His Glu Leu
        595                 600                 605

Ser Ala Gly Phe
    610
```

<210> SEQ ID NO 62
<211> LENGTH: 615
<212> TYPE: PRT
<213> ORGANISM: Artificial Sequence
<220> FEATURE:
<223> OTHER INFORMATION: Amino acid sequence of EVIR-C5

<400> SEQUENCE: 62

```
Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Thr Pro Ser Ser
                20                  25                  30

Leu Pro Val Ser Val Gly Glu Lys Val Thr Met Thr Cys Lys Ser Ser
                35                  40                  45

Gln Thr Leu Leu Tyr Ser Asn Asn Gln Lys Asn Tyr Leu Ala Trp Tyr
    50                  55                  60

Gln Gln Lys Pro Gly Gln Ser Pro Lys Leu Leu Ile Ser Trp Ala Phe
65                  70                  75                  80

Thr Arg Lys Ser Gly Val Pro Asp Arg Phe Thr Gly Ser Gly Ser Gly
                85                  90                  95

Thr Asp Phe Thr Leu Thr Ile Gly Ser Val Lys Ala Glu Asp Leu Ala
                100                 105                 110

Val Tyr Tyr Cys Gln Gln Tyr Ser Asn Tyr Pro Trp Thr Phe Gly Gly
            115                 120                 125

Gly Thr Arg Leu Glu Ile Lys Arg Gly Gly Gly Ser Gly Gly Gly
        130                 135                 140

Gly Ser Gly Gly Gly Gly Ser Gly Gly Gly Gly Ser Glu Val Gln Leu
145                 150                 155                 160

Gln Gln Ser Gly Pro Glu Val Val Lys Thr Gly Ala Ser Val Lys Ile
                165                 170                 175

Ser Cys Lys Ala Ser Gly Tyr Ser Phe Thr Gly Tyr Phe Ile Asn Trp
            180                 185                 190

Val Lys Lys Asn Ser Gly Lys Ser Pro Glu Trp Ile Gly His Ile Ser
            195                 200                 205

Ser Ser Tyr Ala Thr Ser Thr Tyr Asn Gln Lys Phe Lys Asn Lys Ala
    210                 215                 220

Ala Phe Thr Val Asp Thr Ser Ser Thr Ala Phe Met Gln Leu Asn
225                 230                 235                 240

Ser Leu Thr Ser Glu Asp Ser Ala Val Tyr Tyr Cys Val Arg Ser Gly
                245                 250                 255

Asn Tyr Glu Glu Tyr Ala Met Asp Tyr Trp Gly Gln Gly Thr Ser Val
                260                 265                 270

Thr Val Ser Ser Thr Gly Met Ser Ala Pro Cys Gln Lys Ile Asn Val
            275                 280                 285

Lys Gln Ile Ala Ala Gln Leu Leu Pro Pro Leu Tyr Ser Leu Val Phe
    290                 295                 300

Ile Phe Gly Phe Val Gly Asn Met Met Val Phe Leu Ile Leu Ile Ser
305                 310                 315                 320

Cys Lys Lys Leu Lys Ser Val Thr Asp Ile Tyr Leu Leu Asn Leu Ala
                325                 330                 335

Ile Ser Asp Leu Leu Phe Leu Leu Thr Leu Pro Phe Trp Ala His Tyr
                340                 345                 350

Ala Ala Asn Glu Trp Val Phe Gly Asn Ile Met Cys Lys Val Phe Thr
            355                 360                 365
```

-continued

```
Gly Leu Tyr His Ile Gly Tyr Phe Gly Gly Ile Phe Phe Ile Ile Leu
        370                 375                 380

Leu Thr Ile Asp Arg Tyr Leu Ala Ile Val His Ala Val Phe Ala Leu
385                 390                 395                 400

Lys Val Arg Thr Val Asn Phe Gly Val Ile Thr Ser Val Thr Trp
                405                 410                 415

Ala Val Ala Val Phe Ala Ser Leu Pro Glu Ile Ile Phe Thr Arg Ser
                420                 425                 430

Gln Lys Glu Gly Phe His Tyr Thr Cys Ser Pro His Phe Pro His Thr
                435                 440                 445

Gln Tyr His Phe Trp Lys Ser Phe Gln Thr Leu Lys Met Val Ile Leu
        450                 455                 460

Ser Leu Ile Leu Pro Leu Leu Val Met Val Ile Cys Tyr Ser Gly Ile
465                 470                 475                 480

Leu His Thr Leu Phe Arg Cys Arg Asn Glu Lys Lys Arg His Arg Ala
                485                 490                 495

Val Arg Leu Ile Phe Ala Ile Met Ile Val Tyr Phe Leu Phe Trp Thr
        500                 505                 510

Pro Tyr Asn Ile Val Leu Leu Leu Thr Thr Phe Gln Glu Phe Phe Gly
        515                 520                 525

Leu Asn Asn Cys Ser Ser Ser Asn Arg Leu Asp Gln Ala Met Gln Ala
530                 535                 540

Thr Glu Thr Leu Gly Met Thr His Cys Cys Leu Asn Pro Val Ile Tyr
545                 550                 555                 560

Ala Phe Val Gly Glu Lys Phe Arg Ser Tyr Leu Ser Val Phe Phe Arg
                565                 570                 575

Lys His Ile Val Lys Arg Phe Cys Lys Arg Cys Ser Ile Phe Gln Gln
                580                 585                 590

Asp Asn Pro Asp Arg Ala Ser Ser Val Tyr Thr Arg Ser Thr Gly Glu
                595                 600                 605

His Glu Val Ser Thr Gly Leu
        610                 615

<210> SEQ ID NO 63
<211> LENGTH: 607
<212> TYPE: PRT
<213> ORGANISM: Artificial Sequence
<220> FEATURE:
<223> OTHER INFORMATION: Amino acid sequence of EVIR-CX

<400> SEQUENCE: 63

Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Thr Pro Ser Ser
                20                  25                  30

Leu Pro Val Ser Val Gly Glu Lys Val Thr Met Thr Cys Lys Ser Ser
            35                  40                  45

Gln Thr Leu Leu Tyr Ser Asn Asn Gln Lys Asn Tyr Leu Ala Trp Tyr
        50                  55                  60

Gln Gln Lys Pro Gly Gln Ser Pro Lys Leu Leu Ile Ser Trp Ala Phe
65                  70                  75                  80

Thr Arg Lys Ser Gly Val Pro Asp Arg Phe Thr Gly Ser Gly Ser Gly
                85                  90                  95

Thr Asp Phe Thr Leu Thr Ile Gly Ser Val Lys Ala Glu Asp Leu Ala
                100                 105                 110
```

```
Val Tyr Tyr Cys Gln Gln Tyr Ser Asn Tyr Pro Trp Thr Phe Gly Gly
            115                 120                 125

Gly Thr Arg Leu Glu Ile Lys Arg Gly Gly Gly Ser Gly Gly Gly
        130                 135                 140

Gly Ser Gly Gly Gly Ser Gly Gly Gly Ser Glu Val Gln Leu
145                 150                 155                 160

Gln Gln Ser Gly Pro Glu Val Val Lys Thr Gly Ala Ser Val Lys Ile
                165                 170                 175

Ser Cys Lys Ala Ser Gly Tyr Ser Phe Thr Gly Tyr Phe Ile Asn Trp
                180                 185                 190

Val Lys Lys Asn Ser Gly Lys Ser Pro Glu Trp Ile Gly His Ile Ser
            195                 200                 205

Ser Ser Tyr Ala Thr Ser Thr Tyr Asn Gln Lys Phe Lys Asn Lys Ala
210                 215                 220

Ala Phe Thr Val Asp Thr Ser Ser Thr Ala Phe Met Gln Leu Asn
225                 230                 235                 240

Ser Leu Thr Ser Glu Asp Ser Ala Val Tyr Tyr Cys Val Arg Ser Gly
                245                 250                 255

Asn Tyr Glu Glu Tyr Ala Met Asp Tyr Trp Gly Gln Gly Thr Ser Val
            260                 265                 270

Thr Val Ser Ser Thr Gly Phe Arg Asp Glu Asn Val His Phe Asn Arg
        275                 280                 285

Ile Phe Leu Pro Thr Ile Tyr Phe Ile Ile Phe Leu Thr Gly Ile Val
        290                 295                 300

Gly Asn Gly Leu Val Ile Leu Val Met Gly Tyr Gln Lys Lys Leu Arg
305                 310                 315                 320

Ser Met Thr Asp Lys Tyr Arg Leu His Leu Ser Val Ala Asp Leu Leu
                325                 330                 335

Phe Val Ile Thr Leu Pro Phe Trp Ala Val Asp Ala Met Ala Asp Trp
            340                 345                 350

Tyr Phe Gly Lys Phe Leu Cys Lys Ala Val His Ile Ile Tyr Thr Val
        355                 360                 365

Asn Leu Tyr Ser Ser Val Leu Ile Leu Ala Phe Ile Ser Leu Asp Arg
        370                 375                 380

Tyr Leu Ala Ile Val His Ala Thr Asn Ser Gln Arg Pro Arg Lys Leu
385                 390                 395                 400

Leu Ala Glu Lys Ala Val Tyr Val Gly Val Trp Ile Pro Ala Leu Leu
                405                 410                 415

Leu Thr Ile Pro Asp Phe Ile Phe Ala Asp Val Ser Gln Gly Asp Ile
            420                 425                 430

Ser Gln Gly Asp Asp Arg Tyr Ile Cys Asp Arg Leu Tyr Pro Asp Ser
        435                 440                 445

Leu Trp Met Val Val Phe Gln Phe Gln His Ile Met Val Gly Leu Val
        450                 455                 460

Leu Pro Gly Ile Val Ile Leu Ser Cys Tyr Cys Ile Ile Ile Ser Lys
465                 470                 475                 480

Leu Ser His Ser Lys Gly His Gln Lys Arg Lys Ala Leu Lys Thr Thr
                485                 490                 495

Val Ile Leu Ile Leu Ala Phe Phe Ala Cys Trp Leu Pro Tyr Tyr Val
            500                 505                 510

Gly Ile Ser Ile Asp Ser Phe Ile Leu Leu Gly Val Ile Lys Gln Gly
        515                 520                 525
```

Cys Asp Phe Glu Ser Ile Val His Lys Trp Ile Ser Ile Thr Glu Ala
    530                 535                 540

Leu Ala Phe Phe His Cys Cys Leu Asn Pro Ile Leu Tyr Ala Phe Leu
545                 550                 555                 560

Gly Ala Lys Phe Lys Ser Ser Ala Gln His Ala Leu Asn Ser Met Ser
                565                 570                 575

Arg Gly Ser Ser Leu Lys Ile Leu Ser Lys Gly Lys Arg Gly Gly His
                580                 585                 590

Ser Ser Val Ser Thr Glu Ser Glu Ser Ser Phe His Ser Ser
                595                 600                 605

<210> SEQ ID NO 64
<211> LENGTH: 575
<212> TYPE: PRT
<213> ORGANISM: Artificial Sequence
<220> FEATURE:
<223> OTHER INFORMATION: Amino acid sequence of EVIR-S

<400> SEQUENCE: 64

Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Thr Pro Ser Ser
                20                  25                  30

Leu Pro Val Ser Val Gly Glu Lys Val Thr Met Thr Cys Lys Ser Ser
            35                  40                  45

Gln Thr Leu Leu Tyr Ser Asn Asn Gln Lys Asn Tyr Leu Ala Trp Tyr
        50                  55                  60

Gln Gln Lys Pro Gly Gln Ser Pro Lys Leu Leu Ile Ser Trp Ala Phe
65                  70                  75                  80

Thr Arg Lys Ser Gly Val Pro Asp Arg Phe Thr Gly Ser Gly Ser Gly
                85                  90                  95

Thr Asp Phe Thr Leu Thr Ile Gly Ser Val Lys Ala Glu Asp Leu Ala
                100                 105                 110

Val Tyr Tyr Cys Gln Gln Tyr Ser Asn Tyr Pro Trp Thr Phe Gly Gly
            115                 120                 125

Gly Thr Arg Leu Glu Ile Lys Arg Gly Gly Gly Ser Gly Gly Gly
        130                 135                 140

Gly Ser Gly Gly Gly Ser Gly Gly Gly Ser Glu Val Gln Leu
145                 150                 155                 160

Gln Gln Ser Gly Pro Glu Val Val Lys Thr Gly Ala Ser Val Lys Ile
                165                 170                 175

Ser Cys Lys Ala Ser Gly Tyr Ser Phe Thr Gly Tyr Phe Ile Asn Trp
            180                 185                 190

Val Lys Lys Asn Ser Gly Lys Ser Pro Glu Trp Ile Gly His Ile Ser
        195                 200                 205

Ser Ser Tyr Ala Thr Ser Thr Tyr Asn Gln Lys Phe Lys Asn Lys Ala
    210                 215                 220

Ala Phe Thr Val Asp Thr Ser Ser Ser Thr Ala Phe Met Gln Leu Asn
225                 230                 235                 240

Ser Leu Thr Ser Glu Asp Ser Ala Val Tyr Tyr Cys Val Arg Ser Gly
                245                 250                 255

Asn Tyr Glu Glu Tyr Ala Met Asp Tyr Trp Gly Gln Gly Thr Ser Val
                260                 265                 270

Thr Val Ser Ser Thr Gly Ile Ala Thr Thr Asp Pro Thr Ala Pro Gly
            275                 280                 285

```
Thr Gly Gly Thr Ala Val Gly Met Leu Ser Thr Asp Ser Ala Thr Gln
    290                 295                 300

Trp Ser Leu Thr Ser Val Glu Thr Val Gln Pro Ala Ser Thr Glu Val
305                 310                 315                 320

Glu Thr Ser Gln Pro Ala Pro Met Glu Ala Glu Thr Ser Gln Pro Ala
                325                 330                 335

Pro Met Glu Ala Glu Thr Ser Gln Pro Ala Pro Met Glu Ala Asp Thr
                340                 345                 350

Ser Lys Pro Ala Pro Thr Glu Ala Glu Thr Ser Lys Pro Ala Pro Thr
                355                 360                 365

Glu Ala Glu Thr Ser Gln Pro Ala Pro Asn Glu Ala Glu Thr Ser Lys
    370                 375                 380

Pro Ala Pro Thr Glu Ala Glu Thr Ser Lys Pro Ala Pro Thr Glu Ala
385                 390                 395                 400

Glu Thr Thr Gln Leu Pro Arg Ile Gln Ala Val Lys Thr Leu Phe Thr
                405                 410                 415

Thr Ser Ala Ala Thr Glu Val Pro Ser Thr Gly Pro Thr Thr Met Glu
                420                 425                 430

Thr Ala Ser Thr Glu Ser Asn Glu Ser Thr Ile Phe Leu Gly Pro Ser
    435                 440                 445

Val Thr His Leu Pro Asp Ser Gly Leu Lys Lys Gly Leu Ile Val Thr
450                 455                 460

Pro Gly Asn Ser Pro Ala Pro Thr Leu Pro Gly Ser Ser Asp Leu Ile
465                 470                 475                 480

Pro Val Lys Gln Cys Leu Leu Ile Ile Leu Ile Leu Ala Ser Leu Ala
                485                 490                 495

Thr Ile Phe Leu Val Cys Thr Val Val Leu Ala Val Arg Leu Ser Arg
                500                 505                 510

Lys Thr His Met Tyr Pro Val Arg Asn Tyr Ser Pro Thr Glu Met Ile
                515                 520                 525

Cys Ile Ser Ser Leu Leu Pro Glu Gly Gly Asp Gly Ala Pro Val Thr
    530                 535                 540

Ala Asn Gly Gly Leu Pro Lys Val Gln Asp Leu Lys Thr Glu Pro Ser
545                 550                 555                 560

Gly Asp Arg Asp Gly Asp Asp Leu Thr Leu His Ser Phe Leu Pro
                565                 570                 575
```

<210> SEQ ID NO 65
<211> LENGTH: 1620
<212> TYPE: DNA
<213> ORGANISM: Artificial Sequence
<220> FEATURE:
<223> OTHER INFORMATION: Nucleic acid sequence of EVIR-N

<400> SEQUENCE: 65

```
atggatttc aggtccagat tttctccttc ctcctcattt cagccagcgt cattatgtct      60 cgggggata ttgtcctcac acagactccc agctccctgc ctgtgtccgt cggagagaaa    120
gtgaccatga catgcaagtc tagtcagaca ctgctctact ctaacaatca gaagaactac    180
ctcgcatggt atcagcagaa accaggacag agcccaagc tgctcatctc ctgggctttc    240
acccggaaat ccggggtgcc tgaccgcttc acaggtagcg gctccggaac tgatttact    300 ctgaccattg atctgtgaa ggcagaggac ctcgccgtct actattgcca gcagtacagt    360
aattatccat ggactttgg cggagggacc aggctggaaa tcaagagagg tggaggaggg    420
tccggtggag gagggtctgg tggaggaggg agtggtggag gagggtcaga ggtgcagctg    480
```

```
cagcagtctg gccccgaagt ggtcaaaact ggagcttcag tcaaaatcag ctgtaaggca      540
tctgggtaca gcttcaccgg ctacttcatc aactgggtga agaaaaattc agggaagagc      600
cctgagtgga tcggccacat ttcaagctcc tacgccacaa gcacttacaa ccagaagttc      660
aaaaataagg ccgcttttac cgtggacaca tctagttcaa ccgccttcat gcagctgaac      720
tccctcacat ctgaagatag tgctgtgtac tattgtgtca ggagcggcaa ctacgaagaa      780
tatgctatgg attactgggg cagggggacc tccgtgactg tctcaagcac cggtcttctg      840
ggggtgtccc ttggaggtgc caaggaggca tgccccacag gcctgtacac acacagcggt      900
gagtgctgca agcctgcaa cctgggcgag ggtgtggccc agccttgtgg agccaaccag      960
accgtgtgtg agccctgcct ggacagcgtg acgttctccg acgtggtgag cgcgaccgag     1020
ccgtgcaagc cgtgcaccga gtgcgtgggg ctccagagca tgtcggcgcc gtgcgtggag     1080
gccgacgacg ccgtgtgccg ctgcgcctac ggctactacc aggatgagac gactgggcgc     1140
tgcgaggcgt gccgcgtgtg cgaggcgggc tcgggcctcg tgttctcctg ccaggacaag     1200
cagaacaccg tgtgcgagga gtgccccgac ggcacgtatt ccgacgaggc caaccacgtg     1260
gacccgtgcc tgccctgcac cgtgtgcgag gacaccgagc gccagctccg cgagtgcaca     1320
cgctgggccg acgccgagtg cgaggagatc cctggccgtt ggattacacg gtccacaccc     1380
ccagagggct cggacagcac agcccccagc cccaggagc ctgaggcacc tccagaacaa     1440
gacctcatag ccagcacggt ggcaggtgtg gtgaccacag tgatgggcag ctcccagccc     1500
gtggtgaccc gaggcaccac cgacaacctc atccctgtct attgctccat cctggctgct     1560
gtggttgtgg gccttgtggc ctacatagcc ttcaagaggt ggaacagggg gatcctctag     1620

<210> SEQ ID NO 66
<211> LENGTH: 1146
<212> TYPE: DNA
<213> ORGANISM: Artificial Sequence
<220> FEATURE:
<223> OTHER INFORMATION: Nucleic acid sequence of EVIR-G

<400> SEQUENCE: 66
atggattttc aggtccagat tttctccttc ctcctcattt cagccagcgt cattatgtct       60 cgggggggata ttgtcctcac acagactccc agctccctgc ctgtgtccgt cggagagaaa      120
gtgaccatga catgcaagtc tagtcagaca ctgctctact ctaacaatca gaagaactac      180
ctcgcatggt atcagcagaa accaggacag agcccaagc tgctcatctc ctgggctttc      240
acccggaaat ccggggtgcc tgaccgcttc acaggtagcg gctccggaac tgattttact      300
ctgaccattg atctgtgaa ggcagaggac ctcgccgtct actattgcca gcagtacagt      360
aattatccat ggactttgg cggagggacc aggctgaaa tcaagagagg tggaggaggg      420
tccggtggag gagggtctgg tggaggaggg agtggtggag gagggtcaga ggtgcagctg      480
cagcagtctg gccccgaagt ggtcaaaact ggagcttcag tcaaaatcag ctgtaaggca      540
tctgggtaca gcttcaccgg ctacttcatc aactgggtga agaaaaattc agggaagagc      600
cctgagtgga tcggccacat ttcaagctcc tacgccacaa gcacttacaa ccagaagttc      660
aaaaataagg ccgcttttac cgtggacaca tctagttcaa ccgccttcat gcagctgaac      720
tccctcacat ctgaagatag tgctgtgtac tattgtgtca ggagcggcaa ctacgaagaa      780
tatgctatgg attactgggg cagggggacc tccgtgactg tctcaagcac cggtcacgag      840
aactccgaac tgctgattcc taaggcaact cacaacgact ccggctccta tttctgtaga      900
```

| gggctgattg gacataacaa caagagctcc gcctcattca ggattagcct gggcgaccca | 960 |
| gggtctccca gtatgttccc cccttggcac cagatcacct tttgcctgct gattggactg | 1020 |
| ctgttcgcta tcgatacagt gctgtacttt tctgtccgga gaggcctgca gtcacccgtg | 1080 |
| gcagattacg aagaacccaa gattcagtgg agcaaggagc cccaggataa gacgcgtgtc | 1140 |
| gactga | 1146 |

<210> SEQ ID NO 67
<211> LENGTH: 2241
<212> TYPE: DNA
<213> ORGANISM: Artificial Sequence
<220> FEATURE:
<223> OTHER INFORMATION: Nucleic acid sequence of EVIR-F

<400> SEQUENCE: 67

| atggattttc aggtccagat tttctccttc ctcctcattt cagccagcgt cattatgtct | 60 |
| cgggggata ttgtcctcac acagactccc agctccctgc ctgtgtccgt cggagagaaa | 120 |
| gtgaccatga catgcaagtc tagtcagaca ctgctctact ctaacaatca agaaactac | 180 |
| ctcgcatggt atcagcagaa accaggacag agccccaagc tgctcatctc ctgggctttc | 240 |
| acccggaaat ccggggtgcc tgaccgcttc acaggtagcg gctccggaac tgattttact | 300 |
| ctgaccattg gatctgtgaa ggcagaggac ctcgccgtct actattgcca gcagtacagt | 360 |
| aattatccat ggactttggg cggagggacc aggctgaaaa tcaagagagg tggaggaggg | 420 |
| tccggtggag gagggtctgg tggaggaggg agtggtggag gaggtcaga ggtgcagctg | 480 |
| cagcagtctg gccccgaagt ggtcaaaact ggagcttcag tcaaaatcag ctgtaaggca | 540 |
| tctgggtaca gcttcaccgg ctacttcatc aactgggtga agaaaattc agggaagagc | 600 |
| cctgagtgga tcgccacat ttcaagctcc tacgccacaa gcacttacaa ccagaagttc | 660 |
| aaaaataagg ccgcttttac cgtggacaca tctagttcaa ccgccttcat gcagctgaac | 720 |
| tccctcacat ctgaagatag tgctgtgtac tattgtgtca ggagcggcaa ctacgaagaa | 780 |
| tatgctatgg attactgggg gcaggggacc tccgtgactg tctcaagcac cggtccaggc | 840 |
| cccttccctt tcatccaaga caacatctcc ttctatgcga ccattgggct ctgtctcccc | 900 |
| ttcattgttg ttctcattgt gttgatctgc cacaaataca aaaagcaatt taggtacgag | 960 |
| agtcagctgc agatgatcca ggtgactggc ccctggata cgagtacttt ctacgttgac | 1020 |
| ttcagggact atgaatatga ccttaagtgg gagttcccga gagagaactt agagtttggg | 1080 |
| aaggtcctgg gtctggcgc tttcgggagg gtgatgaacg ccacggccta tggcattagt | 1140 |
| aaaacgggag tctcaattca ggtggcggtg aagatgctaa aagagaaagc tgacagctgt | 1200 |
| gaaaagaag ctctcatgtc ggagctcaaa atgatgaccc acctgggaca ccatgacaac | 1260 |
| atcgtgaatc tgctggggc atgcacactg tcagggccag tgtacttgat ttttgaatat | 1320 |
| tgttgctatg gtgacctcct caactaccta agaagtaaaa gagagaagtt cacaggaca | 1380 |
| tggacagaga ttttttaagga acataatttc agttttace ctactttcca ggcacattca | 1440 |
| aattccagca tgcctggttc acgagaagtt cagttacacc cgcccttgga tcagctctca | 1500 |
| gggttcaatg gaatttaat tcattctgaa gatgagattg aatatgaaaa ccagaagagg | 1560 |
| ctggcagaag aagaggagga gatttgaac gtgctgacgt tgaagacct cctttgcttt | 1620 |
| gcgtaccaag tggccaaagg catggaattc ctggagttca gtcgtgtgt ccacagagac | 1680 |
| ctggcagcca gaatgtgtt ggtcacccac gggaaggtgg tgaagatctg tgactttgga | 1740 |
| ctggcccgag acatcctgag cgactccagc tacgtcgtca ggggcaacgc acggctgccg | 1800 |

```
gtgaagtgga tggcacctga gagcttattt gaagggatct acacaatcaa gagtgacgtc    1860
tggtcctacg gcatccttct ctgggagata ttttcactgg gtgtgaaccc ttaccctggc    1920
attcctgtcg acgctaactt ctataaactg attcagagtg gatttaaaat ggagcagcca    1980
ttctatgcca cagaagggat atactttgta atgcaatcct gctgggcttt tgactcaagg    2040
aagcggccat ccttccccaa cctgacttca tttttaggat gtcagctggc agaggcagaa    2100
gaagcgatgt atcagaacat gggtggcaac gtcccagaac atccatccat ctaccaaaac    2160
aggcggcccc tcagcagaga ggcaggctca gagccgccat cgccacaggc ccaggtgaag    2220
attcacggag aaagaagtta g                                              2241
```

<210> SEQ ID NO 68
<211> LENGTH: 1725
<212> TYPE: DNA
<213> ORGANISM: Artificial Sequence
<220> FEATURE:
<223> OTHER INFORMATION: Nucleic acid sequence of EVIR-T

<400> SEQUENCE: 68

```
atggattttc aggtccagat tttctccttc ctcctcattt cagccagcgt cattatgtct      60
cggggggata ttgtcctcac acagactccc agctccctgc ctgtgtccgt cggagagaaa     120
gtgaccatga catgcaagtc tagtcagaca ctgctctact ctaacaatca gaagaactac     180
ctcgcatggt atcagcagaa accaggacag agccccaagc tgctcatctc ctgggctttc     240
acccggaaat ccggggtgcc tgaccgcttc acaggtagcg gctccggaac tgattttact     300
ctgaccattg atctgtgaa ggcagaggac ctcgccgtct actattgcca gcagtacagt     360
aattatccat ggacttttgg cgagggacc aggctggaaa tcaagagagg tggaggaggg     420
tccggtggag gagggtctgg tggaggaggg agtggtggag gagggtcaga ggtgcagctg     480
cagcagtctg gccccgaagt ggtcaaaact ggagcttcag tcaaaatcag ctgtaaggca     540
tctgggtaca gcttcaccgg ctacttcatc aactgggtga agaaaaattc agggaagagc     600
cctgagtgga tcggccacat ttcaagctcc tacgccacaa gcacttacaa ccagaagttc     660
aaaaataagg ccgcttttac cgtggacaca tctagttcaa ccgccttcat gcagctgaac     720
tccctcacat ctgaagatag tgctgtgtac tattgtgtca ggagcggcaa ctacgaagaa     780
tatgctatgg attactgggg gcaggggacc tccgtgactg tctcaagcac cggtcagctg     840
tattccctca gcactcttga ttgcagtttc aatcgcatag acatctaa ggaatactg      900 caacattttc caaagagtct agccttcttc aatcttacta caattctgt tgcttgtata     960 tgtgaacatc agaaattcct gcagtgggtc aaggaacaga agcagttctt ggtgaatgtt    1020
gaacaaatga catgtgcaac acctgtagag atgaatacct ccttagtgtt ggattttaat    1080
aattctacct gttatatgta caagacaatc atcagtgtgt cagtggtcag tgtgattgtg    1140
gtatccactg tagcatttct gatataccac ttctattttc acctgatact tattgctggc    1200
tgtaaaaagt acagcagagg agaaagcatc tatgatgcat ttgtgatcta ctcgagtcag    1260
aatgaggact gggtgagaaa tgagctggta aagaatttag aagaaggagt gcccgctt     1320 caccctctgcc ttcactacag agactttatt cctggtgtag ccattgctgc caacatcatc    1380
caggaaggct tccacaagag ccggaaggtt attgtggtag tgtctagaca ctttattcag    1440
agccgttggt gtatcttga atatgagatt gctcaaacat ggcagtttct gagcagccgc    1500
tctggcatca tcttcattgt ccttgagaag gttgagaagt ccctgctgag gcagcaggtg    1560
```

| | |
|---|---|
| gaattgtatc gccttcttag cagaaacacc tacctggaat gggaggacaa tcctctgggg | 1620 |
| aggcacatct tctggagaag acttaaaaat gccctattgg atggaaaagc ctcgaatcct | 1680 |
| gagcaaacag cagaggaaga acaagaaacg gcaacttgga cctga | 1725 |

<210> SEQ ID NO 69
<211> LENGTH: 1956
<212> TYPE: DNA
<213> ORGANISM: Artificial Sequence
<220> FEATURE:
<223> OTHER INFORMATION: Nucleic acid sequence of EVIR-C2

<400> SEQUENCE: 69

| | |
|---|---|
| atggattttc aggtccagat tttctccttc ctcctcattt cagccagcgt cattatgtct | 60 |
| cgggggata ttgtcctcac acagactccc agctccctgc ctgtgtccgt cggagagaaa | 120 |
| gtgaccatga catgcaagtc tagtcagaca ctgctctact ctaacaatca gaagaactac | 180 |
| ctcgcatggt atcagcagaa accaggacag agccccaagc tgctcatctc ctgggctttc | 240 |
| acccggaaat ccggggtgcc tgaccgcttc acaggtagcg gctccggaac tgatttact | 300 |
| ctgaccattg gatctgtgaa ggcagaggac ctcgccgtct actattgcca gcagtacagt | 360 |
| aattatccat ggactttgg cggagggacc aggctgaaa tcaagagagg tggaggaggg | 420 |
| tccggtggag ggggtctgg tggaggaggg agtggtggag gagggtcaga ggtgcagctg | 480 |
| cagcagtctg gccccgaagt ggtcaaaact ggagcttcag tcaaaatcag ctgtaaggca | 540 |
| tctgggtaca gcttcaccgg ctacttcatc aactgggtga agaaaattc agggaagagc | 600 |
| cctgagtgga tcgccacat ttcaagctcc tacgccacaa gcacttacaa ccagaagttc | 660 |
| aaaaataagg ccgcttttac cgtggacaca tctagttcaa ccgccttcat gcagctgaac | 720 |
| tccctcacat ctgaagatag tgctgtgtac tattgtgtca ggagcggcaa ctacgaagaa | 780 |
| tatgctatgg attactgggg gcaggggacc tccgtgactg tctcaagcac cggtatggaa | 840 |
| gacaataata tgttacctca gttcatccat ggcatactat caacatctca ttctctattt | 900 |
| acacgaagta tccaagagct tgatgaaggg gccaccacac cgtatgacta cgatgatggt | 960 |
| gagccttgtc ataaaaccag tgtgaagcaa attggagctt ggatcctgcc tccactctac | 1020 |
| tccctggtat tcatctttgg ttttgtgggc aacatgttgg tcattataat tctgataggc | 1080 |
| tgtaaaaagc tgaagagcat gactgatatc tatctgctca acctggccat ctctgacctg | 1140 |
| ctcttcctgc tcacattacc attctgggct cactatgctg caaatgagtg ggtctttggg | 1200 |
| aatataatgt gtaaagtatt cacagggctc tatcacattg gttattttgg tggaatcttt | 1260 |
| ttcattatcc tcctgacaat tgataggtac ttggctattg ttcatgctgt gtttgcttta | 1320 |
| aaagccagga cagttacctt tgggggtgata acaagtgtag tcacttgggt ggtggctgtg | 1380 |
| tttgcctctc taccaggaat catatttact aaatccaaac aagatgatca ccattacacc | 1440 |
| tgtggccctt attttacaca actatggaag aatttccaaa caataatgag aaatatcttg | 1500 |
| agcctgatcc tgcctctact tgtcatggtc atctgctact caggaattct ccacaccctg | 1560 |
| tttcgctgta ggaatgagaa gaagaggcac agggctgtga ggctcatctt tgccatcatg | 1620 |
| attgtctact ttctcttctg gactccatac aatattgttc tcttcttgac cacccttccag | 1680 |
| gaatccttgg gaatgagtaa ctgtgtgatt gacaagcact tagaccaggc catgcaggtg | 1740 |
| acagagactc ttggaatgac acactgctgc attaatccig tcatttatgc ctttgttgga | 1800 |
| gagaagttcc gaaggtatct ctccatattt ttcagaaagc acattgctaa acgtctctgc | 1860 |
| aaacagtgcc cagttttcta tagggagaca gcagatcgag tgagctctac attcactcct | 1920 |

```
tccactgggg agcaagaggt ctcggttggg ttgtaa                    1956

<210> SEQ ID NO 70
<211> LENGTH: 1398
<212> TYPE: DNA
<213> ORGANISM: Artificial Sequence
<220> FEATURE:
<223> OTHER INFORMATION: Nucleic acid sequence of EVIR-I

<400> SEQUENCE: 70
atggattttc aggtccagat tttctccttc ctcctcattt cagccagcgt cattatgtct    60 cgggggggata ttgtcctcac acagactccc agctccctgc ctgtgtccgt cggagagaaa   120
gtgaccatga catgcaagtc tagtcagaca ctgctctact ctaacaatca gaagaactac   180
ctcgcatggt atcagcagaa accaggacag agccccaagc tgctcatctc ctgggctttc   240
acccggaaat ccggggtgcc tgaccgcttc acaggtagcg gctccggaac tgattttact   300
ctgaccattg atctgtgaa ggcagaggac ctcgccgtct actattgcca gcagtacagt    360
aattatccat ggacttttgg cggagggacc aggctggaaa tcaagagagg tggaggaggg   420
tccggtggag gagggtctgg tggaggaggg agtggtggag gagggtcaga ggtgcagctg   480
cagcagtctg gccccgaagt ggtcaaaact ggagcttcag tcaaaatcag ctgtaaggca   540
tctgggtaca gcttcaccgg ctacttcatc aactgggtga agaaaaattc agggaagagc   600
cctgagtgga tcggccacat ttcaagctcc tacgccacaa gcacttacaa ccagaagttc   660
aaaaataagg ccgcttttac cgtggacaca tctagttcaa ccgccttcat gcagctgaac   720
tccctcacat ctgaagatag tgctgtgtac tattgtgtca ggagcggcaa ctacgaagaa   780
tatgctatgg attactgggg cagggggacc tccgtgactg tctcaagcac cgtaatgca   840 cggctggtag agtgcagtgg ccgtggccac tgccaatgca acaggtgcat atgtgacgaa   900
ggctaccagc caccgatgtg tgaggattgt cccagctgtg gctcgcactg cagggacaac   960
cacacctctt gtgccgagtg cctgaagttt gataagggcc cttttgagaa gaactgtagt  1020
gttcagtgtg ctggtatgac gctgcagact atccctttga agaaaaagcc ctgcaaggag  1080
agggactcgg aaggctgttg gataacttac actttgcagc agaaggacgg aaggaacatt  1140
tacaacatcc atgtggagga cagtctagag tgtgtgaagg cccccaatgt ggctgccatc  1200
gtagggggca ccgtggtagg tgtcgtactg attggtgtcc tcctcctggt catctggaag  1260
gccctgaccc acctgactga cctcagggag tacaggcgct ttgagaagga gaaactcaag  1320
tcccaatgga caatgacaa ccccctcttc aagagtgcta cgacaacggt catgaacccc   1380
aagtttgctg aaagctag                                                1398

<210> SEQ ID NO 71
<211> LENGTH: 2436
<212> TYPE: DNA
<213> ORGANISM: Artificial Sequence
<220> FEATURE:
<223> OTHER INFORMATION: Nucleic acid sequence of EVIR-C

<400> SEQUENCE: 71
atggattttc aggtccagat tttctccttc ctcctcattt cagccagcgt cattatgtct    60 cgggggggata ttgtcctcac acagactccc agctccctgc ctgtgtccgt cggagagaaa   120
gtgaccatga catgcaagtc tagtcagaca ctgctctact ctaacaatca gaagaactac   180
ctcgcatggt atcagcagaa accaggacag agccccaagc tgctcatctc ctgggctttc   240
```

```
acccggaaat ccggggtgcc tgaccgcttc acaggtagcg gctccggaac tgattttact      300
ctgaccattg gatctgtgaa ggcagaggac ctcgccgtct actattgcca gcagtacagt      360
aattatccat ggacttttgg cggagggacc aggctggaaa tcaagagagg tggaggaggg      420
tccggtggag gagggtctgg tggagggggg agtggtggag gagggtcaga ggtgcagctg      480
cagcagtctg gccccgaagt ggtcaaaact ggagcttcag tcaaaatcag ctgtaaggca      540
tctgggtaca gcttcaccgg ctacttcatc aactgggtga agaaaaattc agggaagagc      600
cctgagtgga tcggccacat ttcaagctcc tacgccacaa gcacttacaa ccagaagttc      660
aaaaataagg ccgcttttac cgtggacaca tctagttcaa ccgccttcat gcagctgaac      720
tccctcacat ctgaagatag tgctgtgtac tattgtgtca ggagcggcaa ctacgaagaa      780
tatgctatgg attactgggg cagggggacc tccgtgactg tctcaagcac cggtactcag      840
aagatggctt actcattcat tgagcacaca ttccaggtcc agtacaagaa gaaatcggac      900
agctgggagg acagcaagac agagaaccta gatcgagccc atagcatgga cctctcccag      960
ctggagccag acacctcata ctgcgccagg gtgagggtca agcccatctc taactacgat     1020
gggatctgga gcaagtggag cgaagagtac acttggaaga ctgactgggt gatgccacg      1080
ctgtggatag tcctcatcct ggtctttctc atcctcacct tgctcctgat ccttcgcttt     1140
ggctgtgtct ctgtatacag gacgtacagg aagtggaagg aaaagatccc caaccccagc     1200
aagagcctcc tgttccagga tggaggtaaa ggtctctggc ctcctggcag catggcagcc     1260
ttcgccacta gaaccccgc tctccagggg ccacagagca ggcttcttgc tgagcaacag      1320
ggggagtcat atgcacattt ggaagacaac aacgtgtcac ctctcactat agaggaccct     1380
aatataattc gagttccacc atccgggcct gatacaaccc cagctgcctc atccgaatcc     1440
acagagcaac ttcccaatgt tcaagtagag ggaccaactc taacagacc taggaagcaa     1500
ttacccagct ttgacttcaa tgggccctac ctggggcctc cccaatccca ctctctgcct     1560
gatctcccag accagctggg ttcccccag gtgggtggga gcctgaagcc agcactgcca      1620
ggctccttgg agtacatgtg tctgccccct ggaggtcaag cgcaactggt tccattgtcc     1680
caggtgatgg ggcagggcca ggctatggat gtgcagtgtg ggtccagcct ggagacctca     1740
gggagccctt ctgtggagcc aaaggagaac cctccagttg agctgagcat ggaggaacag     1800
gaggcacggg acaacccagt gactctgccc ataagctctg ggggccctga gggcagtatg     1860
atggcctctg attatgtcac tcctggagat ccggtgctca ctctgcccac agggcccctg     1920
tctacctctc tgggccctc tctagggttg ccctcagccc aaagccccg tctctgtctt      1980
aagctgccca gggtcccctc tggaagccca gctctagggc caccagggtt tgaggactat     2040
gtggagctgc ctccaagtgt gagccaggct gccaagtccc ctccaggcca tcctgctcct     2100
cctgtggcaa gcagccccac agtgatccca ggagagccca ggaggaagt gggcccagca     2160
tccccacatc ccgaaggcct ccttgttctt cagcaggttg gggactactg cttcctccct     2220
ggcctgggac ctggctccct ctcaccacac agtaagccac cctctccaag tctgtgttct     2280
gagactgagg acctagtcca ggacttgtct gtcaaaaagt ttccctatca gcccatgccc     2340
caggcgccag ccattcagtt tttcaagtcc ctaaagcatc aggactacct gtccctgccc     2400
ccttgggaca atagccagtc tgggaaggtg tgctga                                2436
```

<210> SEQ ID NO 72
<211> LENGTH: 1839
<212> TYPE: DNA
<213> ORGANISM: Artificial Sequence
<220> FEATURE:
<223> OTHER INFORMATION: Nucleic acid sequence of EVIR-C1

<400> SEQUENCE: 72

```
atggattttc aggtccagat tttctccttc ctcctcattt cagccagcgt cattatgtct     60
cgggggata ttgtcctcac acagactccc agctccctgc ctgtgtccgt cggagagaaa    120
gtgaccatga catgcaagtc tagtcagaca ctgctctact ctaacaatca gaagaactac   180
ctcgcatggt atcagcagaa accaggacag agccccaagc tgctcatctc ctgggctttc   240
acccggaaat ccggggtgcc tgaccgcttc acaggtagcg gctccggaac tgattttact   300
ctgaccattg gatctgtgaa ggcagaggac ctcgccgtct actattgcca gcagtacagt   360
aattatccat ggacttttgg cggagggacc aggctggaaa tcaagagagg tggaggaggg   420
tccggtggag gagggtctgg tggagagggg agtggtggag gagggtcaga ggtgcagctg   480
cagcagtctg cccccgaagt ggtcaaaact ggagcttcag tcaaaatcag ctgtaaggca   540
tctgggtaca gcttcaccgg ctacttcatc aactgggtga agaaaaattc agggaagagc   600
cctgagtgga tcggccacat ttcaagctcc tacgccacaa gcacttacaa ccagaagttc   660
aaaaataagg ccgcttttac cgtggacaca tctagttcaa ccgccttcat gcagctgaac   720
tccctcacat ctgaagatag tgctgtgtac tattgtgtca ggagcggcaa ctacgaagaa   780
tatgctatgg attactgggg cagggggacc tccgtgactg tctcaagcac cggtactcca   840
tgccaaaaga ctgctgtaag agcctttggg gctggactcc tgcccccct gtattctcta    900
gtgttcatca ttggagtggt gggcaatgtc ctagtgattc tggtgctcat gcagcatagg   960
aggcttcaaa gcatgaccag catctacctg ttcaacctgg ctgtctctga tctggtcttc  1020
cttttcactt tacctttctg gattgactac aagttgaaag acgactggat ttttggtgat  1080
gccatgtgca agcttctctc tgggttttat tacctgggtt tatacagtga gatcttcttt  1140
atcatcctgt tgacgattga cagatacctg gccattgtcc atgctgtgtt tgccctgagg  1200
gccccgaactg ttacttttgg catcatcacc agtattatca cctgggccct agccatctta  1260
gcttccatgc ctgccttata ctttttttaag gcccagtggg agttcactca ccgtacctgt  1320
agccctcatt tccctacaa gagcctgaag cagtggaaga ggtttcaagc tctaaagcta  1380
aaccttcttg gactaatttt gcctctgtta gtcatgataa tctgctatgc agggatcatc  1440
agaattctgc tcagaagacc cagtgagaag aaggtcaaag ccgtgcgtct gatatttgct  1500
attactcttc tattcttcct cctctggacc ccctacaatc tgagtgtatt tgtttctgct  1560
ttccaagatg ttctattcac caatcagtgt gagcagagta agcaactgga cctggccatg  1620
caggtgactg aggtgattgc ctacacccac tgttgtgtca acccaatcat ttatgttttt  1680
gtgggtgaac ggttctggaa gtaccttcgg cagctgtttc aaaggcatgt ggctatacca  1740
ctggcaaaat ggctgcccct cctctctgtg gaccaactag aaaggaccag ttctatatct  1800
ccatccacag gagaacatga gctctctgct ggcttctga                          1839
```

<210> SEQ ID NO 73
<211> LENGTH: 1848
<212> TYPE: DNA
<213> ORGANISM: Artificial Sequence
<220> FEATURE:
<223> OTHER INFORMATION: Nucleic acid sequence of EVIR-C5

<400> SEQUENCE: 73

```
atggattttc aggtccagat tttctccttc ctcctcattt cagccagcgt cattatgtct     60
```

```
cggggggata ttgtcctcac acagactccc agctccctgc ctgtgtccgt cggagagaaa    120
gtgaccatga catgcaagtc tagtcagaca ctgctctact ctaacaatca gaagaactac    180
ctcgcatggt atcagcagaa accaggacag agccccaagc tgctcatctc ctgggctttc    240
acccggaaat ccggggtgcc tgaccgcttc acaggtagcg gctccggaac tgattttact    300
ctgaccattg gatctgtgaa ggcagaggac ctcgccgtct actattgcca gcagtacagt    360
aattatccat ggacttttgg cggagggacc aggctggaaa tcaagagagg tggaggaggg    420
tccggtggag gagggtctgg tggaggaggg agtggtggag gagggtcaga ggtgcagctg    480
cagcagtctg gccccgaagt ggtcaaaact ggagcttcag tcaaaatcag ctgtaaggca    540
tctgggtaca gcttcaccgg ctacttcatc aactgggtga agaaaaattc agggaagagc    600
cctgagtgga tcggccacat ttcaagctcc tacgccacaa gcacttacaa ccagaagttc    660
aaaaataagg ccgcttttac cgtggacaca tctagttcaa ccgccttcat gcagctgaac    720
tccctcacat ctgaagatag tgctgtgtac tattgtgtca ggagcggcaa ctacgaagaa    780
tatgctatgg attactgggg gcaggggacc tccgtgactg tctcaagcac cggtatgtca    840
gcaccctgcc aaaaaatcaa tgtgaaacaa attgcggctc agctcctgcc cccactctac    900
tccctggtat tcatctttgg ttttgtgggt aacatgatgg tcttcctcat cttgataagc    960
tgcaaaaagc tgaagagcgt gactgatatc tacctgctca acctggccat ctctgacctg   1020
ctcttcctgc tcacactacc attctgggct cactatgctg caaatgagtg ggtctttggg   1080
aacataatgt gtaaagtatt cacagggctc tatcacattg gttattttgg tggaatcttc   1140
ttcattatcc tcctgacaat tgataggtac ttggctattg tccatgctgt gtttgcttta   1200
aaagtcagaa cggtcaactt tggggtgata acaagtgtag tcacttgggc ggtggctgtg   1260
tttgcctctc tcccagaaat aatctttacc agatctcaga aagaaggttt tcattataca   1320
tgcagtcctc attttccaca cactcagtat catttctgga agagtttcca aacattaaag   1380
atggtcatct tgagcctgat cctgcctcta cttgtcatgg tcatctgcta ctcaggaatt   1440
ctccacaccc tgtttcgctg taggaatgag aagaagaggc acagggctgt gaggctcatc   1500
tttgccatca tgattgtcta ctttctcttc tggactccct acaacattgt cctcctcctg   1560
accaccttcc aggaattctt tggactgaat aactgcagta gttctaatag actagaccag   1620
gccatgcagg caacagagac tcttggaatg acacactgct gcctaaaccc tgtcatctat   1680
gcctttgttg gagagaagtt ccggagttat ctctcagtgt tcttccgaaa acacattgtc   1740
aaacgctttt gcaaacggtg ttcaattttc cagcaagaca atcctgatcg tgcaagctca   1800
gtctataccc gatccacagg agaacatgaa gtttctactg gtttatga                1848
```

<210> SEQ ID NO 74
<211> LENGTH: 1824
<212> TYPE: DNA
<213> ORGANISM: Artificial Sequence
<220> FEATURE:
<223> OTHER INFORMATION: Nucleic acid sequence of EVIR-CX

<400> SEQUENCE: 74

```
atggattttc aggtccagat ttctccttc ctcctcattt cagccagcgt cattatgtct      60
cggggggata ttgtcctcac acagactccc agctccctgc ctgtgtccgt cggagagaaa    120
gtgaccatga catgcaagtc tagtcagaca ctgctctact ctaacaatca gaagaactac    180
ctcgcatggt atcagcagaa accaggacag agccccaagc tgctcatctc ctgggctttc    240
acccggaaat ccggggtgcc tgaccgcttc acaggtagcg gctccggaac tgattttact    300
```

```
ctgaccattg gatctgtgaa ggcagaggac ctcgccgtct actattgcca gcagtacagt      360
aattatccat ggacttttgg cggagggacc aggctggaaa tcaagagagg tggaggaggg      420
tccggtggag gagggtctgg tggaggaggg agtggtggag gagggtcaga ggtgcagctg      480
cagcagtctg gccccgaagt ggtcaaaact ggagcttcag tcaaaatcag ctgtaaggca      540
tctgggtaca gcttcaccgg ctacttcatc aactgggtga agaaaattc agggaagagc       600 cctgagtgga tcggccacat ttcaagctcc tacgccacaa gcacttacaa ccagaagttc      660
aaaaataagg ccgcttttac cgtggacaca tctagttcaa ccgccttcat gcagctgaac      720
tccctcacat ctgaagatag tgctgtgtac tattgtgtca ggagcggcaa ctacgaagaa      780
tatgctatgg attactgggg cagggggacc tccgtgactg tctcaagcac cgggttccgg      840
gatgaaaacg tccatttcaa taggatcttc ctgcccacca tctacttcat catcttcttg      900
actggcatag tcggcaatgg gattggtgat cctggtcatg gttaccagaa gaagctaagg      960
agcatgacgg acaagtaccg gctgcacctg tcagtggctg acctcctctt tgtcatcaca     1020 ctcccccttct gggcagttga tgccatggct gactggtact ttgggaaatt tttgtgtaag     1080
gctgtccata tcatctacac tgtcaacctc tacagcagcg ttctcatcct ggccttcatc     1140
agcctggacc ggtacctcgc tattgtccac gccaccaaca gtcagaggcc aaggaaactg     1200
ctggctgaaa aggcagtcta tgtgggcgtc tggatcccag ccctcctcct gactatacct     1260
gacttcatct ttgccgacgt cagccagggg gacatcagtc aggggatga caggtacatc      1320 tgtgaccgcc tttaccccga tagcctgtgg atggtggtgt tcaattcca gcatataatg      1380 gtgggtctcg tcctgcccgg catcgtcatc ctctcctgtt actgcatcat catctctaag     1440
ctgtcacact ccaagggcca ccagaagcgc aaggccctca agacgacagt catcctcatc     1500
ctagcttcct ttgcctgctg gctgccatat tatgtgggga tcagcatcga ctccttcatc     1560
cttttggggg tcatcaagca aggatgtgac ttcgagagca tcgtgcacaa gtggatctcc     1620
atcacagagg ccctcgcctt cttccactgt gcctgaacc ccatcctcta tgccttcctc      1680
ggggccaagt tcaaaagctc tgcccagcat gcactcaact ccatgagcag aggctccagc     1740
ctcaagatcc tttccaaagg aaagcgggtg gacactctt ccgtctccac ggagtcagaa      1800
tcctccagtt ttcactccag ctaa                                            1824
```

<210> SEQ ID NO 75
<211> LENGTH: 1728
<212> TYPE: DNA
<213> ORGANISM: Artificial Sequence
<220> FEATURE:
<223> OTHER INFORMATION: Nucleic acid sequence of EVIR-S

<400> SEQUENCE: 75

```
atggatttc aggtccagat tttctccttc ctcctcattt cagccagcgt cattatgtct        60 cgggggata ttgtcctcac acagactccc agctccctgc ctgtgtccgt cggagagaaa       120
gtgaccatga catgcaagtc tagtcagaca ctgctctact ctaacaatca gaagaactac      180
ctcgcatggt atcagcagaa accaggacag agccccaagc tgctcatctc ctgggctttc     240
acccggaaat ccggggtgcc tgaccgcttc acaggtagcg gctccggaac tgattttact     300
ctgaccattg gatctgtgaa ggcagaggac ctcgccgtct actattgcca gcagtacagt     360
aattatccat ggacttttgg cggagggacc aggctggaaa tcaagagagg tggaggaggg     420
tccggtggag gagggtctgg tggaggaggg agtggtggag gagggtcaga ggtgcagctg     480
```

```
cagcagtctg gccccgaagt ggtcaaaact ggagcttcag tcaaaatcag ctgtaaggca     540
tctgggtaca gcttcaccgg ctacttcatc aactgggtga agaaaaattc agggaagagc     600
cctgagtgga tcggccacat ttcaagctcc tacgccacaa gcacttacaa ccagaagttc     660
aaaaataagg ccgcttttac cgtggacaca tctagttcaa ccgccttcat gcagctgaac     720
tccctcacat ctgaagatag tgctgtgtac tattgtgtca ggagcggcaa ctacgaagaa     780
tatgctatgg attactgggg cagggggacc tccgtgactg tctcaagcac cggtattgcc     840
accactgacc ctactgcccc aggtacagga gggacagctg ttgggatgct gagcacagac     900
tctgccacac agtggagtct aacctcagta gagaccgtcc aaccagcatc cacagaggta     960
gagacctcgc agccagcacc catggaggca gagacctcgc agccagcacc catggaggca    1020
gagacctcgc agccagcacc catggaggca gacacctcaa agccagcacc cacggaggca    1080
gagacctcaa agccagcacc cacggaggca gagacctctc agccagcacc caacgaggca    1140
gagacctcaa aaccagcacc cacggaggca gagacctcaa aaccagcacc cacggaggca    1200
gagaccaccc agcttcccag gattcaggct gtaaaaactc tgtttacaac gtctgcagcc    1260
accgaagtcc cttccacaga acctaccacc atggagacgg cgtccacaga gtctaacgag    1320
tctaccatct tccttgggcc atccgtgact cacttacctg cagcggcct gaagaaaggg    1380 ctgattgtga ccctgggaa ttcacctgcc caaccctgc agggagttc agatctcatc    1440 ccggtgaagc aatgtctgct gattatcctc atccttggctt ctctggccac catcttcctc    1500
gtgtgcacag tggtgctggc ggtccgtctg tcccgtaaga cccacatgta cccagtgcgg    1560
aactactccc ccacggagat gatctgcatc tcgtccctgc tacctgaggg gggagacggg    1620
gcccctgtca cagccaatgg gggcctgccc aaggtccagg acctgaagac agagcccagt    1680
ggggaccggg atggggacga cctcaccctg cacagcttcc tcccttag                 1728
```

<210> SEQ ID NO 76
<211> LENGTH: 748
<212> TYPE: DNA
<213> ORGANISM: Artificial Sequence
<220> FEATURE:
<223> OTHER INFORMATION: Nucleic acid sequence of anti-HER2 scFv
      Trastuzumab

<400> SEQUENCE: 76

```
gatattcaga tgacccagtc ccccagctcc ctgtcagcaa gcgtgggcga ccgagtcact      60
atcacctgcc gagctagcca ggatgtgaac accgcagtcg cctggtacca gcagaagcca     120
gggaaagcac ccaagctgct catctactcc gcctcttttcc tgtattcagg agtgccaagc     180
aggtttagtg gctcaagaag cggaactgac ttcacactga ctatctctag tctccagccc     240
gaggattttg caacctacta ttgccagcag cactatacca caccccctac cttcggtcag     300
ggcacaaaag tggaaattaa gcggaccggc tccacatctg aagtgggaa gccggttcc      360 ggcgagggat ctgaagtgca gctggtcgag tccgaggag gactcgtgca gcctggtggc     420
agtctgaggc tctcatgtgc cgctagcggc ttcaacatca agacacata cattcattgg     480 gtgcgccagg ctcctgggaa gggtctggaa tgggtcgcac gaatctatcc aactaatggg     540
tacacccgat atgctgactc tgtgaaaggc aggttcacaa tttccgccga tacatctaag     600
aacactgctt acctgcagat gaatagtctc agagctgagg atactgcagt ctactattgt     660
agccggtggg gagggatgg cttctatgct atggatgtct gggggcaggg gactctggtg     720
actgtctcaa gtggtaccgg tacgcgtg                                        748
```

<210> SEQ ID NO 77
<211> LENGTH: 726
<212> TYPE: DNA
<213> ORGANISM: Artificial Sequence
<220> FEATURE:
<223> OTHER INFORMATION: Nucleic acid sequence of anti-HER2 scFv
      Pertuzumab

<400> SEQUENCE: 77

| gatattcaga | tgacccagag | cccaagctcc | ctgtcagcta | gcgtgggcga | ccgagtcacc | 60 |
| atcacatgca | aagccagtca | ggatgtgtca | attggcgtcg | cttggtacca | gcagaagccc | 120 |
| ggaaaagctc | ctaagctgct | catctattcc | gcatcttaca | ggtacacagg | cgtgccctct | 180 |
| cgcttcagtg | gttcaggcag | cggaactgac | tttactctga | ccatttctag | tctccagcct | 240 |
| gaggatttcg | caacctacta | ttgtcagcag | tactatatct | acccatatac | ctttgggcag | 300 |
| ggtacaaaag | tggaaattaa | gaacagtc | gcagctccag | gaggaggag | tagcggagga | 360 |
| ggggttccg | gcggagggg | ttctggcgga | gggtagtg | aggtcagct | ggtcgaaagc | 420 |
| ggaggaggac | tcgtgcagcc | tggtggcagc | ctgagactct | cctgcgcagc | ctctggcttc | 480 |
| accttcaccg | actacaccat | ggattgggtg | cggcaggcac | caggaaaggg | actggagtgg | 540 |
| gtggcagacg | tcaaccccaa | ttccggaggg | tctatctaca | accagaggtt | caaggaagg | 600 |
| ttcaccctga | gtgtggatcg | atcaaagaac | accctgtatc | tccagatgaa | ttccctgagg | 660 |
| gccgaagata | cagccgtcta | ttattgtgca | agaaacctgg | gtccatcatt | ttattttgac | 720 |
| tattgg | | | | | | 726 |

<210> SEQ ID NO 78
<211> LENGTH: 727
<212> TYPE: DNA
<213> ORGANISM: Artificial Sequence
<220> FEATURE:
<223> OTHER INFORMATION: Nucleic acid sequence of anti-HER2 scFv FRP5

<400> SEQUENCE: 78

| caggtccagc | tccagcagtc | aggtccagaa | ctcaagaagc | caggggaaac | agtcaaaatc | 60 |
| tcatgtaaag | cctcaggata | cccattcact | aactatggga | tgaattgggt | gaagcaggca | 120 |
| cctggccagg | gactgaaatg | gatgggttgg | atcaacacta | gcaccgggga | gtccacattc | 180 |
| gccgacgatt | ttaagggccg | gttcgacttt | tctctcgaaa | ccagtgcaaa | tacagcctat | 240 |
| ctgcagatta | caatctcaa | tccgaggat | atggccacct | acttctgcgc | tcgctgggaa | 300 |
| gtgtaccacg | gatatgtccc | atactggggg | cagggtacca | cagtgacagt | cagctccgga | 360 |
| ggaggaggtt | caggaggagg | aggtagcgga | ggaggaggtt | ccgacatcca | gctgacacag | 420 |
| tctcataagt | ttctctccac | ttctgtgggc | gacagggtct | ctattacctg | taaagctagt | 480 |
| caggatgtgt | ataacgccgt | cgcttggtac | cagcagaagc | ccggccagag | ccctaaactg | 540 |
| ctcatctata | gcgcctctag | taggtacact | ggagtgccaa | gcagattcac | cggcagtgga | 600 |
| tcagggcccg | acttcacctt | caccatttca | agcgtgcagg | ctgaggatct | ggcagtctac | 660 |
| ttttgccagc | agcattttcg | caccccttc | acctttggaa | gcgggactaa | actggagatt | 720 |
| aagagga | | | | | | 727 |

<210> SEQ ID NO 79
<211> LENGTH: 231
<212> TYPE: PRT
<213> ORGANISM: Artificial Sequence
<220> FEATURE:

<223> OTHER INFORMATION: Amino acid sequence of hinge domain derived
      from dLNGFR

<400> SEQUENCE: 79

Leu Leu Gly Val Ser Leu Gly Gly Ala Lys Glu Ala Cys Pro Thr Gly
1               5                   10                  15

Leu Tyr Thr His Ser Gly Glu Cys Cys Lys Ala Cys Asn Leu Gly Glu
            20                  25                  30

Gly Val Ala Gln Pro Cys Gly Ala Asn Gln Thr Val Cys Glu Pro Cys
        35                  40                  45

Leu Asp Ser Val Thr Phe Ser Asp Val Val Ser Ala Thr Glu Pro Cys
    50                  55                  60

Lys Pro Cys Thr Glu Cys Val Gly Leu Gln Ser Met Ser Ala Pro Cys
65                  70                  75                  80

Val Glu Ala Asp Asp Ala Val Cys Arg Cys Ala Tyr Gly Tyr Tyr Gln
                85                  90                  95

Asp Glu Thr Thr Gly Arg Cys Glu Ala Cys Arg Val Cys Glu Ala Gly
            100                 105                 110

Ser Gly Leu Val Phe Ser Cys Gln Asp Lys Gln Asn Thr Val Cys Glu
        115                 120                 125

Glu Cys Pro Asp Gly Thr Tyr Ser Asp Glu Ala Asn His Val Asp Pro
    130                 135                 140

Cys Leu Pro Cys Thr Val Cys Glu Asp Thr Glu Arg Gln Leu Arg Glu
145                 150                 155                 160

Cys Thr Arg Trp Ala Asp Ala Glu Cys Glu Glu Ile Pro Gly Arg Trp
                165                 170                 175

Ile Thr Arg Ser Thr Pro Pro Glu Gly Ser Asp Ser Thr Ala Pro Ser
            180                 185                 190

Thr Gln Glu Pro Glu Ala Pro Pro Glu Gln Asp Leu Ile Ala Ser Thr
        195                 200                 205

Val Ala Gly Val Val Thr Thr Val Met Gly Ser Ser Gln Pro Val Val
    210                 215                 220

Thr Arg Gly Thr Thr Asp Asn
225                 230

<210> SEQ ID NO 80
<211> LENGTH: 22
<212> TYPE: PRT
<213> ORGANISM: Artificial Sequence
<220> FEATURE:
<223> OTHER INFORMATION: Amino acid sequence of a transmembrane domain
      derived from dLNGFR

<400> SEQUENCE: 80

Leu Ile Pro Val Tyr Cys Ser Ile Leu Ala Ala Val Val Val Gly Leu
1               5                   10                  15

Val Ala Tyr Ile Ala Phe
            20

<210> SEQ ID NO 81
<211> LENGTH: 8
<212> TYPE: PRT
<213> ORGANISM: Artificial Sequence
<220> FEATURE:
<223> OTHER INFORMATION: Amino acid sequence of an intracellular domain
      derived from dLNGFR

<400> SEQUENCE: 81

Lys Arg Trp Asn Arg Gly Ile Leu

```
<210> SEQ ID NO 82
<211> LENGTH: 50
<212> TYPE: PRT
<213> ORGANISM: Artificial Sequence
<220> FEATURE:
<223> OTHER INFORMATION: Amino acid sequence of hinge domain derived
      from FcgRIIIA

<400> SEQUENCE: 82

His Glu Asn Ser Glu Leu Leu Ile Pro Lys Ala Thr His Asn Asp Ser
1               5                   10                  15

Gly Ser Tyr Phe Cys Arg Gly Leu Ile Gly His Asn Asn Lys Ser Ser
            20                  25                  30

Ala Ser Phe Arg Ile Ser Leu Gly Asp Pro Gly Ser Pro Ser Met Phe
        35                  40                  45

Pro Pro
    50

<210> SEQ ID NO 83
<211> LENGTH: 22
<212> TYPE: PRT
<213> ORGANISM: Artificial Sequence
<220> FEATURE:
<223> OTHER INFORMATION: Amino acid sequence of a transmembrane domain
      derived from FcgRIIIA

<400> SEQUENCE: 83

Trp His Gln Ile Thr Phe Cys Leu Leu Ile Gly Leu Leu Phe Ala Ile
1               5                   10                  15

Asp Thr Val Leu Tyr Phe
            20

<210> SEQ ID NO 84
<211> LENGTH: 31
<212> TYPE: PRT
<213> ORGANISM: Artificial Sequence
<220> FEATURE:
<223> OTHER INFORMATION: Amino acid sequence of an intracellular domain
      derived from FcgRIIIA

<400> SEQUENCE: 84

Ser Val Arg Arg Gly Leu Gln Ser Pro Val Ala Asp Tyr Glu Glu Pro
1               5                   10                  15

Lys Ile Gln Trp Ser Lys Glu Pro Gln Asp Lys Thr Arg Val Asp
            20                  25                  30

<210> SEQ ID NO 85
<211> LENGTH: 10
<212> TYPE: PRT
<213> ORGANISM: Artificial Sequence
<220> FEATURE:
<223> OTHER INFORMATION: Amino acid sequence of hinge domain derived
      from FLT3

<400> SEQUENCE: 85

Pro Gly Pro Phe Pro Phe Ile Gln Asp Asn
1               5                   10

<210> SEQ ID NO 86
<211> LENGTH: 22
<212> TYPE: PRT
<213> ORGANISM: Artificial Sequence
<220> FEATURE:
```

<223> OTHER INFORMATION: Amino acid sequence of a transmembrane domain
      derived from FLT3

<400> SEQUENCE: 86

Ile Ser Phe Tyr Ala Thr Ile Gly Leu Cys Leu Pro Phe Ile Val Val
1               5                   10                  15

Leu Ile Val Leu Ile Cys
            20

<210> SEQ ID NO 87
<211> LENGTH: 436
<212> TYPE: PRT
<213> ORGANISM: Artificial Sequence
<220> FEATURE:
<223> OTHER INFORMATION: Amino acid sequence of an intracellular domain
      derived from FLT3

<400> SEQUENCE: 87

His Lys Tyr Lys Lys Gln Phe Arg Tyr Glu Ser Gln Leu Gln Met Ile
1               5                   10                  15

Gln Val Thr Gly Pro Leu Asp Asn Glu Tyr Phe Tyr Val Asp Phe Arg
            20                  25                  30

Asp Tyr Glu Tyr Asp Leu Lys Trp Glu Phe Pro Arg Glu Asn Leu Glu
        35                  40                  45

Phe Gly Lys Val Leu Gly Ser Gly Ala Phe Gly Arg Val Met Asn Ala
    50                  55                  60

Thr Ala Tyr Gly Ile Ser Lys Thr Gly Val Ser Ile Gln Val Ala Val
65                  70                  75                  80

Lys Met Leu Lys Glu Lys Ala Asp Ser Cys Glu Lys Glu Ala Leu Met
                85                  90                  95

Ser Glu Leu Lys Met Met Thr His Leu Gly His His Asp Asn Ile Val
            100                 105                 110

Asn Leu Leu Gly Ala Cys Thr Leu Ser Gly Pro Val Tyr Leu Ile Phe
        115                 120                 125

Glu Tyr Cys Cys Tyr Gly Asp Leu Leu Asn Tyr Leu Arg Ser Lys Arg
    130                 135                 140

Glu Lys Phe His Arg Thr Trp Thr Glu Ile Phe Lys Glu His Asn Phe
145                 150                 155                 160

Ser Phe Tyr Pro Thr Phe Gln Ala His Ser Asn Ser Ser Met Pro Gly
                165                 170                 175

Ser Arg Glu Val Gln Leu His Pro Pro Leu Asp Gln Leu Ser Gly Phe
            180                 185                 190

Asn Gly Asn Leu Ile His Ser Glu Asp Glu Ile Glu Tyr Glu Asn Gln
        195                 200                 205

Lys Arg Leu Ala Glu Glu Glu Glu Asp Leu Asn Val Leu Thr Phe
    210                 215                 220

Glu Asp Leu Leu Cys Phe Ala Tyr Gln Val Ala Lys Gly Met Glu Phe
225                 230                 235                 240

Leu Glu Phe Lys Ser Cys Val His Arg Asp Leu Ala Ala Arg Asn Val
                245                 250                 255

Leu Val Thr His Gly Lys Val Val Lys Ile Cys Asp Phe Gly Leu Ala
            260                 265                 270

Arg Asp Ile Leu Ser Asp Ser Ser Tyr Val Val Arg Gly Asn Ala Arg
        275                 280                 285

Leu Pro Val Lys Trp Met Ala Pro Glu Ser Leu Phe Glu Gly Ile Tyr
    290                 295                 300

```
Thr Ile Lys Ser Asp Val Trp Ser Tyr Gly Ile Leu Trp Glu Ile
305                 310                 315                 320

Phe Ser Leu Gly Val Asn Pro Tyr Pro Gly Ile Pro Val Asp Ala Asn
                325                 330                 335

Phe Tyr Lys Leu Ile Gln Ser Gly Phe Lys Met Glu Gln Pro Phe Tyr
            340                 345                 350

Ala Thr Glu Gly Ile Tyr Phe Val Met Gln Ser Cys Trp Ala Phe Asp
        355                 360                 365

Ser Arg Lys Arg Pro Ser Phe Pro Asn Leu Thr Ser Phe Leu Gly Cys
    370                 375                 380

Gln Leu Ala Glu Ala Glu Ala Met Tyr Gln Asn Met Gly Gly Asn
385                 390                 395                 400

Val Pro Glu His Pro Ser Ile Tyr Gln Asn Arg Arg Pro Leu Ser Arg
                405                 410                 415

Glu Ala Gly Ser Glu Pro Pro Ser Pro Gln Ala Gln Val Lys Ile His
            420                 425                 430

Gly Glu Arg Ser
            435

<210> SEQ ID NO 88
<211> LENGTH: 99
<212> TYPE: PRT
<213> ORGANISM: Artificial Sequence
<220> FEATURE:
<223> OTHER INFORMATION: Amino acid sequence of hinge domain derived
      from TLR4

<400> SEQUENCE: 88

Gln Leu Tyr Ser Leu Ser Thr Leu Asp Cys Ser Phe Asn Arg Ile Glu
1               5                   10                  15

Thr Ser Lys Gly Ile Leu Gln His Phe Pro Lys Ser Leu Ala Phe Phe
            20                  25                  30

Asn Leu Thr Asn Asn Ser Val Ala Cys Ile Cys Glu His Gln Lys Phe
        35                  40                  45

Leu Gln Trp Val Lys Glu Gln Lys Gln Phe Leu Val Asn Val Glu Gln
    50                  55                  60

Met Thr Cys Ala Thr Pro Val Glu Met Asn Thr Ser Leu Val Leu Asp
65                  70                  75                  80

Phe Asn Asn Ser Thr Cys Tyr Met Tyr Lys Thr Ile Ile Ser Val Ser
                85                  90                  95

Val Val Ser

<210> SEQ ID NO 89
<211> LENGTH: 21
<212> TYPE: PRT
<213> ORGANISM: Artificial Sequence
<220> FEATURE:
<223> OTHER INFORMATION: Amino acid sequence of a transmembrane domain
      derived from TLR4

<400> SEQUENCE: 89

Val Ile Val Val Ser Thr Val Ala Phe Leu Ile Tyr His Phe Tyr Phe
1               5                   10                  15

His Leu Ile Leu Ile
            20

<210> SEQ ID NO 90
<211> LENGTH: 176
<212> TYPE: PRT
```

<213> ORGANISM: Artificial Sequence
<220> FEATURE:
<223> OTHER INFORMATION: Amino acid sequence of an intracellular domain derived from TLR4

<400> SEQUENCE: 90

```
Ala Gly Cys Lys Lys Tyr Ser Arg Gly Glu Ser Ile Tyr Asp Ala Phe
1               5                   10                  15

Val Ile Tyr Ser Ser Gln Asn Glu Asp Trp Val Arg Asn Glu Leu Val
            20                  25                  30

Lys Asn Leu Glu Glu Gly Val Pro Arg Phe His Leu Cys Leu His Tyr
        35                  40                  45

Arg Asp Phe Ile Pro Gly Val Ala Ile Ala Asn Ile Ile Gln Glu
    50                  55                  60

Gly Phe His Lys Ser Arg Lys Val Ile Val Val Ser Arg His Phe
65                  70                  75                  80

Ile Gln Ser Arg Trp Cys Ile Phe Glu Tyr Glu Ile Ala Gln Thr Trp
                85                  90                  95

Gln Phe Leu Ser Ser Arg Ser Gly Ile Ile Phe Ile Val Leu Glu Lys
            100                 105                 110

Val Glu Lys Ser Leu Leu Arg Gln Gln Val Glu Leu Tyr Arg Leu Leu
        115                 120                 125

Ser Arg Asn Thr Tyr Leu Glu Trp Glu Asp Asn Pro Leu Gly Arg His
130                 135                 140

Ile Phe Trp Arg Arg Leu Lys Asn Ala Leu Leu Asp Gly Lys Ala Ser
145                 150                 155                 160

Asn Pro Glu Gln Thr Ala Glu Glu Gln Glu Thr Ala Thr Trp Thr
                165                 170                 175
```

<210> SEQ ID NO 91
<211> LENGTH: 55
<212> TYPE: PRT
<213> ORGANISM: Artificial Sequence
<220> FEATURE:
<223> OTHER INFORMATION: Amino acid sequence of hinge domain derived from CCR2

<400> SEQUENCE: 91

```
Met Glu Asp Asn Asn Met Leu Pro Gln Phe Ile His Gly Ile Leu Ser
1               5                   10                  15

Thr Ser His Ser Leu Phe Thr Arg Ser Ile Gln Glu Leu Asp Glu Gly
            20                  25                  30

Ala Thr Thr Pro Tyr Asp Tyr Asp Asp Gly Glu Pro Cys His Lys Thr
        35                  40                  45

Ser Val Lys Gln Ile Gly Ala
    50                  55
```

<210> SEQ ID NO 92
<211> LENGTH: 118
<212> TYPE: PRT
<213> ORGANISM: Artificial Sequence
<220> FEATURE:
<223> OTHER INFORMATION: Amino acid sequence of hinge domain derived from ITGB2

<400> SEQUENCE: 92

```
Asn Ala Arg Leu Val Glu Cys Ser Gly Arg Gly His Cys Gln Cys Asn
1               5                   10                  15

Arg Cys Ile Cys Asp Glu Gly Tyr Gln Pro Pro Met Cys Glu Asp Cys
            20                  25                  30
```

Pro Ser Cys Gly Ser His Cys Arg Asp Asn His Thr Ser Cys Ala Glu
            35                  40                  45

Cys Leu Lys Phe Asp Lys Gly Pro Phe Glu Lys Asn Cys Ser Val Gln
    50                  55                  60

Cys Ala Gly Met Thr Leu Gln Thr Ile Pro Leu Lys Lys Pro Cys
65                  70                  75                  80

Lys Glu Arg Asp Ser Glu Gly Cys Trp Ile Thr Tyr Thr Leu Gln Gln
                85                  90                  95

Lys Asp Gly Arg Asn Ile Tyr Asn Ile His Val Glu Asp Ser Leu Glu
            100                 105                 110

Cys Val Lys Gly Pro Asn
            115

<210> SEQ ID NO 93
<211> LENGTH: 23
<212> TYPE: PRT
<213> ORGANISM: Artificial Sequence
<220> FEATURE:
<223> OTHER INFORMATION: Amino acid sequence of a transmembrane domain
      derived from ITGB2

<400> SEQUENCE: 93

Val Ala Ala Ile Val Gly Gly Thr Val Val Gly Val Val Leu Ile Gly
1               5                   10                  15

Val Leu Leu Leu Val Ile Trp
            20

<210> SEQ ID NO 94
<211> LENGTH: 46
<212> TYPE: PRT
<213> ORGANISM: Artificial Sequence
<220> FEATURE:
<223> OTHER INFORMATION: Amino acid sequence of an intracellular domain
      derived from ITGB2

<400> SEQUENCE: 94

Lys Ala Leu Thr His Leu Thr Asp Leu Arg Glu Tyr Arg Arg Phe Glu
1               5                   10                  15

Lys Glu Lys Leu Lys Ser Gln Trp Asn Asn Asp Asn Pro Leu Phe Lys
            20                  25                  30

Ser Ala Thr Thr Thr Val Met Asn Pro Lys Phe Ala Glu Ser
            35                  40                  45

<210> SEQ ID NO 95
<211> LENGTH: 78
<212> TYPE: PRT
<213> ORGANISM: Artificial Sequence
<220> FEATURE:
<223> OTHER INFORMATION: Amino acid sequence of hinge domain derived
      from CSF2RB

<400> SEQUENCE: 95

Thr Gln Lys Met Ala Tyr Ser Phe Ile Glu His Thr Phe Gln Val Gln
1               5                   10                  15

Tyr Lys Lys Lys Ser Asp Ser Trp Glu Asp Ser Lys Thr Glu Asn Leu
            20                  25                  30

Asp Arg Ala His Ser Met Asp Leu Ser Gln Leu Glu Pro Asp Thr Ser
            35                  40                  45

Tyr Cys Ala Arg Val Arg Val Lys Pro Ile Ser Asn Tyr Asp Gly Ile
        50                  55                  60

Trp Ser Lys Trp Ser Glu Glu Tyr Thr Trp Lys Thr Asp Trp
65                  70                  75

<210> SEQ ID NO 96
<211> LENGTH: 22
<212> TYPE: PRT
<213> ORGANISM: Artificial Sequence
<220> FEATURE:
<223> OTHER INFORMATION: Amino acid sequence of a transmembrane domain
      derived from CSF2RB

<400> SEQUENCE: 96

Val Met Pro Thr Leu Trp Ile Val Leu Ile Val Phe Leu Ile Leu
1               5                   10                  15

Thr Leu Leu Leu Ile Leu
            20

<210> SEQ ID NO 97
<211> LENGTH: 433
<212> TYPE: PRT
<213> ORGANISM: Artificial Sequence
<220> FEATURE:
<223> OTHER INFORMATION: Amino acid sequence of an intracellular domain
      derived from CSF2RB

<400> SEQUENCE: 97

Arg Phe Gly Cys Val Ser Val Tyr Arg Thr Tyr Arg Lys Trp Lys Glu
1               5                   10                  15

Lys Ile Pro Asn Pro Ser Lys Ser Leu Leu Phe Gln Asp Gly Gly Lys
            20                  25                  30

Gly Leu Trp Pro Pro Gly Ser Met Ala Ala Phe Ala Thr Lys Asn Pro
        35                  40                  45

Ala Leu Gln Gly Pro Gln Ser Arg Leu Leu Ala Glu Gln Gln Gly Glu
    50                  55                  60

Ser Tyr Ala His Leu Glu Asp Asn Asn Val Ser Pro Leu Thr Ile Glu
65                  70                  75                  80

Asp Pro Asn Ile Ile Arg Val Pro Pro Ser Gly Pro Asp Thr Thr Pro
                85                  90                  95

Ala Ala Ser Ser Glu Ser Thr Glu Gln Leu Pro Asn Val Gln Val Glu
            100                 105                 110

Gly Pro Thr Pro Asn Arg Pro Arg Lys Gln Leu Pro Ser Phe Asp Phe
        115                 120                 125

Asn Gly Pro Tyr Leu Gly Pro Pro Gln Ser His Ser Leu Pro Asp Leu
    130                 135                 140

Pro Asp Gln Leu Gly Ser Pro Gln Val Gly Gly Ser Leu Lys Pro Ala
145                 150                 155                 160

Leu Pro Gly Ser Leu Glu Tyr Met Cys Leu Pro Pro Gly Gly Gln Ala
                165                 170                 175

Gln Leu Val Pro Leu Ser Gln Val Met Gly Gln Gly Gln Ala Met Asp
            180                 185                 190

Val Gln Cys Gly Ser Ser Leu Glu Thr Ser Gly Ser Pro Ser Val Glu
        195                 200                 205

Pro Lys Glu Asn Pro Pro Val Glu Leu Ser Met Glu Glu Gln Glu Ala
    210                 215                 220

Arg Asp Asn Pro Val Thr Leu Pro Ile Ser Ser Gly Pro Glu Gly
225                 230                 235                 240

Ser Met Met Ala Ser Asp Tyr Val Thr Pro Gly Asp Pro Val Leu Thr
                245                 250                 255

```
Leu Pro Thr Gly Pro Leu Ser Thr Ser Leu Gly Pro Ser Leu Gly Leu
                260                 265                 270

Pro Ser Ala Gln Ser Pro Arg Leu Cys Leu Lys Leu Pro Arg Val Pro
            275                 280                 285

Ser Gly Ser Pro Ala Leu Gly Pro Pro Gly Phe Glu Asp Tyr Val Glu
        290                 295                 300

Leu Pro Pro Ser Val Ser Gln Ala Ala Lys Ser Pro Pro Gly His Pro
305                 310                 315                 320

Ala Pro Pro Val Ala Ser Ser Pro Thr Val Ile Pro Gly Glu Pro Arg
                325                 330                 335

Glu Glu Val Gly Pro Ala Ser Pro His Pro Glu Gly Leu Leu Val Leu
            340                 345                 350

Gln Gln Val Gly Asp Tyr Cys Phe Leu Pro Gly Leu Gly Pro Gly Ser
        355                 360                 365

Leu Ser Pro His Ser Lys Pro Pro Ser Pro Ser Leu Cys Ser Glu Thr
370                 375                 380

Glu Asp Leu Val Gln Asp Leu Ser Val Lys Lys Phe Pro Tyr Gln Pro
385                 390                 395                 400

Met Pro Gln Ala Pro Ala Ile Gln Phe Phe Lys Ser Leu Lys His Gln
                405                 410                 415

Asp Tyr Leu Ser Leu Pro Pro Trp Asp Asn Ser Gln Ser Gly Lys Val
            420                 425                 430

Cys

<210> SEQ ID NO 98
<211> LENGTH: 13
<212> TYPE: PRT
<213> ORGANISM: Artificial Sequence
<220> FEATURE:
<223> OTHER INFORMATION: Amino acid sequence of hinge domain derived
      from CCR1

<400> SEQUENCE: 98

Thr Pro Cys Gln Lys Thr Ala Val Arg Ala Phe Gly Ala
1               5                   10

<210> SEQ ID NO 99
<211> LENGTH: 15
<212> TYPE: PRT
<213> ORGANISM: Artificial Sequence
<220> FEATURE:
<223> OTHER INFORMATION: Amino acid sequence of hinge domain derived
      from CCR5

<400> SEQUENCE: 99

Met Ser Ala Pro Cys Gln Lys Ile Asn Val Lys Gln Ile Ala Ala
1               5                   10                  15

<210> SEQ ID NO 100
<211> LENGTH: 10
<212> TYPE: PRT
<213> ORGANISM: Artificial Sequence
<220> FEATURE:
<223> OTHER INFORMATION: Amino acid sequence of hinge domain derived
      from CXCR4

<400> SEQUENCE: 100

Phe Arg Asp Glu Asn Val His Phe Asn Arg
1               5                   10

<210> SEQ ID NO 101
```

```
<211> LENGTH: 207
<212> TYPE: PRT
<213> ORGANISM: Artificial Sequence
<220> FEATURE:
<223> OTHER INFORMATION: Amino acid sequence of hinge domain derived
      from SELPLG

<400> SEQUENCE: 101

Ile Ala Thr Thr Asp Pro Thr Ala Pro Gly Thr Gly Thr Ala Val
1               5                   10                  15

Gly Met Leu Ser Thr Asp Ser Ala Thr Gln Trp Ser Leu Thr Ser Val
                20                  25                  30

Glu Thr Val Gln Pro Ala Ser Thr Glu Val Glu Thr Ser Gln Pro Ala
            35                  40                  45

Pro Met Glu Ala Glu Thr Ser Gln Pro Ala Pro Met Glu Ala Glu Thr
    50                  55                  60

Ser Gln Pro Ala Pro Met Glu Ala Asp Thr Ser Lys Pro Ala Pro Thr
65                  70                  75                  80

Glu Ala Glu Thr Ser Lys Pro Ala Pro Thr Glu Ala Glu Thr Ser Gln
                85                  90                  95

Pro Ala Pro Asn Glu Ala Glu Thr Ser Lys Pro Ala Pro Thr Glu Ala
            100                 105                 110

Glu Thr Ser Lys Pro Ala Pro Thr Glu Ala Glu Thr Thr Gln Leu Pro
        115                 120                 125

Arg Ile Gln Ala Val Lys Thr Leu Phe Thr Thr Ser Ala Ala Thr Glu
130                 135                 140

Val Pro Ser Thr Glu Pro Thr Thr Met Glu Thr Ala Ser Thr Glu Ser
145                 150                 155                 160

Asn Glu Ser Thr Ile Phe Leu Gly Pro Ser Val Thr His Leu Pro Asp
                165                 170                 175

Ser Gly Leu Lys Lys Gly Leu Ile Val Thr Pro Gly Asn Ser Pro Ala
            180                 185                 190

Pro Thr Leu Pro Gly Ser Ser Asp Leu Ile Pro Val Lys Gln Cys
        195                 200                 205

<210> SEQ ID NO 102
<211> LENGTH: 21
<212> TYPE: PRT
<213> ORGANISM: Artificial Sequence
<220> FEATURE:
<223> OTHER INFORMATION: Amino acid sequence of a transmembrane domain
      derived from SELPLG

<400> SEQUENCE: 102

Leu Leu Ile Ile Leu Ile Leu Ala Ser Leu Ala Thr Ile Phe Leu Val
1               5                   10                  15

Cys Thr Val Val Leu
            20

<210> SEQ ID NO 103
<211> LENGTH: 69
<212> TYPE: PRT
<213> ORGANISM: Artificial Sequence
<220> FEATURE:
<223> OTHER INFORMATION: Amino acid sequence of an intracellular domain
      derived from SELPLG

<400> SEQUENCE: 103

Ala Val Arg Leu Ser Arg Lys Thr His Met Tyr Pro Val Arg Asn Tyr
1               5                   10                  15
```

```
Ser Pro Thr Glu Met Ile Cys Ile Ser Ser Leu Leu Pro Glu Gly Gly
             20                  25                  30

Asp Gly Ala Pro Val Thr Ala Asn Gly Gly Leu Pro Lys Val Gln Asp
         35                  40                  45

Leu Lys Thr Glu Pro Ser Gly Asp Arg Asp Gly Asp Asp Leu Thr Leu
     50                  55                  60

His Ser Phe Leu Pro
 65
```

<210> SEQ ID NO 104
<211> LENGTH: 2
<212> TYPE: PRT
<213> ORGANISM: Artificial Sequence
<220> FEATURE:
<223> OTHER INFORMATION: Amino acid sequence of peptide that facilitates
      DNA engineering

<400> SEQUENCE: 104

```
Thr Gly
 1
```

<210> SEQ ID NO 105
<211> LENGTH: 66
<212> TYPE: DNA
<213> ORGANISM: Artificial Sequence
<220> FEATURE:
<223> OTHER INFORMATION: Nucleic acid sequence of IgK domain (for FRP5
      and trastuzumab)

<400> SEQUENCE: 105

```
atggattttc aggtgcagat tttctctttc ctcctcattt ccgcctcagt gattatgtca      60
aggggg                                                                66
```

<210> SEQ ID NO 106
<211> LENGTH: 66
<212> TYPE: DNA
<213> ORGANISM: Artificial Sequence
<220> FEATURE:
<223> OTHER INFORMATION: Nucleic acid sequence of IgK domain (for
      pertuzumab)

<400> SEQUENCE: 106

```
atggattttc aggtgcagat tttctccttt ctcctcattt cagccagcgt gattatgtct      60
cggggg                                                                66
```

<210> SEQ ID NO 107
<211> LENGTH: 6
<212> TYPE: DNA
<213> ORGANISM: Artificial Sequence
<220> FEATURE:
<223> OTHER INFORMATION: Nucleic acid sequence of a peptide that
      facilitates DNA engineering

<400> SEQUENCE: 107

```
accggt                                                                 6
```

<210> SEQ ID NO 108
<211> LENGTH: 6
<212> TYPE: DNA
<213> ORGANISM: Artificial Sequence
<220> FEATURE:
<223> OTHER INFORMATION: Nucleic acid sequence of a peptide that
      facilitates DNA engineering

<400> SEQUENCE: 108

```
<210> SEQ ID NO 109
<211> LENGTH: 66
<212> TYPE: DNA
<213> ORGANISM: Artificial Sequence
<220> FEATURE:
<223> OTHER INFORMATION: Nucleic acid sequence of IgK domain (for
      EVIR-N1)

<400> SEQUENCE: 109
atggacttcc aggtgcagat cttcagcttc ctgctgatct ccgccagcgt gatcatgagc      60
agaggc                                                                66

<210> SEQ ID NO 110
<211> LENGTH: 66
<212> TYPE: DNA
<213> ORGANISM: Artificial Sequence
<220> FEATURE:
<223> OTHER INFORMATION: Nucleic acid sequence of IgK domain (for
      EVIR-N2)

<400> SEQUENCE: 110
atggattttc aggtgcagat cttcagcttc ctgctgatct ccgccagcgt gatcatgagc      60
agaggc                                                                66

<210> SEQ ID NO 111
<211> LENGTH: 744
<212> TYPE: DNA
<213> ORGANISM: Artificial Sequence
<220> FEATURE:
<223> OTHER INFORMATION: Nucleic acid sequence of anti-TYRP1 scFv TA99

<400> SEQUENCE: 111
gacatccaga tgagccagag ccctgccagc ctgtctgcct ctgtgggcga gacagtgacc      60
atcacctgta gagccagcgg caacatctac aactacctgg cctggtatca gcagaagcag     120
ggcaagagcc cccatctgct ggtgtacgac gccaagacac tggccgacgg cgtgccctct     180
agattctctg gcagcggctc cggcacccag tacagcctga gatcagctc cctgcagacc      240 gaggactccg gcaactacta ctgccagcac ttctggtccc tgcccttcac cttcggcagc     300
ggcaccaagc tggaaatcaa gagaggcggc ggaggctctg gcggaggcgg atctggggc      360 ggaggaagtg gcgggggagg atctgaagtg cagctgcagc agtctggcgc tgagctcgtg     420
cgacctggcg ctctcgtgaa gctgagctgc aagaccagcg gcttcaatat caaggactac     480
ttcctgcact gggtgcgaca gaggcctgac cagggcctgg aatggatcgg ctggatcaac     540
cccgacaacg gcaacaccgt gtacgaccct aagttccagg gcaccgccag cctgacagcc     600
gacacaagct ccaacacagt gtacctgcag ctgagcggcc tgacctccga ggataccgcc     660
gtgtacttct gcaccagaag agactacacc tacgagaagg ccgccctgga ctactggggc     720
cagggaacaa ccgtgaccgt gtcc                                            744

<210> SEQ ID NO 112
<211> LENGTH: 720
<212> TYPE: DNA
<213> ORGANISM: Artificial Sequence
<220> FEATURE:
<223> OTHER INFORMATION: Nucleic acid sequence of anti-GD2 scFv 14G2a

<400> SEQUENCE: 112
```

-continued

```
gaagttcagc tgctgcagag cggacccgaa ctggaaaaac ctggcgcctc cgtgatgatc    60
agctgcaagg cctctggcag ctccttcacc ggctacaaca tgaactgggt ccgacagaac   120
atcggcaaga gcctggaatg gatcggcgcc atcgatcctt actacggcgg caccagctac   180
aaccagaagt tcaagggcag agccacactg accgtggaca gagcagcag cacagcctac    240
atgcatctga agtccctgac cagcgaggac agcgccgtgt actactgtgt gtccggcatg   300
gaatactggg ccagggcac aagcgtgaca gtctcttctg cggcggtgg atctggcgga    360
ggcggaagtg gtggcggcgg atctgatgtg gtcatgacac agaccccctct gagcctgcct   420
gtgtctctgg agatcaggc cagcatcagc tgtagaagca gccagagcct ggtgcacaga   480
aacggcaaca cctacctgca ctggtatctg cagaagcccg gccagtctcc taagctgctg   540
atccacaagg tgtccaacag attcagcggc gtgcccgaca gattctctgg ctctggaagc   600
ggcaccgact tcaccctgaa gattagcaga gtggaagccg aggacctggg cgtgtacttc   660
tgtagccaga gcacacacgt gccacctctg acatttggcg ctggcaccaa gctggaactg   720
```

<210> SEQ ID NO 113
<211> LENGTH: 248
<212> TYPE: PRT
<213> ORGANISM: Artificial Sequence
<220> FEATURE:
<223> OTHER INFORMATION: Amino acid sequence of TA99-based anti-TYRP1 scFv

<400> SEQUENCE: 113

```
Asp Ile Gln Met Ser Gln Ser Pro Ala Ser Leu Ser Ala Ser Val Gly
 1               5                  10                  15

Glu Thr Val Thr Ile Thr Cys Arg Ala Ser Gly Asn Ile Tyr Asn Tyr
            20                  25                  30

Leu Ala Trp Tyr Gln Gln Lys Gln Gly Lys Ser Pro His Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Ser Ser Leu Gln Thr
65                  70                  75                  80

Glu Asp Ser Gly Asn Tyr Tyr Cys Gln His Phe Trp Ser Leu Pro Phe
                85                  90                  95

Thr Phe Gly Ser Gly Thr Lys Leu Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Ala Glu Leu Val Arg Pro Gly Ala
    130                 135                 140

Leu Val Lys Leu Ser Cys Lys Thr Ser Gly Phe Asn Ile Lys Asp Tyr
145                 150                 155                 160

Phe Leu His Trp Val Arg Gln Arg Pro Asp Gln Gly Leu Glu Trp Ile
                165                 170                 175

Gly Trp Ile Asn Pro Asp Asn Gly Asn Thr Val Tyr Asp Pro Lys Phe
            180                 185                 190

Gln Gly Thr Ala Ser Leu Thr Ala Asp Thr Ser Asn Thr Val Tyr
        195                 200                 205

Leu Gln Leu Ser Gly Leu Thr Ser Glu Asp Thr Ala Val Tyr Phe Cys
    210                 215                 220

Thr Arg Arg Asp Tyr Thr Tyr Glu Lys Ala Ala Leu Asp Tyr Trp Gly
225                 230                 235                 240
```

```
Gln Gly Thr Thr Val Thr Val Ser
                245
```

<210> SEQ ID NO 114
<211> LENGTH: 240
<212> TYPE: PRT
<213> ORGANISM: Artificial Sequence
<220> FEATURE:
<223> OTHER INFORMATION: Amino acid sequence of 14G2a-based anti-GD2 scFv

<400> SEQUENCE: 114

```
Glu Val Gln Leu Leu Gln Ser Gly Pro Glu Leu Glu Lys Pro Gly Ala
1               5                   10                  15

Ser Val Met Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Ala Thr Leu Thr Val Asp Lys Ser Ser Ser Thr Ala Tyr
65                  70                  75                  80

Met His Leu Lys Ser Leu Thr Ser Glu Asp Ser Ala Val Tyr Tyr Cys
                85                  90                  95

Val Ser Gly Met Glu Tyr Trp Gly Gln Gly Thr Ser Val Thr Val Ser
            100                 105                 110

Ser Gly Gly Gly Gly Ser Gly Gly Gly Gly Ser Gly Gly Gly Gly Ser
        115                 120                 125

Asp Val Val Met Thr Gln Thr Pro Leu Ser Leu Pro Val Ser Leu Gly
    130                 135                 140

Asp Gln Ala Ser Ile Ser Cys Arg Ser Ser Gln Ser Leu Val His Arg
145                 150                 155                 160

Asn Gly Asn Thr Tyr Leu His Trp Tyr Leu Gln Lys Pro Gly Gln Ser
                165                 170                 175

Pro Lys Leu Leu Ile His Lys Val Ser Asn Arg Phe Ser Gly Val Pro
            180                 185                 190

Asp Arg Phe Ser Gly Ser Gly Ser Gly Thr Asp Phe Thr Leu Lys Ile
        195                 200                 205

Ser Arg Val Glu Ala Glu Asp Leu Gly Val Tyr Phe Cys Ser Gln Ser
    210                 215                 220

Thr His Val Pro Pro Leu Thr Phe Gly Ala Gly Thr Lys Leu Glu Leu
225                 230                 235                 240
```

<210> SEQ ID NO 115
<211> LENGTH: 31
<212> TYPE: DNA
<213> ORGANISM: Artificial Sequence
<220> FEATURE:
<223> OTHER INFORMATION: Nucleic acid sequence of Cxcl9_Fw_XmaI

<400> SEQUENCE: 115
aaaaacccgg gtcactccaa cacagtgact c         31

<210> SEQ ID NO 116
<211> LENGTH: 38
<212> TYPE: DNA
<213> ORGANISM: Artificial Sequence
<220> FEATURE:
<223> OTHER INFORMATION: Nucleic acid sequence of Cxcl9_Rv_SalI/NheI

<400> SEQUENCE: 116
aaaaagtcga cgctagccag ggtgcttgtt ggtaaagt                              38

<210> SEQ ID NO 117
<211> LENGTH: 450
<212> TYPE: DNA
<213> ORGANISM: Artificial Sequence
<220> FEATURE:
<223> OTHER INFORMATION: Nucleic acid sequence of Cxcl9

<400> SEQUENCE: 117
tcactccaac acagtgactc aatagaactc agctctgcca tgaagtccgc tgttcttttc      60
ctcttgggca tcatcttcct ggagcagtgt ggagttcgag aaccctagt gataaggaat      120 gcacgatgct cctgcatcag caccagccga ggcacgatcc actacaaatc cctcaaagac     180
ctcaaacagt ttgccccaag ccccaattgc aacaaaactg aaatcattgc tacactgaag     240
aacggagatc aaacctgcct agatccggac tcggcaaatg tgaagaagct gatgaaagaa     300
tgggaaaaga gatcagcca aagaaaaag caaagagggg gaaaaaaca tcaaaagaac        360 atgaaaaaca gaaacccaa acacccccaa agtcgtcgtc gttcaaggaa gactacataa      420
gagaccatta ctttaccaac aagcaccctg                                      450

<210> SEQ ID NO 118
<211> LENGTH: 32
<212> TYPE: DNA
<213> ORGANISM: Artificial Sequence
<220> FEATURE:
<223> OTHER INFORMATION: Nucleic acid sequence of GM-CSF_Fw_XmaI

<400> SEQUENCE: 118
aaaaacccgg gcagagagaa aggctaaggt cc                                   32

<210> SEQ ID NO 119
<211> LENGTH: 35
<212> TYPE: DNA
<213> ORGANISM: Artificial Sequence
<220> FEATURE:
<223> OTHER INFORMATION: Nucleic acid sequence of  GM-CSF_Rv_SalI/NheI

<400> SEQUENCE: 119
aaaaagtcga cgctagcagt ctgagaagct ggatt                                35

<210> SEQ ID NO 120
<211> LENGTH: 493
<212> TYPE: DNA
<213> ORGANISM: Artificial Sequence
<220> FEATURE:
<223> OTHER INFORMATION: Nucleic acid sequence of GM-CSF

<400> SEQUENCE: 120
cagagagaaa ggctaaggtc ctgaggagga tgtggctgca gaatttactt ttcctgggca      60
ttgtggtcta cagcctctca gcacccaccc gctcacccat cactgtcacc cggccttgga    120
agcatgtaga ggccatcaaa gaagccctga acctcctgga tgacatgcct gtcacgttga    180
atgaagaggt agaagtcgtc tctaacgagt ctctccttca gaagctaaca tgtgtgcaga    240
cccgcctgaa gatattcgag cagggtctac ggggcaattt caccaaactc aagggcgcct    300
tgaacatgac agccagctac taccagacat actgcccccc aactccggaa acggactgtg    360
aaacacaagt taccacctat gcggatttca tagacagcct taaaaccttt ctgactgata    420

```
tcccctttga atgcaaaaaa ccaggccaaa aatgaggaag cccaggccag ctctgaatcc    480
agcttctcag act                                                      493
```

<210> SEQ ID NO 121
<211> LENGTH: 31
<212> TYPE: DNA
<213> ORGANISM: Artificial Sequence
<220> FEATURE:
<223> OTHER INFORMATION: Nucleic acid sequence of IFNg _Fw_XmaI

<400> SEQUENCE: 121

```
aaaaacccgg gagttctggg cttctcctcc t                                  31
```

<210> SEQ ID NO 122
<211> LENGTH: 37
<212> TYPE: DNA
<213> ORGANISM: Artificial Sequence
<220> FEATURE:
<223> OTHER INFORMATION: Nucleic acid sequence of IFNg _Rv_SalI/NheI

<400> SEQUENCE: 122

```
aaaaagtcga cgctagcgac aatctcttcc ccacccc                            37
```

<210> SEQ ID NO 123
<211> LENGTH: 530
<212> TYPE: DNA
<213> ORGANISM: Artificial Sequence
<220> FEATURE:
<223> OTHER INFORMATION: Nucleic acid sequence of IFNg

<400> SEQUENCE: 123

```
agttctgggc ttctcctcct gcggcctagc tctgagacaa tgaacgctac acactgcatc    60
ttggctttgc agctcttcct catggctgtt tctggctgtt actgccacgg cacagtcatt   120
gaaagcctag aaagtctgaa taactatttt aactcaagtg catagatgt ggaagaaaag    180 agtctcttct tggatatctg gaggaactgg caaaaggatg gtgacatgaa atcctgcag   240 agccagatta tctctttcta cctcagactc tttgaagtct tgaaagacaa tcaggccatc    300
agcaacaaca taagcgtcat tgaatcacac ctgattacta ccttcttcag caacagcaag   360
gcgaaaaagg atgcattcat gagtattgcc aagtttgagg tcaacaaccc acaggtccag   420
cgccaagcat tcaatgagct catccgagtg gtccaccagc tgttgccgga atccagcctc   480
aggaagcgga aaaggagtcg ctgctgattc ggggtgggga agagattgtc              530
```

<210> SEQ ID NO 124
<211> LENGTH: 33
<212> TYPE: DNA
<213> ORGANISM: Artificial Sequence
<220> FEATURE:
<223> OTHER INFORMATION: Nucleic acid sequence of LIN28_Fw_BamHI

<400> SEQUENCE: 124

```
aaaaaggatc cctttgcctc cggacttctc tgg                                33
```

<210> SEQ ID NO 125
<211> LENGTH: 32
<212> TYPE: DNA
<213> ORGANISM: Artificial Sequence
<220> FEATURE:
<223> OTHER INFORMATION: Nucleic acid sequence of LIN28_Rv_SalI

<400> SEQUENCE: 125

```
aaaaagtcga caaagacagg gtgacactgg ga                                 32
```

<210> SEQ ID NO 126
<211> LENGTH: 857
<212> TYPE: DNA
<213> ORGANISM: Artificial Sequence
<220> FEATURE:
<223> OTHER INFORMATION: Nucleic acid sequence of LIN28 (PstI and SmaI-
      mouse trophoblast cells)

<400> SEQUENCE: 126

```
ctttgcctcc ggacttctct ggggccagca gccgcccgac ctggggcccg gggccacggg      60
ctcagcagac gaccatgggc tcggtgtcca accagcagtt tgcaggtggc tgcgccaagg     120
cagcggagaa ggcgccagag gaggcgccgc ctgacgcggc ccgagcggca gacgagccgc     180
agctgctgca cggggccggc atctgtaagt ggttcaacgt gcgcatgggg ttcggcttcc     240
tgtctatgac cgcccgcgct ggggtcgcgc tcgaccccc ggtggacgtc tttgtgcacc      300
agagcaagct gcacatggaa gggttccgaa gcctcaagga gggtgaggcg gtggagttca     360
cctttaagaa gtctgccaag ggtctggaat ccatccgtgt cactggccct ggtggtgtgt     420
tctgtattgg aagtgagcgg cggccaaagg ggaagaacat gcagaagcga agatccaaag     480
gagacaggtg ctacaactgc ggtgggctag accatcatgc caaggaatgc aagctgccac     540
cccagcccaa gaagtgccac ttttgccaaa gcatcaacca tatggtggcc tcgtgtccac     600
tgaaggccca gcagggcccc agttctcagg gaaagcctgc ctacttccgg gaggaagagg     660
aagagatcca cagccctgcc ctgctcccag aagcccagaa ttgaggccca ggagtcaggg     720
ttattctttg gctaatgggg agtttaagga aagaggcatc aatctgcaga gtggagaaag     780
tgggggtaag ggtgggttgc gtgggtagct tgcactgccg tgtctcaggc cggggttccc     840
agtgtcaccc tgtctttt                                                   857
```

<210> SEQ ID NO 127
<211> LENGTH: 876
<212> TYPE: DNA
<213> ORGANISM: Artificial Sequence
<220> FEATURE:
<223> OTHER INFORMATION: Nucleic acid sequence of CD40 (GeneArt CD40
      Blunt sites (SmaI - AgeI-blunted) in AfeI/NheI-blunted
      bidirectional)

<400> SEQUENCE: 127

```
gccaccatgg tctctctccc tcggctgtgt gctctgtggg gttgtctgct caccgctgtg      60
catctcggcc agtgtgtgac ttgttctgat aaacagtacc tgcatgacgg gcagtgctgt     120
gatctgtgcc agcccggttc taggctcacc agtcattgta cagccctgga gaagactcag     180
tgccaccctt gtgactcagg ggagttcagc gctcagtgga accgagaaat taggtgccac     240
cagcatagac actgtgagcc taatcagggg ctgcgggtga agaaagaggg taccgcagaa     300
agtgacactg tctgcacctg taaggagggc cagcattgca cctcaaaaga ttgcgaagct     360
tgtgcacagc acacaccttg tatcccaggc ttcggagtga tggagatggc tactgaaacc     420
acagacaccg tgtgccaccc atgtcccgtc ggattctttt ctaaccagag ctccctcttt     480
gagaagtgct atccatggac aagctgtgag gataagaacc tggaagtgct ccagaaaggc     540
acatcccaga ctaatgtcat tgcggactga aaatctcgga tgcgcgccct gctcgtgatc     600
ccagtggtca tgggcatcct cattactatc ttcggagtgt ttctgtacat taagaaagtg     660
gtcaagaaac ccaaggacaa cgagatcctc ccacctgcag ctaggagaca ggaccccag      720 gagatggaag attatcctgg acataataca gcagcccag tgcaggaaac tctgcacggg     780
```

```
tgtcagcccg tcacccagga ggatggcaag gaaagcagaa tctccgtcca ggaaaggcag    840
gtcactgata gcatcgcact ccgcccactc gtctga                              876
```

<210> SEQ ID NO 128
<211> LENGTH: 762
<212> TYPE: DNA
<213> ORGANISM: Artificial Sequence
<220> FEATURE:
<223> OTHER INFORMATION: Nucleic acid sequence of anti-HER2 scFv CHA21
      (1)

<400> SEQUENCE: 128

```
gatattgtcc tcacacagac tcccagctcc ctgcctgtgt ccgtcggaga gaaagtgacc     60
atgacatgca gtctagtca gacactgctc tactctaaca atcagaagaa ctacctcgca    120
tggtatcagc agaaaccagg acagagcccc aagctgctca tctcctgggc tttcacccgg    180
aaatccgggg tgcctgaccg cttcacaggt agcggctccg gaactgattt tactctgacc    240
attggatctg tgaaggcaga ggacctcgcc gtctactatt gccagcagta cagtaattat    300
ccatggactt ttggcggagg gaccaggctg gaaatcaaga gaggtggagg agggtccggt    360
ggaggagggt ctggtggagg agggagtggt ggaggagggt cagaggtgca gctgcagcag    420
tctggccccg aagtggtcaa aactggagct tcagtcaaaa tcagctgtaa ggcatctggg    480
tacagcttca ccggctactt catcaactgg gtgaagaaaa attcagggaa gagccctgag    540
tggatcggcc acatttcaag ctcctacgcc acaagcactt acaaccagaa gttcaaaaat    600
aaggccgctt taccgtggaa cacatctagt tcaaccgcct tcatgcagct gaactccctc    660
acatctgaag atagtgctgt gtactattgt gtcaggagcg gcaactacga agaatatgct    720
atggattact gggggcaggg gacctccgtg actgtctcaa gc                        762
```

<210> SEQ ID NO 129
<211> LENGTH: 66
<212> TYPE: DNA
<213> ORGANISM: Artificial Sequence
<220> FEATURE:
<223> OTHER INFORMATION: Nucleic acid sequence of IgK domain (1)

<400> SEQUENCE: 129

```
atggattttc aggtccagat tttctccttc ctcctcattt cagccagcgt cattatgtct     60
cggggg                                                                66
```

<210> SEQ ID NO 130
<211> LENGTH: 1602
<212> TYPE: DNA
<213> ORGANISM: Artificial Sequence
<220> FEATURE:
<223> OTHER INFORMATION: Nucleic acid sequence of EVIR-N1

<400> SEQUENCE: 130

```
atggacttcc aggtgcagat cttcagcttc ctgctgatct ccgccagcgt gatcatgagc     60
agaggcgaca tccagatgag ccagagccct gccagcctgt ctgcctctgt gggcgagaca    120
gtgaccatca cctgtagagc cagcggcaac atctacaact acctggcctg gtatcagcag    180
aagcagggca gagcccccca tctgctggtg tacgacgcca agacactggc cgacggcgtg    240
ccctctagat ctctggcag cggctccggc acccagtaca gcctgaagat cagctccctg    300
cagaccgagg actccggcaa ctactactgc cagcactttg gtccctgcc cttcaccttc    360 ggcagcggca ccaagctgga aatcaagaga ggcggcggag gctctggcgg aggcggatct    420
```

| | |
|---|---|
| gggggcggag gaagtggcgg gggaggatct gaagtgcagc tgcagcagtc tggcgctgag | 480 |
| ctcgtgcgac ctggcgctct cgtgaagctg agctgcaaga ccagcggctt caatatcaag | 540 |
| gactacttcc tgcactgggt gcgacagagg cctgaccagg gcctggaatg gatcggctgg | 600 |
| atcaaccccg acaacggcaa caccgtgtac gaccctaagt tccagggcac cgccagcctg | 660 |
| acagccgaca caagctccaa cacagtgtac ctgcagctga gcggcctgac ctccgaggat | 720 |
| accgccgtgt acttctgcac cagaagagac tacacctacg agaaggccgc cctggactac | 780 |
| tggggccagg gaacaaccgt gaccgtgtcc accggtcttc tgggggtgtc ccttggaggt | 840 |
| gccaaggagc atgcccccac aggcctgtac acacacagcg tgagtgctg caaagcctgc | 900 |
| aacctgggcg agggtgtggc ccagccttgt ggagccaacc agaccgtgtg tgagccctgc | 960 |
| ctggacagcc tgacgttctc cgacgtggtg agcgcgaccg agccgtgcaa gccgtgcacc | 1020 |
| gagtgcgtgg ggctccagag catgtcggcg ccgtgcgtgg aggccgacga cgccgtgtgc | 1080 |
| cgctgcgcct acggctacta ccaggatgag acgactgggc gctgcgaggc gtgccgcgtg | 1140 |
| tgcgaggcgg gctcgggcct cgtgttctcc tgccaggaca gcagaacac cgtgtgcgag | 1200 |
| gagtgccccg acggcacgta ttccgacgag gccaaccacg tggacccgtg cctgccctgc | 1260 |
| accgtgtgcg aggacaccga cgccagctc cgcgagtgca cacgctgggc cgacgccgag | 1320 |
| tgcgaggaga tccctggccg ttggattaca cggtccacac ccccagaggg ctcggacagc | 1380 |
| acagccccca gcacccagga gcctgaggca cctccagaac aagacctcat agccagcacg | 1440 |
| gtggcaggtg tggtgaccac agtgatgggc agctcccagc ccgtggtgac ccgaggcacc | 1500 |
| accgacaacc tcatccctgt ctattgctcc atcctggctg ctgtggttgt gggccttgtg | 1560 |
| gcctacatag ccttcaagag gtggaacagg gggatcctct ag | 1602 |

<210> SEQ ID NO 131
<211> LENGTH: 1578
<212> TYPE: DNA
<213> ORGANISM: Artificial Sequence
<220> FEATURE:
<223> OTHER INFORMATION: Nucleic acid sequence of EVIR-N2

<400> SEQUENCE: 131

| | |
|---|---|
| atggattttc aggtgcagat cttcagcttc ctgctgatct ccgccagcgt gatcatgagc | 60 |
| agaggcgaag ttcagctgct gcagagcgga cccgaactgg aaaaacctgg cgcctccgtg | 120 |
| atgatcagct gcaaggcctc tggcagctcc ttcaccggct acaacatgaa ctgggtccga | 180 |
| cagaacatcg gcaagagcct ggaatggatc ggcgccatcg atccttacta cggcggcacc | 240 |
| agctacaacc agaagttcaa gggcagagcc acactgaccg tggacaagag cagcagcaca | 300 |
| gcctacatgc atctgaagtc cctgaccagc gaggacagcc ccgtgtacta ctgtgtgtcc | 360 |
| ggcatggaat actggggcca gggcacaagc gtgacagtct cttctggcgg cggtggatct | 420 |
| ggcggaggcg gaagtggtgg cggcggatct gatgtggtca tgacacagac ccctctgagc | 480 |
| ctgcctgtgt ctctgggaga tcaggccagc atcagctgta agcagcca gagcctggtg | 540 |
| cacagaaacg gcaacaccta cctgcactgg tatctgcaga gcccggcca gtctcctaag | 600 |
| ctgctgatcc acaaggtgtc caacagattc agcggcgtgc ccgacagatt ctctggctct | 660 |
| ggaagcggca ccgacttcac cctgaagatt agcagagtgg aagccgagga cctgggcgtg | 720 |
| tacttctgta gccagagcac acacgtgcca cctctgacat ttggcgctgg caccaagctg | 780 |
| gaactgaccg tcttctgggg gtgtcccttg gaggtgccaa ggaggcatg ccccacaggc | 840 |

```
ctgtacacac acagcggtga gtgctgcaaa gcctgcaacc tgggcgaggg tgtggcccag    900
ccttgtggag ccaaccagac cgtgtgtgag ccctgcctgg acagcgtgac gttctccgac    960
gtggtgagcg cgaccgagcc gtgcaagccg tgcaccgagt gcgtggggct ccagagcatg   1020
tcggcgccgt gcgtggaggc cgacgacgcc gtgtgccgct cgccctacgg ctactaccag   1080
gatgagacga ctgggcgctg cgaggcgtgc cgcgtgtgcg aggcgggctc gggcctcgtg   1140
ttctcctgcc aggacaagca gaacaccgtg tgcgaggagt gccccgacgg cacgtattcc   1200
gacgaggcca accacgtgga cccgtgcctg ccctgcaccg tgtgcgagga caccgagcgc   1260
cagctccgcg agtgcacacg ctgggccgac gccgagtgcg aggagatccc tggccgttgg   1320
attacacggt ccacaccccc agagggctcg gacagcacag cccccagcac ccaggagcct   1380
gaggcacctc cagaacaaga cctcatagcc agcacggtgg caggtgtggt gaccacagtg   1440
atgggcagct cccagcccgt ggtgacccga ggcaccaccg acaacctcat ccctgtctat   1500
tgctccatcc tggctgctgt ggttgtgggc cttgtggcct acatagcctt caagaggtgg   1560
aacaggggga tcctctag                                                  1578
```

<210> SEQ ID NO 132
<211> LENGTH: 533
<212> TYPE: PRT
<213> ORGANISM: Artificial Sequence
<220> FEATURE:
<223> OTHER INFORMATION: Amino acid sequence of EVIR-N1

<400> SEQUENCE: 132

```
Met Asp Phe Gln Val Gln Ile Phe Ser Phe Leu Leu Ile Ser Ala Ser
1               5                   10                  15

Val Ile Met Ser Arg Gly Asp Ile Gln Met Ser Gln Ser Pro Ala Ser
            20                  25                  30

Leu Ser Ala Ser Val Gly Glu Thr Val Thr Ile Thr Cys Arg Ala Ser
        35                  40                  45

Gly Asn Ile Tyr Asn Tyr Leu Ala Trp Tyr Gln Gln Lys Gln Gly Lys
    50                  55                  60

Ser Pro His Leu Leu Val Tyr Asp Ala Lys Thr Leu Ala Asp Gly Val
65                  70                  75                  80

Pro Ser Arg Phe Ser Gly Ser Gly Ser Gly Thr Gln Tyr Ser Leu Lys
                85                  90                  95

Ile Ser Ser Leu Gln Thr Glu Asp Ser Gly Asn Tyr Tyr Cys Gln His
            100                 105                 110

Phe Trp Ser Leu Pro Phe Thr Phe Gly Ser Gly Thr Lys Leu Glu Ile
        115                 120                 125

Lys Arg Gly Gly Gly Gly Ser Gly Gly Gly Gly Ser Gly Gly Gly Gly
    130                 135                 140

Ser Gly Gly Gly Gly Ser Glu Val Gln Leu Gln Gln Ser Gly Ala Glu
145                 150                 155                 160

Leu Val Arg Pro Gly Ala Leu Val Lys Leu Ser Cys Lys Thr Ser Gly
                165                 170                 175

Phe Asn Ile Lys Asp Tyr Phe Leu His Trp Val Arg Gln Arg Pro Asp
            180                 185                 190

Gln Gly Leu Glu Trp Ile Gly Trp Ile Asn Pro Asp Asn Gly Asn Thr
        195                 200                 205

Val Tyr Asp Pro Lys Phe Gln Gly Thr Ala Ser Leu Thr Ala Asp Thr
    210                 215                 220

Ser Ser Asn Thr Val Tyr Leu Gln Leu Ser Gly Leu Thr Ser Glu Asp
```

```
            225                 230                 235                 240
Thr Ala Val Tyr Phe Cys Thr Arg Arg Asp Tyr Thr Tyr Glu Lys Ala
                245                 250                 255
Ala Leu Asp Tyr Trp Gly Gln Gly Thr Thr Val Thr Val Ser Thr Gly
                260                 265                 270
Leu Leu Gly Val Ser Leu Gly Ala Lys Glu Ala Cys Pro Thr Gly
            275                 280                 285
Leu Tyr Thr His Ser Gly Glu Cys Cys Lys Ala Cys Asn Leu Gly
            290                 295                 300
Gly Val Ala Gln Pro Cys Gly Ala Asn Gln Thr Val Cys Glu Pro Cys
305                 310                 315                 320
Leu Asp Ser Val Thr Phe Ser Asp Val Val Ser Ala Thr Glu Pro Cys
                325                 330                 335
Lys Pro Cys Thr Glu Cys Val Gly Leu Gln Ser Met Ser Ala Pro Cys
                340                 345                 350
Val Glu Ala Asp Asp Ala Val Cys Arg Cys Ala Tyr Gly Tyr Tyr Gln
                355                 360                 365
Asp Glu Thr Thr Gly Arg Cys Glu Ala Cys Arg Val Cys Glu Ala Gly
            370                 375                 380
Ser Gly Leu Val Phe Ser Cys Gln Asp Lys Gln Asn Thr Val Cys Glu
385                 390                 395                 400
Glu Cys Pro Asp Gly Thr Tyr Ser Asp Glu Ala Asn His Val Asp Pro
                405                 410                 415
Cys Leu Pro Cys Thr Val Cys Glu Asp Thr Glu Arg Gln Leu Arg Glu
                420                 425                 430
Cys Thr Arg Trp Ala Asp Ala Glu Cys Glu Glu Ile Pro Gly Arg Trp
            435                 440                 445
Ile Thr Arg Ser Thr Pro Pro Glu Gly Ser Asp Ser Thr Ala Pro Ser
            450                 455                 460
Thr Gln Glu Pro Glu Ala Pro Pro Glu Gln Asp Leu Ile Ala Ser Thr
465                 470                 475                 480
Val Ala Gly Val Val Thr Thr Val Met Gly Ser Ser Gln Pro Val Val
                485                 490                 495
Thr Arg Gly Thr Thr Asp Asn Leu Ile Pro Val Tyr Cys Ser Ile Leu
                500                 505                 510
Ala Ala Val Val Val Gly Leu Val Ala Tyr Ile Ala Phe Lys Arg Trp
            515                 520                 525
Asn Arg Gly Ile Leu
            530

<210> SEQ ID NO 133
<211> LENGTH: 525
<212> TYPE: PRT
<213> ORGANISM: Artificial Sequence
<220> FEATURE:
<223> OTHER INFORMATION: Amino acid sequence of EVIR-N2

<400> SEQUENCE: 133

Met Asp Phe Gln Val Gln Ile Phe Ser Phe Leu Leu Ile Ser Ala Ser
1               5                   10                  15
Val Ile Met Ser Arg Gly Glu Val Gln Leu Leu Gln Ser Gly Pro Glu
                20                  25                  30
Leu Glu Lys Pro Gly Ala Ser Val Met Ile Ser Cys Lys Ala Ser Gly
            35                  40                  45
Ser Ser Phe Thr Gly Tyr Asn Met Asn Trp Val Arg Gln Asn Ile Gly
```

```
              50                  55                  60
Lys Ser Leu Glu Trp Ile Gly Ala Ile Asp Pro Tyr Tyr Gly Gly Thr
 65                  70                  75                  80

Ser Tyr Asn Gln Lys Phe Lys Gly Arg Ala Thr Leu Thr Val Asp Lys
                     85                  90                  95

Ser Ser Ser Thr Ala Tyr Met His Leu Lys Ser Leu Thr Ser Glu Asp
                100                 105                 110

Ser Ala Val Tyr Tyr Cys Val Ser Gly Met Glu Tyr Trp Gly Gln Gly
                115                 120                 125

Thr Ser Val Thr Val Ser Ser Gly Gly Gly Ser Gly Gly Gly Gly
                130                 135                 140

Ser Gly Gly Gly Gly Ser Asp Val Val Met Thr Gln Thr Pro Leu Ser
145                 150                 155                 160

Leu Pro Val Ser Leu Gly Asp Gln Ala Ser Ile Ser Cys Arg Ser Ser
                165                 170                 175

Gln Ser Leu Val His Arg Asn Gly Asn Thr Tyr Leu His Trp Tyr Leu
                180                 185                 190

Gln Lys Pro Gly Gln Ser Pro Lys Leu Leu Ile His Lys Val Ser Asn
                195                 200                 205

Arg Phe Ser Gly Val Pro Asp Arg Phe Ser Gly Ser Gly Ser Gly Thr
                210                 215                 220

Asp Phe Thr Leu Lys Ile Ser Arg Val Glu Ala Glu Asp Leu Gly Val
225                 230                 235                 240

Tyr Phe Cys Ser Gln Ser Thr His Val Pro Pro Leu Thr Phe Gly Ala
                245                 250                 255

Gly Thr Lys Leu Glu Leu Thr Gly Leu Leu Gly Val Ser Leu Gly Gly
                260                 265                 270

Ala Lys Glu Ala Cys Pro Thr Gly Leu Tyr Thr His Ser Gly Glu Cys
                275                 280                 285

Cys Lys Ala Cys Asn Leu Gly Glu Gly Val Ala Gln Pro Cys Gly Ala
                290                 295                 300

Asn Gln Thr Val Cys Glu Pro Cys Leu Asp Ser Val Thr Phe Ser Asp
305                 310                 315                 320

Val Val Ser Ala Thr Glu Pro Cys Lys Pro Cys Thr Glu Cys Val Gly
                325                 330                 335

Leu Gln Ser Met Ser Ala Pro Cys Val Glu Ala Asp Asp Ala Val Cys
                340                 345                 350

Arg Cys Ala Tyr Gly Tyr Tyr Gln Asp Glu Thr Thr Gly Arg Cys Glu
                355                 360                 365

Ala Cys Arg Val Cys Glu Ala Gly Ser Gly Leu Val Phe Ser Cys Gln
                370                 375                 380

Asp Lys Gln Asn Thr Val Cys Glu Glu Cys Pro Asp Gly Thr Tyr Ser
385                 390                 395                 400

Asp Glu Ala Asn His Val Asp Pro Cys Leu Pro Cys Thr Val Cys Glu
                405                 410                 415

Asp Thr Glu Arg Gln Leu Arg Glu Cys Thr Arg Trp Ala Asp Ala Glu
                420                 425                 430

Cys Glu Glu Ile Pro Gly Arg Trp Ile Thr Arg Ser Thr Pro Pro Glu
                435                 440                 445

Gly Ser Asp Ser Thr Ala Pro Ser Thr Gln Glu Pro Glu Ala Pro Pro
                450                 455                 460

Glu Gln Asp Leu Ile Ala Ser Thr Val Ala Gly Val Val Thr Thr Val
465                 470                 475                 480
```

```
Met Gly Ser Ser Gln Pro Val Val Thr Arg Gly Thr Thr Asp Asn Leu
                485                 490                 495

Ile Pro Val Tyr Cys Ser Ile Leu Ala Ala Val Val Gly Leu Val
            500                 505                 510

Ala Tyr Ile Ala Phe Lys Arg Trp Asn Arg Gly Ile Leu
        515                 520                 525

<210> SEQ ID NO 134
<211> LENGTH: 34
<212> TYPE: DNA
<213> ORGANISM: Artificial Sequence
<220> FEATURE:
<223> OTHER INFORMATION: Nucleic acid sequence of TYRP1 Fw

<400> SEQUENCE: 134
aaaaaaaccg gtgacctgtg ttctgaactc ttgc                            34

<210> SEQ ID NO 135
<211> LENGTH: 32
<212> TYPE: DNA
<213> ORGANISM: Artificial Sequence
<220> FEATURE:
<223> OTHER INFORMATION: Nucleic acid sequence of TYRP1 Rv

<400> SEQUENCE: 135
aaaaaagtcg acactgtcat cactggagag ca                              32

<210> SEQ ID NO 136
<211> LENGTH: 103
<212> TYPE: DNA
<213> ORGANISM: Artificial Sequence
<220> FEATURE:
<223> OTHER INFORMATION: Nucleic acid sequence of the anti-B2m gRNA

<400> SEQUENCE: 136
ggtcgtcagc atggctcgct gttttagagc tagaaatagc aagttaaaat aaggctagtc    60
cgttatcaac ttgaaaaagt ggcaccgagt cggtgctttt ttt                     103
```